United States Patent
Edmondson et al.

(10) Patent No.: US 9,018,224 B2
(45) Date of Patent: Apr. 28, 2015

(54) SUBSTITUTED CYCLOPROPYL COMPOUNDS USEFUL AS GPR119 AGONISTS

(71) Applicant: Merck Sharp & Dohme Corp., Rahway, NJ (US)

(72) Inventors: Scott Edmondson, Clark, NJ (US); Zhiyong Hu, Livingston, NJ (US); Ping Liu, Westfield, NJ (US); Gregori J. Morriello, Randolph, NJ (US); Jason W. Szewczyk, Collegeville, PA (US); Bowei Wang, Westfield, NJ (US); Liping Wang, Cranbury, NJ (US); Harold B. Wood, Westfield, NJ (US); Cheng Zhu, Edison, NJ (US); Yuping Zhu, Basking Ridge, NJ (US); Zhiqiang Guo, Morganville, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/358,241

(22) PCT Filed: Nov. 9, 2012

(86) PCT No.: PCT/US2012/064274
§ 371 (c)(1),
(2) Date: May 15, 2014

(87) PCT Pub. No.: WO2013/074388
PCT Pub. Date: May 23, 2013

(65) Prior Publication Data
US 2014/0329798 A1    Nov. 6, 2014

Related U.S. Application Data

(60) Provisional application No. 61/559,897, filed on Nov. 15, 2011.

(51) Int. Cl.
| | | |
|---|---|---|
| *A01N 43/54* | (2006.01) | |
| *A61K 31/505* | (2006.01) | |
| *C07D 513/04* | (2006.01) | |
| *C07D 401/14* | (2006.01) | |
| *C07D 405/14* | (2006.01) | |
| *C07D 413/14* | (2006.01) | |
| *C07D 401/04* | (2006.01) | |
| *C07D 417/14* | (2006.01) | |
| *C07D 471/04* | (2006.01) | |
| *C07D 487/04* | (2006.01) | |
| *C07D 495/04* | (2006.01) | |
| *C07D 498/04* | (2006.01) | |
| *C07D 239/42* | (2006.01) | |
| *C07D 403/12* | (2006.01) | |

(Continued)

(52) U.S. Cl.
CPC ........... *C07D 513/04* (2013.01); *C07D 401/14* (2013.01); *C07D 405/14* (2013.01); *C07D 413/14* (2013.01); *C07D 401/04* (2013.01); *C07D 417/14* (2013.01); *C07D 471/04* (2013.01); *C07D 487/04* (2013.01); *C07D 495/04* (2013.01); *C07D 498/04* (2013.01); *C07D 239/42* (2013.01); *C07D 403/12* (2013.01); *C07D 403/14* (2013.01); *C07D 405/12* (2013.01); *C07D 409/12* (2013.01)

(58) Field of Classification Search
USPC .......... 514/318, 326, 256, 275; 544/180, 182, 544/238, 295, 296, 322, 324, 328, 357, 544/405; 546/194
See application file for complete search history.

(56) References Cited

U.S. PATENT DOCUMENTS

| | | |
|---|---|---|
| 6,054,587 A | 4/2000 | Reddy et al. |
| 6,110,903 A | 8/2000 | Kasibhatla et al. |

(Continued)

FOREIGN PATENT DOCUMENTS

| | | |
|---|---|---|
| WO | 98/04528 A2 | 2/1998 |
| WO | 99/01423 A1 | 1/1999 |

(Continued)

OTHER PUBLICATIONS

T. Overton et al., 153 British Journal of Pharmacology, 576-581 (2008).*
R.M. Jones et al., 19 Expert Opinion on Therapeutic Patents, 1339-1359 (2009).*
Z-L Chu et al., 24 Molecular Endocrinology, 161-170 (2010).*
S. Yoshida et al., 400 Biochemical and Biophysical Research Communications, 745-751 (2010).*
J. Szewczyk et al., 21 Bioorganic & Medicinal Chemistry Letters 2665-2669 (2011).*

(Continued)

*Primary Examiner* — Alexander R Pagano
(74) *Attorney, Agent, or Firm* — Anna L. Cocuzzo; Catherine D. Fitch

(57) ABSTRACT

Substituted cyclopropyl compounds of the formula (I): and pharmaceutically acceptable salts thereof are disclosed as useful for treating or preventing type 2 diabetes and similar conditions. The compounds are useful as agonists of the G-protein coupled receptor GPR-119. Pharmaceutical compositions and methods of treatment are also included.

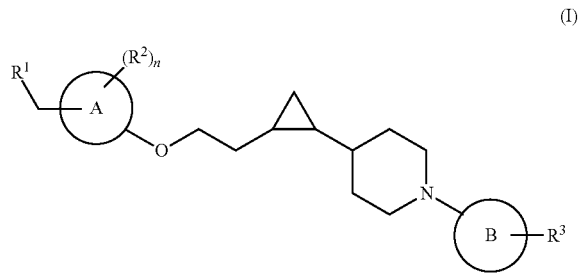

(I)

25 Claims, No Drawings

(51) Int. Cl.
*C07D 403/14* (2006.01)
*C07D 405/12* (2006.01)
*C07D 409/12* (2006.01)

(56) References Cited

U.S. PATENT DOCUMENTS

| | | |
|---|---|---|
| 6,284,748 B1 | 9/2001 | Dang et al. |
| 6,399,782 B1 | 6/2002 | Kasibhatla et al. |
| 6,489,476 B1 | 12/2002 | Dang et al. |
| 6,699,871 B2 | 3/2004 | Edmondson et al. |
| 6,730,690 B2 | 5/2004 | Olson et al. |
| 2009/0270409 A1 | 10/2009 | Alper et al. |
| 2010/0022591 A1 | 1/2010 | Bertram et al. |
| 2010/0286112 A1 | 11/2010 | Barba et al. |
| 2011/0028501 A1 | 2/2011 | Wood et al. |
| 2011/0212939 A1 | 9/2011 | Bartram et al. |
| 2012/0053180 A1 | 3/2012 | Kang et al. |
| 2012/0142706 A1 | 6/2012 | Wood et al. |

FOREIGN PATENT DOCUMENTS

| | | |
|---|---|---|
| WO | 00/39088 A1 | 7/2000 |
| WO | 00/69810 A1 | 11/2000 |
| WO | 02/08188 A1 | 1/2002 |
| WO | 02/060388 A2 | 8/2002 |
| WO | 03/104207 A2 | 12/2003 |
| WO | 2004/019869 A2 | 3/2004 |
| WO | 2004/020408 A1 | 3/2004 |
| WO | 2004/020409 A1 | 3/2004 |
| WO | 2004/058741 A1 | 7/2004 |
| WO | 2004/066963 A2 | 8/2004 |
| WO | 2006/067531 A1 | 6/2006 |
| WO | 2006/067532 A1 | 6/2006 |
| WO | 2007/003962 A2 | 1/2007 |
| WO | 2007/003964 A1 | 1/2007 |
| WO | 2009/011836 A1 | 1/2009 |
| WO | 2009/034388 A1 | 3/2009 |
| WO | 2009/042053 A2 | 4/2009 |
| WO | 2009/129036 A1 | 10/2009 |
| WO | WO 2009129036 A1 * | 10/2009 |
| WO | 2009/000087 A1 | 12/2009 |
| WO | 2010/004343 A1 | 1/2010 |
| WO | 2010/004344 A1 | 1/2010 |
| WO | 2010/004346 A1 | 1/2010 |
| WO | 2010/004347 A1 | 1/2010 |
| WO | 2010/004348 A1 | 1/2010 |
| WO | 2010/146605 A1 | 12/2010 |
| WO | 2011/008663 A2 | 1/2011 |
| WO | 2011/019538 A1 | 2/2011 |
| WO | 2011/113947 A1 | 9/2011 |
| WO | 2012/138845 A1 | 10/2012 |
| WO | 2012/173917 A1 | 12/2012 |
| WO | 2013/048916 A1 | 4/2013 |
| WO | 2013/062838 A1 | 5/2013 |
| WO | 2013/122821 A1 | 8/2013 |
| WO | 2014/052379 A1 | 4/2014 |

OTHER PUBLICATIONS

Charette, et al., Enantioselective Cyclpropanation of Allylic Alcohols with Dioxaborolane Ligands: Scope and Synthetic Applications, vol. 120, pp. 11943-11952 (1998).

Charette, et al., Stability, Reactivity, Solution, and Solid-State Structure of Halomethylzinc Alkoxides, vol. 123, pp. 12160-12167 (2001).

Costanzi, et al., "On the applicability of GPRC Homology Models . . . ", J. Med. Chem., vol. 51, pp. 2907-2914 (2008).

Eymery, et al., "The Usefullness of Phosphorus Compounds in Alkyne Synthesis", Synthesis, No. 2, pp. 185-213 (2000).

Lima, et al., "Bioisosterism: A Useful Strategy for Molecular Modification and Drug Design", Current Medicinal Chemistry, vol. 12, pp. 23-49 (2005).

Chaki, et al., "Recent Advances in feeding suppressing agents: potential therapeutic strategy for the treatment of obesity", Expert Opinion Ther. Patents, vol. 11, No. 11, pp. 1677-1692 (2001).

Spanswick, et al., "Emerging antiobesity drugs", Expert Opinion Emerging Drugs, vol. 8, No. 1, pp. 217-237 (2003).

Fernandez-Lopez, et al., "Pharmacological Approaches for the Treatment of Obesity", Drugs, vol. 62, No. 6, pp. 915-944 (2002).

Gadde, et al., "Combination pharmaceutical therapies for obesity", Expert Opin. Pharmacother., vol. 10, No. 6, pp. 921-925 (2009).

Szewczyk, et al., "Design of potent and selective GPR119 agonists for type II diabetes", Bioorganic & Medicinal Chemistry Letters, vol. 21, pp. 2665-2668 (2011).

International Search Report for PCT/US2012/64274, mailed Feb. 4, 2013.

Written Opinion for PCT/US2012/64274, dated Dec. 23, 2012.

* cited by examiner

SUBSTITUTED CYCLOPROPYL COMPOUNDS USEFUL AS GPR119 AGONISTS

CROSS-REFERENCE TO RELATED APPLICATIONS

This application is a U.S. National Phase application under 35 U.S.C. §371 of PCT/US2012/064274, filed Nov. 9, 2012, which published as WO 2013/074388 on May 23, 2013, which claims priority from U.S. provisional application 61/559,897, filed Nov. 15, 2011.

BACKGROUND OF THE INVENTION

The present invention relates to G-protein coupled receptor agonists. In particular, the present invention is directed to agonists of GPR 119 that are useful for the treatment of diabetes, especially type 2 diabetes, as well as related diseases and conditions such as obesity and metabolic syndrome.

Diabetes is a disease derived from multiple causative factors. It is characterized by elevated levels of plasma glucose (hyperglycemia) in the fasting state or after administration of glucose during an oral glucose tolerance test. There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin-dependent diabetes mellitus (T2DM), insulin is still produced in the body, and patients demonstrate resistance to the effects of insulin in stimulating glucose and lipid metabolism in the main insulin-sensitive tissues, namely, muscle, liver and adipose tissue. These patients often have normal levels of insulin, and may have hyperinsulinemia (elevated plasma insulin levels), as they compensate for the reduced effectiveness of insulin by secreting increased amounts of insulin.

There has been renewed focus on pancreatic islet-based insulin secretion that is controlled by glucose-dependent insulin secretion (GDIS). In this regard, several orphan G-protein coupled receptors (GPCR's) have recently been identified that are preferentially expressed in the β-cell and are implicated in GDIS. GPR119 is a cell-surface GPCR that is highly expressed in human (and rodent) islets as well as in insulin-secreting cell lines. Synthetic GPR119 agonists augment the release of insulin from isolated static mouse islets only under conditions of elevated glucose, and improve glucose tolerance in diabetic mice and diet-induced obese (DIO) C57/B6 mice without causing hypoglycemia. Novel GPR119 agonists therefore have the potential to function as anti-hyperglycemic agents that produce weight loss.

SUMMARY OF THE INVENTION

The present invention relates to compounds represented by the formula:

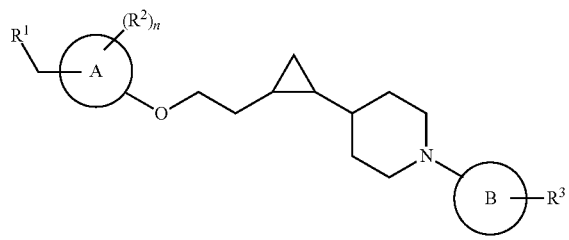

(I)

as well as pharmaceutically acceptable salts thereof.

The present invention further relates to methods of treating diabetes and related diseases and conditions.

DETAILED DESCRIPTION OF THE INVENTION

The present invention relates to compounds represented by the formula:

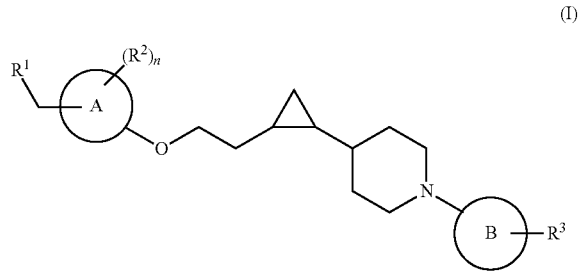

(I)

or a pharmaceutically acceptable salt thereof, wherein:
ring A is a 6-membered heteroaryl containing 1-3 N, or phenyl;
ring B is a 6-membered heteroaryl containing 1-3 N;
$R^1$ is selected from the group consisting of
  (1) 5- or 6-membered heteroaryl containing 1-4 O, S, or N, optionally substituted by $C_{1-3}$alkyl,
  (2) 3-8 membered heterocyclyl containing 1-3 O, S, or N,
  (3) $C_{1-3}$alkyl-OH,
  (4) $C(O)_2C_{1-3}$alkyl, and
  (5) $C(O)NR^4R^5$;
each $R^2$ is selected from the group consisting of
  (1) $C_{1-3}$alkyl,
  (2) $C_{1-3}$alkoxy,
  (3) halo$C_{1-3}$alkyl,
  (4) halo $C_{1-3}$ alkoxy,
  (5) halo, and
  (6) cyano;
$R^3$ is selected from the group consisting of
  (1) CN,
  (2) halo,
  (3) —$C_{1-6}$alkyl,
  (4) -halo$C_{1-6}$alkyl,
  (5) —$C_{1-6}$alkoxy,
  (6) -halo$C_{1-6}$alkoxy
  (7) —$C_{1-6}$alkyl-OH,
  (8) —$C_{1-3}$alkyl-O—$C_{1-3}$alkyl, and
  (9) —$C_{1-3}$alkyl-S—$C_{1-3}$alkyl;
$R^4$ and $R^5$ are independently selected from the group consisting of
  (1) hydrogen,
  (2) hydroxy,
  (3) $C_{1-6}$alkyl,
  (4) $C_{1-6}$alkyl-OH,
  (5) $C_{1-6}$alkyl-O—$C_{1-3}$alkyl,
  (6) halo$C_{1-6}$alkyl,
  (7) $C_{1-6}$alkoxy,
  (8) $C_{3-6}$cycloalkyl,
  (9) $C_{1-3}$alkyl-$C_{3-6}$cycloalkyl, wherein the alkyl group is optionally substituted by hydroxy, or 1-3 fluoro,
  (10) $C_{1-3}$alkyl($C_{3-6}$cycloalkyl)$_2$,
  (11) $C_{1-3}$alkyl-$C_{3-5}$heterocyclyl containing 1-3 N, O, or S, wherein the heterocyclyl is optionally substituted by 1-2 oxo,
  (12) $C_{3-5}$heterocyclyl containing 1-3 N, O or S, wherein the heterocyclyl is optionally substituted by 1-2 oxo,

(13) $C_{1-3}$alkyl-C(O)NH$_2$,
(14) $C_{1-3}$alkyl-S(O)$_2$C$_{1-3}$alkyl,
(15) $C_{1-3}$alkyl-C(O)$_2$C$_{1-3}$alkyl,
(16) C(O)C$_{1-6}$alkyl,
(17) C(O)C$_{3-6}$cycloalkyl,
(18) S(O)$_2$C$_{1-6}$alkyl, and
(19) S(O)$_2$C$_{3-6}$cycloalkyl,
or $R^4$ and $R^5$ are linked together with the nitrogen to which they are both attached to form a 3-9 membered monocyclic or bicyclic heterocyclic ring, comprising C, O, N, and S ring atoms, wherein the heterocyclic ring is optionally substituted with 1-3 $R^6$;

each $R^6$ is selected from the group consisting of:
(1) $C_{1-3}$alkyl,
(2) halo$C_{1-3}$alkyl,
(3) $C_{1-3}$alkoxy,
(4) $C_{1-3}$alkyl-OH,
(5) $C_{1-3}$alkyl-O—C$_{1-3}$alkyl,
(6) halo,
(7) hydroxy,
(8) oxo,
(9) C(O)$_2$C$_{1-3}$alkyl,
(10) C(O)NH$_2$,
(11) C(O)N(H)C$_{1-6}$alkyl,
(12) C(O)C$_{3-6}$cycloalkyl,
(13) $C_{3-6}$cycloalkyl,
(14) $C_{1-3}$alkyl-phenyl,
(15) phenyl,
(16) 5- or 6-membered heteroaryl, containing 1-3 N, O, or S; and n is 0, 1, 2, or 3.

In one embodiment, the invention relates to compounds of formula I, or a pharmaceutically acceptable salt, thereof, ring A is a 6-membered heteroaryl containing 1-3 N, or phenyl.

In one class of this embodiment,

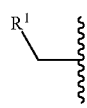

is para with respect to the ether linkage of ring A.

In one class of this embodiment, ring A is pyridinyl, pyrimidinyl, pyridazinyl, pyrazinyl, triazinyl, or phenyl.

In one sub-subclass of this class,

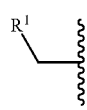

is para with respect to the ether linkage of ring A.

In another class of this embodiment, ring A is pyridinyl, pyrimidinyl, or phenyl.

In a subclass of this class, ring A is pyridinyl.

In one sub-subclass of this class,

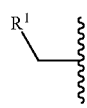

is para with respect to the ether linkage of pyridinyl.

In another subclass of this class, ring A is pyrimidinyl.

In one sub-subclass of this class,

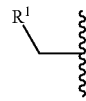

is para with respect to the ether linkage of pyrimidinyl.

In yet another subclass of this class, ring A is phenyl.

In one sub-subclass of this class, X and

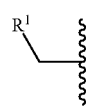

is para with respect to the ether linkage of phenyl.

In one class of this embodiment, $R^3$ and the piperidinyl group in formula I are in the para orientation.

In one embodiment, the invention relates to compounds of formula I, or a pharmaceutically acceptable salt, thereof, wherein ring B is a 6-membered heteroaryl containing 1-3 N.

In one class of this embodiment, $R^3$ and the piperidinyl group in formula I are in the para orientation.

In one class of this embodiment, ring B is pyridinyl, pyrimidinyl, pyridazinyl, pyrazinyl, or triazinyl.

In one subclass of this class, $R^3$ and the piperidinyl group in formula I are in the para orientation.

In a class of this embodiment, ring B is pyridinyl or pyrimidinyl.

In one subclass of this class, $R^3$ and the piperidinyl group in formula I are in the para orientation.

In a class of this embodiment, ring B is pyridinyl.

In one subclass of this class, $R^3$ and the piperidinyl group in formula I are in the para orientation.

In another class of this embodiment, ring B is pyrimidinyl.

In one subclass of this class, $R^3$ and the piperidinyl group in formula I are in the para orientation.

In another class of this embodiment, ring B is pyidazinyl.

In one subclass of this class, $R^3$ and the piperidinyl group in formula I are in the para orientation.

In another class of this embodiment, ring B is pyrazinyl.

In one subclass of this class, $R^3$ and the piperidinyl group in formula I are in the para orientation.

In yet another class of this embodiment, ring B is triazinyl.

In one subclass of this class, $R^3$ and the piperidinyl group in formula I are in the para orientation.

In one class of this embodiment, ring B is selected from the group consisting of:

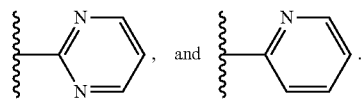 [SMILES: *c1ncccn1 ; *c1ccccn1]

In one subclass of this class, $R^3$ and the piperidinyl group in formula I are in the para orientation.

In a class of this embodiment, ring B is

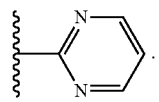

In one subclass of this class, $R^3$ and the piperidinyl group in formula I are in the para orientation.

In a subclass of this embodiment, ring B is

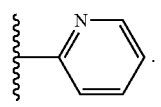

In one subclass of this class, $R^3$ and the piperidinyl group in formula I are in the para orientation.

In one embodiment, the invention relates to compounds of formula I, or a pharmaceutically acceptable salt, thereof, wherein $R^1$ is selected from the group consisting of 5- or 6-membered heteroaryl containing 1-3 O, S, or N, optionally substituted by $C_{1-3}$alkyl; 3-8 membered heterocyclyl containing 1-3 O, S, or N; $C_{1-3}$alkyl-OH; $C(O)_2C_{1-3}$alkyl; and $C(O)NR^4R^5$.

In one class of this embodiment, $R^1$ is a 5-membered heteroaryl containing 1-4 O, S, or N, optionally substituted by $C_{1-3}$alkyl.

In one subclass of this class, $R^1$ is selected from the group consisting of

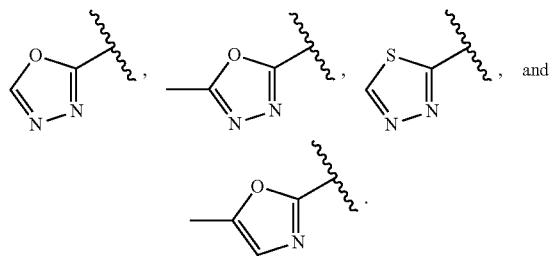

In one class of this embodiment, $R^1$ is a 6-membered heteroaryl containing 1-4 O, S, or N, optionally substituted by $C_{1-3}$alkyl.

In a subclass of this class, $R^1$ is pyridinyl, pyrimidinyl, pyridazinyl, pyrazinyl, or triazinyl.

In one class of this embodiment, $R^1$ is a 3-8 membered heterocyclyl containing 1-3 O, S, or N.

In one class of this embodiment, $R^1$ is —$C(O)_2C_{1-3}$alkyl.

In one subclass of this class, $R^1$ is —$CH_2C(O)_2Me$.

In one class of this embodiment, $R^1$ is $C_{1-3}$alkyl-OH.

In one subclass of this class, $R^1$ is —$CH_2OH$.

In one class of this embodiment, $R^1$ is —$C(O)NR^4R^5$; and $R^4$ and $R^5$ are independently selected from the group consisting of hydrogen; hydroxy; $C_{1-6}$ alkyl; $C_{1-6}$alkyl-OH; $C_{1-6}$alkyl-O—$C_{1-3}$alkyl; halo$C_{1-6}$alkyl; $C_{1-6}$alkoxy; $C_{3-6}$cycloalkyl; $C_{1-3}$alkyl-$C_{3-6}$cycloalkyl, wherein the alkyl group is optionally substituted with hydroxy, or 1-3 fluoro; $C_{1-3}$ alkyl($C_{3-6}$cycloalkyl)$_2$; $C_{1-3}$alkyl-$C_{3-5}$heterocyclyl containing 1-3 N, O, or S, wherein the heterocyclyl is optionally substituted by 1-2 oxo; $C_{3-5}$heterocyclyl containing 1-3 N, O or S, wherein the heterocyclyl is optionally substituted by 1-2 oxo; $C_{1-3}$alkyl-$C(O)NH_2$; $S(O)_2C_{1-3}$ alkyl; $C_{1-3}$ alkyl-$C(O)_2C_{1-3}$ alkyl; $C(O)C_{1-6}$alkyl; $C(O)C_{3-6}$cycloalkyl; $S(O)_2C_{1-6}$alkyl; and $S(O)_2C_{3-6}$cycloalkyl; or $R^4$ and $R^5$ are linked together with the nitrogen to which they are both attached to form a 3-9 membered monocyclic or bicyclic heterocyclic ring, comprising C, O, N, and S ring atoms, wherein the heterocyclic ring is optionally substituted with 1-3 $R^6$.

In a subclass of this class, $R^1$ is

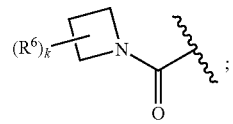

and k is 0-3.

In one class of this embodiment, $R^1$ is selected from the group consisting of

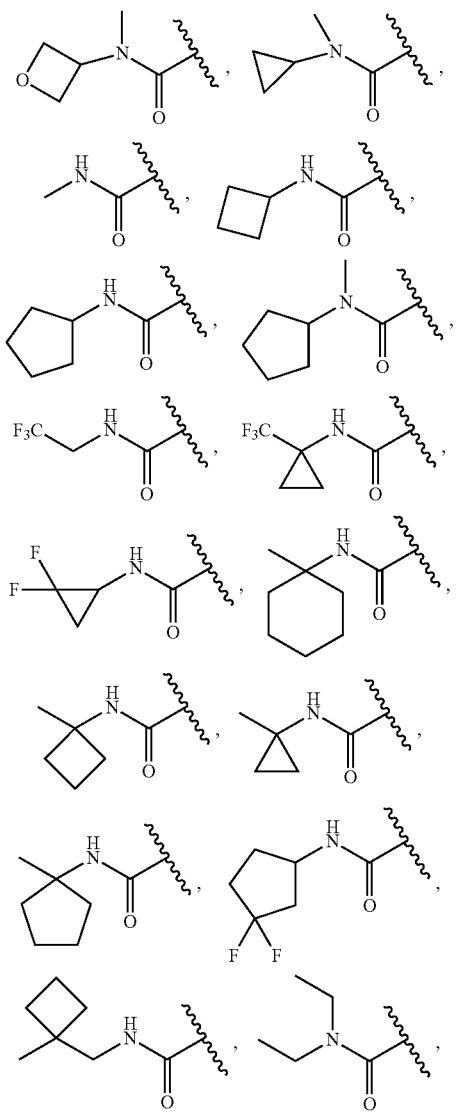

-continued
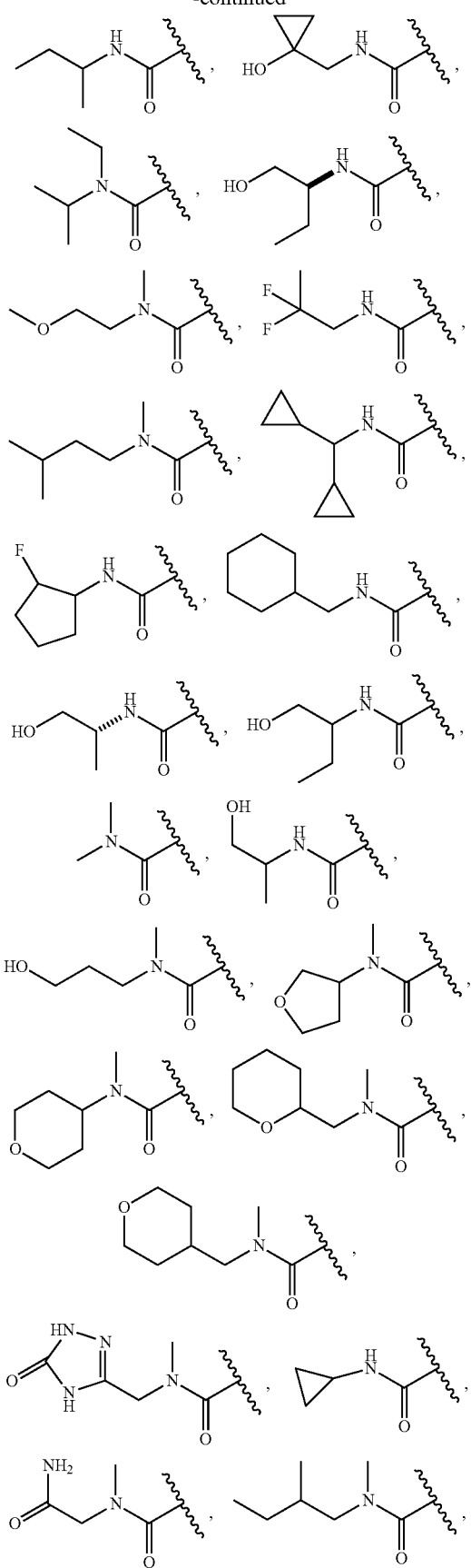
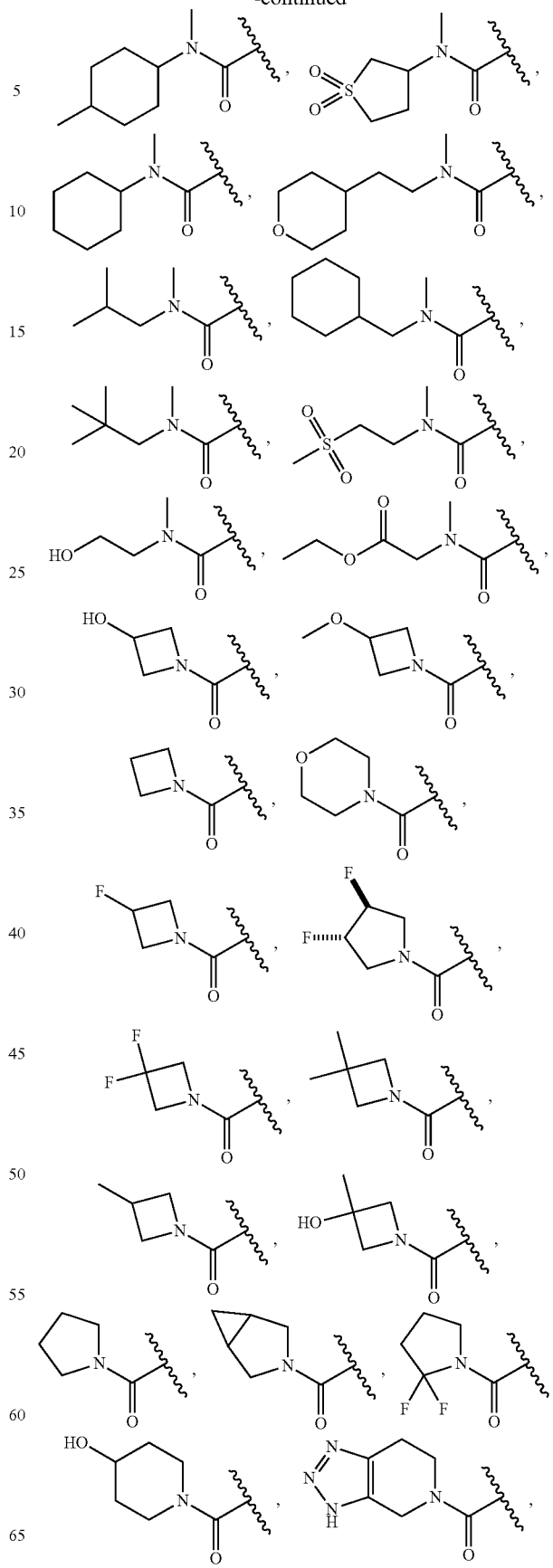

-continued
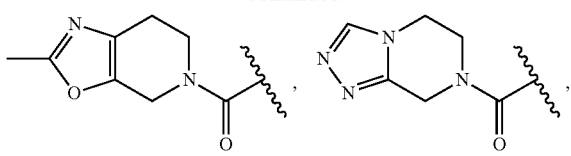
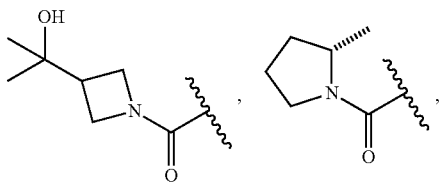
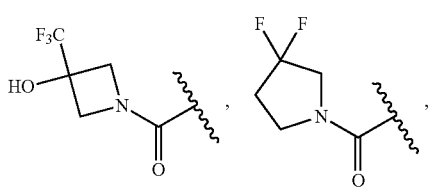
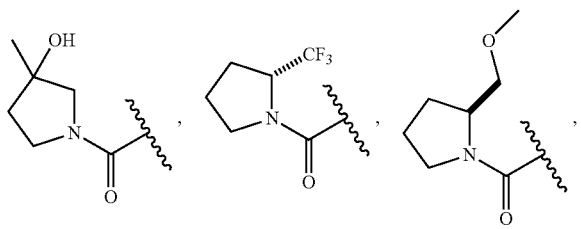
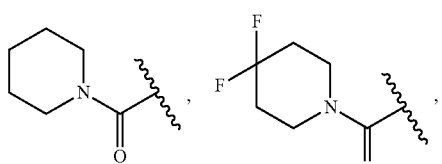
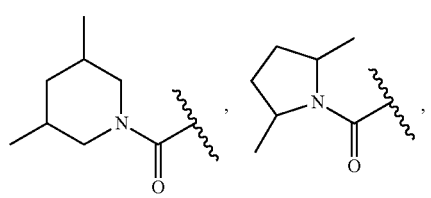
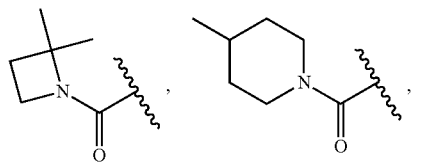
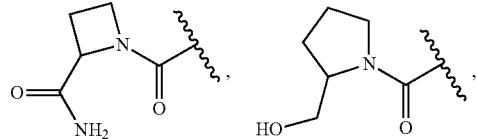
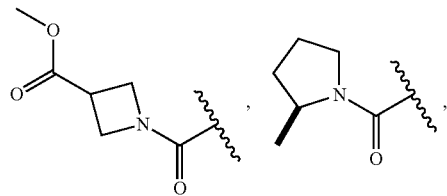
-continued
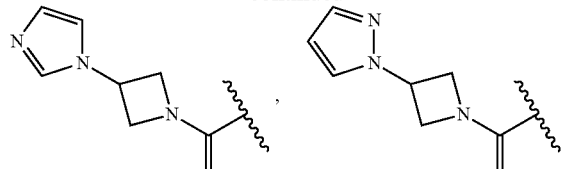
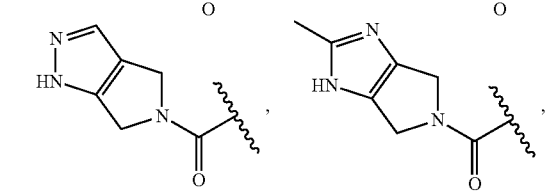
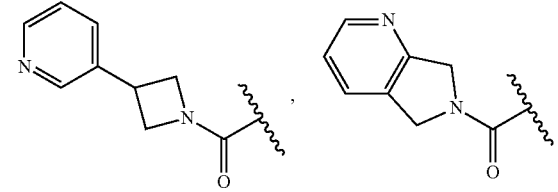
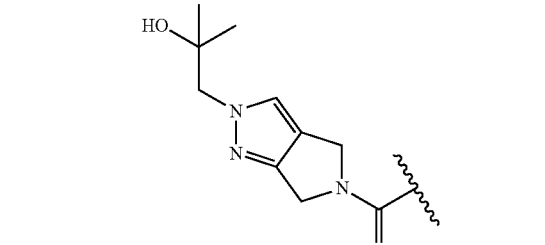
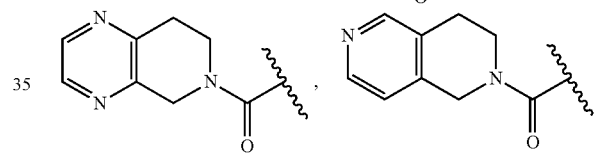
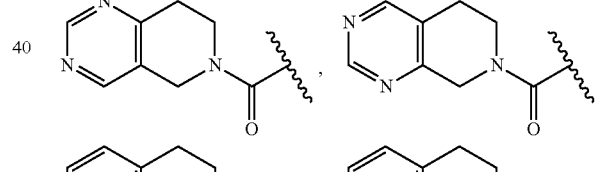
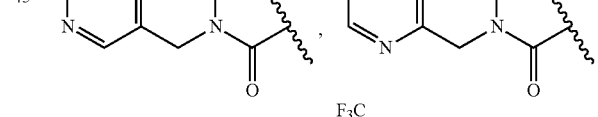
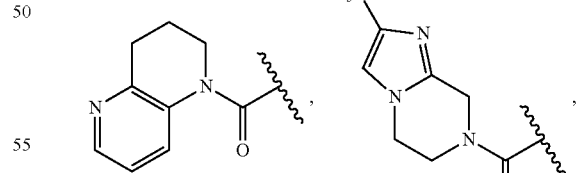
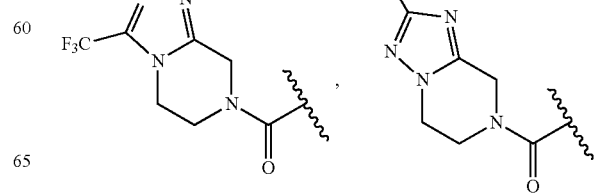

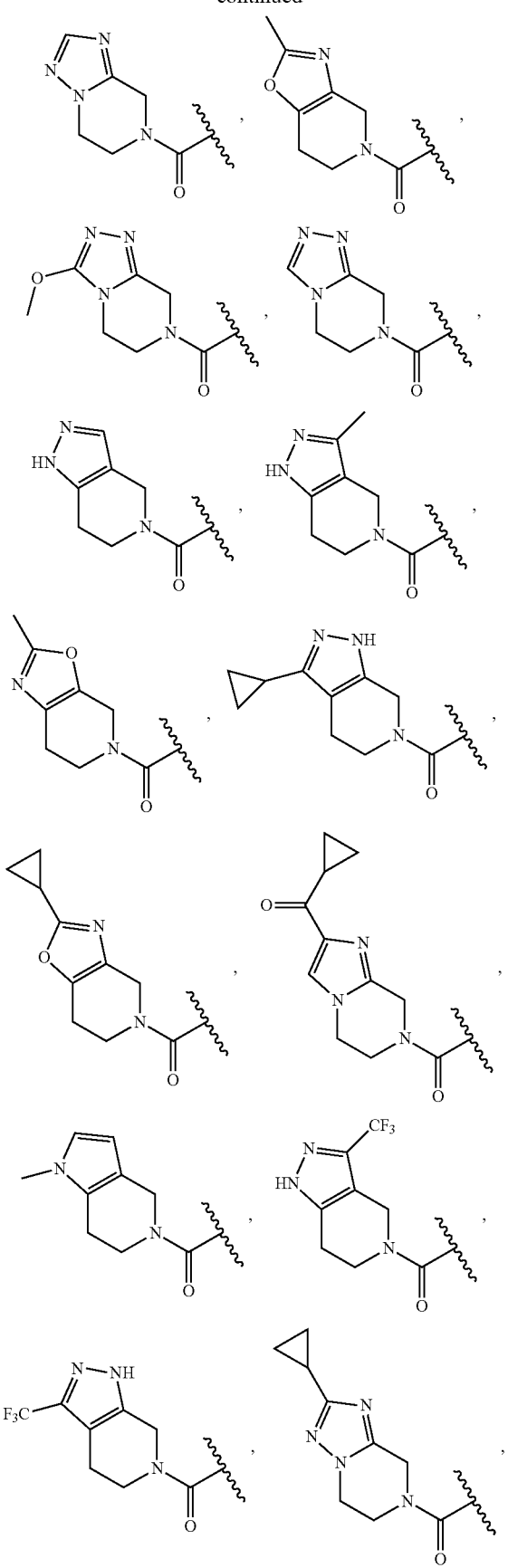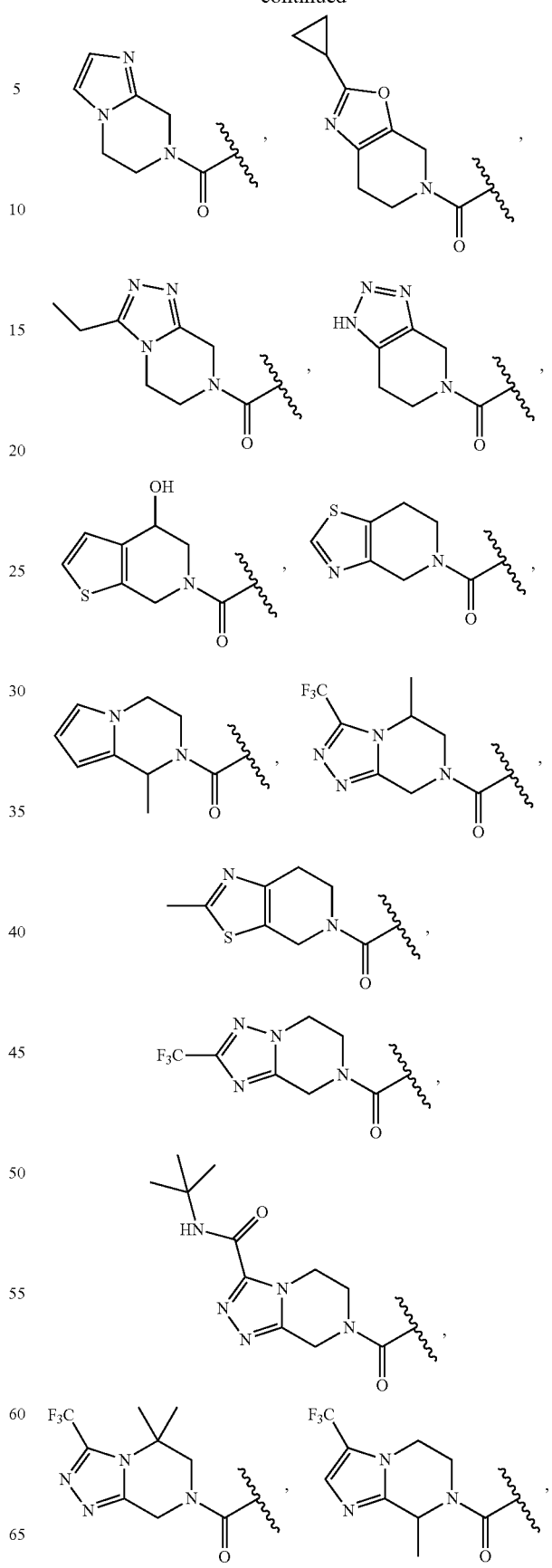

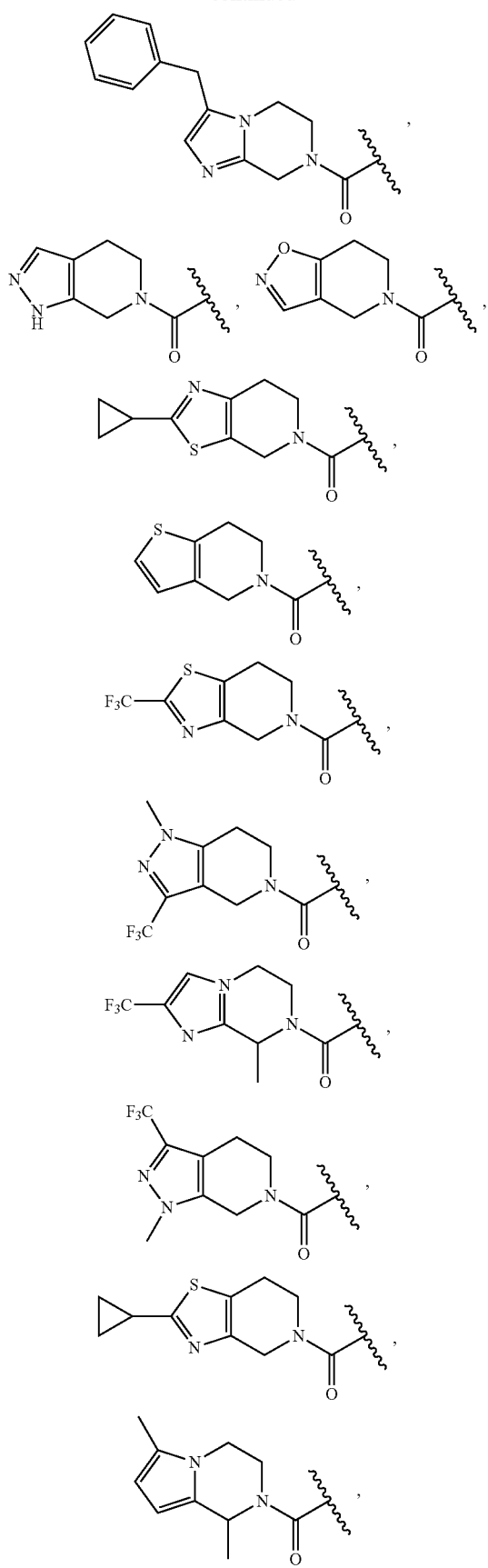

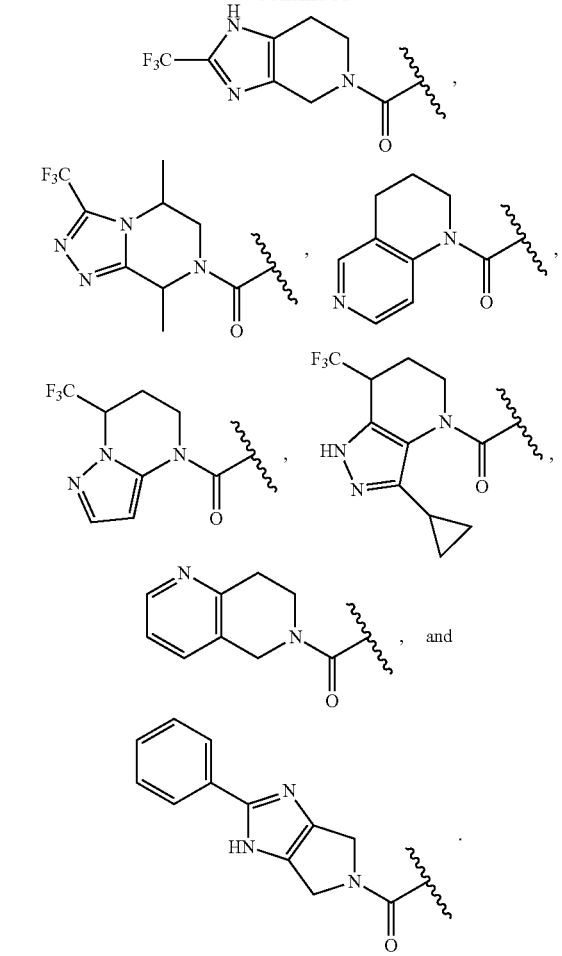

In one embodiment, the invention relates to compounds of formula I, or a pharmaceutically acceptable salt, thereof, wherein each $R^2$ is selected from the group consisting of $C_{1-3}$alkyl, $C_{1-3}$alkoxy, halo$C_{1-3}$alkyl, halo$C_{1-3}$alkoxy, halo, and cyano.

In one class of this embodiment, each $R^2$ is selected from the group consisting of Cl, F, methyl, methoxy, and cyano.

In one embodiment, the invention relates to compounds of formula I, or a pharmaceutically acceptable salt, thereof, wherein $R^3$ is selected from the group consisting of CN, halo, —$C_{1-6}$alkyl, -halo$C_{1-6}$alkyl, —$C_{1-6}$alkoxy, -halo$C_{1-6}$alkoxy, —$C_{1-6}$alkyl-OH, —$C_{1-3}$alkyl-O—$C_{1-3}$alkyl, and —$C_{1-3}$alkyl-S—$C_{1-3}$ alkyl.

In one embodiment, the invention relates to compounds of formula I, or a pharmaceutically acceptable salt, thereof, wherein $R^3$ is selected from the group consisting of halo, —$C_{1-6}$alkyl, —$C_{1-6}$alkoxy, —$C_{1-6}$alkyl-OH, —$C_{1-3}$alkyl-O—$C_{1-3}$alkyl, and —$C_{1-3}$alkyl-S—$C_{1-3}$alkyl.

In one class of this embodiment, $R^3$ is selected from the group consisting of:

-continued

[chemical structures: ~O~, ~O~/, and ~C(CH3)2-OH]

In one embodiment, the invention relates to compounds of formula I, or a pharmaceutically acceptable salt, thereof, wherein the cyclopropyl ring is the cis cyclopropyl isomer.

In one class of this embodiment, the cyclopropyl ring of formula I has the 1S and 2S stereocenters.

In one class of this embodiment, the cyclopropyl ring of formula I has the 1R and 2R stereocenters.

In one class of this embodiment, the cyclopropyl ring of formula I has the 1S and 2R stereocenters.

In one subclass of this class, the compound is present in at least 90% diastereomeric excess.

In one subclass of this class, the compound is present in at least 95% diastereomeric excess.

In one subclass of this class, the compound is present in at least 99% diastereomeric excess.

In one embodiment, the invention relates to compounds of formula I, or a pharmaceutically acceptable salt, thereof, wherein ring A is phenyl.

In one class of this embodiment, ring B is pyrimidinyl.

In one class of this embodiment, ring B is pyridinyl.

In one class of this embodiment, ring B is pyrimidinyl; and $R^3$ is halo.

In a subclass of this class, $R^1$ is a 5- or 6-membered heteroaryl containing 1-4 O, S, or N, optionally substituted by $C_{1-3}$alkyl.

In a subclass of this class, $R^1$ is a 5-membered heteroaryl containing 1-4 O, S, or N, optionally substituted by $C_{1-3}$alkyl.

In another subclass of this class, $R^1$ is —$C(O)_2C_{1-3}$alkyl.

In another subclass of this class, $R^1$ is $C_{1-3}$alkyl-OH.

In another subclass of this class, $R^1$ is —$C(O)NR^4R^5$; and $R^4$ and $R^5$ are independently selected from the group consisting of hydrogen; hydroxy; $C_1$. 6alkyl; $C_{1-6}$alkyl-OH; $C_{1-6}$alkyl-O—$C_{1-3}$alkyl; halo$C_{1-6}$alkyl; $C_{1-6}$alkoxy; $C_{3-6}$cycloalkyl; $C_{1-3}$alkyl-$C_{3-6}$cycloalkyl, wherein the alkyl group is optionally substituted with hydroxy, or 1-3 fluoro; $C_1$-3alkyl ($C_{3-6}$cycloalkyl)$_2$; $C_{1-3}$alkyl-$C_{3-5}$heterocyclyl containing 1-3 N, O, or S, wherein the heterocyclyl is optionally substituted by 1-2 oxo; $C_{3-5}$heterocyclyl containing 1-3 N, O or S, wherein the heterocyclyl is optionally substituted by 1-2 oxo; $C_{1-3}$alkyl-C(O)NH$_2$; $C_{1-3}$alkyl-S(O)$_2C_{1-3}$alkyl; $C_{1-3}$alkyl-C(O)$_2C_{1-3}$alkyl; C(O)$C_{1-6}$alkyl; C(O)$C_{3-6}$cycloalkyl; S(O)$_2$ $C_{1-6}$alkyl; and S(O)$_2C_{3-6}$cycloalkyl; or $R^4$ and $R^5$ are linked together with the nitrogen to which they are both attached to form a 3-9 membered monocyclic or bicyclic heterocyclic ring, comprising C, O, N, and S ring atoms, wherein the heterocyclic ring is optionally substituted with 1-3 $R^6$.

In another subclass of this class, $R^1$ is —$C(O)NR^4R^5$; and $R^4$ and $R^5$ are linked together with the nitrogen to which they are both attached to form a 3-9 membered monocyclic or bicyclic heterocyclic ring, comprising C, O, N, and S ring atoms, wherein the heterocyclic ring is optionally substituted with 1-3 $R^6$.

In a subclass of this class, $R^1$ is

[chemical structure: azetidine ring with $(R^6)_k$ substituent, N-C(O)- attachment]

and k is 0-3.

In one class of this embodiment, ring B is pyrimidinyl; and $R^3$ is —$C_{1-6}$alkoxy.

In another subclass of this class, $R^1$ is a 5- or 6-membered heteroaryl containing 1-4 O, S, or N, optionally substituted by $C_{1-3}$alkyl.

In another subclass of this class, $R^1$ is a 5-membered heteroaryl containing 1-4 O, S, or N, optionally substituted by $C_{1-3}$alkyl.

In another subclass of this class, $R^1$ is —$C(O)_2C_{1-3}$alkyl.

In another subclass of this class, $R^1$ is $C_{1-3}$alkyl-OH.

In another subclass of this class, $R^1$ is —$C(O)NR^4R^5$; and $R^4$ and $R^5$ are independently selected from the group consisting of hydrogen; hydroxy; $C_{1-6}$alkyl; $C_{1-6}$alkyl-OH; $C_{1-6}$alkyl-O—$C_{1-3}$alkyl; halo$C_{1-6}$alkyl; $C_{1-6}$alkoxy; $C_{3-6}$cycloalkyl; $C_{1-3}$alkyl-$C_{3-6}$cycloalkyl, wherein the alkyl group is optionally substituted with hydroxy, or 1-3 fluoro; $C_{1-3}$ alkyl ($C_{3-6}$cycloalkyl)$_2$; $C_{1-3}$alkyl-$C_{3-5}$heterocyclyl containing 1-3 N, O, or S, wherein the heterocyclyl is optionally substituted by 1-2 oxo; $C_{3-5}$heterocyclyl containing 1-3 N, O or S, wherein the heterocyclyl is optionally substituted by 1-2 oxo; $C_{1-3}$alkyl-C(O)NH$_2$; $C_{1-3}$alkyl-S(O)$_2C_{1-3}$alkyl; $C_{1-3}$alkyl-C(O)$_2C_{1-3}$alkyl; C(O)$C_{1-6}$alkyl; C(O)$C_{3-6}$cycloalkyl; S(O)$_2$ $C_{1-6}$alkyl; and S(O)$_2C_{3-6}$cycloalkyl; or $R^4$ and $R^5$ are linked together with the nitrogen to which they are both attached to form a 3-9 membered monocyclic or bicyclic heterocyclic ring, comprising C, O, N, and S ring atoms, wherein the heterocyclic ring is optionally substituted with 1-3 $R^6$.

In another subclass of this class, $R^1$ is —$C(O)NR^4R^5$; and $R^4$ and $R^5$ are linked together with the nitrogen to which they are both attached to form a 3-9 membered monocyclic or bicyclic heterocyclic ring, comprising C, O, N, and S ring atoms, wherein the heterocyclic ring is optionally substituted with 1-3 $R^6$.

In a subclass of this class, $R^1$ is

[chemical structure: azetidine ring with $(R^6)_k$ substituent, N-C(O)- attachment]

and k is 0-3.

In one class of this embodiment, ring B is pyrimidinyl; and $R^3$ is —$C_{1-3}$alkyl-O—$C_{1-3}$alkyl.

In a subclass of this class, $R^1$ is a 5- or 6-membered heteroaryl containing 1-4 O, S, or N, optionally substituted by $C_{1-3}$alkyl.

In a subclass of this class, $R^1$ is a 5-membered heteroaryl containing 1-4 O, S, or N, optionally substituted by $C_{1-3}$alkyl.

In another subclass of this class, $R^1$ is —$C(O)_2C_{1-3}$alkyl.

In another subclass of this class, $R^1$ is $C_{1-3}$alkyl-OH.

In another subclass of this class, $R^1$ is —$C(O)NR^4R^5$; and $R^4$ and $R^5$ are independently selected from the group consisting of hydrogen; hydroxy; $C_{1-6}$alkyl; $C_{1-6}$alkyl-OH; $C_{1-6}$alkyl-O—$C_{1-3}$alkyl; halo $C_{1-6}$alkyl; $C_{1-6}$alkoxy; $C_{3-6}$cycloalkyl; $C_{1-3}$alkyl-$C_{3-6}$cycloalkyl, wherein the alkyl group is optionally substituted with hydroxy, or 1-3 fluoro; $C_{1-3}$ alkyl $(C_{3-6}$cycloalkyl$)_2$; $C_{1-3}$alkyl-$C_{3-5}$heterocyclyl containing 1-3 N, O, or S, wherein the heterocyclyl is optionally substituted by 1-2 oxo; $C_{3-5}$heterocyclyl containing 1-3 N, O or S, wherein the heterocyclyl is optionally substituted by 1-2 oxo; $C_{1-3}$alkyl-C(O)NH$_2$; $C_{1-3}$alkyl-S(O)$_2$C$_{1-3}$ alkyl; $C_{1-3}$alkyl-C(O)$_2$C$_{1-3}$alkyl; C(O)C$_{1-6}$alkyl; C(O)C$_{3-6}$cycloalkyl; S(O)$_2$C$_{1-6}$alkyl; and S(O)$_2$C$_{3-6}$cycloalkyl; or $R^4$ and $R^5$ are linked together with the nitrogen to which they are both attached to form a 3-9 membered monocyclic or bicyclic heterocyclic ring, comprising C, O, N, and S ring atoms, wherein the heterocyclic ring is optionally substituted with 1-3 $R^6$.

In another subclass of this class, $R^1$ is —C(O)NR$^4$R$^5$; and $R^4$ and $R^5$ are linked together with the nitrogen to which they are both attached to form a 3-9 membered monocyclic or bicyclic heterocyclic ring, comprising C, O, N, and S ring atoms, wherein the heterocyclic ring is optionally substituted with 1-3 $R^6$.

In a subclass of this class, $R^1$ is

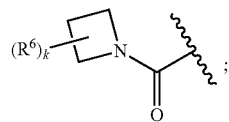

and k is 0-3.

In one class of this embodiment, ring B is pyrimidinyl; and $R^3$ is —$C_{1-6}$alkyl-OH.

In another subclass of this class, $R^1$ is a 5- or 6-membered heteroaryl containing 1-4 O, S, or N, optionally substituted by $C_{1-3}$alkyl.

In a subclass of this class, $R^1$ is a 5-membered heteroaryl containing 1-4 O, S, or N, optionally substituted by $C_{1-3}$alkyl.

In another subclass of this class, $R^1$ is —C(O)$_2$C$_{1-3}$alkyl.

In another subclass of this class, $R^1$ is $C_{1-3}$alkyl-OH.

In another subclass of this class, $R^1$ is —C(O)NR$^4$R$^5$; and $R^4$ and $R^5$ are independently selected from the group consisting of hydrogen; hydroxy; $C_1$-6alkyl; $C_{1-6}$alkyl-OH; $C_{1-6}$alkyl-O—$C_{1-3}$alkyl; halo$C_{1-6}$alkyl; $C_{1-6}$alkoxy; $C_{3-6}$cycloalkyl; $C_{1-3}$alkyl-$C_{3-6}$cycloalkyl, wherein the alkyl group is optionally substituted with hydroxy, or 1-3 fluoro; $C_{1-3}$ alkyl $(C_{3-6}$cycloalkyl$)_2$; $C_{1-3}$alkyl-$C_{3-5}$heterocyclyl containing 1-3 N, O, or S, wherein the heterocyclyl is optionally substituted by 1-2 oxo; $C_{3-5}$heterocyclyl containing 1-3 N, O or S, wherein the heterocyclyl is optionally substituted by 1-2 oxo; $C_{1-3}$alkyl-C(O)NH$_2$; $C_{1-3}$alkyl-S(O)$_2$C$_{1-3}$alkyl; $C_{1-3}$alkyl-C(O)$_2$C$_{1-3}$alkyl; C(O)C$_{1-6}$alkyl; C(O)C$_{3-6}$cycloalkyl; S(O)$_2$C$_{1-6}$alkyl; and S(O)$_2$C$_{3-6}$cycloalkyl; or $R^4$ and $R^5$ are linked together with the nitrogen to which they are both attached to form a 3-9 membered monocyclic or bicyclic heterocyclic ring, comprising C, O, N, and S ring atoms, wherein the heterocyclic ring is optionally substituted with 1-3 $R^6$.

In another subclass of this class, $R^1$ is —C(O)NR$^4$R$^5$; and $R^4$ and $R^5$ are linked together with the nitrogen to which they are both attached to form a 3-9 membered monocyclic or bicyclic heterocyclic ring, comprising C, O, N, and S ring atoms, wherein the heterocyclic ring is optionally substituted with 1-3 $R^6$.

In a subclass of this class, $R^1$ is

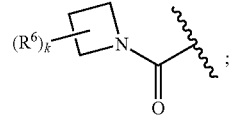

and k is 0-3.

In one class of this embodiment, ring B is pyrimidinyl; and $R^3$ is $C_{1-6}$alkyl.

In another subclass of this class, $R^1$ is a 5- or 6-membered heteroaryl containing 1-4 O, S, or N, optionally substituted by $C_{1-3}$alkyl.

In a subclass of this class, $R^1$ is a 5-membered heteroaryl containing 1-4 O, S, or N, optionally substituted by $C_{1-3}$alkyl.

In another subclass of this class, $R^1$ is —C(O)$_2$C$_{1-3}$alkyl.

In another subclass of this class, $R^1$ is $C_{1-3}$alkyl-OH.

In another subclass of this class, $R^1$ is —C(O)NR$^4$R$^5$; and $R^4$ and $R^5$ are independently selected from the group consisting of hydrogen; hydroxy; $C_{1-6}$alkyl; $C_{1-6}$alkyl-OH; $C_{1-6}$alkyl-O—$C_{1-3}$alkyl; halo$C_{1-6}$alkyl; $C_{1-6}$alkoxy; $C_{3-6}$cycloalkyl; $C_{1-3}$alkyl-$C_{3-6}$cycloalkyl, wherein the alkyl group is optionally substituted with hydroxy, or 1-3 fluoro; $C_1$-3alkyl $(C_{3-6}$cycloalkyl$)_2$; $C_{1-3}$alkyl-$C_{3-5}$heterocyclyl containing 1-3 N, O, or S, wherein the heterocyclyl is optionally substituted by 1-2 oxo; $C_{3-5}$heterocyclyl containing 1-3 N, O or S, wherein the heterocyclyl is optionally substituted by 1-2 oxo; $C_{1-3}$alkyl-C(O)NH$_2$; $C_{1-3}$alkyl-S(O)$_2$C$_{1-3}$alkyl; $C_{1-3}$alkyl-C(O)$_2$C$_{1-3}$alkyl; C(O)C$_{1-6}$alkyl; C(O)C$_{3-6}$cycloalkyl; S(O)$_2$C$_{1-6}$alkyl; and S(O)$_2$C$_{3-6}$cycloalkyl; or $R^4$ and $R^5$ are linked together with the nitrogen to which they are both attached to form a 3-9 membered monocyclic or bicyclic heterocyclic ring, comprising C, O, N, and S ring atoms, wherein the heterocyclic ring is optionally substituted with 1-3 $R^6$.

In another subclass of this class, $R^1$ is —C(O)NR$^4$R$^5$; and $R^4$ and $R^5$ are linked together with the nitrogen to which they are both attached to form a 3-9 membered monocyclic or bicyclic heterocyclic ring, comprising C, O, N, and S ring atoms, wherein the heterocyclic ring is optionally substituted with 1-3 $R^6$.

In a subclass of this class, $R^1$ is

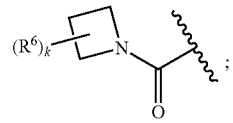

and k is 0-3.

In one embodiment, the invention relates to compounds of formula I, or a pharmaceutically acceptable salt, thereof, wherein ring A is pyridinyl.

In one class of this embodiment, ring B is pyrimidinyl.
In a subclass of this class, $R^3$ is halo.
In a subclass of this class, $R^3$ is —$C_{1-6}$alkoxy.
In a subclass of this class, $R^3$ is —$C_{1-3}$alkyl-O—$C_{1-3}$alkyl.
In a subclass of this class, $R^3$ is —$C_{1-6}$alkyl-OH.
In a subclass of this class, $R^3$ is $C_{1-6}$alkyl.
In one class of this embodiment, ring B is pyridinyl.
In one embodiment, the invention relates to compounds of formula I, or a pharmaceutically acceptable salt, thereof, wherein ring A is pyrimidinyl.
In one class of this embodiment, ring B is pyrimidinyl.

In a subclass of this class, $R^3$ is halo.
In a subclass of this class, $R^3$ is —$C_{1-6}$alkoxy.
In a subclass of this class, $R^3$ is —$C_{1-3}$alkyl-O—$C_{1-3}$alkyl.
In a subclass of this class, $R^3$ is —$C_{1-6}$alkyl-OH.
In a subclass of this class, $R^3$ is $C_{1-6}$alkyl.
In one class of this embodiment, ring B is pyridinyl.
In one embodiment, the present invention relates to compounds represented by the formula Ia:

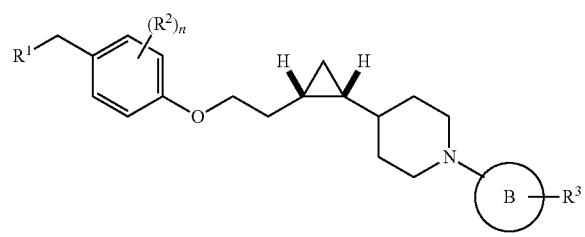

Ia or a pharmaceutically acceptable salt, wherein Ring B, $R^1$, $R^2$, $R^3$ and n are previously defined.
In a class of this embodiment, $R^1$ is

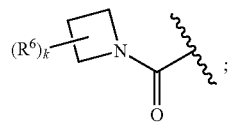

k is 0-3, and $R^6$ is previously defined.
In one embodiment, the present invention relates to compounds represented by the formula Ib:

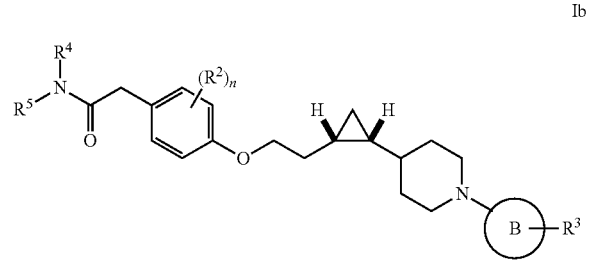

Ib or a pharmaceutically acceptable salt, wherein Ring B, $R^2$, $R^3$, $R^4$, $R^5$, and n are previously defined.
In one class of this embodiment, $R^4$ and $R^5$ are linked together with the nitrogen to which they are both attached to form a 3-9 membered monocyclic or bicyclic heterocyclic ring, comprising C, O, N, and S ring atoms, wherein the heterocyclic ring is optionally substituted with 1-3 $R^6$.
In a subclass of this class, $R^4$ and $R^5$ together form the following:

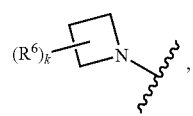

wherein k is 0-3, and $R^6$ is previously defined.

In one embodiment, the present invention relates to compounds represented by the formula Ic:

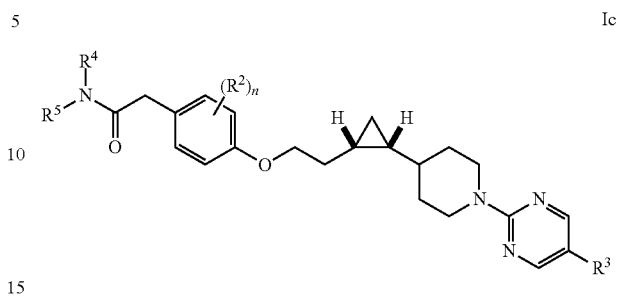

Ic or a pharmaceutically acceptable salt, wherein $R^2$, $R^3$, $R^4$, $R^5$, and n are previously defined.
In one class of this embodiment, $R^4$ and $R^5$ are linked together with the nitrogen to which they are both attached to form a 3-9 membered monocyclic or bicyclic heterocyclic ring, comprising C, O, N, and S ring atoms, wherein the heterocyclic ring is optionally substituted with 1-3 $R^6$.
In a subclass of this class, $R^4$ and $R^5$ together form the following:

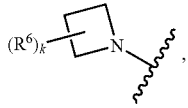

wherein k is 0-3, and $R^6$ is previously defined.
In one subclass of this class, $R^3$ is —$C_{1-3}$alkyl-O—$C_{1-3}$alkyl.
In one embodiment, the present invention relates to compounds represented by the formula Id:

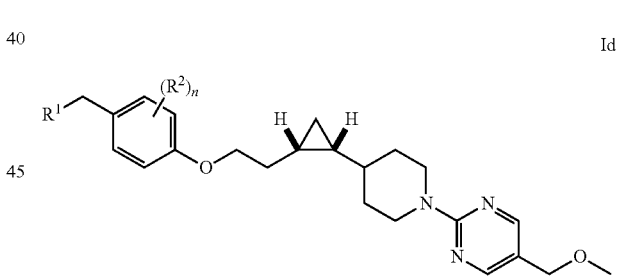

Id or a pharmaceutically acceptable salt, wherein $R^1$, $R^2$, and n are previously defined.
In a class of this embodiment, $R^1$ is

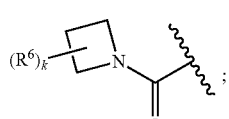

k is 0-3, and $R^6$ is previously defined.
The invention is described herein in detail using the terms defined below unless otherwise specified.
"Alkyl", as well as other groups having the prefix "alk", such as alkoxy, and the like, means carbon chains which may be linear or branched, or combinations thereof, containing the indicated number of carbon atoms. If no number is specified, 1-6 carbon atoms are intended for linear and 3-7 carbon atoms for branched alkyl groups. Examples of alkyl groups include methyl, ethyl, propyl, isopropyl, butyl, sec- and tert-butyl, pentyl, hexyl, heptyl, octyl, nonyl and the like.

"Alkyl-OH" or "hydroxyalkyl" means an alkyl group linked to a hydroxy group.

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

As used herein, "cycloalkyl" means a saturated cyclic hydrocarbon radical having the number of carbon atoms designated if no number of atoms is specified, 3-7 carbon atoms are intended, forming 1-3 carbocyclic rings that are fused. "Cycloalkyl" also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl and the like.

"Alkoxy" refers to an alkyl group linked to oxygen.

"Haloalkoxy" and "haloalkylO" are used interchangeably and refer to halo substituted alkyl groups linked through the oxygen atom. Haloalkoxy include mono-substituted as well as multiple halo substituted alkoxy groups, up to perhalo substituted alkoxy. For example, trifluoromethoxy is included.

"Haloalkyl" include mono-substituted as well as multiple halo substituted alkyl groups, up to perhalo substituted alkyl. For example, trifluoromethyl is included.

As used herein, "heterocyclyl" "heterocycle" or "heterocyclic" refers to nonaromatic cyclic ring structures in which one or more atoms in the ring, the heteroatom(s), is an element other than carbon. Heteroatoms are typically O, S or N atoms. Examples of heterocyclyl groups include: piperidine, piperazine, morpholine, pyrrolidine, tetrahydrofuran, azetidine, oxirane, or aziridine, and the like.

"Heteroaryl" (HAR) unless otherwise specified, means an aromatic or partially aromatic ring system that contains at least one ring heteroatom selected from O, S and N. Heteroaryls thus includes heteroaryls fused to other kinds of rings, such as aryls, cycloalkyls and heterocyclyls that are not aromatic. Examples of heteroaryl groups include: pyrrolyl or pyrrole, isoxazolyl or isoxazole, isothiazolyl or isothiazole, pyrazolyl or pyrazole, pyridyl, oxazolyl or oxazole, oxadiazolyl or oxadiazole, thiadiazolyl or thiadiazole, thiazolyl or thiazole, imidazolyl or imidazole, triazolyl or triazole, tetrazolyl or tetrazole, furyl, triazinyl, thienyl, pyrimidyl, benzisoxazolyl or benzisoxazole, benzoxazolyl or benzoazole, benzothiazolyl or benzothiazole, benzothiadiazolyl or benzothiadiazole, dihydrobenzofuranyl or dihydrobenzofurane, indolinyl or indoline, pyridazinyl or pyridazine, indazolyl or indazole, isoindolyl or isoindole, dihydrobenzothienyl, indolizinyl or indolizine, cinnolinyl or cinnoline, phthalazinyl or phthalazine, quinazolinyl or quinazoline, naphthyridinyl or naphthyridine, carbazolyl or carbazole, benzodioxolyl or benzodioxole, quinoxalinyl or quinoxaline, purinyl or purine, furazanyl or furazane, isobenzylfuranyl or isobenzylfurane, benzimidazolyl or benzimidazole, benzofuranyl or benzofurane, benzothienyl or benzothiene, quinolyl or quinoline, oxo-dihydroqunoline, indolyl or indole, oxindole, isoquinolyl or isoquinoline, dibenzofuranyl or dibenzofurane, and the like. For heterocyclic and heteroaryl groups, rings and ring systems containing from 3-15 atoms are included, forming 1-3 rings.

"Halogen" (Halo) includes fluorine, chlorine, bromine and iodine.

In the compounds described herein, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the formulas described herein. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within the formulas described herein can be prepared without undue experimentation by conventional techniques well known to those skilled in the art or by processes analogous to those described in the Schemes and Examples herein using appropriate isotopically-enriched reagents and/or intermediates.

The individual tautomers of the compounds of the formulas described herein, as well as mixture thereof, are encompassed with compounds of the formulas described herein. Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers.

Compounds of the formulas described herein may be separated into diastereoisomeric pairs of enantiomers by, for example, fractional crystallization from a suitable solvent. The pair of enantiomers thus obtained may be separated into individual stereoisomers by conventional means, for example by the use of an optically active amine or acid as a resolving agent or on a chiral HPLC column.

Alternatively, any enantiomer of a compound of the formulas described herein may be obtained by stereospecific synthesis using optically pure starting materials or reagents of known configuration.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Compounds described herein may contain an asymmetric center and may thus exist as enantiomers. Where the compounds according to the invention possess two or more asymmetric centers, they may additionally exist as diastereomers. When bonds to the chiral carbon are depicted as straight lines in the formulas of the invention, it is understood that both the (R) and (S) configurations of the chiral carbon, and hence both enantiomers and mixtures thereof, are embraced within the formulas. The present invention includes all such possible stereoisomers as substantially pure resolved enantiomers, racemic mixtures thereof, as well as mixtures of diastereomers. Except where otherwise specified, the formulae encompassing compounds of the present invention are shown without a definitive stereochemistry at certain positions. The present invention therefore may be understood to include all stereoisomers of compounds of Formula I and pharmaceutically acceptable salts thereof.

Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I or Ia may be obtained by stereospecific synthesis using optically pure starting materials or reagents of known configuration.

Furthermore, some of the crystalline forms for compounds of the present invention may exist as polymorphs and as such are intended to be included in the present invention. In addition, some of the compounds of the instant invention may form solvates with water or common organic solvents. Solvates, and in particular, the hydrates of the compounds of the structural formulas described herein are also included in the present invention.

Compounds of the present invention are potent agonists of the GPR 119 receptor. These compounds and pharmaceutically acceptable salts thereof are modulators of the receptor known as GPR 119, and are therefore useful in the treatment of diseases that are modulated by GPR119 ligands and agonists. Many of these diseases are summarized below. Said compounds may be used for the manufacture of a medicament for treating one or more of diseases or conditions, including, without limitation:

(1) noninsulin dependent diabetes mellitus (type 2 diabetes);
(2) hyperglycemia;
(3) metabolic syndrome/syndrome X;
(4) obesity;
(5) ischemia and myocardial infarction;
(6) neurological disorders such as Alzheimer's disease, schizophrenia, and impaired cognition;
(5) hypercholesterolemia;
(6) hypertriglyceridemia (elevated levels of triglyceride-rich-lipoproteins);
(7) mixed or diabetic dyslipidemia;
(8) low HDL cholesterol;
(9) high LDL cholesterol;
(10) Hyperapobetalipoproteinemia; and
(11) atherosclerosis.

Because the compounds are agonists of the GPR119 receptor, the compounds will be useful for lowering glucose, lipids, and insulin resistance in diabetic patients and in non-diabetic patients who have impaired glucose tolerance and/or are in a pre-diabetic condition. The compounds are useful to ameliorate hyperinsulinemia, which often occurs in diabetic or pre-diabetic patients, by modulating the swings in the level of serum glucose that often occurs in these patients. The compounds are useful for treating or reducing insulin resistance. The compounds are useful for treating or preventing gestational diabetes.

Additionally, by keeping hyperglycemia under control, the compounds are useful to delay or for preventing vascular restenosis and diabetic retinopathy.

The compounds of this invention are useful in improving or restoring β-cell function, so that they may be useful in treating type 1 diabetes or in delaying or preventing a patient with type 2 diabetes from needing insulin therapy.

The compounds, compositions, and medicaments as described herein are further useful for reducing the risks of adverse sequelae associated with metabolic syndrome, or Syndrome X, and in reducing the risk of developing atherosclerosis, delaying the onset of atherosclerosis, and/or reducing the risk of sequelae of atherosclerosis. Sequelae of atherosclerosis include angina, claudication, heart attack, stroke, and others.

The compounds may be useful for reducing appetite and body weight in obese subjects and may therefore be useful in reducing the risk of co-morbidities associated with obesity such as hypertension, atherosclerosis, diabetes, and dyslipidemia.

By elevating levels of active GLP-1 in vivo, the compounds are useful in treating neurological disorders such as Alzheimer's disease, multiple sclerosis, and schizophrenia.

One aspect of the invention provides a method for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound of the formulas described herein or a pharmaceutically acceptable salt thereof. The compound may be used alone or advantageously may be administered with a cholesterol biosynthesis inhibitor, particularly an HMG-CoA reductase inhibitor (e.g., simvastatin, atorvastatin, and the like). The compound may also be used advantageously in combination with other lipid lowering drugs such as cholesterol absorption inhibitors (e.g., stanol esters, sterol glycosides or azetidinones such as ezetimibe), ACAT inhibitors (e.g., avasimibe), CETP inhibitors (e.g. anacetrapib), niacin, bile acid sequestrants, microsomal triglyceride transport inhibitors, and bile acid reuptake inhibitors. Such combination treatments are useful for the treatment or control of conditions such hypercholesterolemia, atherosclerosis, hyperlipidemia, hypertriglyceridemia, dyslipidemia, high LDL, and low HDL.

Another aspect of the invention provides a method for the treatment and control of obesity or metabolic syndrome, which comprises administering to a patient in need of such treatment a therapeutically effective amount of a compound having the formulas described herein or a pharmaceutically acceptable salt thereof. The compound may be used alone or advantageously may be administered with an anti-obesity agent, such as a lipase inhibitor (e.g., orlistat,) or a monoamine neurotransmitter uptake inhibitor (e.g., sibutramine or phentermine). The compound may also be used advantageously in combination with CB-1 inverse agonists or antagonists (e.g., rimonabant or taranabant).

The present invention further relates to a method of treating hyperglycemia, diabetes or insulin resistance in a mammalian patient in need of such treatment which comprises administering to said patient a compound in accordance with the formulas described herein or a pharmaceutically acceptable salt thereof in an amount that is effective to treat hyperglycemia, diabetes or insulin resistance.

Yet another aspect of the invention that is of interest relates to a method of treating atherosclerosis in a mammalian patient in need of such treatment, comprising administering to said patient a compound in accordance with a compound in accordance with the formulas described herein or a pharmaceutically acceptable salt thereof in an amount that is effective to treat atherosclerosis.

Yet another aspect of the invention that is of interest relates to a method of delaying the onset of one of the aforementioned conditions and disorders where insulin resistance is a component in a mammalian patient in need thereof, comprising administering to the patient a compound in accordance with the formulas described herein or a pharmaceutically acceptable salt thereof in an amount that is effective to delay the onset of said condition.

Yet another aspect of the invention that is of interest relates to a method of reducing the risk of developing one of the aforementioned conditions and disorders where insulin resistance is a component in a mammalian patient in need thereof, comprising administering to the patient a compound in accordance with the formulas described herein or a pharmaceutically acceptable salt thereof in an amount that is effective to reduce the risk of developing said condition.

Yet another aspect of the invention that is of interest relates to a method of treating a condition or reducing the risk of developing a condition or delaying the onset of a condition selected from the group consisting of (1) hyperglycemia, (2) impaired glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension and other conditions and disorders where insulin resistance is a component, in a mammalian patient in need of such treatment, comprising administering to the patient a compound in accordance with the formulas described herein or a pharmaceutically acceptable salt thereof in an amount that is effective to treat said condition, and a compound selected from the group consisting of:

(a) DPP-IV inhibitors;
(b) insulin sensitizers selected from the group consisting of (i) PPAR agonists and (ii) biguanides;
(c) insulin and insulin mimetics;
(d) sulfonylureas and other insulin secretagogues;
(e) α-glucosidase inhibitors;
(f) glucagon receptor antagonists;
(g) GLP-1, GLP-1 mimetics, and GLP-1 receptor agonists (e.g., exenatide, liraglutide, lixisenatide);
(h) GIP, GIP mimetics, and GIP receptor agonists;
(i) PACAP, PACAP mimetics, and PACAP receptor 3 agonists;
(j) cholesterol lowering agents selected from the group consisting of
    (i) HMG-CoA reductase inhibitors, (ii) sequestrants, (iii) nicotinyl alcohol, nicotinic acid and salts thereof, (iv) PPARα agonists, (v) PPAR α/γ dual agonists, (vi) inhibitors of cholesterol absorption, (vii) acyl CoA: cholesterol acyltransferase inhibitors, and (viii) anti-oxidants;
(k) PPARδ agonists;
(l) SGLT inhibitors (e.g., dapagliflozin, canagliflozin, BI-10773, PF-729, tofogliflozin, ipragliflozin, LX-4211);
(m) antiobesity compounds;
(n) ileal bile acid transporter inhibitors;
(o) anti-inflammatory agents excluding glucocorticoids;
(p) protein tyrosine phosphatase-1B (PTP-1B) inhibitors; and
(q) antihypertensives including those acting on the angiotensin or renin systems, such as angiotensin converting enzyme inhibitors, angiotensin II receptor antagonists or renin inhibitors, (e.g., lisinopril, losartan); said compounds being administered to the patient in an amount that is effective to treat said condition.

For dosing purposes, any suitable route of administration may be employed for providing a mammal, especially a human, with an effective amount of a compound of the present invention. Dosage forms may include tablets, troches, dispersions, suspensions, solutions, capsules, creams, ointments, aerosols, and the like. Most preferably, compounds of the formulas described herein or a pharmaceutically acceptable salt thereof are administered orally. The effective dosage of active ingredient employed may vary depending on the particular compound employed, the mode of administration, the condition being treated and the severity of the condition being treated. Such dosage may be ascertained readily by a person skilled in the art.

When treating or controlling diabetes mellitus or other diseases for which compounds of the formulas described herein are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams. In the case of a 70 kg adult human, the total daily dose will generally be from about 1 milligram to about 350 milligrams. For a particularly potent compound, the dosage for an adult human may be as low as 0.1 mg. The dosage regimen may be adjusted within this range or even outside of this range to provide the optimal therapeutic response. Oral administration will usually be carried out using tablets or capsules. Examples of doses in tablets and capsules are 0.1 mg, 0.25 mg, 0.5 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 12 mg, 15 mg, 20 mg, 25 mg, 50 mg, 100 mg, 200 mg, 350 mg, 500 mg, 700 mg, 750 mg, 800 mg and 1000 mg. Other oral forms may also have the same or similar dosages.

Another aspect of the invention that is of interest is a pharmaceutical composition comprised of a compound of the formulas described herein or a pharmaceutically acceptable salt thereof in combination with a pharmaceutically acceptable carrier. The pharmaceutical compositions of the present invention comprise a compound of the formulas described herein or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

Salts of basic compounds encompassed within the term "pharmaceutically acceptable salt" refer to non-toxic salts of the compounds described herein which are generally prepared by reacting the free base with a suitable organic or inorganic acid. Representative salts of basic compounds described herein include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, formate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, palmitate, pamoate (embonate), pantothenate, phosphate/diphosphate, polygalacturonate, salicylate, stearate, sulfate, subacetate, succinate, tannate, tartrate, teoclate, tosylate, triethiodide and valerate. Furthermore, where the compounds described herein carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

A pharmaceutical composition may also comprise a prodrug, or a pharmaceutically acceptable salt thereof, if a prodrug is administered.

The compositions are typically suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the condition being treated and on the particular active ingredient selected. They may be conveniently presented in unit dosage form and prepared by any of the methods well-known in the art.

In practical use, compounds of the formulas described herein, or the pharmaceutically acceptable salts thereof can be combined as the active ingredient in intimate admixture with the pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage form. Solid pharmaceutical carriers are therefore typically employed. If desired, tablets may be coated by standard aqueous or nonaqueous techniques. Such compositions and preparations typically comprise at least about 0.1 percent of active compound, the remainder of the composition being the carrier. The percentage of active compound in these compositions may, of course, be varied and is conveniently between about 2 percent to about 60 percent of the weight of the dosage form. The amount of active compound in such therapeutically useful compositions is such that an effective dosage will be delivered.

Alternatively, the active compound can be administered intranasally as, for example, in the form of liquid drops or a spray.

The tablets, capsules and the like also typically contain a binder. Examples of suitable binders include gum tragacanth, acacia, gelatin and a synthetic or semisynthetic starch derivative, such as hydroxypropylmethylcellulose (HPMC); excipients such as dicalcium phosphate; a disintegrating agent such as corn starch, potato starch, alginic acid; a lubricant such as magnesium stearate; and in some instances, a sweetening agent such as sucrose, lactose or saccharin. When the dosage form employed is a capsule, it may contain, in addition to the components described above, a liquid carrier such as fatty oil.

Various other materials may be present as coatings or to modify the physical form of the dosage unit. For instance, tablets may be coated with shellac, sugar or both. Syrups and elixirs typically contain, in addition to the active ingredient, sucrose as a sweetening agent, methyl or propylparabens as a preservative, a dye and a flavoring such as cherry or orange flavor.

The compound of the formulas described herein or a pharmaceutically acceptable salt thereof may also be administered parenterally. Solutions or suspensions of these active compounds can be prepared in water, saline or another biocompatible vehicle, suitably mixed with a surfactant, buffer, and the like. Dispersions can also be prepared in glycerol, liquid polyethylene glycols and mixtures thereof in an oil. Under ordinary conditions of storage and use, these preparations can also contain a preservative to prevent the growth of microorganisms.

The pharmaceutical forms suitable for injectable use include sterile aqueous solutions and dispersions, and sterile powders for the extemporaneous preparation of sterile injectable solutions and dispersions. The preparation should be prepared under sterile conditions and be fluid to the extent that easy syringability exists. It should be sufficiently stable under the conditions of manufacture and storage and preserved against the growth of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and suitable oils.

As discussed supra, compounds of the present invention may be used in combination with other drugs that may also be useful in the treatment or amelioration of the diseases and conditions described herein. Such other drugs may be administered by a route and in an amount commonly used therefore, contemporaneously or sequentially with a compound of the formulas described herein or a pharmaceutically acceptable salt thereof. In the treatment of patients who have type 2 diabetes, insulin resistance, obesity, metabolic syndrome, neurological disorders, and co-morbidities that accompany these diseases, more than one drug is commonly administered. The compounds of this invention may generally be administered to a patient who is already taking one or more other drugs for these conditions.

When a compound of the formulas described herein is used contemporaneously with one or more other drugs, a pharmaceutical composition in unit dosage form containing such other drugs and the compound of the formulas described herein is preferred. However, the combination therapy also includes therapies in which a compound of the formulas described herein and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of the formulas described herein.

Examples of other active ingredients that may be administered separately or in the same pharmaceutical composition in combination with a compound of the formulas described herein include, but are not limited to:

(1) dipeptidyl peptidase-IV (DPP-4) inhibitors;

(2) insulin sensitizers, including (i) PPARγ agonists, such as the glitazones (e.g. pioglitazone), and other PPAR ligands, including (1) PPARα/γ dual agonists (e.g., muraglitazar,); (2) PPARα agonists, such as fenofibric acid derivatives (e.g., gemfibrozil), (3) selective PPARγ modulators (SPPARγM's); and (4) PPARγ partial agonists;

(ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors;
(3) insulin or insulin analogs;
(4) leptin and leptin derivatives and agonists;
(5) amylin and amylin analogs, such as pramlintide;
(6) sulfonylurea and non-sulfonylurea insulin secretagogues;
(7) α-glucosidase inhibitors (e.g., acarbose);
(8) glucagon receptor antagonists;
(9) incretin mimetics, such as GLP-1, GLP-1 analogs, derivatives, and mimetics; and GLP-1 receptor agonists (e.g., exenatide, liraglutide, lixisenatide);
(10) LDL cholesterol lowering agents such as (i) HMG-CoA reductase inhibitors (e.g., simvastatin), (ii) bile acid sequestering agents (e.g., cholestyramine), (iii) inhibitors of cholesterol absorption, (e.g., ezetimibe), and (iv) acyl CoA:cholesterol acyltransferase inhibitors, (e.g., avasimibe);
(11) HDL-raising drugs, (e.g., niacin and nicotinic acid receptor agonists);
(12) antiobesity compounds;
(13) agents intended for use in inflammatory conditions, such as aspirin, non-steroidal anti-inflammatory drugs or NSAIDs, glucocorticoids, and selective cyclooxygenase-2 or COX-2 inhibitors;
(14) antihypertensive agents, such as ACE inhibitors (e.g., lisinopril), A-II receptor blockers (e.g., losartan), renin inhibitors (e.g., aliskiren), beta blockers, and calcium channel blockers;
(15) glucokinase activators (GKAs);
(16) inhibitors of 11β-hydroxysteroid dehydrogenase type 1, (e.g., those disclosed in U.S. Pat. No. 6,730,690);
(17) CETP inhibitors (e.g., anacetrapib);
(18) inhibitors of fructose 1,6-bisphosphatase, (e.g., those disclosed in U.S. Pat. No. 6,054,587);
(19) inhibitors of acetyl CoA carboxylase-1 or 2;
(20) AMP-activated Protein Kinase (AMPK) activators;
(21) other agonists of the G-protein-coupled receptors: GPR-109, GPR-119, and GPR-40;
(22) SSTR3 antagonists;
(23) neuromedin U receptor agonists;
(24) SCD inhibitors;
(2S) GPR-105 antagonists;
(26) SGLT inhibitors (e.g., dapagliflozin, canagliflozin, BI-10773, PF-729, tofogliflozin, ipragliflozin, LX-4211);
(27) inhibitors of acyl coenzyme A:diacylglycerol acyltransferase 1 and 2 (DGAT-1 and DGAT-2);
(28) inhibitors of fatty acid synthase;
(29) inhibitors of acetyl-CoA carboxylase-1 and 2 (ACC-1 and ACC-2);
(30) inhibitors of acyl coenzyme A:monoacylglycerol acyltransferase 1 and 2 (MGAT-1 and MGAT-2);
(31) agonists of the TGR5 receptor (also known as GPBAR1, BG37, GPCR19, GPR131, and M-BAR);
(32) ileal bile acid transporter inhibitors;
(33) PACAP, PACAP mimetics, and PACAP receptor 3 agonists;
(34) PPAR agonists;
(35) protein tyrosine phosphatase-1B (PTP-1B) inhibitors; and
(36) bromocriptine mesylate and rapid-release formulations thereof.

Of particular interest are dipeptidyl peptidase-IV (DPP-4) inhibitors that can be used in combination with compounds of the present invention. Such inhibitors include, without limitation, sitagliptin (disclosed in U.S. Pat. No. 6,699,871), MK-3102, SYR-472, teneligliptin, KRP104, TS021, AMG222, SK0403, LC15-0444, vildagliptin, saxagliptin, alogliptin, denagliptin, carmegliptin, dutogliptin, melogliptin, linagliptin, and pharmaceutically acceptable salts thereof, and fixed-dose combinations of these compounds with metformin hydrochloride, pioglitazone, rosiglitazone, simvastatin, atorvastatin, or a sulfonylurea.

Other dipeptidyl peptidase-IV (DPP-4) inhibitors that can be used in combination with compounds of the formulas described herein include, but are not limited to:

(2R,3S,5R)-5-(1-methyl-4,6-dihydropyrrolo[3,4-c]pyrazol-5(1H)-yl)-2-(2,4,5-trifluorophenyl)tetrahydro-2H-pyran-3-amine;

(2R,3S,5R)-5-(1-methyl-4,6-dihydropyrrolo[3,4-c]pyrazol-5(1H)-yl)-2-(2,4,5-trifluorophenyl)tetrahydro-2H-pyran-3-amine;

(2R,3S,5R)-2-(2,5-difluorophenyl)tetrahydro-5-(4,6-dihydropyrrolo[3,4-c]pyrazol-5(1H)-yl)tetrahydro-2H-pyran-3-amine;

(3R)-4-[(3R)-3-amino-4-(2,4,5-trifluorophenyl)butanoyl]-hexahydro-3-methyl-2H-1,4-diazepin-2-one;

4-[(3R)-3-amino-4-(2,5-difluorophenyl)butanoyl]hexahydro-1-methyl-2H-1,4-diazepin-2-one hydrochloride; and (3R)-4-[(3R)-3-amino-4-(2,4,5-trifluorophenyl)butanoyl]-hexahydro-3-(2,2,2-trifluoroethyl)-2H-1,4-diazepin-2-one; and pharmaceutically acceptable salts thereof.

Another aspect of the invention that is of interest relates to the use of a compound in accordance with the formulas described herein or a pharmaceutically acceptable salt thereof in the manufacture of a medicament for use in treating a disease or condition described herein.

Compounds of the present invention were shown to be biologically active in one or more of the following assays:

Measurement of GPR119 Signaling Using LANCE 384-Well cAMP Kit

Human embryonic kidney (HEK) 293 cell lines stably transfected with human GPR119 were maintained in DMEM media containing FBS, penicillin-streptomycin, HEPES, and hygromycin. For the cAMP assay, the transfected cells were harvested using a non-enzymatic cell dissociation solution (GIBCO 2672), pelleted and resuspended in stimulation buffer (DMEM, 25 mM Hepes, 0.1% BSA, pH 7.4 in the presence of 100 μM phosphodiesterase inhibitors). The adenylate cyclase assay was constructed following the LANCE™ cAMP Kit (Perkin Elmer, AD0264) instructions. Briefly, cells with Alexa Fluor® 647-anti cAMP antibody were incubated with 10 point series diluted test article in stimulation buffer with a final concentration of 2.5% DMSO for 45 minutes. The reaction was stopped by incubating with the supplied detection buffer containing the europium chelate of the Eu-SA/Biotin-cAMP tracer for 3 hours. The assay was performed in duplicate in a 384 well plate for duplicate plates. Fluorescence at 665 nm was measured using a PHERAstar instrument. Basal activity was determined using a DMSO control and maximum response was defined as cAMP stimulation produced by an internal agonist control. Standard cAMP concentrations were assayed concurrently for conversion of fluorescence signal to cAMP level. The data was analyzed using 4-parameter curve fit in Microsoft Excel Measurement of GPR119 Signaling Using a Cyclic AMP (cAMP) Homogenous Time Resolved Fluorescence (HTRF) Assay Chinese hamster ovary (CHO) cell lines stably transfected with the permissive guanine nucleotide binding protein alpha 15 (Gα15) and murine GPR119 were maintained in DMEM media containing FBS, penicillin-streptomycin, puromycin, and G418 (geneticin). Alternatively, human embryonic kidney (HEK)293 Flp-In cells (Invitrogen, Carlsbad, Calif.) were stably transfected with a human SNP variant (S309L) of GPR119 and maintained in DMEM media containing FBS, penicillin-streptomycin, and hygromycin. Agonist activation of the GPR119 receptor was measured in receptor transfected cells described above, treated with compounds of this invention, using a commercial homogenous time resolved fluorescence (HTRF) kit for measurement of cAMP (CisBio, Bedford, Mass.). The assay was performed in 96-well half-volume plates (murine) or 384-well plates (human) following the manufacturers instructions. Briefly, suspended cells were incubated with a dose titration of test compound at room temperature for 60 min, lysed, and incubated with HTRF reagents for an additional 60 min. The plate was read using an Envision multilabel reader (Perkin Elmer) adjusted to read time resolved fluorescence and the cAMP concentrations were extrapolated from a cAMP calibration curve. GPR119 agonists will exhibit a concentration-dependent increase in intracellular cAMP. The concentration of test compound required to stimulate a half-maximal response (EC50), and efficacy as compared to an internal agonist control, was determined from a sigmoidal 4-parameter curve fit of the resulting plot of normalized activity versus compound concentration.
Evaluation of Glucose Dependent Insulin Secretion (GDIS) in Static Isolated Mouse Islets.

Pancreatic islets of Langerhans were isolated from the pancreata of 10-12 wk-old C57BL/6 mice by collagenase digestion and discontinuous Ficoll gradient separation, a modification of the original method of Lacy and Kostianovsky (Lacy & Kostianovsky, 1967 Diabetes 16-35-39). The islets were cultured overnight in RPMI 1640 medium (11 mM glucose, 10% FCS) before experimental treatment. The acute effects of compounds of this invention on GDIS were determined by 60-min static incubation with islets in Krebs-Ringers' bicarbonate (KRB) medium. The KRB medium contained, in mM, 143.5 Na$^+$, 5.8 K$^+$, 2.5 Ca$^{2+}$, 1.2 Mg$^{2+}$, 124.1 Cl$^-$, 1.2 PO$_4^{3-}$, 1.2 SO$_4^{2+}$, 25 CO$_3^{2-}$, and 10 HEPES, pH 7.4, in addition to 2 mg/ml bovine serum albumin, and either 2 (G2) or 16 (G16) mM glucose (pH 7.4). The static incubation was performed with round-bottomed 96-well plates (one islet/well with 200 µl KRB medium). The compounds were added to KRB medium just before the initiation of the 60-min incubation. Insulin concentration in aliquots of the incubation buffer was measured by the ultra-sensitive rat insulin EIA kit from ALPCO Diagnostics (Windham, N.H.).

The compounds of the invention can be prepared using the synthetic schemes described herein as well as any of several alternate methods which will be apparent to a chemist skilled in the art.

The following abbreviations may be used in the synthetic schemes or Examples: BOP is benzotriazol-1-yloxy-tris-(dimethylamino)-phosphonium hexafluorophosphate; BuTMDOB is trans 2-butyl-N,N,N,N-tetramethyl-1,3,2-dioxaborolane-4,5-dicarboxamide, as specified R,R or S,S; DCM is dichloromethane; DEAD is diethyl azodicarboxylate; DIAD is diisopropylazodicarboxylate; DIPEA is N,N-Diisopropylethylamine, or Hünig's base; DMAP is dimethylaminopyridine; DMF is N,N-dimethylformamide; DMSO is dimethyl sulfoxide; EDC is 1-ethyl-3-[3-(dimethylamino)propyl]-carbodiimide HCl; EtOAc is ethyl acetate; EtOH is ethanol; HCl is hydrochloric acid; HOBt is 1-hydroxybenzotriazole; HPLC is high performance liquid chromatography; iPrOAc is isopropyl acetate; LRMS is low resolution mass spectrometry; M is molar; mmol is millimole; n-BuLi is n-butyllithium; room temperature is RT; TEA is triethylamine; TFA is trifluoroacetic acid; THF is tetrahydrofuran; TLC is thin layer chromatography; TPAP is tetrapropylammonium perruthenate.

Reaction Schemes below illustrate the methods employed in the synthesis of the compounds of the present invention of Formula I. All substituents are as defined above unless indicated otherwise. The synthesis of the novel compounds of the present invention may be accomplished by one or more of synthetic scheme.

General Schemes

Substituted aryl and heteroaryl coupling intermediates shown in the schemes are commercially available or may be prepared from readily accessible aryl, heterocyclic, or other congeners via a host of routes.

The cyclopropyl residue in the connecting chain of the present examples may be introduced by any of several methods. A particularly convenient method is outlined in Scheme 1 below. Conversion of the readily available hydroxymethyl piperidine to the acetylene by a multistep protocol allows ready access to the indicated cis olefins after Lindlar reduction. (see, e.g., Eymery, et al, *Synth* 2000, 185-213 at page 196 for a convenient protocol). Charette's Et$_2$Zn/CH$_2$I$_2$ cyclopropanation affords racemic, diasteromerically enriched or enatiomerically enriched cyclopropyl analogs. (Charette et al, *JACS* 1998, 120, 11943-11952; further details in Charette, et al, *JACS,* 2001, 123, 12160-12167.) In the absence of an auxiliary chiral Lewis acid the cis allylic olefin affords good yields of the desired racemic analog. Also in the absence of an auxiliary chiral Lewis acid, the chiral alcohol derived from the opening of R or S glycidyl epoxide affords reasonable ratios the chiral diasteromeric cyclopropanation products.

With the addition of the auxiliary chiral Lewis acid RR or SS BuTMDOB, the same cyclopropanation protocol leads to very good ratios of the desired enantiomer in either the allylic or homoallylic cyclopropanation. The depicted chiral homoallylic alcohol requires the "matched" dioxaborolane in the double diasteroselection protocol.

SCHEME 1:

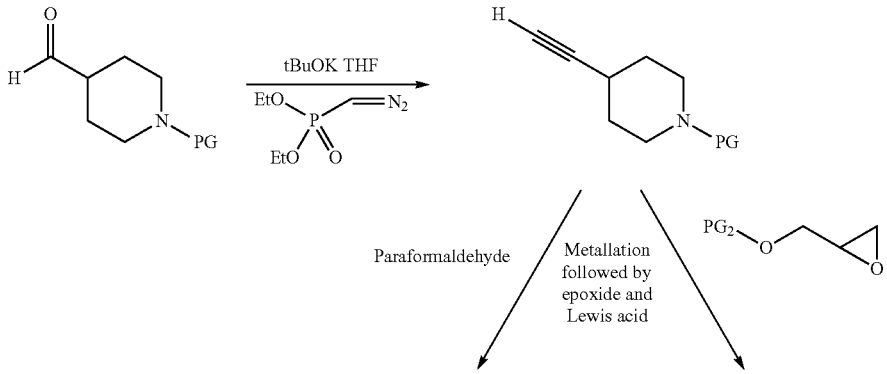

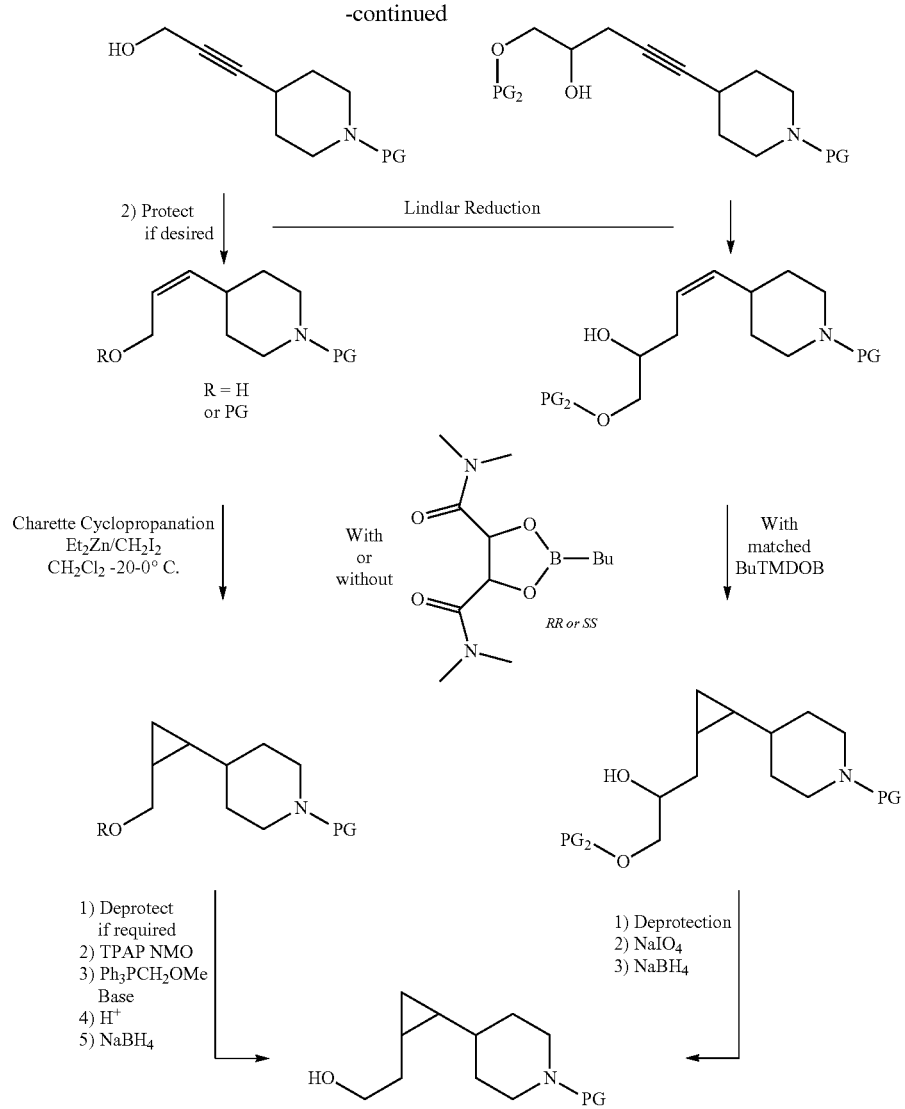

With the starting alcohol available from the above described procedures, many analogs can be made via several different routes. Depending on the amino protecting group, several methods can be used for removal which will be apparent to the skilled artisan. For example, t-butylcarbonyl can be removed via treatment with an acid, such as HCl or TFA. Another commonly used protecting group is carboxybenzyl, which can be removed via hydrogenation. Direct displacement of labile heteroaryl halides or other leaving groups can often be used to introduce the nitrogen substituent directly as shown in Scheme 2.

SCHEME 2:

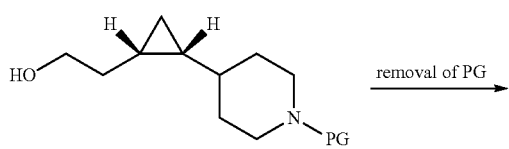

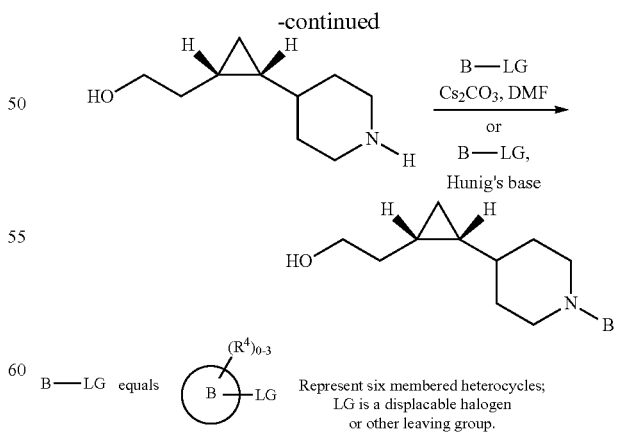

Scheme 3 outlines a particularly convenient method for conversion of the cyclopropyl alcohol to substituted aryl/heteroaryl ethers via Mitsunobu reaction with phenols. A mixture of the cyclopropyl alcohol and phenol can be treated with DIAD or DEAD in the presence of triphenylphosphine and a suitable solvent (such as THF, dichloromethane) to afford substituted aryl ethers.

SCHEME 3:

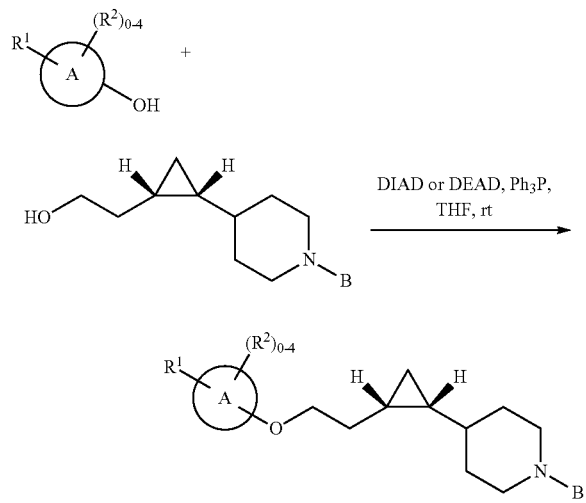

Scheme 4 outlines another convenient method for conversion of the cyclopropyl alcohol to substituted aryl/heteroaryl ethers via treatment with aryl/heteroaryl halides in the presence of a base, such as sodium hydride, heated to between 40-100° C., for a period of 2 to 24 hours.

SCHEME 4:

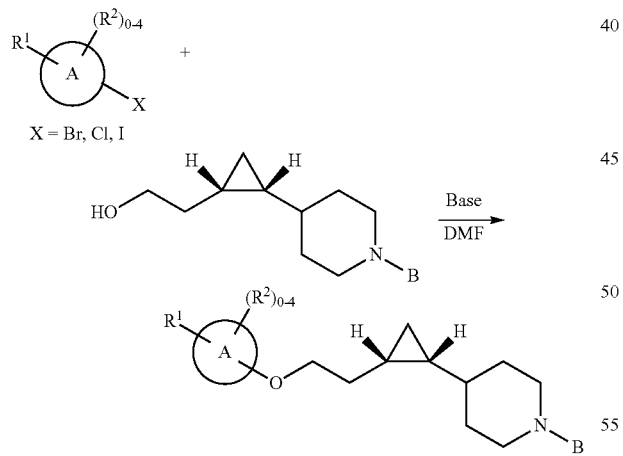

Phenols can also be used in a nucleophilic displacement via the activated cyclopropyl alcohol intermediate (Scheme 4A). The cyclopropyl alcohol can be converted to a tosylate or mesylate via treatment with tosyl or mesyl chloride in the presence of an organic base, such as TEA, and an activating agent, such as DMAP, in the appropriate solvent. This tosyl/mesylate can then be treated with the choice of substituted phenols in the presence of base, such as sodium hydride to form the desired phenoxy-ethers.

SCHEME 4A:

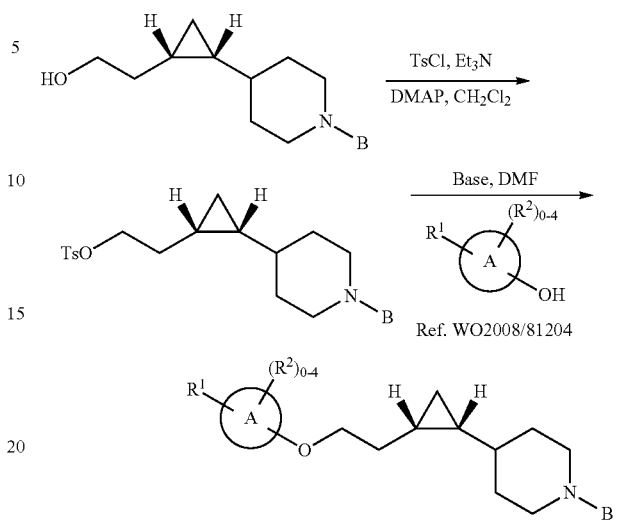

Ref. WO2008/81204

The order of introduction of aryl ether and piperidine N-substituents can be easily inverted by using protected cyclopropyl alcohol (from Scheme 1) and introducing the aryl/heteroaryl (A ring) first, then derivatisation of the piperidine nitrogen (Scheme 5). Similar chemistry is used as represented in the prior schemes, which will be apparent to the skilled artisan.

SCHEME 5:

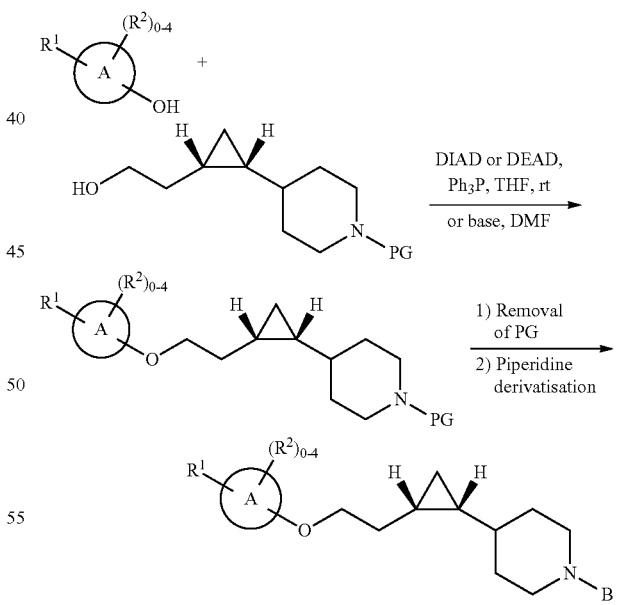

The ethers formed from the schemes 3 to 5 are either final GPR119 agonists or can be used in the final synthesis of GPR119 agonists via transformations apparent to the skilled artisan. When 0-Aryl or O-heteroaryl residue is substituted with an X group (where X=Cl, Br, I or OTf), it is possible to functionalize the residue by utilizing palladium mediated coupling reactions (Scheme 6).

SCHEME 6:

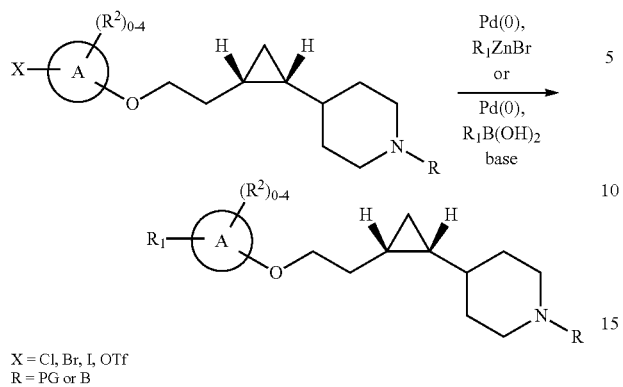

X = Cl, Br, I, OTf
R = PG or B

INTERMEDIATES

Intermediate 1

Preparation of rac cis tert-butyl 4-[2-(2-hydroxyethyl)cyclopropyl]piperidine-1-carboxylate, i.e. (tert-butyl 4-[(1S,2R)-2-(2-hydroxyethyl)cyclopropyl]piperidine-1-carboxylate and tert-butyl 4-[(1R,2S)-2-(2-hydroxyethyl)cyclopropyl]piperidine-1-carboxylate)

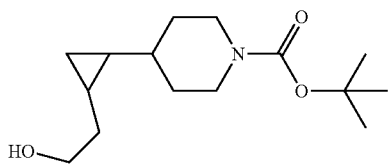 [SMILES: CC(C)(C)OC(=O)N1CCC(C2CC2CCO)CC1]

Step A: Preparation of racemic tert-butyl 4-[(1Z)-4-(benzyloxy)but-1-en-1-yl]piperidine-1-carboxylate

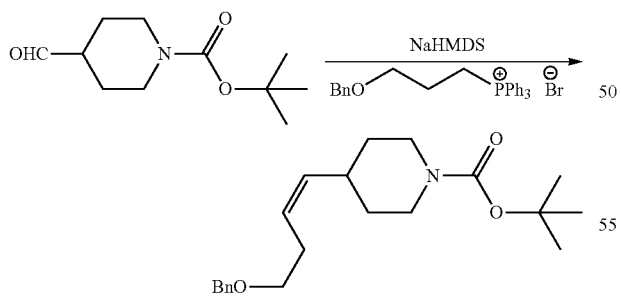

(3-Benzyloxypropyl)triphenylphosphonium bromide (2.88 g, 5.86 mmol) was suspended in 15 mL THF and cooled to 0° C. Sodium bis(trimethylsilyl)amide (1M in THF, 5.63 mL, 5.63 mmol) was added dropwise. The mixture turned deep orange. tert-Butyl 4-formylpiperidine-1-carboxylate (1 g, 4.69 mmol) in 3 mL THF was added after 5 minutes. Color faded to slight yellow. The reaction was stirred at RT for 1.5 hours, before quenching with saturated aqueous ammonium chloride solution. The aqueous layer was extracted twice with ethyl acetate. The organic layers were combined, washed with water and brine, dried over sodium sulfate, filtered, concentrated and purified by passing through a 40 gram Biotage silica gel cartridge using 20% EtOAc/hexanes to afford the product as colorless oil. NMR integration indicated >20:1 Z/E selectivity. LRMS calc: 345.2; obs: 346.5 (M+1).

Step B: rac-tert-butyl 4-{2-[2-(benzyloxy)ethyl]cyclopropyl}piperidine-1-carboxylate, i.e., (tert-butyl 4-{(1S,2R)-2-[2-(benzyloxy)ethyl]cyclopropyl}piperidine-1-carboxylate and tert-butyl 4-{(1R,2S)-2-[2-(benzyloxy)ethyl]cyclopropyl}piperidine-1-carboxylate)

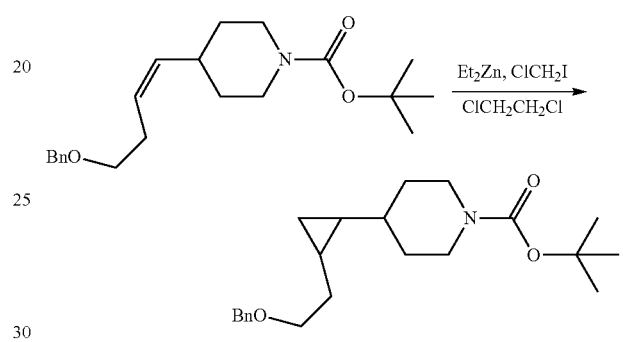

Dichloroethane (5 mL) was degassed and purged with argon three times before diethylzinc solution (1M in hexanes, 1.74 mL, 1.74 mmol) was added. The solution was cooled to −20° C. Chloroiodomethane (613 mg, 3.47 mmol) was added dropwise while maintaining internal temperature below −15° C. After stirring for 10 minutes at −20° C., tert-butyl 4-[(1Z)-4-(benzyloxy)but-1-en-1-yl]piperidine-1-carboxylate (from step 1, this Example 200 mg, 0.579 mmol) in degassed dichloroethane (1 mL) was added dropwise. The reaction was stirred at −20° for 10 minutes before slowly warming to RT. The reaction mixture was cooled to −10° C. after 1 hour. A 1:4 mixture of saturated aqueous ammonium chloride and aqueous ammonium hydroxide (28% w/w) was slowly introduced to quench excess reagents. The mixture was stirred at RT for 3 hours. The aqueous layer was separated and extracted twice with dichloromethane. The combined organic layers were washed with brine, dried over sodium sulfate, concentrated and purified by column chromatography eluting with 25% EtOAc/hexanes to give the product as colorless oil. LRMS calc: 359.25; obs: 360.5 (M+1).

Step C: rac cis tert-Butyl 4-[2-(2-hydroxyethyl)cyclopropyl]piperidine-1-carboxylate, i.e. (tert-butyl 4-[(1S,2R)-2-(2-hydroxyethyl)cyclopropyl]piperidine-1-carboxylate and tert-butyl 4-[(1R,2S)-2-(2-hydroxyethyl)cyclopropyl]piperidine-1-carboxylate)

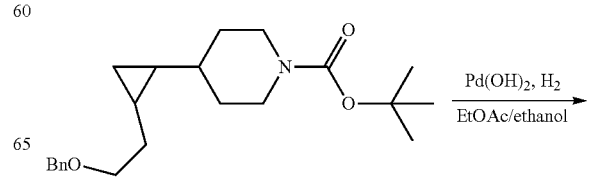

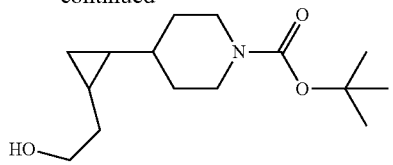

Racemic-cis tert-butyl 4-{2-[2-(benzyloxy)ethyl]cyclopropyl}piperidine-1-carboxylate from step 2 (140 mg, 0.39 mmol) was dissolved in 5 mL ethyl acetate and ethanol (1:1). The solution was degassed and purged with nitrogen 3 times, before palladium hydroxide (20% on carbon, 54.6 mg, 0.08 mmol) was added. The mixture was degassed and purged with hydrogen three times. The reaction was stirred under a hydrogen balloon at RT for 1 hour and filtered through a small plug of silica gel to remove catalyst. The silica gel plug was thoroughly washed with acetone. The eluent was concentrated to give the crude product, which was used without further purification. LRMS calc: 269.2; obs: 270.2 (M+1).

Intermediate 2

Preparation of benzyl 4-[(1R,2S)-2-(2-hydroxyethyl)cyclopropyl]piperidine-1-carboxylate

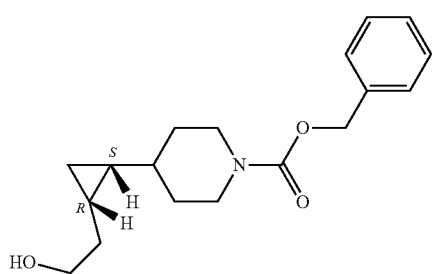

Step A: Preparation of tert-butyl 4-[(4R)-5-(benzyloxy)-4-hydroxypent-1-yn-1-yl]piperidine-1-carboxylate

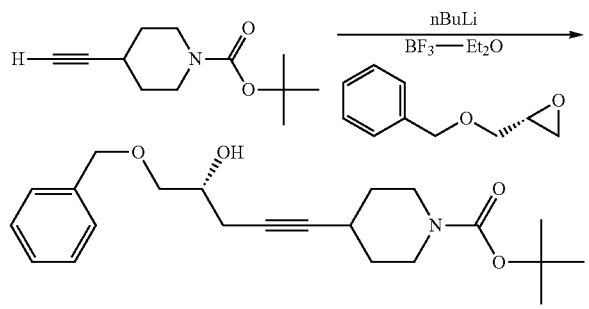

Commercially available tert-butyl 4-ethynylpiperidine-1-carboxylate was dissolved in 40 ml of THF and cooled to −78° C. forming a white slurry. Titrated n-BuLi (2.2 M in hexanes, 23.9 ml, 52.6 mmol) was added dropwise with stirring. The clear colorless solution was stirred at −78° C. for 5 minutes. A solution of the R-(+) benzyl glycidyl epoxide (8.63 g, 52.6 mmol) in THF (20 ml) was added dropwise. BF₃ etherate (8.43 g, 59.7 mmol) was then added dropwise with a syringe and the solution stirred at −78° C. for 1 hour. Sat'd aq. NH₄Cl was added (100 ml), the mixture warmed to RT, diluted with water to dissolve any remaining solids, and extracted with iPrOAc (3×100 ml). The organic fractions were combined, washed with brine, dried over MgSO₄, filtered and stripped. Crude product was purified by chromatography on SiO₂ eluting with 30% EtOAc:Hexanes. The alcohol was repurified by chromatography on a C18 reversed phase column (12-100% water: acetonitrile 0.1% TFA as two runs.). Product containing fractions were combined, reduced in volume by approximately 50%,—made basic by addition of sat'd aq. NaHCO₃, water was added to dissolve some white solids, and the mixture extracted with iPrOAc (3×100). The organic fractions were combined, washed with brine, dried over MgSO₄, filtered, and stripped.

Step B: Preparation of tert-butyl 4-[(1Z,4R)-5-(benzyloxy)-4-hydroxypent-1-en-1-yl]piperidine-1-carboxylate

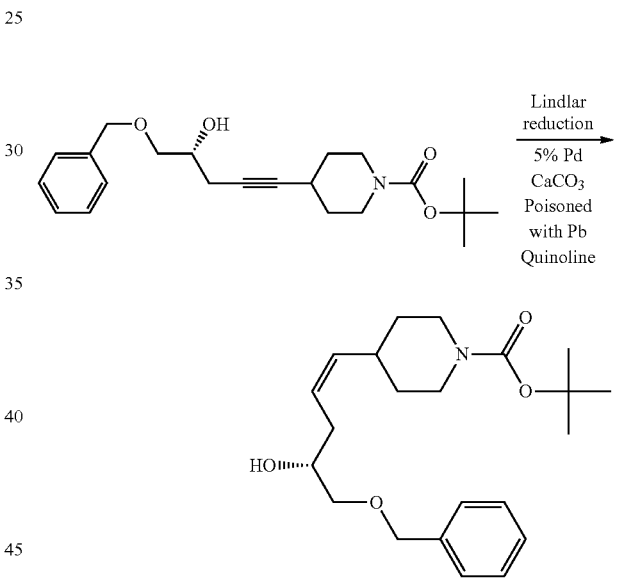

The alcohol from step 1 of this example (9.1 g, 24.4 mmol) was dissolved in EtOAc (100 ml) and quinoline (0.48 ml, 4.03 mmol) was added. Lindlar's catalyst (1.04 g) was added and the vessel evacuated and refilled three times with H₂. The slurry was stirred under a H₂ atmosphere for 40 min. The starting material was completely consumed. The mixture was filtered through celite and rinsed with EtOAc (4×50 ml). The volume of EtOAc was reduced ~80% in vac. The remaining solution was diluted with ether (100 ml) and washed with 2N HCl (100 ml). The aqueous fraction was re-extracted with ether (2×50 ml), organics combined and washed with 15 ml 2 N HCl. The organic fraction was washed with sat'd aq. NaHCO₃, brine, dried over MgSO₄, filtered, and stripped. The resulting oil was purified by chromatography on SiO₂ 30% eluting with EtOAc:Hexanes.

Step C. Preparation of cis tert-butyl 4-{2-[(2R)-3-(benzyloxy)-2-hydroxypropyl]cyclopropyl}piperidine-1-carboxylate

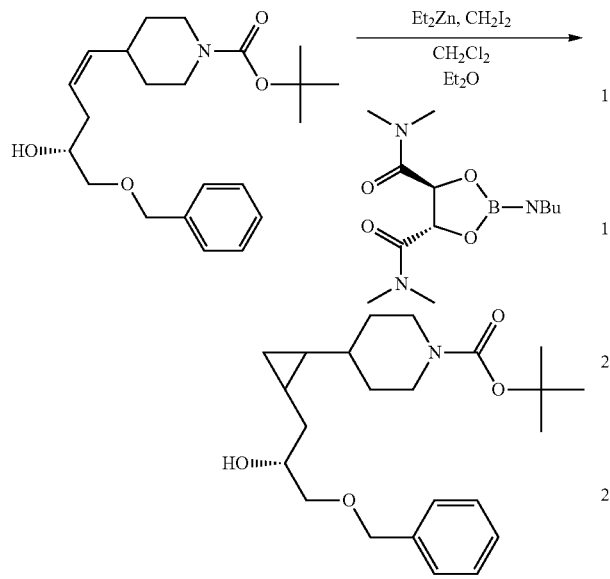

Dichloromethane stabilized with EtOH was distilled from CaH$_2$ under N$_2$ and sparged with N$_2$ to maintain oxygen free solvents. A 500 ml three neck round bottom flask was equipped with an addition funnel topped with a 3 way stopcock and internal thermal couple. The apparatus was evacuated and backfilled with N$_2$ 4 times. 20 mL DCM, Diethyl Ether (5.06 g, transferred by weight) and a solution of Et$_2$Zn (8.43 g, 68.2 mmol, in 30 ml DCM) was added to this degassed vessel under a N$_2$ atmosphere. The solution was cooled to −20° C. and a solution of CH$_2$I$_2$ (36.5 g, 136 mmol, in 20 ml DCM) was added dropwise. The temperature was monitored with an internal temperature probe. The rate of addition was altered to maintain a constant −20° C. internal temperature. A fine precipitate formed after the addition was ~80% complete. The mixture was stirred for 10 minutes.

A solution of the commercially available (S,S) dioxaborolane ligand (7.37 g, 27.3 mmol) in DCM (20 mL) was added. The mixture was stirred for 10 minutes. The precipitate dissolves yielding a clear solution. A solution of the alkene from step B of this example (8.53 g, 22.7 mmol) in DCM (20 mL) was added. The solution was warmed to 0° C. and stirred for 24 hours. The solution remains clear after stirring for 24 hours. The reaction was quenched after 24 hr by addition of 50 ml of sat'd aq. NH$_4$Cl. The mixture was placed in a separatory funnel, 250 ml DCM and 200 ml 10% HCl (aq) added, shaken, and the layers separated. The aqueous layer was re-extracted with DCM (2×150 ml), the organic layers combined, transferred to a Morton flask. 2N NaOH (300 ml) and 50 ml of 30% H$_2$O$_2$ were added. The biphasic solution was stirred vigorously for 12 hours. The layers were separated and the aqueous phase was re-extracted with DCM (2×150 ml), the organic phases were combined, washed with 10% HCl (aq, 250 ml), 1N Na$_2$S$_2$O$_3$ (250 ml), sat'd NaHCO$_3$ (250 ml), brine (250 ml), dried over MgSO$_4$, filtered and stripped. The material was purified by chromatography on SiO$_2$ eluting with 30% EtOAc:Hexanes. The desired product is obtained as a mixture with the minor diastereomer and the residual SM. The desired diastereomer was isolated by Chiralpak IA stationary phase chromatography.

Step D: Preparation of cis tert-butyl 4-[2-(2-hydroxyethyl)cyclopropyl]piperidine-1-carboxylate

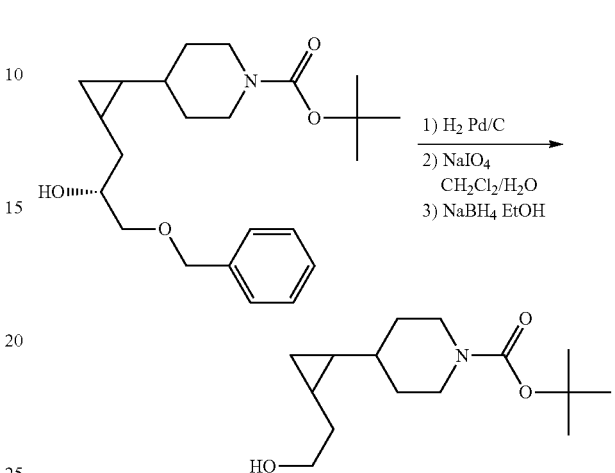

The tert-butyl 4-{2-[(2R)-3-(benzyloxy)-2-hydroxypropyl]cyclopropyl}piperidine-1-carboxylate from step C of this example (4.3 g, 11 mmol) was transferred to a Parr shaker pressure tube in 55 ml 1:1 EtOAc/Ethanol with 0.88 trigs Aldrich palladium hydroxide (20% wt on carbon-Degussa type E101). The mixture was shaken at 50 psig hydrogen on a Parr shaker. HPLC check at 30 min. indicated complete conversion. The product was filtered through Celite, washed with ethanol, and reduced to an oil in vacuo.

The crude debenzylation product was dissolved in CH$_2$Cl$_2$ (56 ml) and cooled in ice. Sodium periodate (4.77 g, 22.3 mmol) was dissolved in water (56 ml) and added slowly dropwise. The milky mixture was stirred vigorously at 0° C. HPLC indicated complete cleavage at 30 min. at 0° C. The reaction mixture was diluted with brine and CH$_2$Cl$_2$. The mixture was extracted three times with CH$_2$Cl$_2$, dried over MgSO$_4$ and reduced in vacuo.

The crude aldehyde was redissolved in EtOH (56 ml), sodium borohydride (0.422 g, 11.2 mmol) was added as a solid and the mixture stirred at RT. The reduction is complete in 30 min. Saturated aq NH$_4$Cl aq (70 ml) was added to quench, and the mixture reduced to a paste i. vac. The result was diluted with water (350 ml), and iPrOAc. The mixture was extracted with iPrOAc (3×), washed with brine, dried over MgSO$_4$, filtered and reduced i. vac. The crude product was purified by chromatography on SiO$_2$ eluting with 40% EtOAc:Hexanes.

Step E: benzyl 4[-2-(2-hydroxyethyl)cyclopropyl]piperidine-1-carboxylate

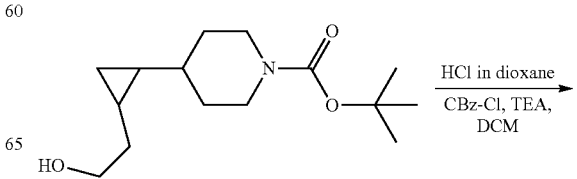

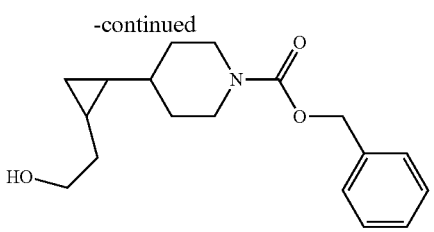

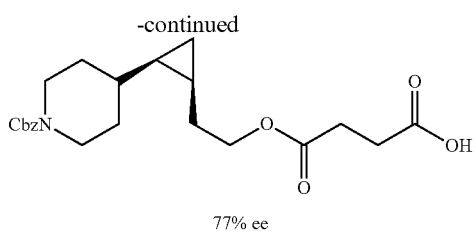

77% ee

Cis tert-butyl 4-[2-(2-hydroxyethyl)cyclopropyl]piperidine-1-carboxylate (2.0 g, 7.44 mmol) was treated with 4M HCl in dioxane (200 mL) at room temperature for 2 hours. The mixture was concentrated under reduced pressure and the residue taken up in 200 mL DCM. To this solution was added TEA (10.0 mL, 7.64 mmol) followed by benzylchloroformate (1.30 g, 7.64 mmol) and the resulting mixture stirred at room temperature overnight. The mixture was washed with 1N aqueous HCl (75 mL), followed by saturated aqueous sodium bicarbonate (75 mL) and brine (75 mL). The organics were dried over sodium sulfate, filtered, and concentrated under reduced pressure. The residue was purified via Biotage (40M+ silica gel) eluting with a gradient of 0-80% ethyl acetate to afford the title compound (2.06 g, 91%) as a viscous oil.

Step F: Separation of benzyl 4-[(1R,2S)-2-(2-hydroxyethyl)cyclopropyl]piperidine-1-carboxylate and benzyl 4-[(1S,2R)-2-(2-hydroxyethyl)cyclopropyl]piperidine-1-carboxylate

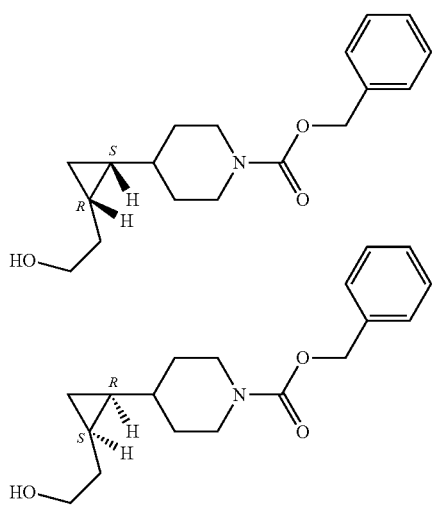

Separation of the cis isomers to afford the pure diastereomers were done via an enzymatic enantiomeric excess (ee) enrichment.

Step F-1: Preparation of 4-[2-(2-{1-[(benzylox)carbonyl]piperidin-4-yl}cyclopropyl)ethyoxy]-4-oxobutanoic acid

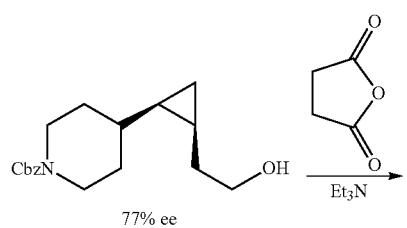

77% ee

To a solution of benzyl 4[-2-(2-hydroxyethyl)cyclopropyl]piperidine-1-carboxylate (2 g, 6.70 mmol) and TEA (10.0 mL, 7.60 mmol) in ethyl acetate (40 mL) was added succinamide (760 mg, 7.60 mmol) and the resulting mixture was heated to reflux via oil bath for 4 hours. The mixture was allowed to cool to room temperature over 1 hour and then the mixture was quenched with 1N HCl. The organics were separated and washed with water followed by brine. The organics were dried over sodium sulfate, filtered, and the filtrate was concentrate to dryness under reduced pressure to afford the product (2.61 g, 87%).

Step F-2: Preparation of benzyl 4-[(1R,2S)-2-(2-hydroxyethyl)cyclopropyl]piperidine-1-carboxylate

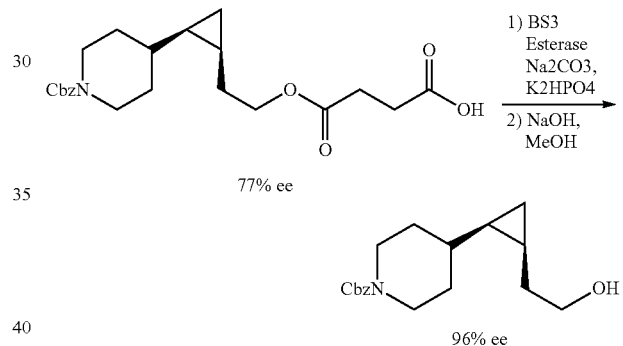

77% ee

96% ee

A solution of potassium phosphate (dibasic; 1.05 g, 6.00 mmol) and sodium carbonate (610 mg, 5.76 mmol) in water (60 mL) was premixed and aged until all solids were dissolved. The solution was cooled to 0° C. via ice/water bath and a solution of 4-[2-(2-{1-[(benzylox)carbonyl]piperidin-4-yl}cyclopropyl)ethyoxy]-4-oxobutanoic acid (2.60 g, 6.47 mmol) in DMSO/methanol (1:3, 20 mL) was added via syringe. The pH of the solution was checked to make sure it was between 7 and 8 to ensure the proper condition for the enzyme. Codexis BS3 (110 mg, ~5% by wt of the starting material) was added and the reaction temperature was monitored to make sure it did not exceed 25° C. The reaction mixture was then aged at 21° C. for 7 hours and then the pH was adjusted to 11 by addition of a solution of potassium carbonate in water. The solution was diluted with ethyl acetate and the aqueous was separated. The organics were washed with aqueous potassium carbonate solution (25 mL) and all the aqueous cuts were combined. The combined aqueous was then cooled to 5° C. and treated with 47% sodium hydroxide solution (5 mL) keeping the temperature at less than 40° C. The pH of the mixture was ~14 and >99% hydrolysis had occurred after 30 minutes of treatment based on HPLC. The mixture was then cooled to room temperature and diluted with ethyl acetate (75 mL). The biphasic mixture was filtered through a pad of Solka Floc and the clarified phases separated. The organics were separate, dried over sodium sulfate, filtered, and the filtrate concentrated to dryness under reduced pressure to afford the title compound (1.40 g, 71%) with an ee of 96%. $^1$H NMR (500 MHz, CDCl$_3$) δ 7.46-7.30 (m, 51-1), 5.16 (s, 2H), 4.20 (br s, 2H), 3.82-3.70 (m, 2H), 2.77 (br s, 2H), 1.95-1.87 (m, 1H), 1.76-1.72 (m, 2H), 1.46-1.23 (m, 4H), 1.02-0.87 (m, 1H), 0.86-0.76 (m, 1H), 0.67-0.61 (m, 1H), 0.60-0.52 (m, 1H), −0.18 (q, J=4.5 Hz, 1H).

Intermediate 3

Preparation of 2-((1S,2R)-2-(piperidin-4-yl)cyclopropyl)ethanol

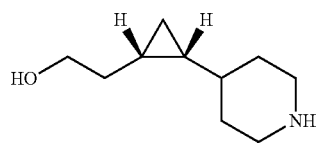 [SMILES: OCC[C@@H]1C[C@@H]1C1CCNCC1]

Benzyl 4-((1R,2S)-2-(2-hydroxyethyl)cyclopropyl)piperidine-1-carboxylate (7.50 g, 24.7 mmol) and palladium on activated carbon (10%, wet, 1.00 g) in methanol (130 mL) were stirred under an atmosphere of hydrogen (1 atm) at RT for 48 h. The mixture was filtered through Celite® and the filter cake washed with methanol. The filtrate was concentrated to dryness under reduced pressure to afford the title compound (3.87 g, 93%) as a white solid. $^1$H NMR (500 MHz, CDCl$_3$) δ 3.74 (m, 2H), 3.15-3.05 (m, 2H), 2.56 (m, 2H), 1.91-1.87 (m, 2H), 1.76-1.72 (m, 3H), 1.36-1.28 (m, 3H), 0.92-0.87 (m, 1H), 0.84-0.76 (m, 1H), 0.67-0.61 (m, 1H), 0.60-0.56 (m, 1H), −0.18 (q, J=4.5 Hz, 1H).

Intermediate 4

Preparation of 2-{(1S,2R)-2-[1-(5-chloropyrimidin-2-yl)piperidin-4-yl]cyclopropyl}ethanol Step A: Preparation of 2,5-dichloropyrimidine

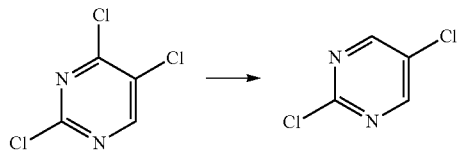 [SMILES: Clc1ncc(Cl)c(Cl)n1 ; Clc1cnc(Cl)nc1]

2,4,5-Trichloropyrimidine (25 g, 136 mmol) and zinc (26.7 g, 409 mmol, granular) were combined and THF (100 ml) added. The slurry was stirred at RT, glacial acetic acid was added (11.7 ml, 204 mmol) and the mixture heated at reflux for 2 hours. The mixture was cooled to RT, diluted with DCM (100 ml) and filtered through CELITE. The solution was then concentrated in vacuum. The crude material was dissolved in DCM (100 ml), saturated NaHCO$_3$ was added in small portions and shaken until the pH of the aqueous phase was 8. Then the pH was adjusted to 10 using 1N NaOH (aq), shaken and the layers separated. The organic fraction was dried over MgSO$_4$, filtered, and the volatiles removed in vacuum. The material was purified by chromatography on SiO$_2$ eluting with 2% EtOAc:Hexanes to give the titled compound.

Step B: 2-{(1S,2R)-2-[1-(5-chloropyrimidin-2-yl)piperidin-4-yl]cyclopropyl}ethanol

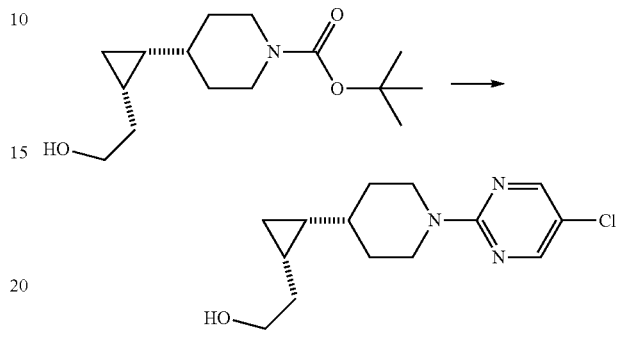

Tert-butyl 4-[(1R,2S)-2-(2-hydroxyethyl)cyclopropyl]piperidine-1-carboxylate (1.07 g, 3.95 mmol) was dissolved in DCM (20 ml) and cooled to 0° C. Excess TFA (20 ml) was added drop wise and the solution was stirred at 0° C. for 30 minutes. The volatiles were removed under vacuum. Residual TFA was further removed by stripping twice from DCM followed by drying in vacuum. The resulting material was transferred to a pear-shaped flask in DCM and the volatiles removed in vacuum.

The crude piperidine was dissolved in DMF (9 ml, 0.44 M) with the dichloropyrimidine from step A of this example (0.59 g, 3.95 mmol) and cesium carbonate (7.08 g, 21.7 mmol, 5.5 eq) was added. The mixture was stirred at RT for 6.0 hrs. The mixture was poured into 150 ml water and extracted with iPrOAc (3×100 ml). The organic phases were washed with brine, dried over Na$_2$SO$_4$, filtered and stripped. Crude material was purified by column chromatography on SiO$_2$ eluting with 40% EtOAc:Hexanes to give the titled compound. LRMS calc: 281.1; obs: 282.2 (M+1).

Intermediate 5

Preparation of 2-{(1S,2R)-2-[1-(5-ethylpyrimidin-2-yl)piperidin-4-yl]cyclopropyl}ethanol

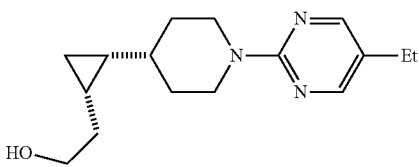

2-{(1S,2R)-2-[1-(5-ethylpyrimidin-2-yl)piperidin-4-yl]cyclopropyl}ethanol was synthesized from 2-((1S,2R)-2-(piperidin-4-yl)cyclopropyl)ethanol according to the method described for 2-{(1S,2R)-2-[1-(5-chloropyrimidin-2-yl)piperidin-4-yl]cyclopropyl}ethanol employing 2-chloro-5-ethylpyrimidine. MS (ESI) m/z 276.1 (M+H).

Intermediate 6

Preparation of 2-[(1S,2R)-2-{1-[5-(methoxymethyl)pyrimidin-2-yl]piperidin-4-yl}cyclopropyl]ethanol Step A: Preparation of 2-chloro-5-(methoxymethyl)pyrimidine

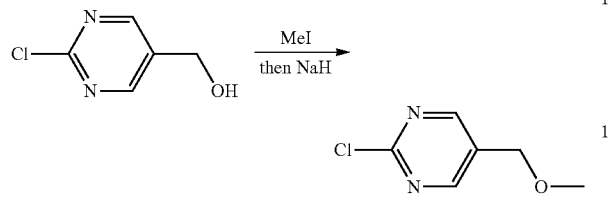

To a solution of 2-chloro-5-hydroxymethyl-pyrimidine (9.0 g, 62 mmol) in 70 ml of anhydrous DMF was added methyl iodide (6 eq. 370 mmol, 23 ml). The mixture was cooled to 0° C., then NaH (2.61 g, 1.05 eq.) was added in portions over 5 mins. The resulting mixture was stirred 25 min. at 0° C., then 25 min. at rt. The reaction mixture was then cooled in ice bath, and quenched by addition of saturated NH$_4$Cl aq. solution (200 ml), extracted with ether (150 ml×3). The combined organic layers were washed by brine, dried over Na$_2$SO$_4$, filtered and concentrated in vacuo. The residue was purified by ISCO column (330 g of silica gel) using ethyl acetate in hexane (0-90% ethyl acetate, 2500 ml, then 1000 ml of ethyl acetate) to give 6.5 g (66%) of the title compound: MS (ESI) m/z 159.2 (M+H); $^1$H NMR (500 MHz, CDCl$_3$) δ 8.60 (s, 2H), 4.48 (s, 2H), 3.45 (s, 3H).

Step B: Preparation of 2-[(1S,2R)-2-{1-[5-(methoxymethyl)pyrimidin-2-yl]piperidin-4-yl}cyclopropyl]ethanol

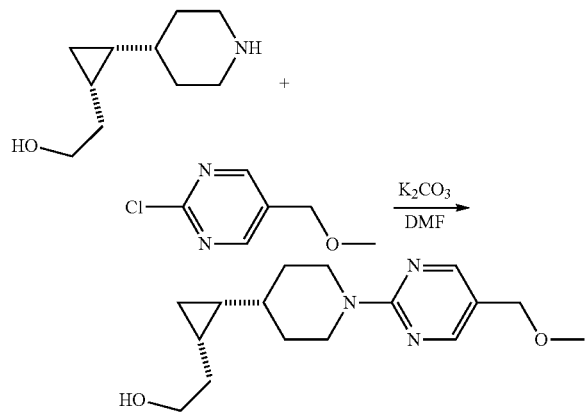

2-((1S,2R)-2-(piperidin-4-yl)cyclopropyl)ethanol (6.30 g, 37.2 mmol) was added to a solution of 2-chloro-5-(methoxymethyl)pyrimidine (5.90 g, 37.2 mmol) from step A of this example in DMF (35 ml). Potassium carbonate (6.68 g, 48.4 mmol) was added and the mixture stirred at RT overnight. The mixture was diluted with 120 ml of brine, extracted with EtOAc (150 ml×3), the organic layers combined, dried over Na$_2$SO$_4$, filtered and the volatiles removed in vacuo. Purification by silica gel chromatography eluting with EtOAc:Hexanes (0-70% then 70% EtOAc in hexanes) afforded the title compound (9.7 g, 90%). MS (ESI) ink 292.4 (M+H).

EXAMPLES

Example 1

Preparation of 1-(azetidin-1-yl)-2-[4-(2-{(1S,2R)-2-[1-(5-chloropyrimidin-2-yl)piperidin-4-yl]cyclopropyl}ethoxy)phenyl]ethanone

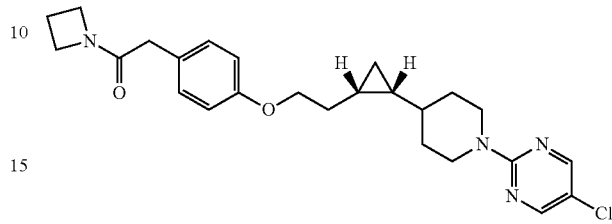

Step A: Methyl [4-(2-{(1S,2R)-2-[1-(5-chloropyrimidin-2-yl)piperidin-4-yl]cyclopropyl}ethoxy)phenyl]acetate

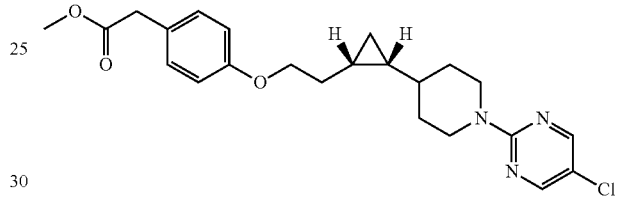

To a solution of methyl (4-hydroxyphenyl)acetate (106 mg, 0.639 mmol) in 5 ml anhydrous dichloromethane at RT was added a solution of 2-{(1S,2R)-2-[1-(5-chloropyrimidin-2-yl)piperidin-4-yl]cyclopropyl}ethanol (150 mg, 0.532 mmol) in 5 ml anhydrous dichloromethane, triphenylphosphine (polymer-bound, 419 mg, 1.21 mmol), and di-test-butyl azodicarboxylate (245 mg, 1.07 mmol). The reaction mixture was stirred at RT for 3 hours. It was filtered by Celite® and concentrated. The residue was purified by column chromatography on silica gel (50 g) using a gradient eluent of 0-50% ethyl acetate in hexanes (1000 ml) to afford the title compound. LC/MS (m/z) 430.3 (M+H)$^+$.

Step B: [4-(2-{(1S,2R)-2-[1-(5-chloropyrimidin-2-yl)piperidin-4-yl]cyclopropyl}ethoxy)phenyl]acetic acid

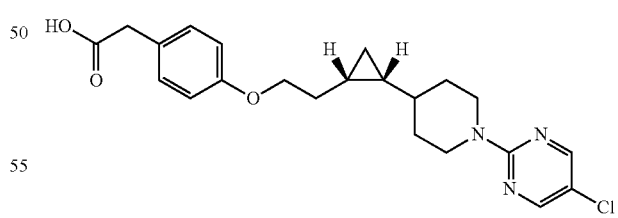

Methyl [4-(2-{(1S,2R)-2-[1-(5-chloropyrimidin-2-yl)piperidin-4-yl]cyclopropyl}ethoxy)phenyl]acetate (20 mg, 0.047 mmol) in 3 ml THF was added 1 ml methanol and 1 ml water. Lithium hydroxide (5.6 mg, 0.23 mmol) was added to the mixture, and the mixture was stirred at RT overnight. 1 M hydrochloric acid was added to adjust the pH to 4. The volatiles were removed under vacuum, and the remaining aqueous layer was extracted with dichloromethane (3×10 ml). The organics were combined, dried over magnesium sulphate, filtered, and the filtrate concentrated under reduced pressure to afford the title compound. LC/MS (m/z) 416.3 (M+H)⁺.

Step C: 1-(azetidin-1-yl)-2-[4-(2-{(1S,2R)-2-[1-(5-chloropyrimidin-2-yl)piperidin-4-yl]cyclopropyl}ethoxy)phenyl)ethanone

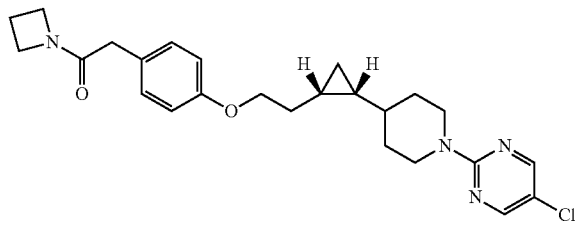 [SMILES: O=C(Cc1ccc(OCC[C@@H]2C[C@@H]2C2CCN(c3ncc(Cl)cn3)CC2)cc1)N1CCC1]

[4-(2-(1S,2R)-2-[1-(5-chloropyrimidin-2-yl)piperidin-4-yl]cyclopropyl ethoxy)phenyl]acetic acid (150 mg, 0.361 mmol), 1-hydroxybenzotriazole hydrate (55.2 mg, 0.361 mmol), and (E)-3-(ethyldiazenyl)-N,N-dimethylpropan-1-amine hydrochloride (83 mg, 0.433 mmol) were dissolved in $CH_2Cl_2$ (5 ml). The mixture was stirred at RT for 5 min. and azetidine (20.6 mg, 0.361 mmol) was added. The mixture was stirred at RT overnight and loaded directly onto a silica gel column that was developed with 50~100% EtOAc in hexane. The desired product (Rf=0.30 @ 70% EtOAc in hexane) was collected to give the title compound. $^1$H NMR (500 MHz, $CDCl_3$) δ 8.12 (s, 2H), 7.20 (d, 2H), 6.84 (d, 2H), 4.65 (m, 2H), 4.15 (t, 2H), 4.03 (m, 4H), 3.40 (s, 2H), 2.92 (m, 2H), 2.25 (m, 3H), 1.90 (m, 2H), 1.55 (m, 1H), 1.40 (m, 2H), 0.95-1.05 (m, 2H), 0.68 (m, 2H), −0.40 (m, 1H). LC/MS (m/z): 455 (M+H)⁺, GPR119 Human $EC_{50}$: 0.79 nM.

The Examples in Table 1 were synthesized according to the methods described in the prior example (1) employing the appropriate reagents and solvents.

TABLE 1

| Example # | Chemical Structure | Observed Mass [M + H]⁺ | GPR119 Human $EC_{50}$ (nM) |
|---|---|---|---|
| 2 | 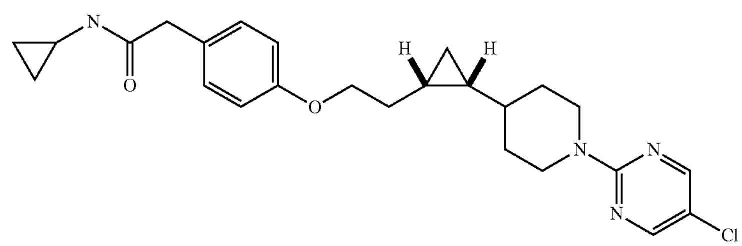 [SMILES: O=C(Cc1ccc(OCC[C@@H]2C[C@@H]2C2CCN(c3ncc(Cl)cn3)CC2)cc1)NC1CC1] | 455 | 1.8 |
| 3 | 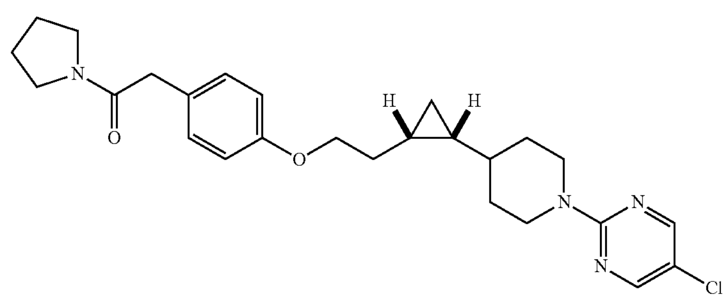 [SMILES: O=C(Cc1ccc(OCC[C@@H]2C[C@@H]2C2CCN(c3ncc(Cl)cn3)CC2)cc1)N1CCCC1] | 469 | 2.1 |
| 5 | 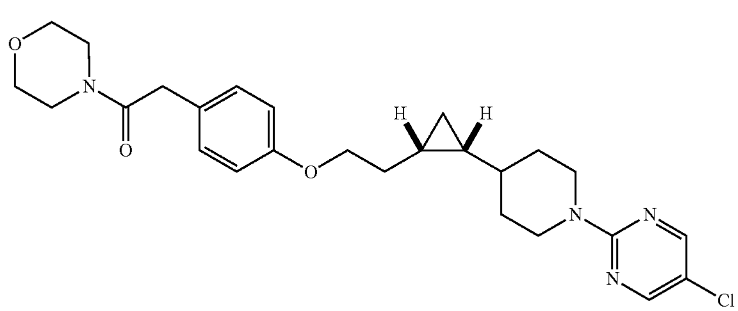 [SMILES: O=C(Cc1ccc(OCC[C@@H]2C[C@@H]2C2CCN(c3ncc(Cl)cn3)CC2)cc1)N1CCOCC1] | 486 | 3.6 |

TABLE 1-continued

| Example # | Chemical Structure | Observed Mass [M + H]+ | GPR119 Human EC$_{50}$ (nM) |
|---|---|---|---|
| 6 | 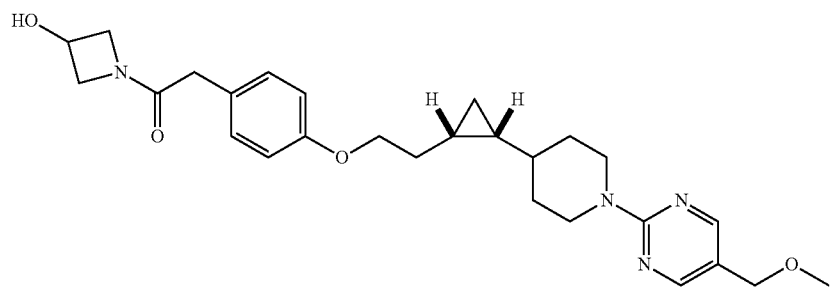 [SMILES: COCc1cnc(N2CCC([C@H]3C[C@H]3CCOc3ccc(CC(=O)N4CC(O)C4)cc3)CC2)nc1] | 473 | 0.89 |

Example 7

Preparation of 1-(3-hydroxyazetidin-1-yl)-2-(4-{2-[(1S,2R)-2-{1-[5-(methoxymethyl)pyrimidin-2-yl]piperidin-4-yl}cyclopropyl]ethoxy}phenyl)ethanone Step A: methyl (4-{2-[(1S,2R)-2-{1-[5-(methoxymethyl)pyrimidin-2-yl]piperidin-4-yl]}cyclopropyl]ethoxy}phenyl)acetate

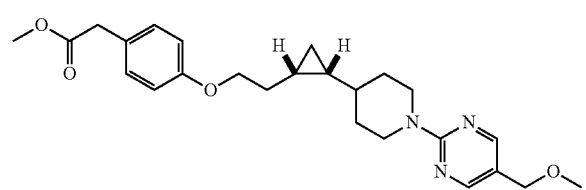

2-((1S,2R)-2-(1-(5-(Methoxymethyl)pyrimidin-2-yl)piperidin-4-yl)cyclopropyl)ethanol (1.2 g, 4.12 mmol), methyl 4-hydroxyphenylacetate (0.82 g, 4.94 mmol) and triphenylphosphine (1.62 g, 6.18 mmol) were dissolved in dichloromethane (20 ml). The mixture was stirred at RT under N$_2$ for 5 min and diisopropyl azodicarboxylate (1.21 ml, 6.18 mmol) was added. The mixture was stirred at RT overnight. The mixture was diluted with DCM (50 ml), washed with water, dried and evaporated. The crude material was purified by silica gel column (50 g SNAP, 15~50% EtOAc in hexane) to afford the desired product. This material was used for the next step without further purification. LC/MS (m/z): 440 (M+H)+. Rf was 0.4 @ 30% EtOAc in hexanes.

Step B: (4-{2-[(1S,2R)-2-{1-[5-(methoxymethyl)pyrimidin-2-yl]piperidin-4-yl}cyclopropyl]ethoxy}phenyl)acetic acid

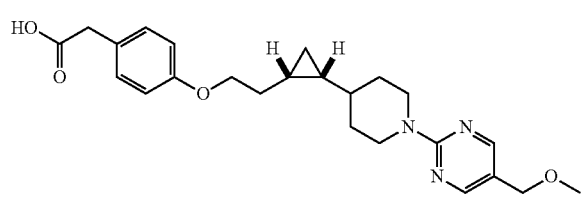 [SMILES: COCc1cnc(N2CCC([C@H]3C[C@H]3CCOc3ccc(CC(=O)O)cc3)CC2)nc1]

Methyl (4-{2-[(1S,2R)-2-{1-[5-(methoxymethyl)pyrimidin-2-yl]piperidin-4-yl]}cyclopropyl]ethoxy}phenyl)acetate (1.8 g, 4.1 mmol) was dissolved in MeOH (15 ml) and sodium hydroxide (5 M, 4.1 ml, 20.5 mmol) was added. The mixture was stirred at RT for 1 h and neutralized to pH 5 with 5 M HCl (5 ml), extracted with EtOAc (50 ml). The EtOAc phase was dried over MgSO$_4$, and concentrated in vacuo to afford the title product. LC/MS (m/z): 426 (M+H)+.

Step C: 1-(3-hydroxyazetidin-1-yl)-2-(4-{2-[(1S,2R)-2-{1-[5-(methoxymethyl)pyrimidin-2-yl]piperidin-4-yl}cyclopropyl]ethoxy}phenyl)ethanone

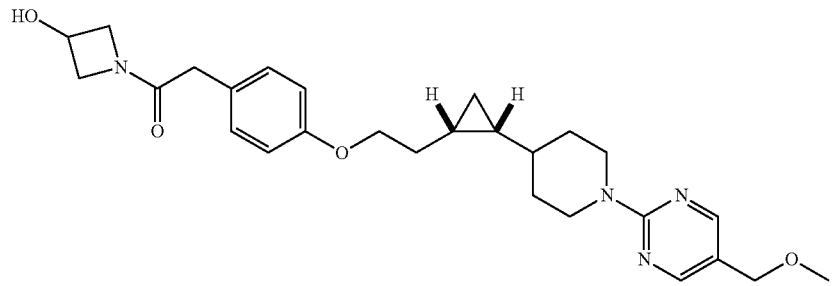 [SMILES: COCc1cnc(N2CCC([C@H]3C[C@H]3CCOc3ccc(CC(=O)N4CC(O)C4)cc3)CC2)nc1]

(4-{2-[(1S,2R)-2-{1-[5-(methoxymethyl)pyrimidin-2-yl]piperidin-4-yl}cyclopropyl]ethoxy}phenyl)acetic acid (70 mg, 0.165 mmol), 1-hydroxybenzotriazole hydrate (37.8 mg, 0.247 mmol), 3-hydroxyazetidine hydrochloride (27 mg, 0.247 mmol) and (E)-3-(ethyldiazenyl)-N,N-dimethylpropan-1-amine hydrochloride (44.3 mg, 0.247 mmol) were dissolved in $CH_2Cl_2$ (4 ml). The mixture was stirred at RT for 5 min. and triethylamine (0.078 ml, 0.556 mmol) added. The mixture was stirred at RT overnight and the mixture loaded directly onto a preparative TLC plate that was developed with 10% MeOH in EtOAc. The desired product (Rf=0.35 @ 10% MeOH in EtOAc) was collected to give the title compound. $^1H$ NMR (500 MHz, $CDCl_3$) δ 8.30 (s, 2H), 7.20 (d, 2H), 6.85 (d, 2H), 4.70 (m, 2H), 4.55 (broad, s, 1H), 4.22 (s, 2H), 4.10 (m, 1H), 4.05 (m, 2H), 3.85 (m, 2H), 3.40 (s, 2H), 3.35 (s, 3H), 2.85 (m, 2H), 2.05 (m, 1H), 1.95 (m, 2H), 1.55 (m, 1H), 1.38 (m, 2H), 1.10 (m, 1H), 0.95 (m, 1H), 0.68 (m, 2H), −0.40 (m, 1H). LC/MS (m/z): 481 $(M+H)^+$, GPR119 Human $EC_{50}$: 7.7 nM.

The Examples in Table 2 were synthesized according to the methods described in the prior example (7) employing the appropriate reagents and solvents.

TABLE 2

| Example # | Chemical Structure | Observed Mass $[M + H]^+$ | GPR119 Human $EC_{50}$ (nM) |
|---|---|---|---|
| 8 | 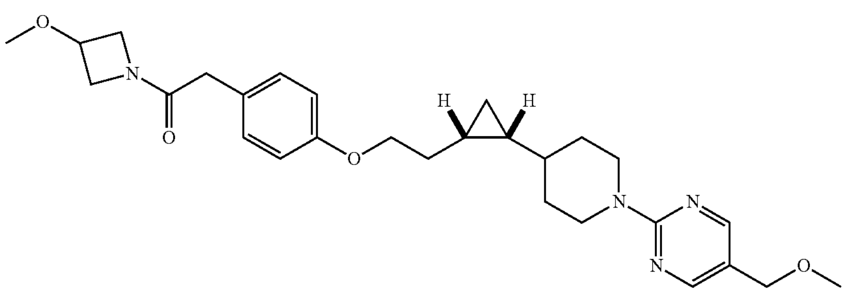 | 495 | 2.9 |
| 9 | 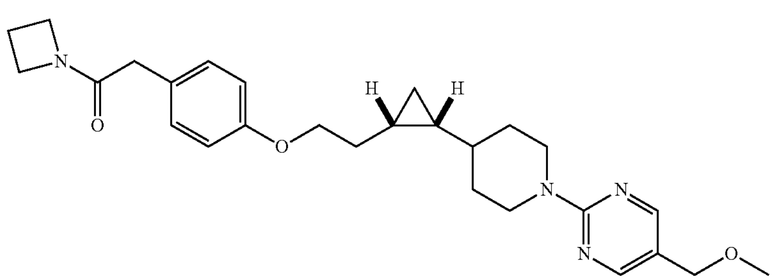 [SMILES: COCc1cnc(N2CCC([C@H]3C[C@H]3CCOc3ccc(CC(=O)N4CCC4)cc3)CC2)nc1] | 465 | 3.8 |

TABLE 2-continued
| Example # | Chemical Structure | Observed Mass [M + H]+ | GPR119 Human EC$_{50}$ (nM) |
|---|---|---|---|
| 10 | 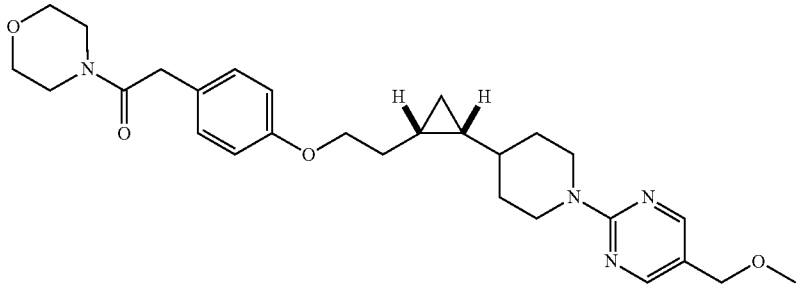 [SMILES: COCc1cnc(N2CCC([C@H]3C[C@H]3CCOc3ccc(CC(=O)N4CCOCC4)cc3)CC2)nc1] | 495 | 8.3 |
| 11 | 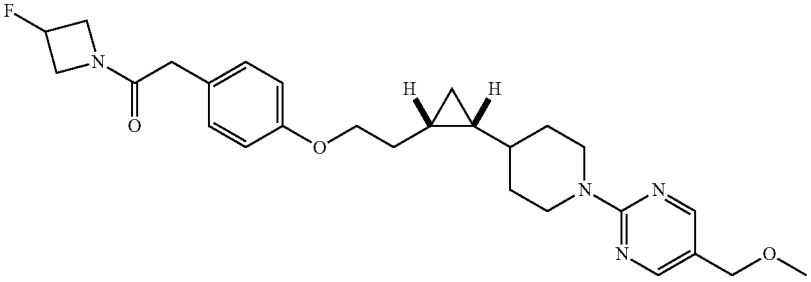 [SMILES: COCc1cnc(N2CCC([C@H]3C[C@H]3CCOc3ccc(CC(=O)N4CC(F)C4)cc3)CC2)nc1] | 483 | 2.9 |
| 12 | 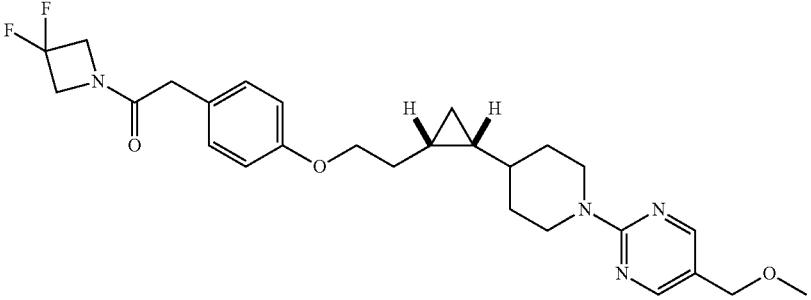 [SMILES: COCc1cnc(N2CCC([C@H]3C[C@H]3CCOc3ccc(CC(=O)N4CC(F)(F)C4)cc3)CC2)nc1] | 501 | 3.0 |
| 13 | 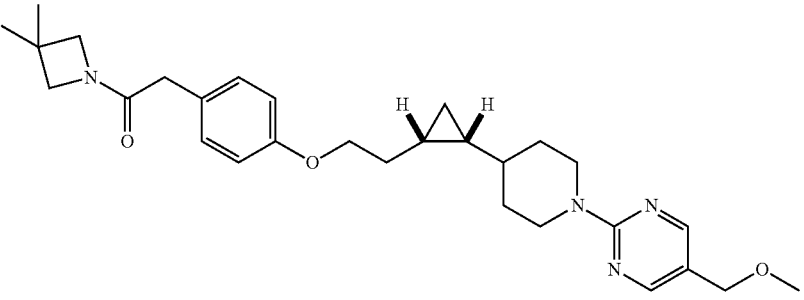 | 493 | 5.2 |
| 14 | 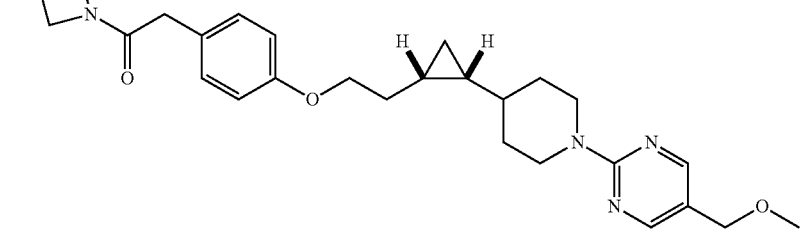 | 479 | 5.5 |

Example 15

Preparation of 1-(azetidin-1-yl)-2-[4-(2-{(1S,2R)-2-[1-(5-chloropyrimidin-2-yl)piperidin-4-yl]cyclopropyl}ethoxy)-2-methylphenyl]ethanone

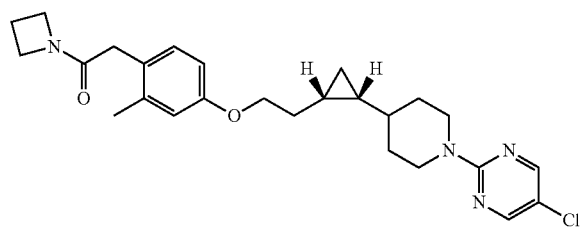 [SMILES: Cc1cc(OCC[C@@H]2C[C@@H]2C2CCN(c3ncc(Cl)cn3)CC2)ccc1CC(=O)N1CCC1]

Step A: tert-butyl [4-(benzyloxy)-2-methylphenyl]acetate

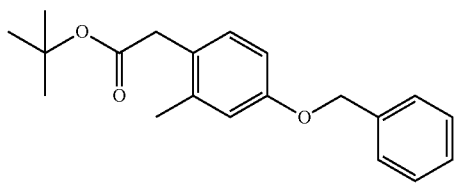 [SMILES: Cc1cc(OCc2ccccc2)ccc1CC(=O)OC(C)(C)C]

To a solution of 5-benzyloxy-2-bromotoluene (1 g, 3.61 mmol) in THF (10 ml) was added 2-tert-butoxy-2-oxoethylzinc chloride (18.04 ml, 9.02 mmol). Nitrogen gas bubbled through the mixture for 10 min. then Pd$_2$(dba)$_3$ (0.165 g, 0.180 mmol) and X-PHOS (0.172 g, 0.361 mmol) were added and the resulting mixture heated at 60° C. for 50 min. The mixture was cooled, diluted with ethyl acetate (20 mL), washed with aqueous ammonium chloride (saturated, 1×15 mL), dried over MgSO$_4$, filtered and the solvent evaporated under reduced pressure. The residue was purified by column chromatography on silica gel (Biotage 50M), using a gradient eluant of EtOAc/Hexane (0-20%) to afford the title compound. LC/MS (m/z): 335 (M+Na)$^+$.

Step B: [4-(benzyloxy)-2-methylphenyl]acetic acid

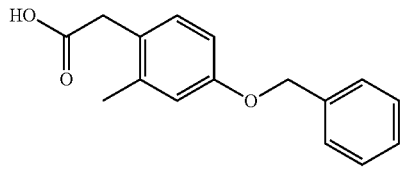 [SMILES: Cc1cc(OCc2ccccc2)ccc1CC(=O)O]

A solution of tert-butyl [4-(benzyloxy)-2-methylphenyl]acetate (1.05 g, 3.36 mmol) in DCM (8 ml) was treated with TFA (7.77 ml, 101 mmol) and the mixture stirred at RT for 30 min. The volatiles were removed in vacuo to afford the title compound. LC/MS (m/z): 257 (M+H)$^+$.

Step C: 1-(azetidin-1-yl)-2-[4-(benzyloxy)-2-methylphenyl]ethanone

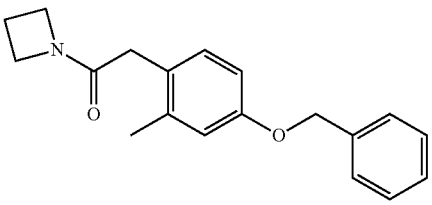 [SMILES: Cc1cc(OCc2ccccc2)ccc1CC(=O)N1CCC1]

[4-(benzyloxy)-2-methylphenyl]acetic acid (0.5 g, 1.951 mmol) was dissolved in DMF (1 ml). Azetidine (0.167 g, 2.93 mmol), DIEA (0.511 ml, 2.93 mmol), and HATU (1.484 g, 3.90 mmol) were added and the mixture stirred at RT for 1 hr. The reside was purified by column chromatography using a Biotage RP C18 cartridge (30 g) using a gradient eluant of 10-100% water:acetonitrile+0.05% formic acid to afford the title compound. LC/MS (m/z): 296 (M+H)$^+$.

Step D: 1-(azetidin-1-yl)-2-(4-hydroxy-2-methylphenyl)ethanone

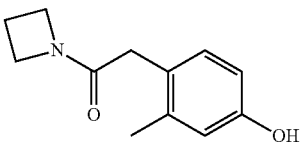

1-(azetidin-1-yl)-2-[4-(benzyloxy)-2-methylphenyl]ethanone (440 mg, 1.490 mmol) was dissolved in ethanol (3 ml) and palladium hydroxide on carbon (20%) (105 mg, 0.149 mmol) added. The mixture was stirred under an atmosphere of hydrogen gas at RT overnight. The mixture was filtered and the filtrate concentrated under reduced pressure to afford the title compound. LC/MS (m/z): 206 (M+H)$^+$.

Step E: 1-(azetidin-1-yl)-2-[4-(2-{(1S,2R)-2-[1-(5-chloropyrimidin-2-yl)piperidin-4-yl]cyclopropyl}ethoxy)-2-methylphenyl]ethanone

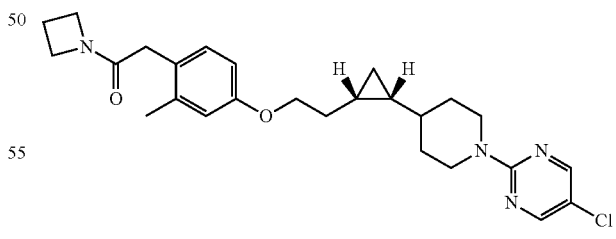

2-{(1S,2R)-2-[1-(5-chloropyrimidin-2-yl)piperidin-4-yl]cyclopropyl}ethanol (50 mg, 0.177 mmol) was dissolved in toluene (1 ml) and 1-(azetidin-1-yl)-2-(4-hydroxy-2-methylphenyl)ethanone (36.4 mg, 0.177 mmol), triphenylphosphine (55.8 mg, 0.213 mmol), and DIAD (41.4 μl, 0.213 mmol) added and the mixture stirred at RT overnight. The mixture was diluted with ethyl acetate (20 mL), washed with brine (10 ml), dried over MgSO$_4$, filtered and the solvent removed in vacuo. The residue was purified by chromatography on silica gel, Biotage 25M, eluting with a gradient eluant of 0-100% EtOAc/Hexane to afford afford the title compound. LC/MS (m/z): 469 (M+H)$^+$. GPR119 Human EC50: 0.73 nM.

The Examples in Table 3 were synthesized according to the methods described in the prior example (15) employing the appropriate reagents and solvents.

[4-(benzyloxy)-2-methylphenyl]acetic acid (1.1 g, 4.29 mmol) was dissolved in DMF (5 ml) and dimethylamine (6.44 ml, 12.88 mmol), DIEA (2.25 ml, 12.88 mmol), and HATU (3.26 g, 5.58 mmol) added. The mixture was stirred at RT for overnight. The residue was purified by column chromatography using a Biotage RP C18 cartridge (30 g) using a gradient eluant of 10-100% water:acetonitrile+0.05% formic acid. to afford the title compound. LC/MS (m/z): 284 (M+H)$^+$.

TABLE 3

| Example # | Chemical Structure | Observed Mass [M + H]$^+$ | GPR119 Human EC$_{50}$ (nM) |
|---|---|---|---|
| 16 | 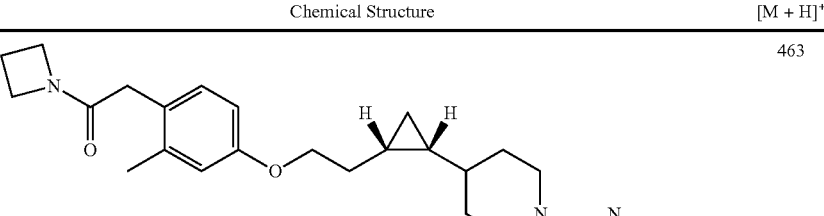 | 463 | 1.1 |
| 17 | 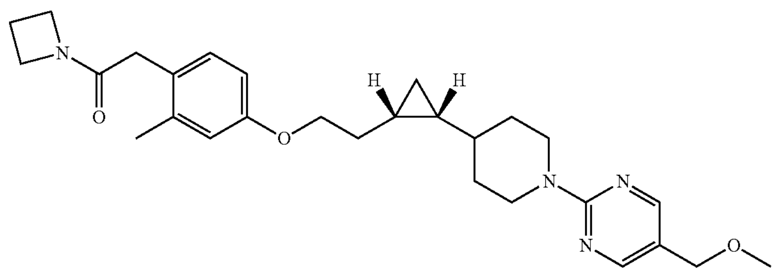 [SMILES: COCc1cnc(N2CCC([C@H]3C[C@H]3CCOc3ccc(CC(=O)N4CCC4)c(C)c3)CC2)nc1] | 515 | 1.2 |

Example 18

Preparation of 2-[4-(2-{(1S,2R)-2-[1-(5-chloropyrimidin-2-yl)piperidin-4-yl]cyclopropyl}ethoxy)-2-methylphenyl]-N,N-dimethylacetamide

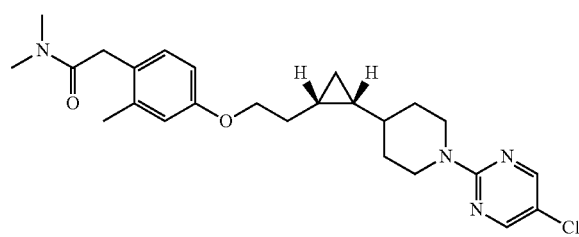 [SMILES: Cc1cc(OCC[C@@H]2C[C@@H]2C2CCN(c3ncc(Cl)cn3)CC2)ccc1CC(=O)N(C)C]

Step A: 2-[4-(benzyloxy)-2-methylphenyl]-N,N-dimethylacetamide

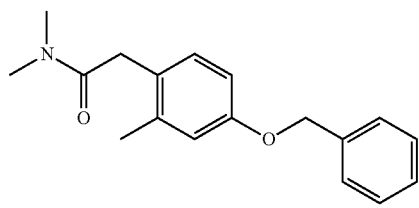 [SMILES: Cc1cc(OCc2ccccc2)ccc1CC(=O)N(C)C]

Step B: 2-(4-hydroxy-2-methylphenyl)-N,N-dimethylacetamide

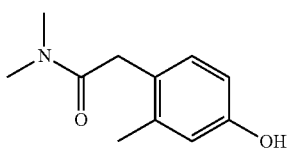

2-[4-(benzyloxy)-2-methylphenyl]-N,N-dimethylacetamide (680 mg, 2.40 mmol) was dissolved in ethanol (4 ml) and palladium hydroxide on carbon (20%) (169 mg, 0.240 mmol) added. The mixture was stirred under an atmosphere of hydrogen gas at RT overnight. The mixture was filtered and the filtrate concentrated under reduced pressure to afford the title compound. LC/MS (m/z): 194 (M+H)$^+$.

Step C: 2-[4-(2-{(1S,2R)-2-[1-(5-chloropyrimidin-2-yl)piperidin-4-yl]cyclopropyl}ethoxy)-2-methylphenyl]-N,N-dimethylacetamide

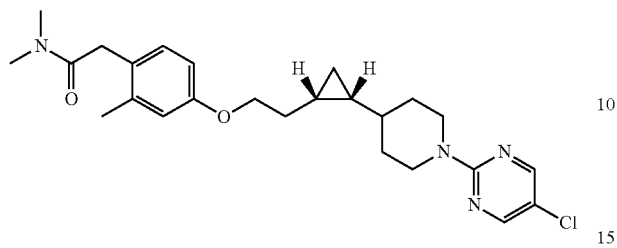

2-{(1S,2R)-2-[1-(5-chloropyrimidin-2-yl)piperidin-4-yl]cyclopropyl}ethanol (90 mg, 0.319 mmol) was dissolved in toluene (1 ml) and 2-(4-hydroxy-2-methylphenyl)-N,N-dimethylacetamide (62 mg, 0.319 mmol), triphenylphosphine (126 mg, 0.479 mmol), and DIAD (93 µl, 0.479 mmol) added and the mixture stirred at RT overnight. The mixture was concentrated in vacuo and the residue purified by chromatography using a Biotage RP C18 cartridge (30 g) using a gradient eluant of 10-100% water:acetonitrile+0.1% TFA to afford the title compound. LC/MS (m/z): 457 (M+H)$^+$. GPR119 Human EC50: 1.7 nM.

The Example in Table 4 was synthesized according to the methods described in the prior example (18) employing the appropriate reagents and solvents.

Step A: 4-(benzyloxy)-1-bromo-2-chlorobenzene

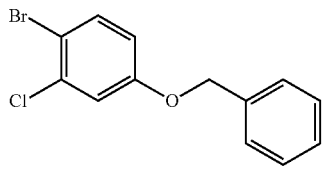

4-Bromo-3-chlorophenol (1 g, 4.82 mmol) was dissolved in DMF (10 ml) and K$_2$CO$_3$ (1.332 g, 9.64 mmol) and benzyl bromide (0.630 ml, 5.30 mmol) added. The mixture was stirred under N$_2$ for 1 hr at RT. The mixture was diluted with water (15 mL) and extracted with EtOAc (2×10 mL). The organic fractions were combined, washed with brine (saturated, 1×8 mL), dried over MgSO$_4$, filtered and the volatiles removed in vacuo. The residue was purified by column chromatography on silica gel Biotage 25M, using a gradient eluant of EtOAc/Hexane (0-50%) to afford the title compound. LC/MS (m/z): 297 (M+H)$^+$.

TABLE 4

| Example # | Chemical Structure | Observed Mass [M + H]$^+$ | GPR119 Human EC$_{50}$ (nM) |
| --- | --- | --- | --- |
| 19 | 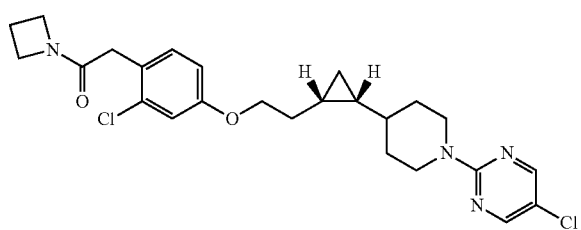 | 451 | 2.3 |

Example 20

Preparation of 1-(azetidin-1-yl)-2-[2-chloro-4-(2-{(1S,2R)-2-[1-(5-chloropyrimidin-2-yl)piperidin-4-yl]cyclopropyl}ethoxy)phenyl]ethanone Step B: tert-butyl [4-(benzyloxy)-2-chlorophenyl]acetate

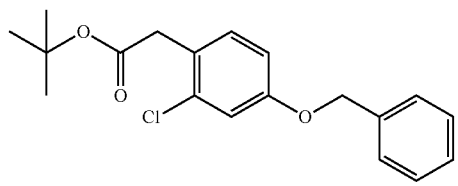 [SMILES: CC(C)(C)OC(=O)Cc1ccc(OCc2ccccc2)cc1Cl]

To a solution of 4-(benzyloxy)-1-bromo-2-chlorobenzene (1 g, 3.36 mmol) in THF (10 ml) was added 2-tert-butoxy-2-oxoethylzinc chloride (13.44 ml, 6.72 mmol). Nitrogen gas bubbled through the mixture for 10 min. Pd$_2$(dba)$_3$ (0.154 g, 0.180 mmol) and X-PHOS (0.160 g, 0.336 mmol) were added and the resulting mixture heated at 60° C. for 50 min. The mixture was cooled, diluted with ethyl acetate (20 mL), washed with aqueous ammonium chloride (saturated, 1×15 mL), dried over MgSO$_4$, filtered and the solvent evaporated under reduced pressure. The residue was purified by column chromatography on silica gel Biotage 50M, using a gradient eluant of EtOAc/Hexane (0-20%) to afford the title compound. LC/MS (m/z): 333 (M+H)$^+$.

Step C: [4-(benzyloxy)-2-chlorophenyl]acetic acid

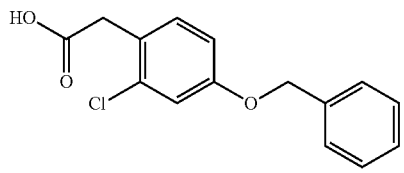

A solution of tert-butyl [4-(benzyloxy)-2-chlorophenyl] acetate (1.0 g, 3.00 mmol) in DCM (8 ml) was treated with TFA (6.94 ml, 90 mmol) and the mixture stirred at RT for 30 min. The volatiles were removed in vacuo to afford the title compound. LC/MS (m/z): 299 (M+Na)$^+$.

Step D: 1-(azetidin-1-yl)-2-[4-(benzyloxy)-2-chlorophenyl]ethanone

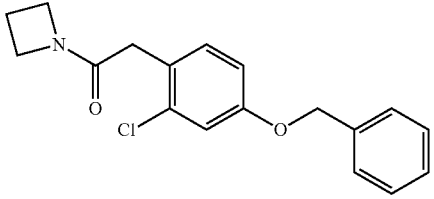 [SMILES: O=C(Cc1ccc(OCc2ccccc2)cc1Cl)N1CCC1]

[4-(Benzyloxy)-2-chlorophenyl]acetic acid (0.52 g, 1.88 mmol) was dissolved in DMF (1 ml) and azetidine (0.161 g, 2.82 mmol), DIEA (0.99 ml, 5.64 mmol), and HATU (1.43 g, 3.76 mmol) added. The mixture was stirred at RT for 1 hr. The solution was loaded directly onto a Biotage RP C18 cartridge (30 g) and purified using a gradient eluant of 10-100% water: acetonitrile+0.05% formic acid. The volatiles were removed in vacuo to afford the title compound. LC/MS (m/z): 316 (M+H)$^+$.

Step E: 1-(azetidin-1-yl)-2-(2-chloro-4-hydroxyphenyl)ethanone

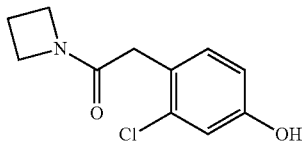

1-(azetidin-1-yl)-2-[4-(benzyloxy)-2-chlorophenyl]ethanone (520 mg, 1.65 mmol) was dissolved in ethanol (2 ml) and palladium hydroxide on carbon (20%) (116 mg, 0.165 mmol) added. The mixture was stirred under an atmosphere of hydrogen gas at RT overnight. The mixture was filtered and the filtrate concentrated under reduced pressure. The reside was purified by column chromatography using a Biotage RP C18 cartridge (30 g) using a gradient eluant of 10-100% water:acetonitrile+0.05% formic acid. to afford the title compound. LC/MS (m/z): 226 (M+H)$^+$.

Step F: 1-(azetidin-1-yl)-2-[2-chloro-4-(2-{(1S,2R)-2-[1-(5-chloropyrimidin-2-yl)piperidin-4-yl] cyclopropyl}ethoxy)phenyl]ethanone 2-{(1S,2R)-2-[1-(5-chloropyrimidin-2-yl)piperidin-4-yl] cyclopropyl}ethanol (25 mg, 0.089 mmol) was dissolved in toluene (1 ml) and 1-(azetidin-1-yl)-2-(4-hydroxy-2-methylphenyl)ethanone (20 mg, 0.089 mmol), triphenylphosphine (28 mg, 0.106 mmol), and DIAD (21 μl, 0.106 mmol) added. The mixture was stirred at RT overnight, diluted with ethyl acetate (20 mL), washed with brine (10 ml), dried over MgSO$_4$, filtered and the solvent removed in vacuo. The reside was purified by column chromatography using a Biotage RP C18 cartridge (30 g) using a gradient eluant of 10-100% water: acetonitrile+0.05% formic acid to afford the title compound. LC/MS (m/z): 489 (M+H)$^+$. GPR119 Human EC50: 0.32 nM.

The Examples in Table 5 were synthesized according to the methods described in the prior example (20) employing the appropriate reagents and solvents.

TABLE 5

| Example # | Chemical Structure | Observed Mass [M + H]$^+$ | GPR119 Human EC$_{50}$ (nM) |
|---|---|---|---|
| 21 | 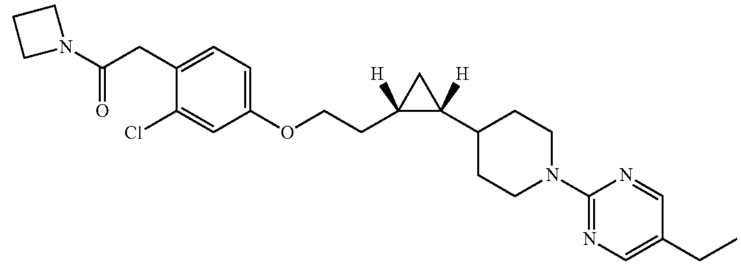 [SMILES: CCc1cnc(N2CCC([C@H]3C[C@H]3CCOc3ccc(CC(=O)N4CCC4)c(Cl)c3)CC2)nc1] | 483 | 0.19 |

TABLE 5-continued

| Example # | Chemical Structure | Observed Mass [M + H]+ | GPR119 Human EC50 (nM) |
|---|---|---|---|
| 22 | 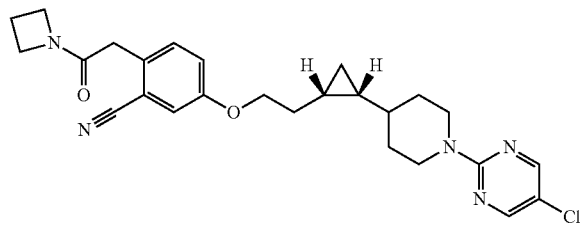 [SMILES: N#Cc1cc(OCC[C@@H]2C[C@@H]2C2CCN(c3ncc(Cl)cn3)CC2)ccc1CC(=O)N1CCC1] | 499 | 0.83 |

Example 23

Preparation of 2-[2-(azetidin-1-yl)-2-oxoethyl]-5-(2-{(1S,2R)-2-[1-(5-chloropyrimidin-2-yl)piperidin-4-yl]cyclopropyl}ethoxy)benzonitrile

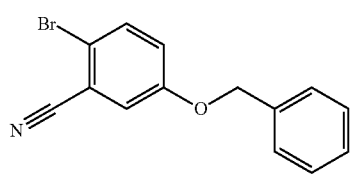 [SMILES: N#Cc1cc(OCc2ccccc2)ccc1Br]

Step A: 5-(benzyloxy)-2-bromobenzonitrile

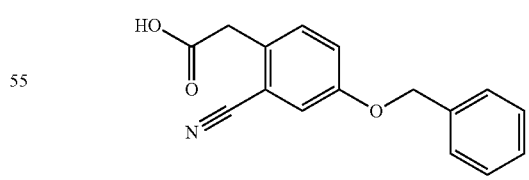

4-bromo-3-cyanophenol (1 g, 5.05 mmol) was dissolved in DMF (10 ml) and $K_2CO_3$ (1.40 g, 10.10 mmol) and benzyl bromide (0.66 ml, 5.56 mmol) added. The mixture was stirred under $N_2$ for 1 hr at RT. The mixture was diluted with water (15 mL) and extracted with EtOAc (2×10 mL). The organic fractions were combined, washed with brine (saturated, 1×8 mL), dried over $MgSO_4$, filtered and the volatiles removed in vacuo. The residue was purified by chromatography on silica gel Biotage 25M, using a gradient eluant of EtOAc/Hexane (0-50%) to afford the title compound. LC/MS (m/z): 289 (M+H)+.

Step B: tert-butyl [4-(benzyloxy)-2-cyanophenyl]acetate

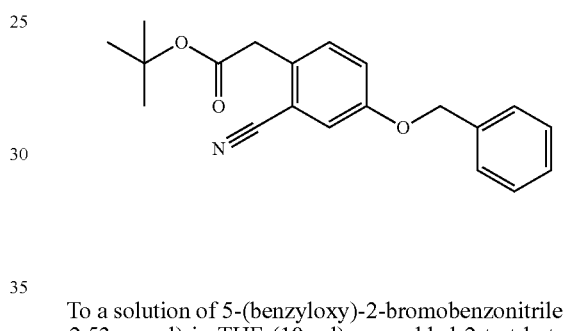

To a solution of 5-(benzyloxy)-2-bromobenzonitrile (0.73 g, 2.53 mmol) in THF (10 ml) was added 2-tert-butoxy-2-oxoethylzinc chloride (10.13 ml, 5.07 mmol). Nitrogen gas bubbled through the mixture for 10 min. then $Pd_2(dba)_3$ (0.116 g, 0.127 mmol) and X-PHOS (0.121 g, 0.253 mmol) were added and the resulting mixture heated at 60° C. for 50 min. The mixture was cooled, diluted with ethyl acetate (20 mL), washed with aqueous ammonium chloride (saturated, 1×15 mL), dried over $MgSO_4$, filtered and the solvent evaporated under reduced pressure. The residue was purified by column chromatography on silica gel Biotage 50M, using a gradient eluant of EtOAc/Hexane (0-15%) to afford the title compound. LC/MS (m/z): 346 (M+H)+.

Step C: [4-(benzyloxy)-2-cyanophenyl]acetic acid

A solution of tert-butyl [4-(benzyloxy)-2-cyanophenyl]acetate (0.48 g, 1.48 mmol) in DCM (7 ml) was treated with TFA (3.43 ml, 44.5 mmol) and the mixture stirred at RT for 30 min. The volatiles were removed in vacuo to afford the title compound. LC/MS (m/z): 268 (M+H)+.

Step D: 2-[2-(azetidin-1-yl)-2-oxoethyl]-5-(benzyloxy)benzonitrile

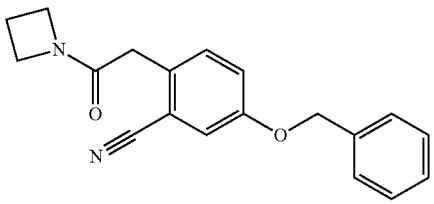 [SMILES: N#Cc1cc(OCc2ccccc2)ccc1CC(=O)N1CCC1]

[4-(Benzyloxy)-2-cyanophenyl]acetic acid (0.40 g, 1.50 mmol) was dissolved in DMF (5 ml) and azetidine (0.128 g, 2.25 mmol), DIEA (0.78 ml, 4.49 mmol), and HATU (1.14 g, 2.99 mmol) added. The mixture was stirred at RT for 1 hr. The solution was loaded directly onto a Biotage RP C18 cartridge (30 g) and purified using a gradient eluant of 10-100% water: acetonitrile+0.05% formic acid. The volatiles were removed in vacuo to afford the title compound. LC/MS (m/z): 307 (M+H)$^+$.

Step E: 2-[2-(azetidin-1-yl)-2-oxoethyl]-5-hydroxybenzonitrile

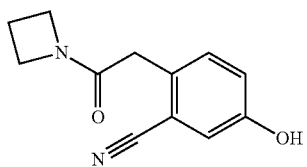 [SMILES: N#Cc1cc(O)ccc1CC(=O)N1CCC1]

2-[2-(azetidin-1-yl)-2-oxoethyl]-5-(benzyloxy)benzonitrile (410 mg, 1.34 mmol) was dissolved in ethanol (2 ml) and palladium hydroxide on carbon (20%) (94 mg, 0.134 mmol) added. The mixture was stirred under an atmosphere of hydrogen gas at RT overnight. The mixture was filtered and the filtrate concentrated under reduced pressure. The reside was purified by column chromatography using a Biotage RP C18 cartridge (30 g) using a gradient eluant of 0-25% water: acetonitrile+0.05% formic acid. to afford the title compound. LC/MS (m/z): 217 (M+H)$^+$.

Step F: 2-[2-(azetidin-1-yl)-2-oxoethyl]-5-(2-{(1S, 2R)-2-[1-(5-chloropyrimidin-2-yl)piperidin-4-yl]cyclopropyl}ethoxy)benzonitrile

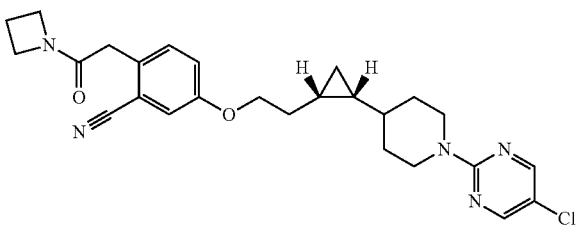 [SMILES: N#Cc1cc(OCC[C@@H]2C[C@@H]2C2CCN(c3ncc(Cl)cn3)CC2)ccc1CC(=O)N1CCC1]

2-{(1S,2R)-2-[1-(5-chloropyrimidin-2-yl)piperidin-4-yl]cyclopropyl}ethanol (22 mg, 0.076 mmol) was dissolved in toluene (1 ml) and 2-[2-(azetidin-1-yl)-2-oxoethyl]-5-hydroxybenzonitrile (15 mg, 0.069 mmol), triphenylphosphine (36 mg, 0.139 mmol), and DIAD (27 μl, 0.139 mmol) added and the mixture stirred at RT overnight. The mixture was diluted with ethyl acetate (20 mL), washed with brine (10 ml), dried over MgSO$_4$, filtered and the solvent removed in vacuo. The reside was purified by column chromatography using a Biotage SiO2 cartridge (25 g) using a gradient eluant of 10-100% EtOAc:hexanes to afford the title compound. LC/MS (m/z): 480 (M+H)$^+$. GPR119 Human EC50: 0.32 nM.

The Examples in Table 6 were synthesized according to the methods described in the prior example (23) employing the appropriate reagents and solvents.

TABLE 6

| Example # | Chemical Structure | Observed Mass [M + H]$^+$ | GPR119 Human EC$_{50}$ (nM) |
|---|---|---|---|
| 24 | 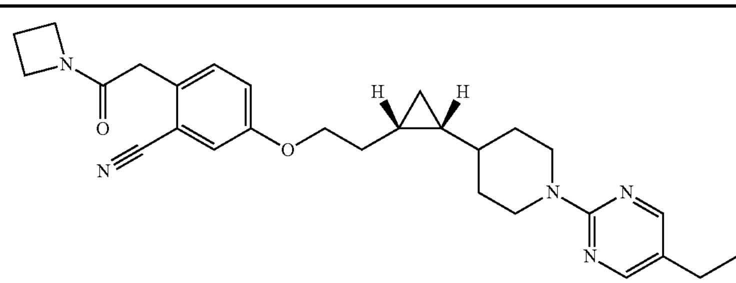 | 474 | 0.40 |
| 25 | 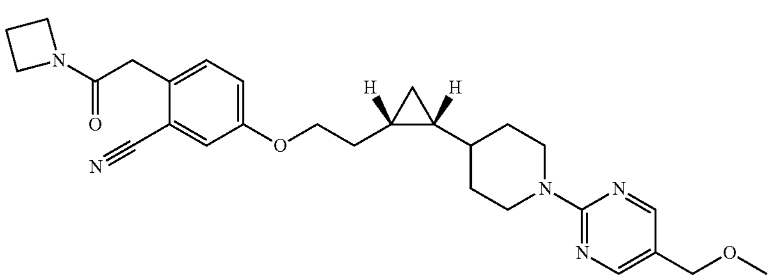 [SMILES: COCc1cnc(N2CCC([C@H]3C[C@H]3CCOc3ccc(CC(=O)N4CCC4)c(C#N)c3)CC2)nc1] | 490 | 1.4 |

Example 26

Preparation of 1-(azetidin-1-yl)-2-[4-(2-{(1S,2R)-2-[1-(5-chloropyrimidin-2-yl)piperidin-4-yl]cyclopropyl}ethoxy)-2-methoxyphenyl]ethanone

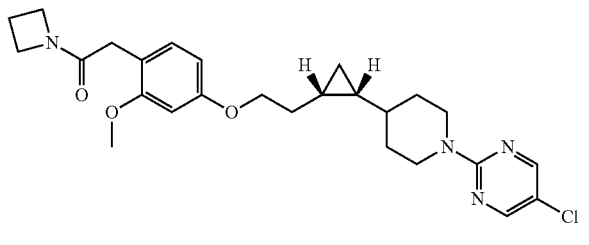 [SMILES: COc1cc(OCC[C@@H]2C[C@@H]2C2CCN(c3ncc(Cl)cn3)CC2)ccc1CC(=O)N1CCC1]

Step A: tert-butyl [4-(benzyloxy)-2-methoxyphenyl]acetate

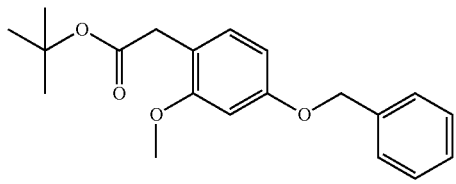 [SMILES: COc1cc(OCc2ccccc2)ccc1CC(=O)OC(C)(C)C]

To a solution of 4-(benzyloxy)-1-bromo-2-methoxybenzene (2.0 g, 6.82 mmol) in THF (20 ml) was added 2-tert-butoxy-2-oxoethylzinc chloride (27.3 ml, 13.64 mmol). Nitrogen gas bubbled through the mixture for 10 min. then Pd$_2$(dba)$_3$ (0.312 g, 0.341 mmol) and X-PHOS (0.325 g, 0.682 mmol) were added and the resulting mixture heated at 60° C. for 30 min. The mixture was cooled, diluted with ethyl acetate (20 mL), washed with aqueous ammonium chloride (saturated, 1×15 mL), dried over MgSO$_4$, filtered and the solvent evaporated under reduced pressure. The residue was purified by column chromatography on silica gel Biotage 50M, using a gradient eluant of EtOAc/Hexane (0-50%) to afford the title compound (2.2 g, 98%). LC/MS (m/z): 351 (M+Na)$^+$.

Step B: [4-(benzyloxy)-2-methoxyphenyl]acetic acid

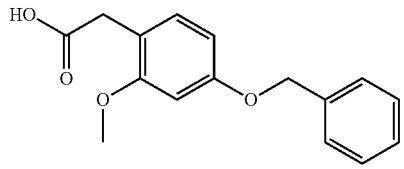 [SMILES: COc1cc(OCc2ccccc2)ccc1CC(=O)O]

A solution of tert-butyl [4-(benzyloxy)-2-methoxyphenyl] acetate (2.2 g, 6.70 mmol) in DCM (10 ml) was treated with TFA (10.3 ml, 134 mmol) and the mixture stirred at RT for 30 min. The volatiles were removed in vacuo to afford the title compound. LC/MS (m/z): 273 (M+H)$^+$.

Step D: 1-(azetidin-1-yl)-2-[4-(benzyloxy)-2-methoxyphenyl]ethanone

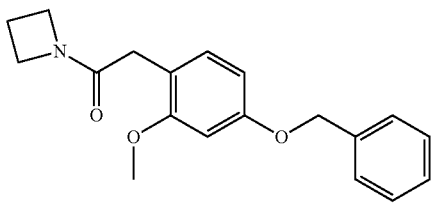 [SMILES: COc1cc(OCc2ccccc2)ccc1CC(=O)N1CCC1]

[4-(benzyloxy)-2-methoxyphenyl]acetic acid (1.8 g, 6.61 mmol) was dissolved in DMF (5 ml) and azetidine (0.566 g, 9.92 mmol), DIEA (3.46 ml, 19.8 mmol), and HATU (4.02 g, 10.6 mmol) added. The mixture was stirred at RT for 1 hr. The solution was loaded directly onto a Biotage RP C18 cartridge (30 g) and purified using a gradient eluant of 10-100% water:acetonitrile+0.05% formic acid. The volatiles were removed in vacuo to afford the title compound. LC/MS (m/z): 312 (M+H)$^+$.

Step E: 1-(azetidin-1-yl)-2-(4-hydroxy-2-methoxyphenyl)ethanone

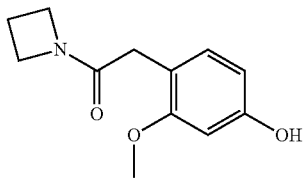 [SMILES: COc1cc(O)ccc1CC(=O)N1CCC1]

1-(azetidin-1-yl)-2-[4-(benzyloxy)-2-methoxyphenyl]ethanone (1.26 g, 4.05 mmol) was dissolved in ethanol (10 ml) and palladium hydroxide on carbon (20%) (284 mg, 0.405 mmol) added. The mixture was stirred under an atmosphere of hydrogen gas at RT overnight. The mixture was filtered and the filtrate concentrated under reduced pressure. The reside was purified by column chromatography using a Biotage RP C18 cartridge (30 g) using a gradient eluant of 0-30% water: acetonitrile+0.05% formic acid to afford the title compound. LC/MS (m/z): 222 (M+H)$^+$.

Step F: 1-(azetidin-1-yl)-2-[4-(2-{(1S,2R)-2-[1-(5-chloropyrimidin-2-yl)piperidin-4-yl]cyclopropyl}ethoxy)-2-methoxyphenyl]ethanone

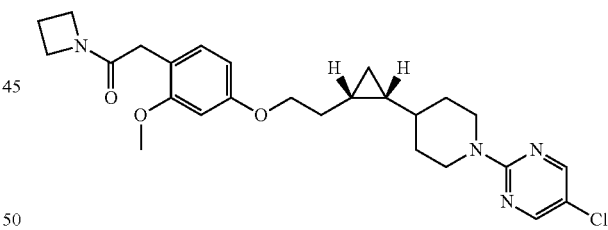

2-{(1S,2R)-2-[1-(5-chloropyrimidin-2-yl)piperidin-4-yl]cyclopropyl}ethanol (75 mg, 0.266 mmol) was dissolved in toluene (1 ml) and 1-(azetidin-1-yl)-2-(4-hydroxy-2-methoxyphenyl)ethanone (59 mg, 0.069 mmol), triphenylphosphine (105 mg, 0.399 mmol), and DIAD (78 µl, 0.399 mmol) added and the mixture stirred at RT overnight. The mixture was concentrated in vacuo and the residue purified by column chromatography using a Biotage RP C18 cartridge (30 g) using a gradient eluant of 0-100% water:acetonitrile+0.1% TFA to afford the title compound. LC/MS (m/z): 485 (M+H)$^+$. GPR119 Human EC50: 7.1 nM.

The Example in Table 7 was synthesized according to the methods described in the prior example (26) employing the appropriate reagents and solvents.

TABLE 7

| Example # | Chemical Structure | Observed Mass [M + H]⁺ | GPR119 Human EC$_{50}$ (nM) |
|---|---|---|---|
| 27 | 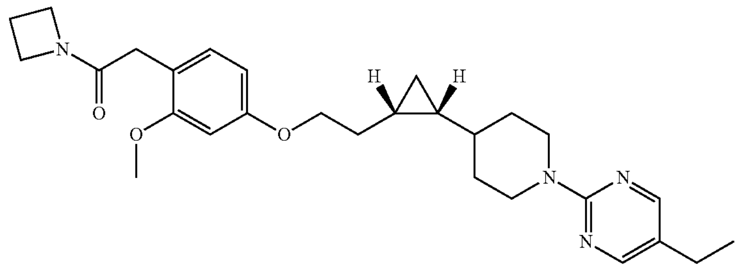 [SMILES: CCc1cnc(N2CCC([C@H]3C[C@H]3CCOc3ccc(CC(=O)N4CCC4)c(OC)c3)CC2)nc1] | 479 | 3.2 |

Example 28

Preparation of 2-(2-chloro-4-{2-[(1S,2R)-2-{1-[5-(methoxymethyl)pyrimidin-2-yl]piperidin-4-yl}cyclopropyl]ethoxy}phenyl)-N,N-dimethylacetamide Step A: 2-(4-{(1R,2S)-2-[2-(4-bromo-3-chlorophenoxy)ethyl]cyclopropyl}piperidin-1-yl)-5-(methoxymethyl)pyrimidine 2-[(1S,2R)-2-{1-[5-(methoxymethyl)pyrimidin-2-yl]piperidin-4-yl}cyclopropyl]ethanol (670 mg, 2.30 mmol) was dissolved in toluene (5 ml) and 4-bromo-3-chlorophenol (525 mg, 2.53 mmol), triphenylphosphine (905 mg, 3.45 mmol), and DIAD (671 µl, 3.45 mmol) added and the mixture stirred at RT overnight. The mixture was concentrated in vacuo and the residue purified by column chromatography on SiO$_2$ using a Biotage 50M cartridge using a gradient eluant of 0-50% EtOAc:hexanes to afford the title compound. LC/MS (m/z): 481 (M+H)⁺.

Step B: tert-butyl (2-chloro-4-{2-[(1S,2R)-2-{1-[5-(methoxymethyl)pyrimidin-2-yl]piperidin-4-yl}cyclopropyl]ethoxy}phenyl)acetate To a solution of 2-(4-{(1R,2S)-2-[2-(4-bromo-3-chlorophenoxy)ethyl]cyclopropyl}piperidin-1-yl)-5-(methoxymethyl)pyrimidine (0.91 g, 1.89 mmol) in THF (10 ml) was added 2-tert-butoxy-2-oxoethylzinc chloride (9.46 ml, 4.73 mmol). Nitrogen gas bubbled through the mixture for 10 min. then Pd$_2$(dba)$_3$ (0.087 g, 0.189 mmol) and X-PHOS (0.090 g, 0.189 mmol) were added and the resulting mixture heated at 60° C. for 30 min. The mixture was cooled, diluted with ethyl acetate (20 mL), washed with aqueous ammonium chloride (saturated, 1×15 mL), dried over MgSO$_4$, filtered and the solvent evaporated under reduced pressure. The residue was purified by column chromatography on silica gel Biotage 50M, using a gradient eluant of EtOAc/Hexane (0-50%) to afford the title compound. LC/MS (m/z): 516 (M+H)⁺.

Step C: (2-chloro-4-{2-[(1S,2R)-2-{1-[5-(methoxymethyl)pyrimidin-2-yl]piperidin-4-yl}cyclopropyl]ethoxy}phenyl)acetic acid

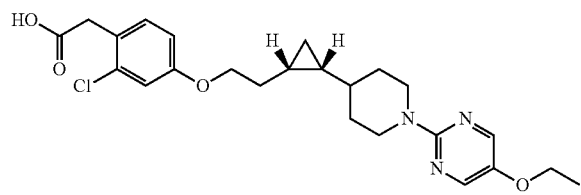 [SMILES: CCOc1cnc(N2CCC([C@H]3C[C@H]3CCOc3ccc(CC(=O)O)c(Cl)c3)CC2)nc1]

A solution of tert-butyl (2-chloro-4-{2-[(1S,2R)-2-{1-[5-(methoxymethyl)pyrimidin-2-yl]piperidin-4-yl}cyclopropyl]ethoxy}phenyl)acetate (0.96 g, 1.86 mmol) in DCM (10 ml) was treated with TFA (10.0 ml, 130 mmol) and the mixture stirred at RT for 50 min. The volatiles were removed and the residue purified by column chromatography using a Biotage RP C18 cartridge (30 g) using a gradient eluant of 0-100% water:acetonitrile+0.05% formic acid. to afford the title compound.

Step D: 2-(2-chloro-4-{2-[(1S,2R)-2-{1-[5-(methoxymethyl)pyrimidin-2-yl]piperidin-4-yl}cyclopropyl]ethoxy}phenyl)-N,N-dimethylacetamide

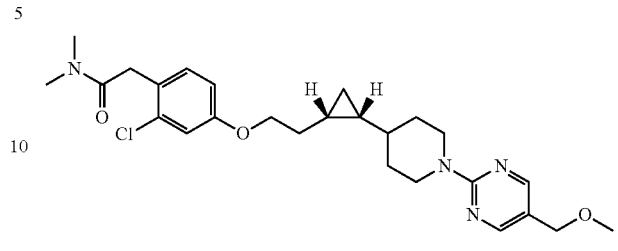

(2-chloro-4-{2-[(1S,2R)-2-{1-[5-(methoxymethyl)pyrimidin-2-yl]piperidin-4-yl}cyclopropyl]ethoxy}phenyl)acetic acid (50 mg, 109 mmol) was dissolved in DMF (1 ml) and dimethylamine (0.163 g, 0.326 mmol), DIEA (0.057 ml, 0.326 mmol), and HATU (62 mg, 0.163 mmol) added. The mixture was stirred at RT overnight. The solution was loaded directly onto a Biotage RP C18 cartridge (30 g) and purified using a gradient eluant of 10-100% water:acetonitrile+0.05% formic acid. The volatiles were removed in vacuo to afford the title compound. LC/MS (m/z): 487 (M+H)+. GPR119 Human EC50: 2.3 nM.

The Examples in Table 8 were synthesized according to the methods described in the prior example (28) employing the appropriate reagents and solvents.

TABLE 8

| Example # | Chemical Structure | Observed Mass [M + H]+ | GPR119 Human EC$_{50}$ (nM) |
|---|---|---|---|
| 29 | ![structure] | 515 | 2.4 |
| 30 | ![structure] | 529 | 0.86 |

TABLE 8-continued

| Example # | Chemical Structure | Observed Mass [M + H]+ | GPR119 Human EC50 (nM) |
|---|---|---|---|
| 31 | 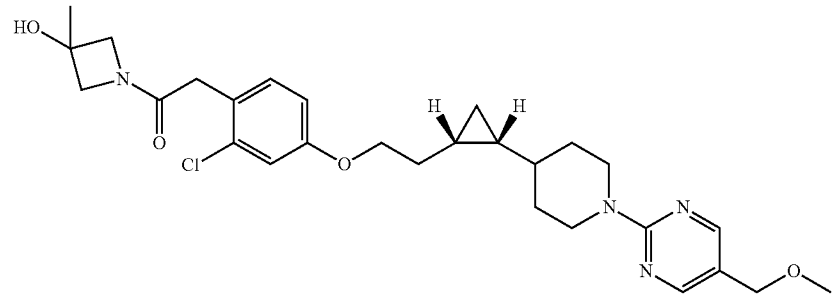 [SMILES: COCc1cnc(N2CCC([C@H]3C[C@H]3CCOc3ccc(CC(=O)N4CC(C)(O)C4)c(Cl)c3)CC2)nc1] | 529 | 1.5 |
| 32 | 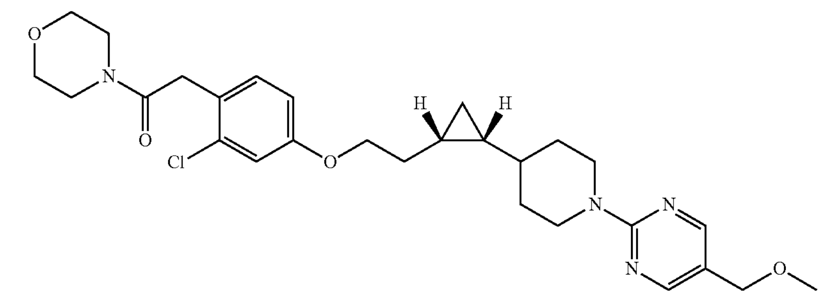 [SMILES: COCc1cnc(N2CCC([C@H]3C[C@H]3CCOc3ccc(CC(=O)N4CCOCC4)c(Cl)c3)CC2)nc1] | 529 | 1.1 |

Example 33

Preparation of 2-[2-fluoro-4-(2-{(1S,2R)-2-[1-(5-methoxypyrimidin-2-yl)piperidin-4-yl]cyclopropyl}ethoxy)phenyl]-1-(3-hydroxyazetidin-1-yl)ethanone

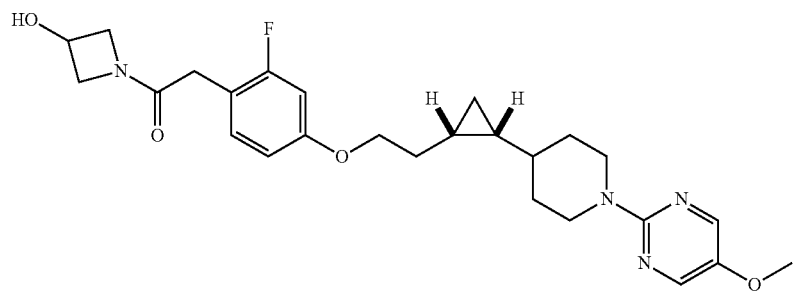 [SMILES: COc1cnc(N2CCC([C@H]3C[C@H]3CCOc3ccc(CC(=O)N4CC(O)C4)c(F)c3)CC2)nc1]

Step A: 2-{(1S,2R)-2-[1-(5-methoxypyrimidin-2-yl)piperidin-4-yl]cyclopropyl}ethanol

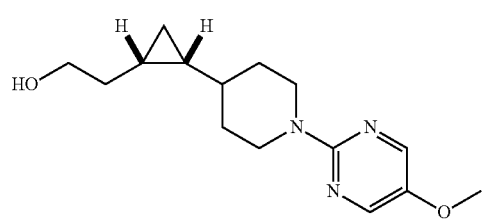 [SMILES: COc1cnc(N2CCC([C@H]3C[C@H]3CCO)CC2)nc1]

2-((1S,2R)-2-(Piperidin-4-yl)cyclopropyl)ethanol (2.5 g, 14.77 mmol) was dissolved in DMF (30 ml) at RT under $N_2$ and cesium carbonate (7.22 g, 22.15 mmol) was added. The mixture was stirred at RT for 5 min and 2-chloro-5-methoxypyrimidine (2.56 g, 17.72 mmol) was added. The mixture was stirred at 100° C. overnight. The mixture was diluted with EtOAc (100 ml), washed with sat. $NH_4Cl$ (100 ml), dried over $MgSO_4$, and the concentrated in vacuo. The crude material was purified by silica gel column (100 g SNAP, 2060% EtOAc in hexane) to afford the title compound as a white solid. LC/MS (m/z): 278 (M+H)+. Rf was 0.4 @ 50% EtOAc in hexanes (blue spot on CAM stain).

Step B: Methyl [2-fluoro-4-(2-{(1S,2R)-2-[1-(5-methoxypyrimidin-2-yl)piperidin-4-yl]cyclopropyl}ethoxy)phenyl]acetate

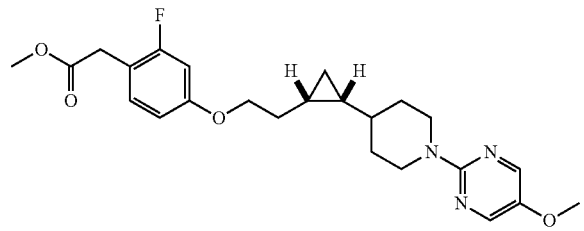

2-{(1S,2R)-2-[1-(5-Methoxypyrimidin-2-yl)piperidin-4-yl]cyclopropyl}ethanol (1.2 g, 4.33 mmol), methyl 2-(2-fluoro-4-hydroxyphenyl)acetate (0.956 g, 5.19 mmol) and triphenylphosphine (1.702 g, 6.49 mmol) were dissolved in dichloromethane (20 ml). The mixture was stirred at RT under N₂ for 5 min and diisopropyl azodicarboxylate (1.274 ml, 6.49 mmol) was added. The mixture was stirred at RT overnight. The mixture was diluted with DCM (50 ml), washed with water, dried and evaporated. The crude material was purified by column chromatography on silica gel (50 g SNAP, 5~30% EtOAc in hexane) to afford the desired product which contains some impurities. This material was re-purified by column chromatography on silica gel (50 g SNAP, 2~5% EtOAc in DCM) to afford the title compound. LC/MS (m/z): 444 (M+H)⁺. Rf was 0.4 @ 30% EtOAc in hexanes (blue spot on CAM stain).

Step C: [2-fluoro-4-(2-{(1S,2R)-2-[1-(5-methoxypyrimidin-2-yl)piperidin-4-yl]cyclopropyl}ethoxy)phenyl]acetic acid

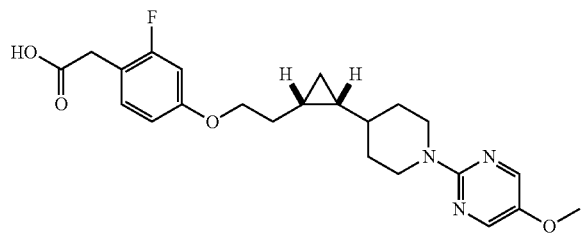 [SMILES: COc1cnc(N2CCC([C@H]3C[C@H]3CCOc3ccc(CC(=O)O)c(F)c3)CC2)nc1]

Methyl [2-fluoro-4-(2-{(1S,2R)-2-[1-(5-methoxypyrimidin-2-yl)piperidin-4-yl]cyclopropyl}ethoxy)phenyl]acetate (1.41 g, 3.28 mmol) was dissolved in MeOH (15 ml) and sodium hydroxide (5 M, 3.18 ml, 15.9 mmol) was added. The mixture was stirred at RT for 1 h and neutralized to pH 5 with 5 M HCl (5 ml), extracted with EtOAc (50 ml). The organic phase was dried over MgSO₄, and evaporated to afford the title compound. LC/MS (m/z): 430 (M+H)⁺.

Step D: 2-[2-fluoro-4-(2-{(1S,2R)-2-[1-(5-methoxypyrimidin-2-yl)piperidin-4-yl]cyclopropyl}ethoxy)phenyl]-1-(3-hydroxyazetidin-1-yl)ethanone

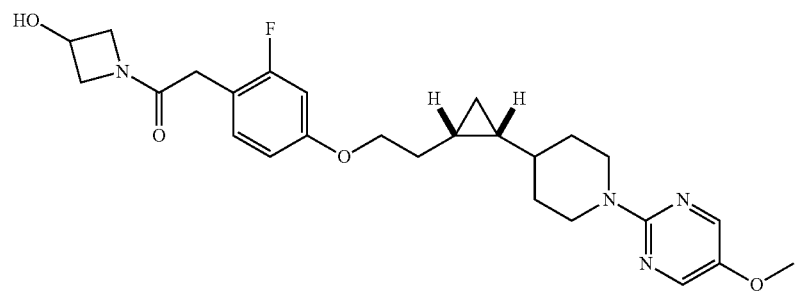 [SMILES: COc1cnc(N2CCC([C@H]3C[C@H]3CCOc3ccc(CC(=O)N4CC(O)C4)c(F)c3)CC2)nc1]

[2-Fluoro-4-(2-{(1S,2R)-2-[1-(5-methoxypyrimidin-2-yl)piperidin-4-yl]cyclopropyl}ethoxy)phenyl]acetic acid (80 mg, 0.186 mmol), 1-hydroxybenzotriazole hydrate (42.8 mg, 0.279 mmol), 3-hydroxyazetidine hydrochloride (30.6 mg, 0.279 mmol) and (E)-3-(ethyldiazenyl)-N,N-dimethylpropan-1-amine hydrochloride (50.2 mg, 0.279 mmol) were dissolved in CH₂Cl₂ (4 ml). The mixture was stirred at RT for 5 min. and triethylamine (0.078 ml, 0.556 mmol) was added. The mixture was stirred at RT overnight and loaded directly on Preparative TLC that was developed with pure EtOAc. The desired product (Rf=0.35 @ pure EtOAc) was collected to give the title compound. ¹H NMR (500 MHz, CDCl₃) δ 8.1 (s, 2H), 7.21 (m, 1H), 6.65 (m, 2H), 4.60 (m, 3H), 4.30 (m, 2H), 4.05 (m, 3H), 3.90 (m, 1H), 3.80 (s, 3H), 3.72 (s, broad, 1H), 3.41 (s, 2H), 2.83 (m, 2H), 2.15 (m, 1H), 2.05 (s, broad, 1H), 1.92 (m, 2H), 1.55 (m, 1H), 1.40 (m, 2H), 0.95 (m, 2H), 0.68 (m, 2H), −0.40 (m, 1H). LC/MS (m/z): 485 (M+H)⁺. GPR119 Human EC₅₀: 2.1 nM.

The Examples in Table 9 were synthesized according to the methods described in the prior example (33) employing the appropriate reagents and solvents.

TABLE 9

| Example # | Chemical Structure | Observed Mass [M + H]⁺ | GPR119 Human EC$_{50}$ (nM) |
|---|---|---|---|
| 34 | 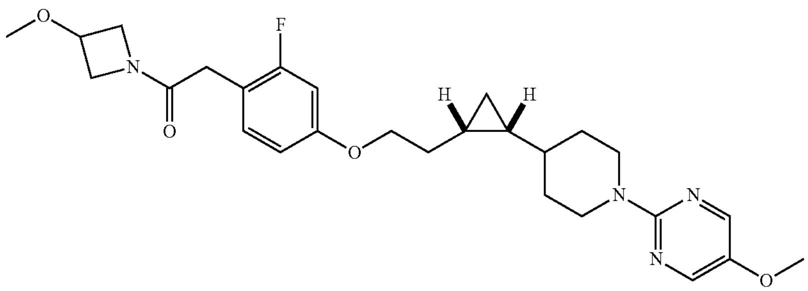 | 499 | 0.98 |
| 35 | 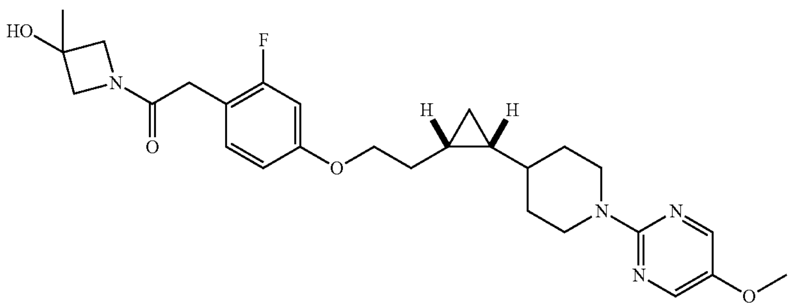 [SMILES: COc1cnc(N2CCC([C@H]3C[C@H]3CCOc3ccc(CC(=O)N4CC(C)(O)C4)c(F)c3)CC2)nc1] | 499 | 2.2 |
| 36 | 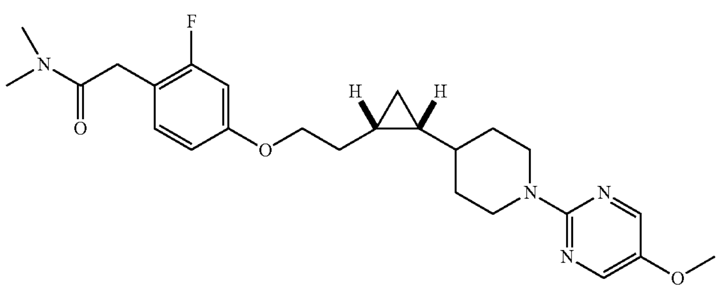 | 457 | 1.7 |
| 37 | 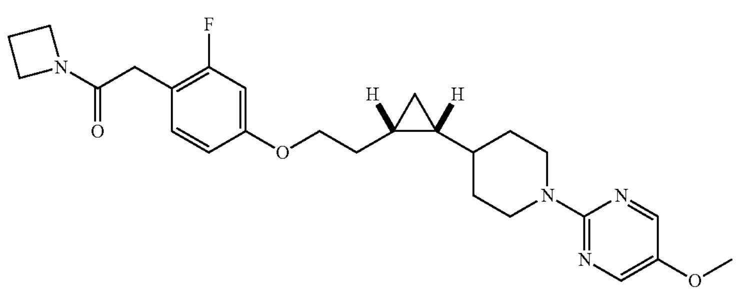 [SMILES: COc1cnc(N2CCC([C@H]3C[C@H]3CCOc3ccc(CC(=O)N4CCC4)c(F)c3)CC2)nc1] | 469 | 0.94 |
| 38 | 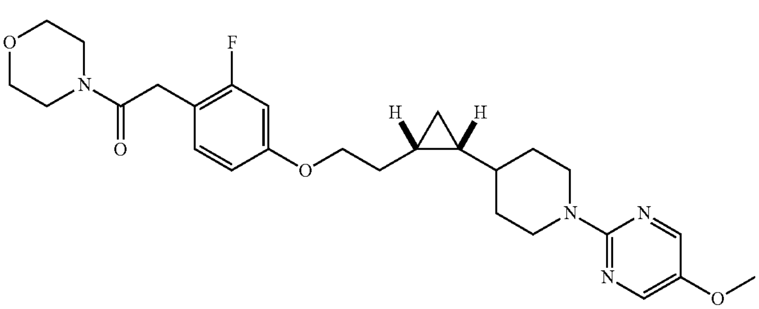 [SMILES: COc1cnc(N2CCC([C@H]3C[C@H]3CCOc3ccc(CC(=O)N4CCOCC4)c(F)c3)CC2)nc1] | 499 | 1.4 |

TABLE 9-continued

| Example # | Chemical Structure | Observed Mass [M + H]+ | GPR119 Human EC50 (nM) |
|---|---|---|---|
| 39 | 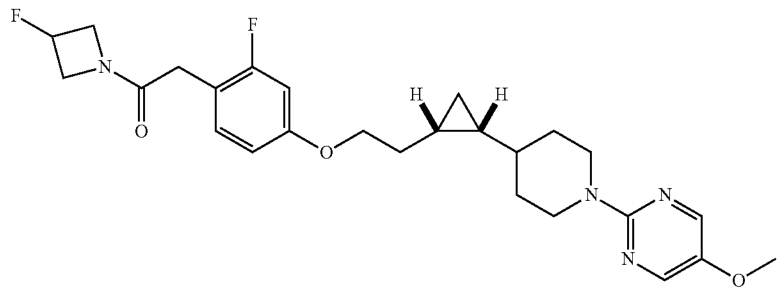 [SMILES: COc1cnc(N2CCC([C@H]3C[C@H]3CCOc3ccc(CC(=O)N4CC(F)C4)c(F)c3)CC2)nc1] | 487 | 0.48 |
| 40 | 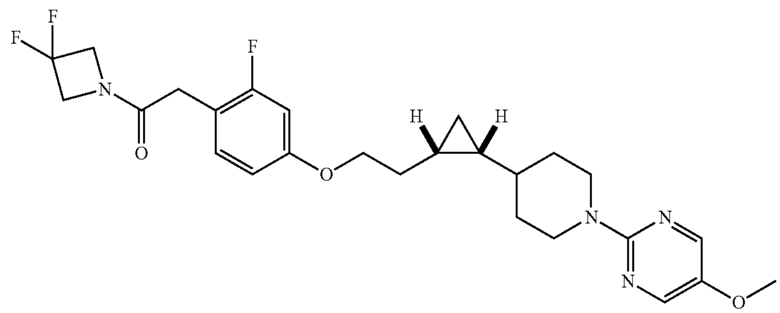 [SMILES: COc1cnc(N2CCC([C@H]3C[C@H]3CCOc3ccc(CC(=O)N4CC(F)(F)C4)c(F)c3)CC2)nc1] | 505 | 0.42 |

Example 41

Preparation of 1-(azetidin-1yl)-2-(2-fluoro-4-{2 [(1S, 2R)-2-{1-[5-(methoxylmethyl)pyrimidin-2yl]piperidin-4-yl}cyclopropyl]ethoxyl}phenyl)ethanone

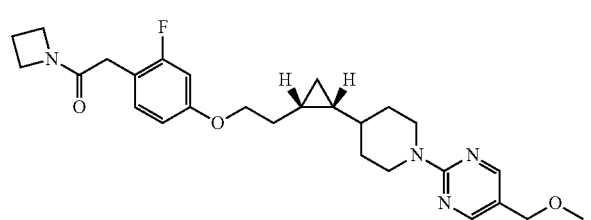 [SMILES: COCc1cnc(N2CCC([C@H]3C[C@H]3CCOc3ccc(CC(=O)N4CCC4)c(F)c3)CC2)nc1]

Step A: methyl (2-fluoro-4-hydroxyphenyl) acetate

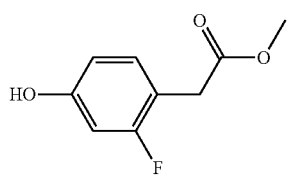

To a solution of (2-fluoro-4-hoxylphenyl) acetic acid (10 g, 58.8 mmol) in 400 ml methanol was added sulfuric acid (15.7 ml, 294 mmol). The reaction mixture was refluxed overnight. The mixture was concentrated under reduced pressure, diluted with water, adjusted pH-7 with 1N NaOH, extracted with EtOAc (3×250 ml), washed with brine, the organic layers combined, dried over magnesium sulphate, filtered, and concentrated under reduced pressure. The residue was purified by column chromatography (100 g silica gel) using a gradient eluent of 10-100% ethyl acetate in hexanes (2500 ml) to afford the title compound. LC/MS (m/z) 185.2 (M+H)+.

Step B: Methyl{2-fluoro-4-[2-((1S,2R)-2-{1-[5-(methoxymethyl)pyrimidin-2-yl]piperidin-4-yl}cyclopropyl)ethoxy]phenyl}acetate

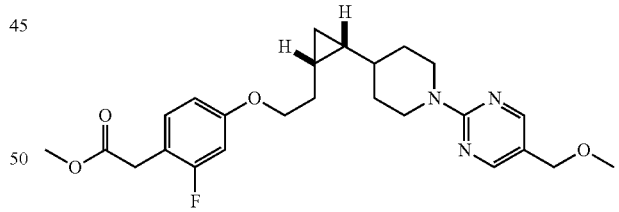

To an RT solution of methyl (2-fluoro-4-hydroxyphenyl) acetate (1.60 g, 5.49 mmol) in 15 ml of anhydrous dichloromethane was added a solution of 2-((1S,2R)-2-{1-[5-(methoxymethyl)pyrimidin-2-yl]piperidin-4-yl}cyclopropyl)ethanol (2.10 g, 7.22 mmol) in 20 ml anhydrous dichloromethane, followed by triphenylphosphine (polymer-bound, 4.32 g, 16.5 mmol), and di-tert-butyl azodicarboxylate (2.53 g, 11.0 mmol). The mixture was stirred at RT for 3 hours, filtered through Celite and concentrated. The residue was purified by column chromatography (50 g silica gel) using a gradient eluent of 0-50% ethyl acetate:hexanes (1000 ml) to afford the title compound. LC/MS (m/z) 458.3 (M+H)+.

Step C: {2-fluoro-4-[2-((1S,2R)-2-{1-[5-(methoxymethyl)pyrimidin-2-yl]piperidin-4-yl}cyclopropyl)ethoxy]phenyl]acetic acid

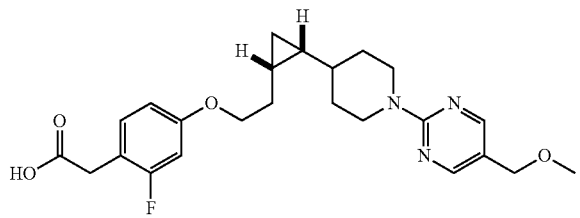 [SMILES: COCc1cnc(N2CCC([C@H]3C[C@H]3CCOc3ccc(CC(=O)O)c(F)c3)CC2)nc1]

To a solution of methyl{2-fluoro-4-[2-((1S,2R)-2-{1-[5-(methoxymethyl)pyrimidin-2-yl]piperidin-4-yl}cyclopropyl)ethoxy]phenyl}acetate (1.50 g, 3.28 mmol) in 21 ml of tetrahydrofuran was added 14 ml of methanol and 14 ml of water. Lithium hydroxide (0.393 g, 16.4 mmol) was added to the mixture, and stirred at RT overnight. 1 M hydrochloric acid was added to adjust the pH to 4. The volatiles were removed in vacuo, and the remaining aqueous layer extracted with dichloromethane (3×30 ml). The organic fractions were combined, dried over magnesium sulphate, filtered and concentrated under reduced pressure. The residue was purified by column chromatography (50 g silica gel) using a gradient eluent of 0-70% ethyl acetate in hexanes (1000 ml) to afford the title compound. LC/MS (m/z) 444.4 (M+H)$^+$.

Step D: 1-(azetidin-1yl)-2-(2-fluoro-4-{2[(1S,2R)-2-{1-[5-(methoxylmethyl)pyrimidin-2yl]piperidin-4-yl}cyclopropyl]ethoxyl}phenyl)ethanone

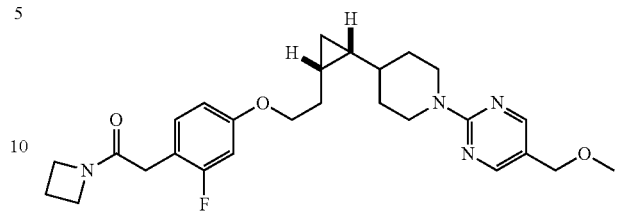

To a solution of {2-fluoro-4-[2-((1S,2R)-2-{1-[5-(methoxymethyl)pyrimidin-2-yl]piperidin-4-yl}cyclopropyl)ethoxy]phenyl}acetic acid (500 mg, 1.13 mmol) in 8 ml of anhydrous DMF at RT was added azetidine (129 mg, 2.26 mmol) and N,N-diisopropylethylamine (0.591 ml, 3.38 mmol). o-(7-Azabenzotriazol-1-yl)-N,N,N',N'-tetramethyluronium hexafluorophosphate (643 mg, 1.69 mmol) was added to the solution and stirred at RT for 4 hrs. The mixture was purified by column chromatography by loading directly to a preparative biotage reverse phase column (C-18) (50 g column) and eluting with Acetonitrile/Water+0.1% formic acid (35% to 90%). The material was further purified by column chromatography on silica gel Biotage 40S, eluting with EtOAc/hexanes (30% to 90%) to give the title compound. $^1$H NMR (500 MHz, CDCl$_3$) δ 8.29 (s, 2H), 7.27 (t, J=8.4 Hz, 1H), 6.64 (d, J=2.1 Hz, 1H), 6.20 (d, J=2.3 Hz, 1H), 4.74 (t, J=13.2 Hz, 2H), 4.27 (s, 2H), 4.17 (t, J=7.7 Hz, 2H), 4.04 (m, 4H), 3.40 (s, 2H), 3.35 (s, 3H), 2.85 (m, 2H), 2.14-2.29 (m, 3H), 1.85 (m, 2H), 1.41 (m, 1H), 1.36 (m, 2H), 1.11 (m, 1H), 0.93 (m, 1H), 0.60-0.71 (m, 2H), −0.08 (m, 1H). LC/MS (m/z): 482.4 (M+H)$^+$. GPR119 Human EC50: 0.77 nM The Examples in Table 10 were synthesized according to the methods described in the prior example (41) employing the appropriate reagents and solvents.

TABLE 10

| Example # | Chemical Structure | Observed Mass [M + H]$^+$ | GPR119 Human EC$_{50}$ (nM) |
|---|---|---|---|
| 42 | 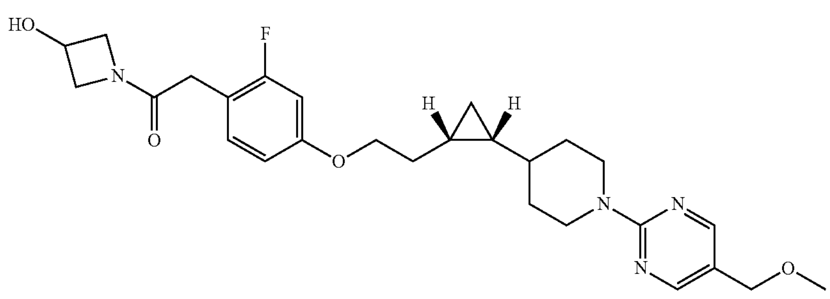 [SMILES: COCc1cnc(N2CCC([C@H]3C[C@H]3CCOc3ccc(CC(=O)N4CC(O)C4)c(F)c3)CC2)nc1] | 499 | 3.4 |
| 43 | 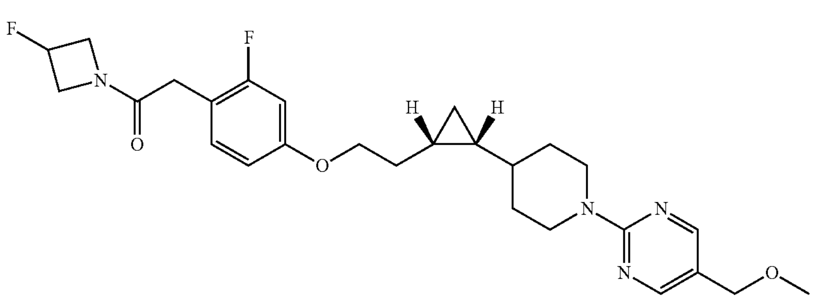 [SMILES: COCc1cnc(N2CCC([C@H]3C[C@H]3CCOc3ccc(CC(=O)N4CC(F)C4)c(F)c3)CC2)nc1] | 501 | 0.54 |

TABLE 10-continued

| Example # | Chemical Structure | Observed Mass [M + H]⁺ | GPR119 Human EC$_{50}$ (nM) |
|---|---|---|---|
| 44 | 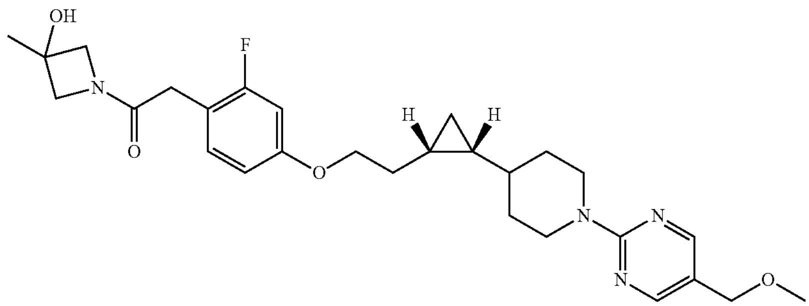 | 513 | 3.6 |
| 45 | 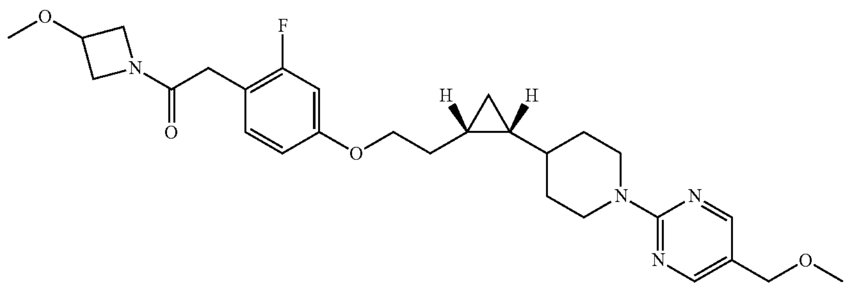 | 513 | 0.81 |
| 46 | 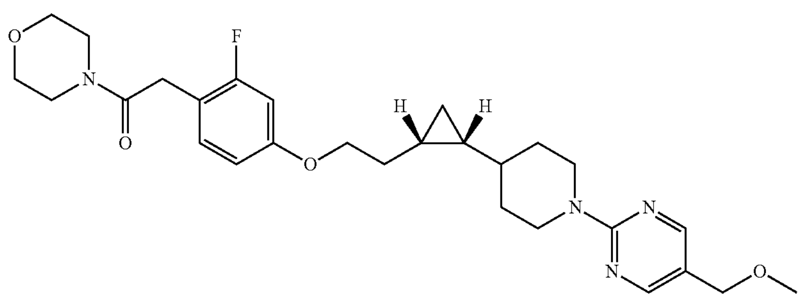 [SMILES: COCc1cnc(N2CCC([C@H]3C[C@H]3CCOc3ccc(CC(=O)N4CCOCC4)c(F)c3)CC2)nc1] | 513 | 1.8 |
| 47 | 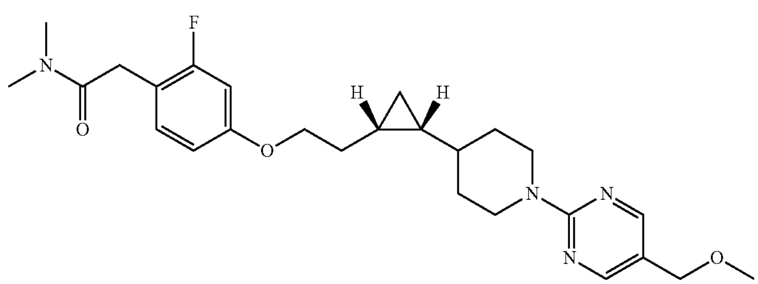 | 471 | 1.3 |
| 48 | 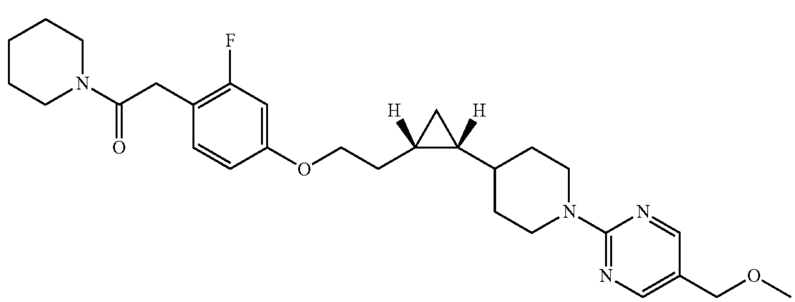 [SMILES: COCc1cnc(N2CCC([C@H]3C[C@H]3CCOc3ccc(CC(=O)N4CCCCC4)c(F)c3)CC2)nc1] | 511 | 0.99 |

TABLE 10-continued

| Example # | Chemical Structure | Observed Mass [M + H]+ | GPR119 Human EC$_{50}$ (nM) |
| --- | --- | --- | --- |
| 49 | 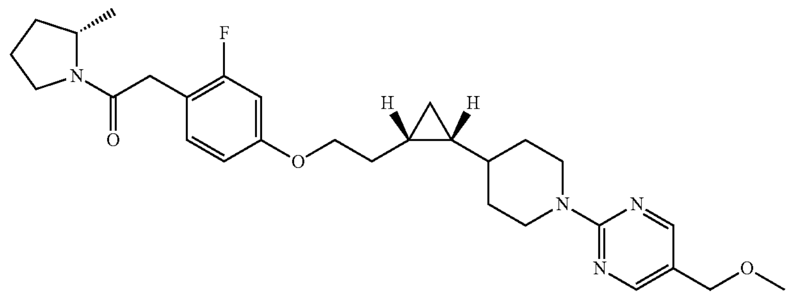 [SMILES: COCc1cnc(N2CCC([C@H]3C[C@H]3CCOc3ccc(CC(=O)N4CCC[C@@H]4C)c(F)c3)CC2)nc1] | 511 | 1.6 |
| 50 | 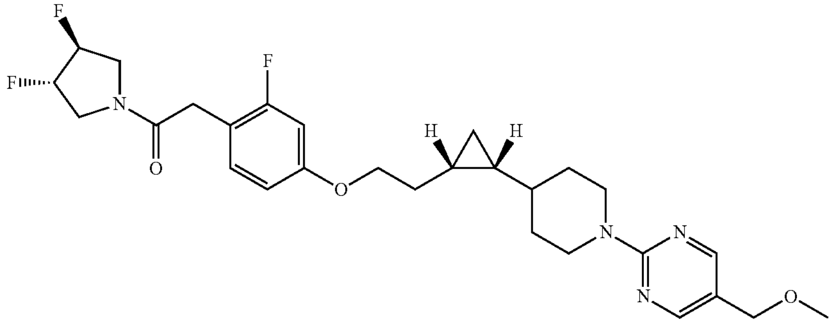 [SMILES: COCc1cnc(N2CCC([C@H]3C[C@H]3CCOc3ccc(CC(=O)N4C[C@H](F)[C@@H](F)C4)c(F)c3)CC2)nc1] | 533 | 1.0 |
| 51 | 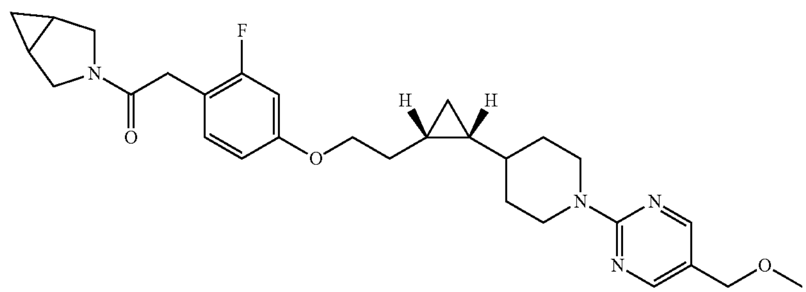 [SMILES: COCc1cnc(N2CCC([C@H]3C[C@H]3CCOc3ccc(CC(=O)N4CC5CC5C4)c(F)c3)CC2)nc1] | 509 | 0.98 |
| 52 | 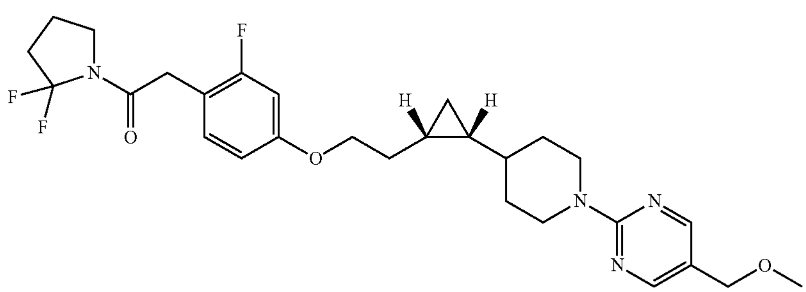 [SMILES: COCc1cnc(N2CCC([C@H]3C[C@H]3CCOc3ccc(CC(=O)N4CCCC4(F)F)c(F)c3)CC2)nc1] | 533 | 0.36 |
| 53 | 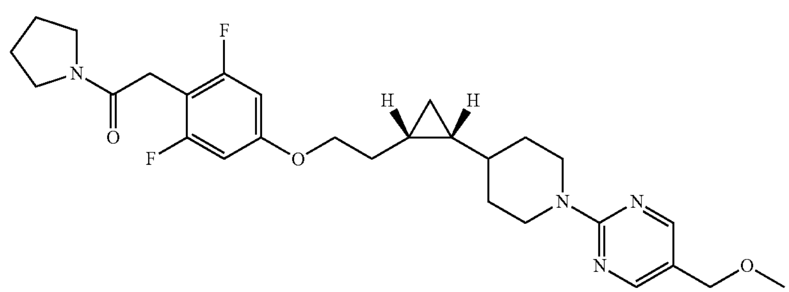 [SMILES: COCc1cnc(N2CCC([C@H]3C[C@H]3CCOc3cc(F)c(CC(=O)N4CCCC4)c(F)c3)CC2)nc1] | 497 | 3.8 |

TABLE 10-continued

| Example # | Chemical Structure | Observed Mass [M + H]+ | GPR119 Human EC$_{50}$ (nM) |
|---|---|---|---|
| 54 | 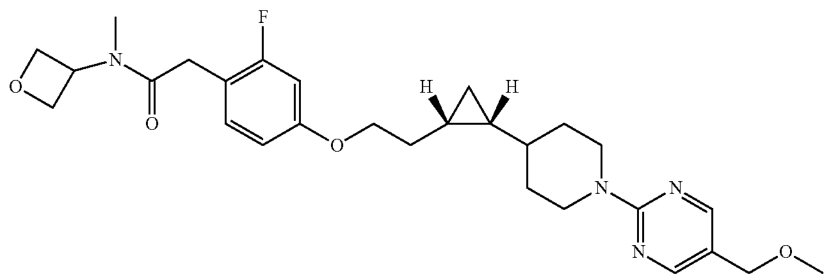 [SMILES: COCc1cnc(N2CCC([C@H]3C[C@H]3CCOc3ccc(CC(=O)N(C)C4COC4)c(F)c3)CC2)nc1] | 513 | 2.5 |
| 55 | 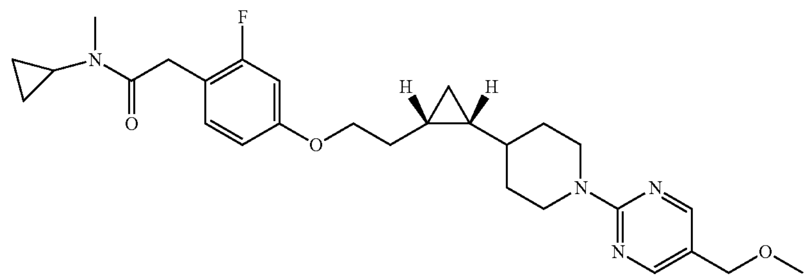 [SMILES: COCc1cnc(N2CCC([C@H]3C[C@H]3CCOc3ccc(CC(=O)N(C)C4CC4)c(F)c3)CC2)nc1] | 497 | 4.4 |
| 56 | 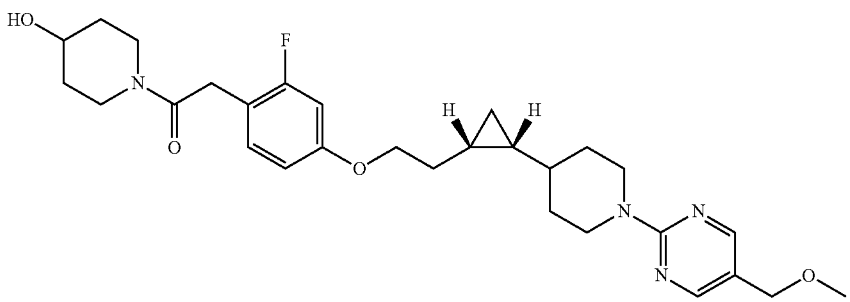 [SMILES: COCc1cnc(N2CCC([C@H]3C[C@H]3CCOc3ccc(CC(=O)N4CCC(O)CC4)c(F)c3)CC2)nc1] | 527 | 3.7 |
| 57 | 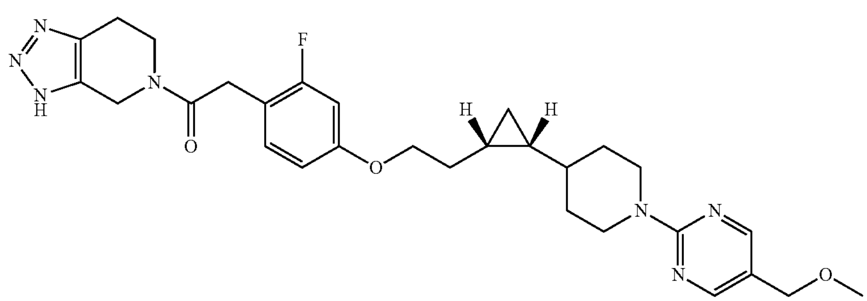 [SMILES: COCc1cnc(N2CCC([C@H]3C[C@H]3CCOc3ccc(CC(=O)N4CCc5nn[nH]c5C4)c(F)c3)CC2)nc1] | 550 | 3.0 |
| 58 | 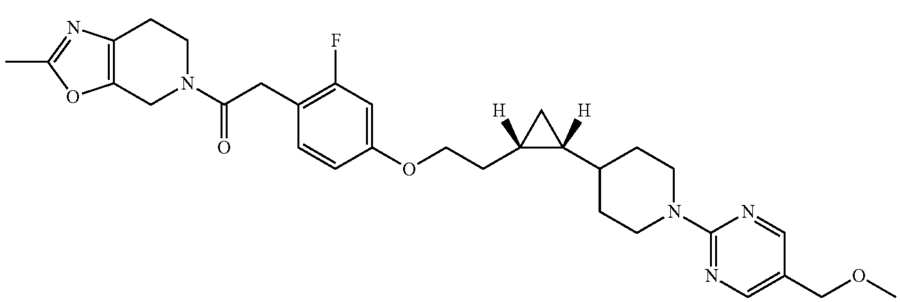 | 564 | 1.2 |

TABLE 10-continued

| Example # | Chemical Structure | Observed Mass [M + H]+ | GPR119 Human EC$_{50}$ (nM) |
|---|---|---|---|
| 59 | 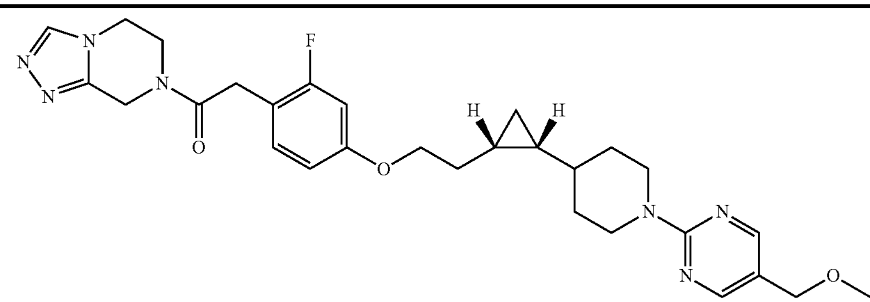 | 550 | 7.3 |

Example 60

Preparation of 1-(azetidin-1-yl)-2-[4-(2-{(1S,2R)-2-[1-(5-chloropyrimidin-2-yl)piperidin-4-yl]cyclopropyl}ethoxy)-2-fluorophenyl]ethanone

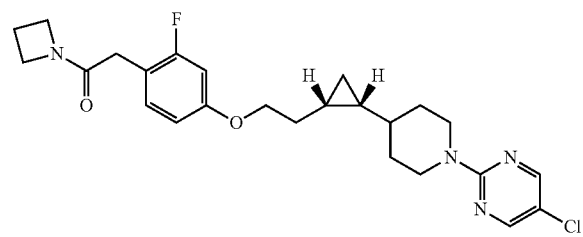 [SMILES: O=C(Cc1ccc(OCC[C@@H]2C[C@@H]2C2CCN(c3ncc(Cl)cn3)CC2)cc1F)N1CCC1]

Step A: Methyl [4-(2-{(1S,2R)-2-[1-(5-chloropyrimidin-2-yl)piperidin-4-yl]cyclopropyl}ethoxy)-2-fluorophenyl]acetate

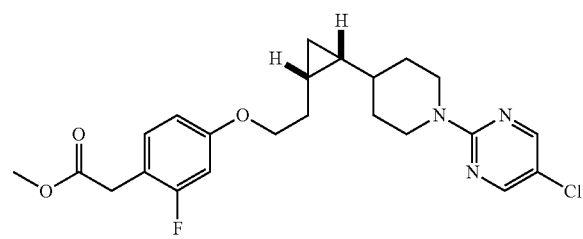 [SMILES: COC(=O)Cc1ccc(OCC[C@@H]2C[C@@H]2C2CCN(c3ncc(Cl)cn3)CC2)cc1F]

To a solution of methyl (2-fluoro-4-hydroxyphenyl)acetate (1.3 g, 4.61 mmol) in 15 ml anhydrous dichloromethane at RT was added a solution of 2-{(1S,2R)-2-[1-(5-chloropyrimidin-2-yl)piperidin-4-yl]cyclopropyl}ethanol (1.02 g, 1.70 mmol) in 5 ml of anhydrous dichloromethane, followed by triphenylphosphine (polymer-bound, 3.63 g, 10.5 mmol) and di-tert-butyl azodicarboxylate (2.13 g, 9.23 mmol). The mixture was stirred at RT for 3 hours, filtered through Celite and concentrated. The residue was purified by column chromatography on silica gel (Biotage 100 g) using a gradient eluent of 0-50% ethyl acetate in hexanes (1500 ml) to afford the title compound. LC/MS (m/z) 448.2 (M+H)+.

Step B: [4-(2-{(1S,2R)-2-[1-(5-chloropyrimidin-2-yl)piperidin-4-yl]cyclopropyl}ethoxy)-2-fluorophenyl]acetic acid

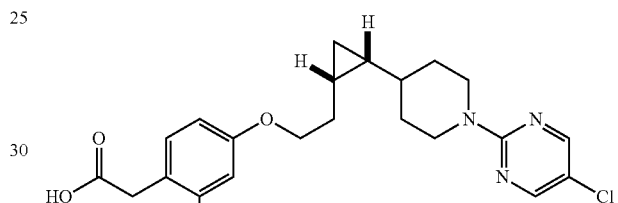

To a solution of methyl [4-(2-{(1S,2R)-2-[1-(5-chloropyrimidin-2-yl)piperidin-4-yl]cyclopropyl}ethoxy)-2-fluorophenyl]acetate (1.50 g, 3.25 mmol) in 21 ml of tetrahydrofuran was added 14 ml of methanol and 14 ml of water. Lithium hydroxide (0.401 g, 16.7 mmol) was added to the reaction mixture, and the reaction mixture was stirred at RT overnight. 1 M hydrochloric acid was added to adjust the pH to 4. The volatiles were removed under reduced pressure, and the remaining aqueous solution was extracted with dichloromethane (3×20 ml). The organic fractions were combined, dried over magnesium sulphate, filtered, and concentrated under reduced pressure. The residue was purified by column chromatography on silica gel (Biotage 100 g) using a gradient eluent of 0-70% ethyl acetate in hexanes (700 ml) to afford the title compound. LC/MS (m/z) 434.1 (M+H)+.

Step C: 1-(azetidin-1-yl)-2-[4-(2-{(1S,2R)-2-[1-(5-chloropyrimidin-2-yl)piperidin-4-yl]cyclopropyl}ethoxy)-2-fluorophenyl]ethanone

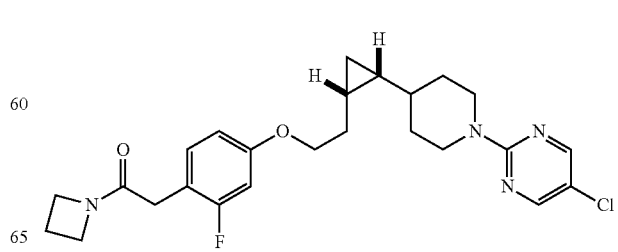

To a solution of [4-(2-{(1S,2R)-2-[1-(5-chloropyrimidin-2-yl)piperidin-4-yl]cyclopropyl}ethoxy)-2-fluorophenyl]acetic acid (100 mg, 0.230 mmol) in 1 ml of anhydrous DMF at RT was added azetidine (13.2 mg, 0.230 mmol) and N,N-diisopropylethylamine (0.201 ml, 1.15 mmol). o-(7-Azabenzotriazol-1-yl)-N,N,N',N'-tetramethyluronium hexafluorophosphate (175 mg, 0.461 mmol) was added to the solution and the mixture stirred at RT for 4 hrs. The mixture was filtered and purified by reverse-phase HPLC (SunFire Prep C18 OBD 5 um 19×100 mm column; 35-75% acetonitrile in 0.1% formic acid in water gradient) to give the title compound. LC/MS (m/z): 473.1 (M+H)+. GPR119 Human EC50: 0.19 nM The Examples in Table 11 were synthesized according to the methods described in the prior example (60) employing the appropriate reagents and solvents.

TABLE 11

| Example # | Chemical Structure | Observed Mass [M + H]+ | GPR119 Human EC$_{50}$ (nM) |
|---|---|---|---|
| 61 | 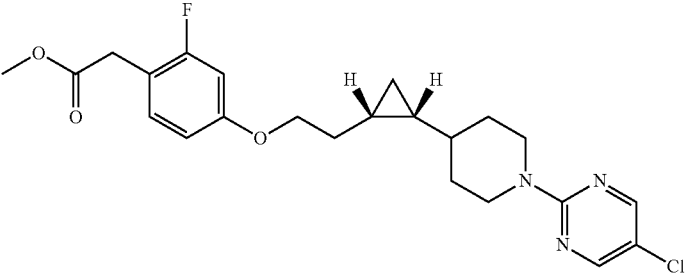 [SMILES: COC(=O)Cc1ccc(OCC[C@@H]2C[C@@H]2C2CCN(c3ncc(Cl)cn3)CC2)cc1F] | 448 | 0.70 |
| 62 | 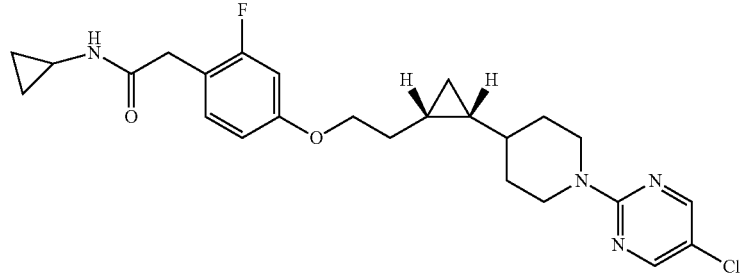 [SMILES: O=C(Cc1ccc(OCC[C@@H]2C[C@@H]2C2CCN(c3ncc(Cl)cn3)CC2)cc1F)NC1CC1] | 473 | 1.4 |
| 63 | 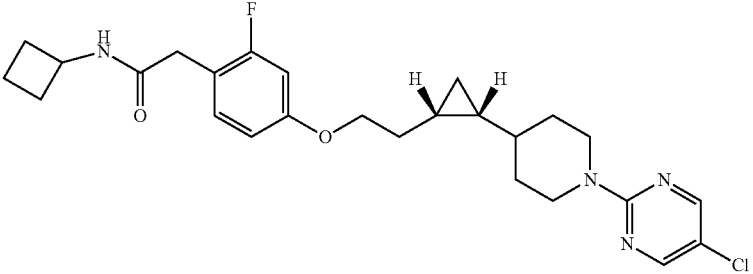 [SMILES: O=C(Cc1ccc(OCC[C@@H]2C[C@@H]2C2CCN(c3ncc(Cl)cn3)CC2)cc1F)NC1CCC1] | 487 | 4.2 |
| 64 | 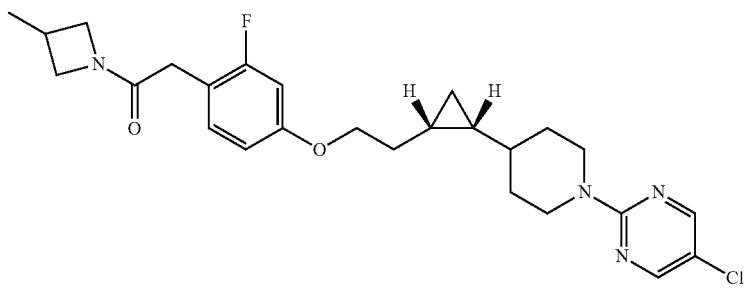 [SMILES: CC1CN(C(=O)Cc2ccc(OCC[C@@H]3C[C@@H]3C3CCN(c4ncc(Cl)cn4)CC3)cc2F)C1] | 487 | 0.95 |

TABLE 11-continued

| Example # | Chemical Structure | Observed Mass [M + H]⁺ | GPR119 Human EC$_{50}$ (nM) |
| --- | --- | --- | --- |
| 65 | 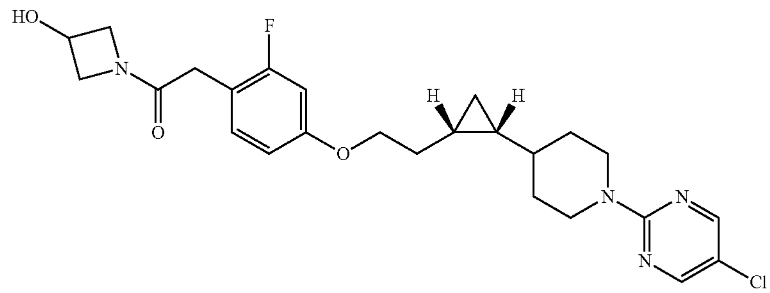 [SMILES: O=C(Cc1ccc(OCC[C@@H]2C[C@@H]2C2CCN(c3ncc(Cl)cn3)CC2)cc1F)N1CC(O)C1] | 489 | 0.22 |
| 66 | 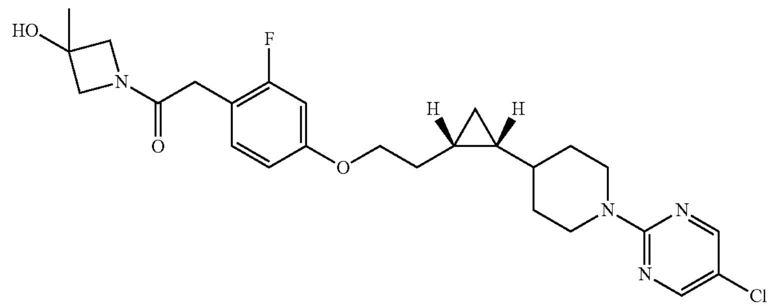 [SMILES: CC1(O)CN(C(=O)Cc2ccc(OCC[C@@H]3C[C@@H]3C3CCN(c4ncc(Cl)cn4)CC3)cc2F)C1] | 503 | 0.40 |
| 67 | 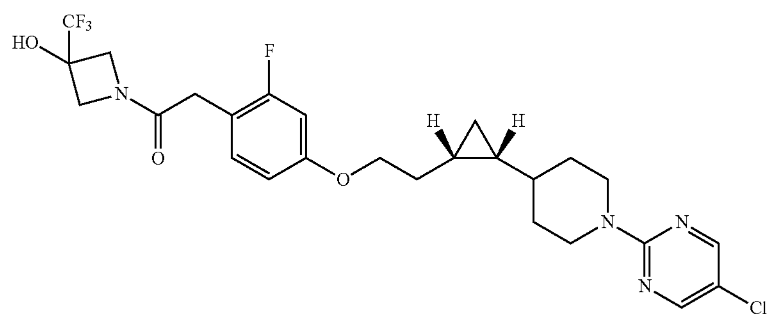 [SMILES: O=C(Cc1ccc(OCC[C@@H]2C[C@@H]2C2CCN(c3ncc(Cl)cn3)CC2)cc1F)N1CC(O)(C(F)(F)F)C1] | 557 | 0.68 |
| 68 | 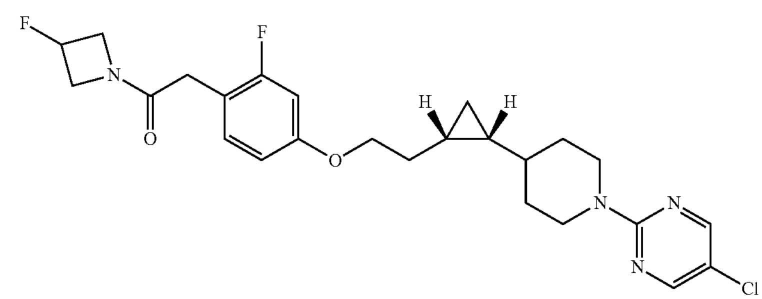 [SMILES: O=C(Cc1ccc(OCC[C@@H]2C[C@@H]2C2CCN(c3ncc(Cl)cn3)CC2)cc1F)N1CC(F)C1] | 491 | 0.33 |
| 69 | 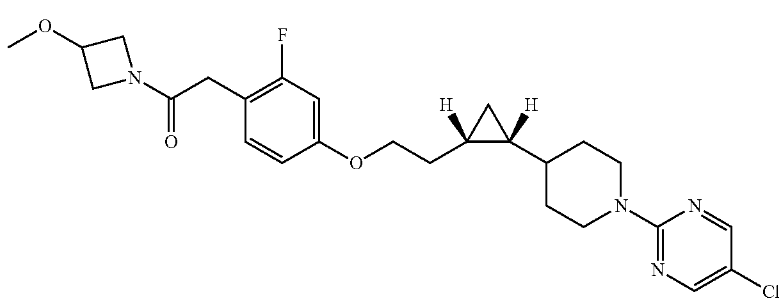 [SMILES: COC1CN(C(=O)Cc2ccc(OCC[C@@H]3C[C@@H]3C3CCN(c4ncc(Cl)cn4)CC3)cc2F)C1] | 503 | 0.17 |

TABLE 11-continued

| Example # | Chemical Structure | Observed Mass [M + H]+ | GPR119 Human EC50 (nM) |
|---|---|---|---|
| 70 | 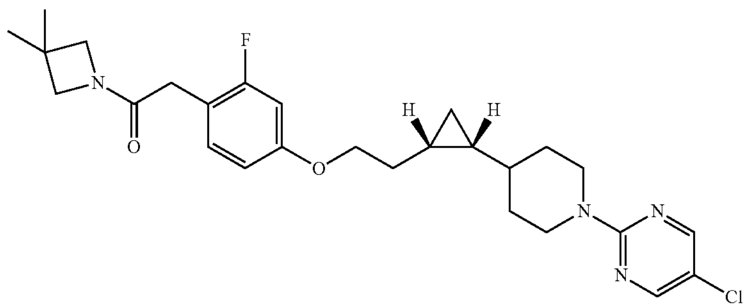 [SMILES: CC1(C)CN(C(=O)Cc2ccc(OCC[C@@H]3C[C@@H]3C3CCN(c4ncc(Cl)cn4)CC3)cc2F)C1] | 501 | 0.80 |
| 71 | 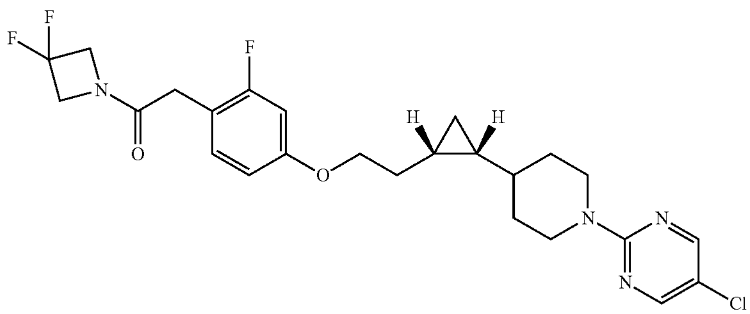 [SMILES: O=C(Cc1ccc(OCC[C@@H]2C[C@@H]2C2CCN(c3ncc(Cl)cn3)CC2)cc1F)N1CC(F)(F)C1] | 509 | 1.2 |
| 72 | 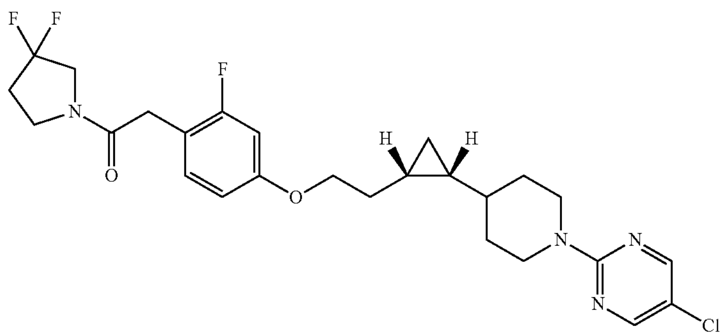 [SMILES: O=C(Cc1ccc(OCC[C@@H]2C[C@@H]2C2CCN(c3ncc(Cl)cn3)CC2)cc1F)N1CCC(F)(F)C1] | 523 | 0.50 |
| 73 | 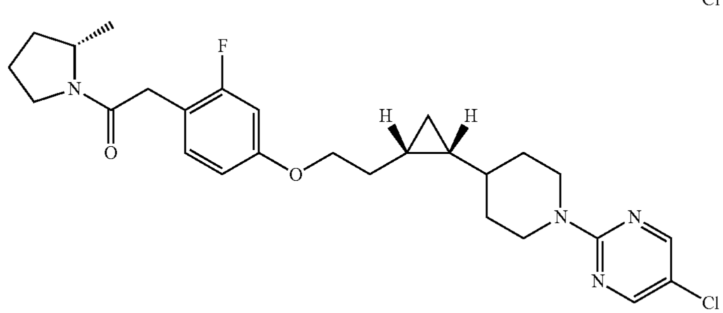 | 501 | 2.7 |
| 74 | 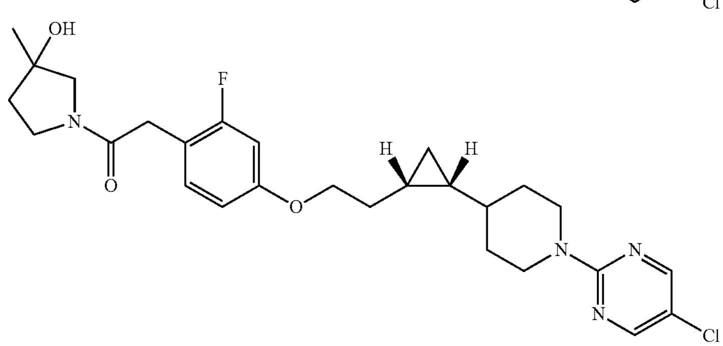 | 517 | 4.2 |

TABLE 11-continued

| Example # | Chemical Structure | Observed Mass [M + H]+ | GPR119 Human EC50 (nM) |
|---|---|---|---|
| 75 | 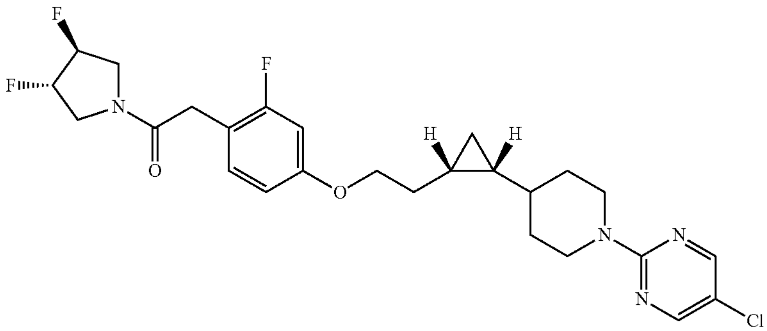 [SMILES: O=C(Cc1ccc(OCC[C@@H]2C[C@@H]2C2CCN(c3ncc(Cl)cn3)CC2)cc1F)N1C[C@H](F)[C@@H](F)C1] | 523 | 0.78 |
| 76 | 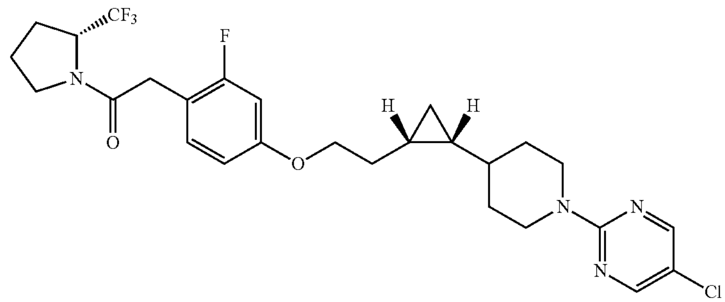 [SMILES: O=C(Cc1ccc(OCC[C@@H]2C[C@@H]2C2CCN(c3ncc(Cl)cn3)CC2)cc1F)N1CCC[C@@H]1C(F)(F)F] | 555 | 2.4 |

Example 77

Preparation of 2-[4-(2-(1S,2R)-2-[1-(5-chloropyrimidin-2-yl)piperidin-4-yl]cyclopropyl ethoxy)-2-fluorophenyl]-N-(cyclopropylmethyl)acetamide

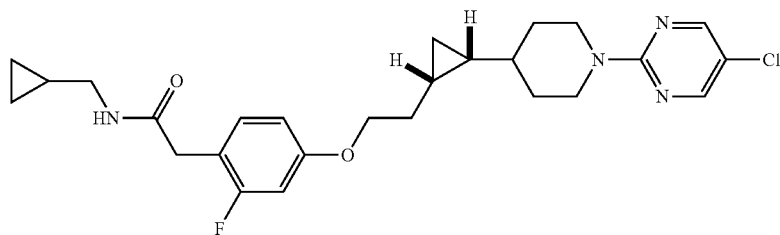 [SMILES: O=C(Cc1ccc(OCC[C@@H]2C[C@@H]2C2CCN(c3ncc(Cl)cn3)CC2)cc1F)NCC1CC1]

Step A: 2-[4-(2-{(1S,2R)-2-[1-(5-chloropyrimidin-2-yl)piperidin-4-yl]cyclopropyl}ethoxy)-2-fluorophenyl]-N-(cyclopropylmethyl)acetamide

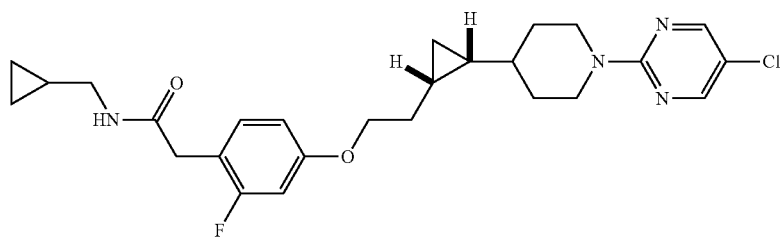 [SMILES: O=C(Cc1ccc(OCC[C@@H]2C[C@@H]2C2CCN(c3ncc(Cl)cn3)CC2)cc1F)NCC1CC1]

[4-(2-(1S,2R)-2-[1-(5-chloropyrimidin-2-yl)piperidin-4-yl]cyclopropyl ethoxy)-2-fluorophenyl]acetic acid (25 mg, 0.06 mmol), Hunig's Base (0.030 ml, 0.17 mmol) and 1-cyclopropylmethanamine (6 mg, 0.09 mmol) were dissolved in DMF (2 ml). The mixture was stirred at RT for 10 min, HBTU (43 mg, 0.12 mmol) added, and the mixture stirred at RT overnight. The reaction mixture was filtered and purified by reverse-phase HPLC (SunFire Prep C18 OBD 5 um 19×100 mm column; 35-75% acetonitrile in 0.16% formic acid in water gradient) to give the title compound. LC/MS (m/z): 487 (M+H)⁺. GPR119 Human EC50: 1.5 nM The Examples in Table 12 were synthesized according to the methods described in the prior example (77) employing the appropriate reagents and solvents.

TABLE 12

| Example # | Chemical Structure | Observed Mass [M + H]$^+$ | GPR119 Human EC$_{50}$ (nM) |
|---|---|---|---|
| 78 | 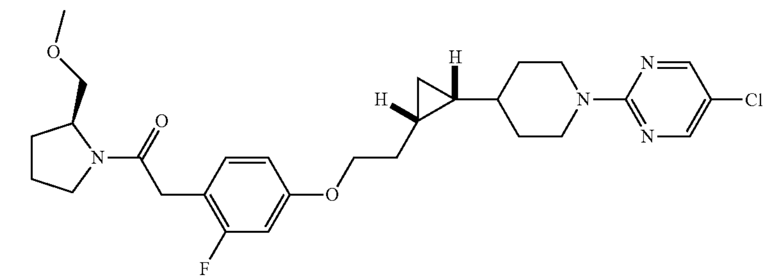 [SMILES: COC[C@@H]1CCCN1C(=O)Cc1ccc(OCC[C@@H]2C[C@@H]2C2CCN(c3ncc(Cl)cn3)CC2)cc1F] | 531 | 3.8 |
| 79 | 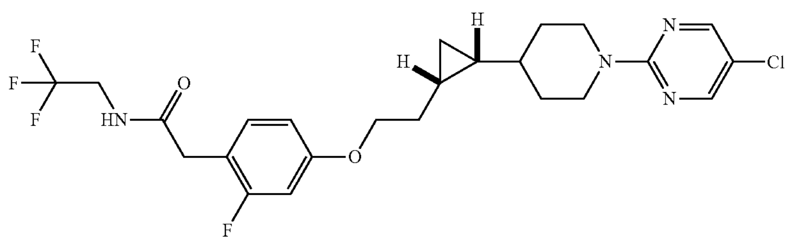 [SMILES: O=C(Cc1ccc(OCC[C@@H]2C[C@@H]2C2CCN(c3ncc(Cl)cn3)CC2)cc1F)NCC(F)(F)F] | 515 | 1.6 |
| 80 | 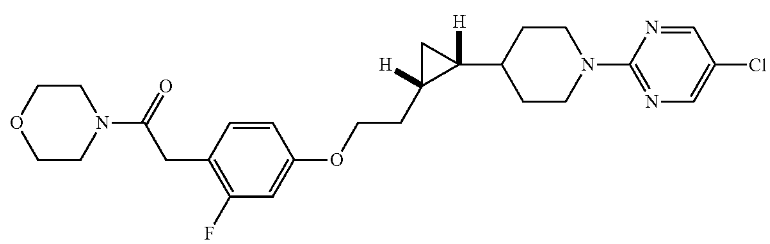 [SMILES: O=C(Cc1ccc(OCC[C@@H]2C[C@@H]2C2CCN(c3ncc(Cl)cn3)CC2)cc1F)N1CCOCC1] | 503 | 0.76 |
| 81 | 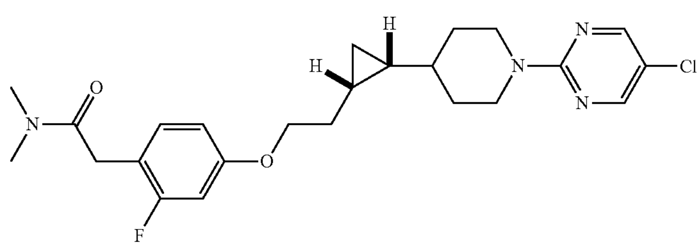 [SMILES: CN(C)C(=O)Cc1ccc(OCC[C@@H]2C[C@@H]2C2CCN(c3ncc(Cl)cn3)CC2)cc1F] | 461 | 0.63 |
| 82 | 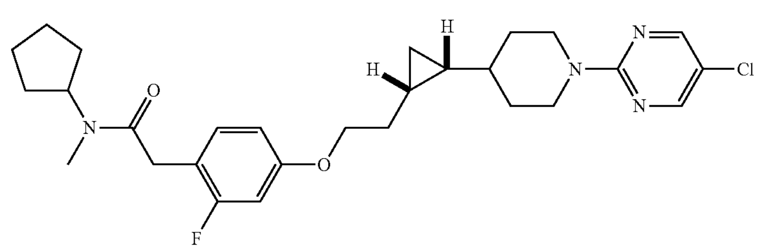 [SMILES: CN(C(=O)Cc1ccc(OCC[C@@H]2C[C@@H]2C2CCN(c3ncc(Cl)cn3)CC2)cc1F)C1CCCC1] | 515 | 2.9 |

TABLE 12-continued

| Example # | Chemical Structure | Observed Mass [M + H]+ | GPR119 Human EC$_{50}$ (nM) |
|---|---|---|---|
| 83 | (cyclopentyl-NH-C(O)-CH$_2$-phenyl(F)-O-CH$_2$CH$_2$-cyclopropyl-piperidine-pyrimidine-Cl) | 501 | 1.3 |
| 84 | (piperidine-C(O)-CH$_2$-phenyl(F)-O-CH$_2$CH$_2$-cyclopropyl-piperidine-pyrimidine-Cl) | 501 | 1.5 |
| 85 | (pyrrolidine-C(O)-CH$_2$-phenyl(F)-O-CH$_2$CH$_2$-cyclopropyl-piperidine-pyrimidine-Cl) | 487 | 0.61 |
| 86 | (4,4-difluoropiperidine-C(O)-CH$_2$-phenyl(F)-O-CH$_2$CH$_2$-cyclopropyl-piperidine-pyrimidine-Cl) | 537 | 0.80 |
| 87 | (1-trifluoromethylcyclopropyl-NH-C(O)-CH$_2$-phenyl(F)-O-CH$_2$CH$_2$-cyclopropyl-piperidine-pyrimidine-Cl) | 541 | 3.6 |
| 88 | (2,2-difluorocyclopropyl-NH-C(O)-CH$_2$-phenyl(F)-O-CH$_2$CH$_2$-cyclopropyl-piperidine-pyrimidine-Cl) | 509 | 1.7 |

TABLE 12-continued

| Example # | Chemical Structure | Observed Mass [M + H]+ | GPR119 Human EC50 (nM) |
|---|---|---|---|
| 89 | 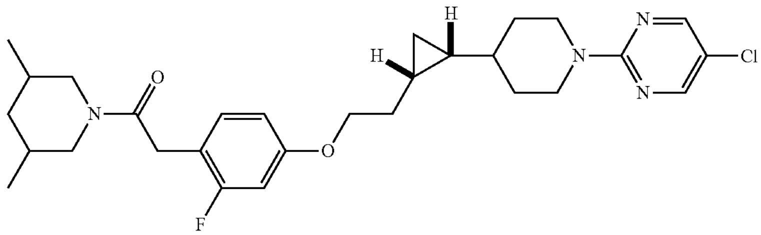 [SMILES: CC1CC(C)CN(C(=O)Cc2ccc(OCC[C@@H]3C[C@@H]3C3CCN(c4ncc(Cl)cn4)CC3)cc2F)C1] | 529 | 8.6 |
| 90 | 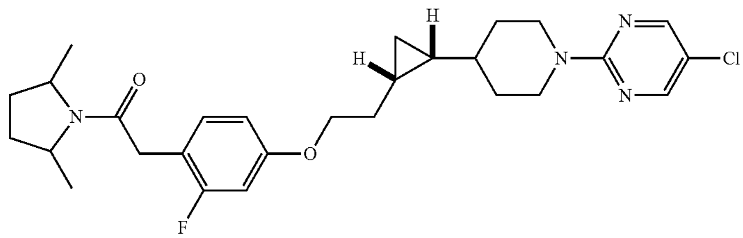 [SMILES: CC1CCC(C)N1C(=O)Cc1ccc(OCC[C@@H]2C[C@@H]2C2CCN(c3ncc(Cl)cn3)CC2)cc1F] | 515 | 7.2 |
| 91 | 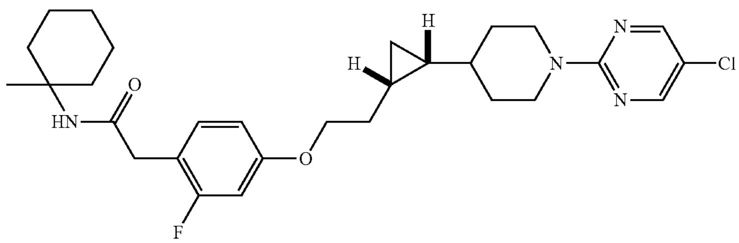 [SMILES: CC1(NC(=O)Cc2ccc(OCC[C@@H]3C[C@@H]3C3CCN(c4ncc(Cl)cn4)CC3)cc2F)CCCCC1] | 529 | 9.3 |
| 92 | 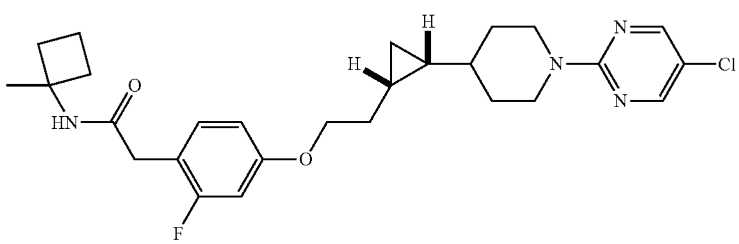 [SMILES: CC1(NC(=O)Cc2ccc(OCC[C@@H]3C[C@@H]3C3CCN(c4ncc(Cl)cn4)CC3)cc2F)CCC1] | 501 | 4.0 |
| 93 | 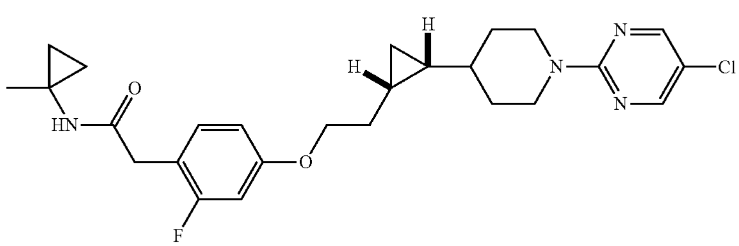 [SMILES: CC1(NC(=O)Cc2ccc(OCC[C@@H]3C[C@@H]3C3CCN(c4ncc(Cl)cn4)CC3)cc2F)CC1] | 487 | 3.7 |
| 94 | 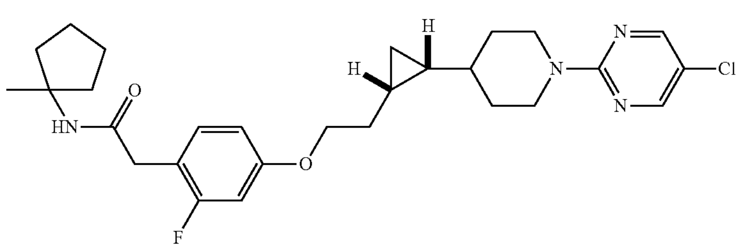 [SMILES: CC1(NC(=O)Cc2ccc(OCC[C@@H]3C[C@@H]3C3CCN(c4ncc(Cl)cn4)CC3)cc2F)CCCC1] | 515 | 6.5 |

TABLE 12-continued

| Example # | Chemical Structure | Observed Mass [M + H]+ | GPR119 Human EC50 (nM) |
|---|---|---|---|
| 95 | 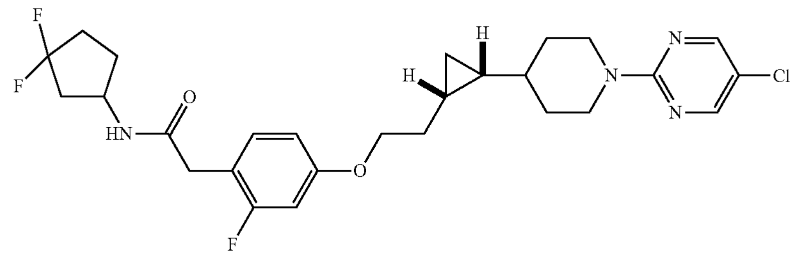 [SMILES: O=C(Cc1ccc(OCC[C@@H]2C[C@@H]2C2CCN(c3ncc(Cl)cn3)CC2)cc1F)NC1CCC(F)(F)C1] | 537 | 2.3 |
| 96 | 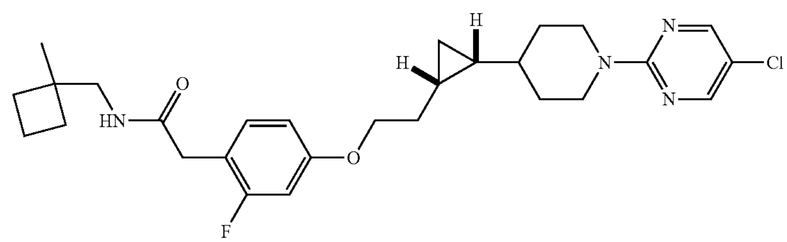 [SMILES: CC1(CNC(=O)Cc2ccc(OCC[C@@H]3C[C@@H]3C3CCN(c4ncc(Cl)cn4)CC3)cc2F)CCC1] | 515 | 5.1 |
| 97 | 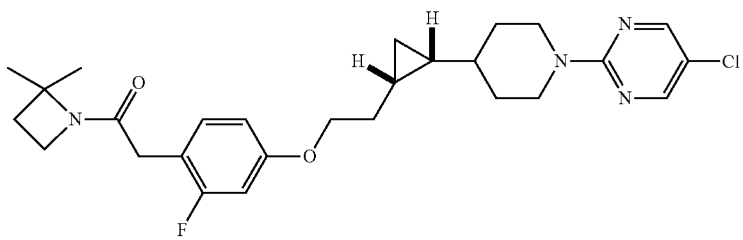 [SMILES: CC1(C)CCN1C(=O)Cc1ccc(OCC[C@@H]2C[C@@H]2C2CCN(c3ncc(Cl)cn3)CC2)cc1F] | 501 | 3.2 |
| 98 | 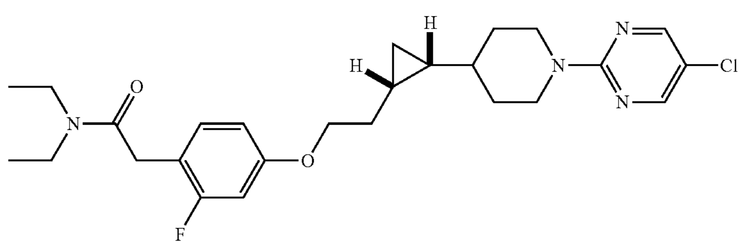 [SMILES: CCN(CC)C(=O)Cc1ccc(OCC[C@@H]2C[C@@H]2C2CCN(c3ncc(Cl)cn3)CC2)cc1F] | 489 | 9.2 |
| 99 | 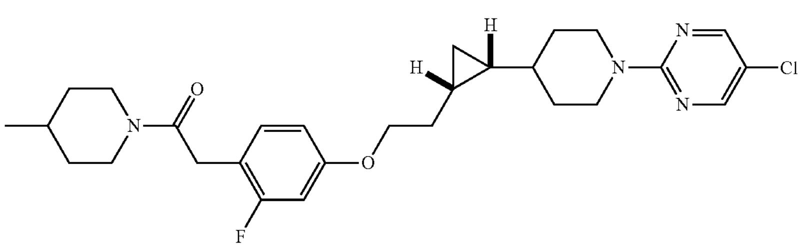 [SMILES: CC1CCN(C(=O)Cc2ccc(OCC[C@@H]3C[C@@H]3C3CCN(c4ncc(Cl)cn4)CC3)cc2F)CC1] | 515 | 4.0 |
| 100 | 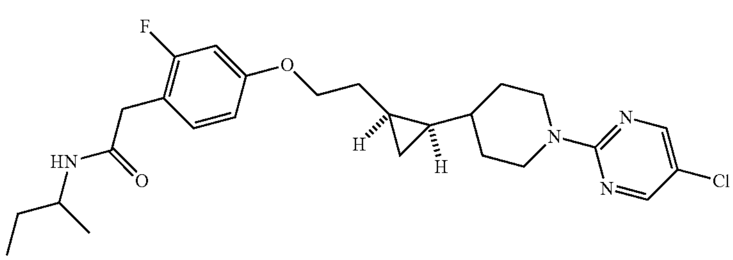 [SMILES: CCC(C)NC(=O)Cc1ccc(OCC[C@@H]2C[C@@H]2C2CCN(c3ncc(Cl)cn3)CC2)cc1F] | 489 | 1.8 |

TABLE 12-continued

| Example # | Chemical Structure | Observed Mass [M + H]+ | GPR119 Human EC$_{50}$ (nM) |
|---|---|---|---|
| 101 | 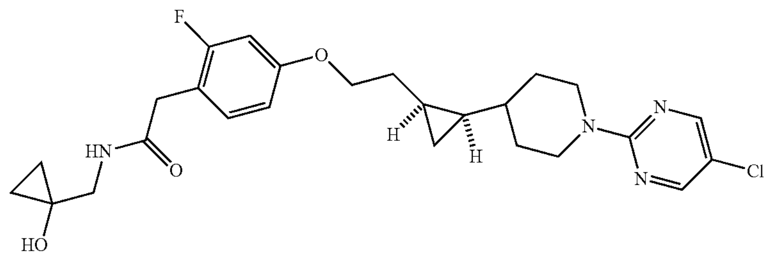 [SMILES: O=C(Cc1ccc(OCC[C@@H]2C[C@@H]2C2CCN(c3ncc(Cl)cn3)CC2)cc1F)NCC1(O)CC1] | 503 | 5.2 |
| 102 | 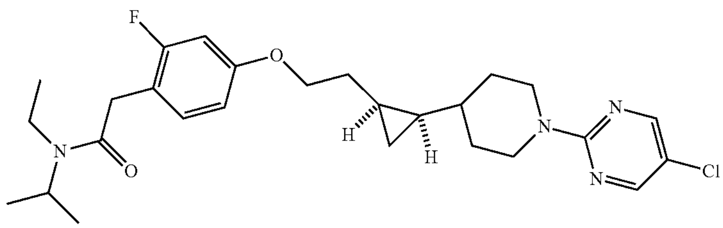 [SMILES: CCN(C(=O)Cc1ccc(OCC[C@@H]2C[C@@H]2C2CCN(c3ncc(Cl)cn3)CC2)cc1F)C(C)C] | 503 | 3.0 |
| 103 | 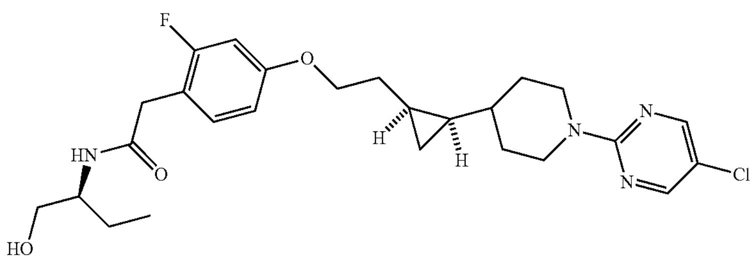 [SMILES: CC[C@@H](CO)NC(=O)Cc1ccc(OCC[C@@H]2C[C@@H]2C2CCN(c3ncc(Cl)cn3)CC2)cc1F] | 505 | 9.7 |
| 104 | 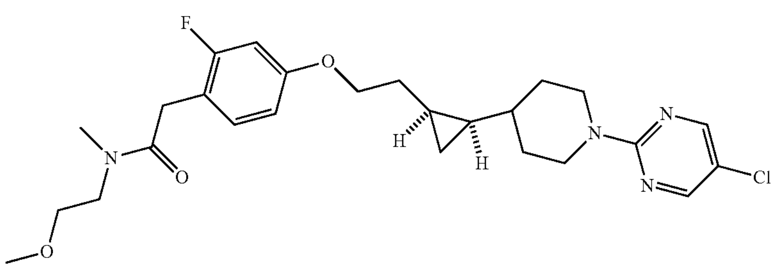 [SMILES: COCCN(C)C(=O)Cc1ccc(OCC[C@@H]2C[C@@H]2C2CCN(c3ncc(Cl)cn3)CC2)cc1F] | 505 | 1.3 |
| 105 | 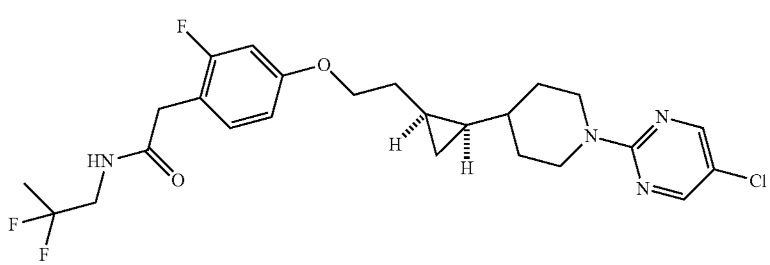 [SMILES: CC(F)(F)CNC(=O)Cc1ccc(OCC[C@@H]2C[C@@H]2C2CCN(c3ncc(Cl)cn3)CC2)cc1F] | 511 | 1.5 |
| 106 | 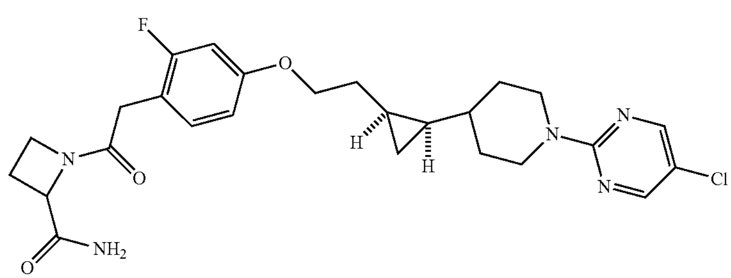 [SMILES: NC(=O)C1CCN1C(=O)Cc1ccc(OCC[C@@H]2C[C@@H]2C2CCN(c3ncc(Cl)cn3)CC2)cc1F] | 516 | 4.3 |

TABLE 12-continued
| Example # | Chemical Structure | Observed Mass [M + H]+ | GPR119 Human EC50 (nM) |
|---|---|---|---|
| 107 | 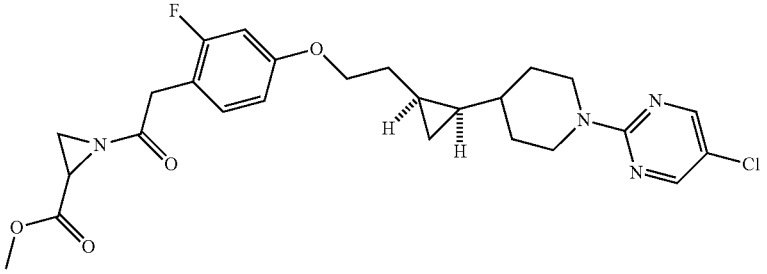 [SMILES: COC(=O)C1CN1C(=O)Cc1ccc(OCC[C@@H]2C[C@@H]2C2CCN(c3ncc(Cl)cn3)CC2)cc1F] | 517 | 8.9 |
| 108 | 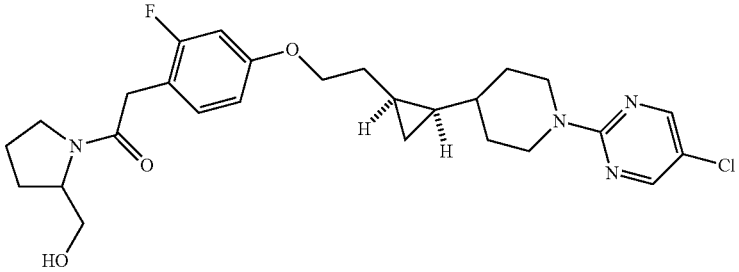 [SMILES: O=C(Cc1ccc(OCC[C@@H]2C[C@@H]2C2CCN(c3ncc(Cl)cn3)CC2)cc1F)N1CCCC1CO] | 517 | 2.5 |
| 109 | 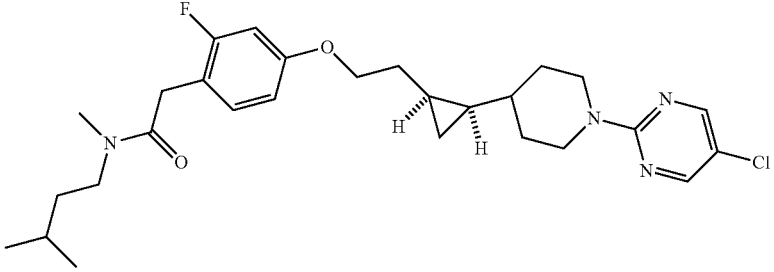 [SMILES: CC(C)CCN(C)C(=O)Cc1ccc(OCC[C@@H]2C[C@@H]2C2CCN(c3ncc(Cl)cn3)CC2)cc1F] | 517 | 10.3 |
| 110 | 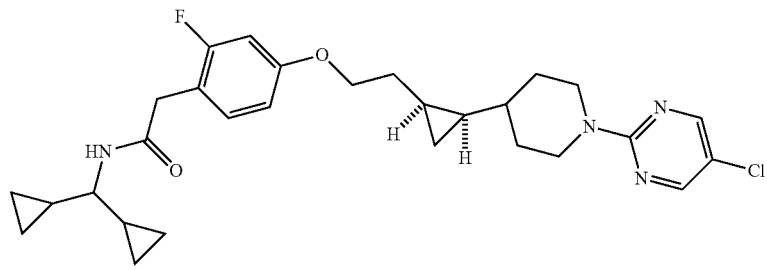 [SMILES: O=C(Cc1ccc(OCC[C@@H]2C[C@@H]2C2CCN(c3ncc(Cl)cn3)CC2)cc1F)NC(C1CC1)C1CC1] | 527 | 5.8 |
| 111 | 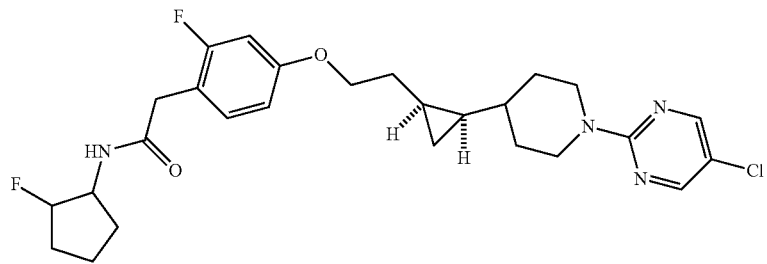 [SMILES: O=C(Cc1ccc(OCC[C@@H]2C[C@@H]2C2CCN(c3ncc(Cl)cn3)CC2)cc1F)NC1CCCC1F] | 519 | 3.0 |

TABLE 12-continued

| Example # | Chemical Structure | Observed Mass [M + H]+ | GPR119 Human EC$_{50}$ (nM) |
|---|---|---|---|
| 112 | 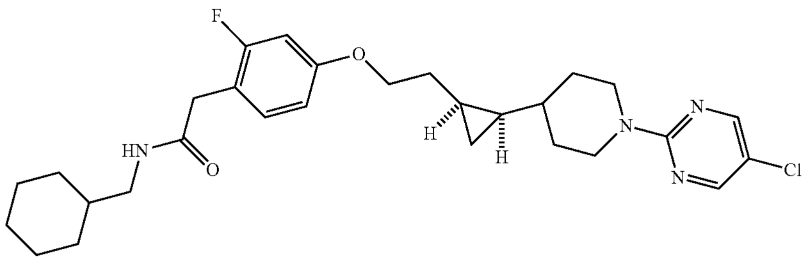 [SMILES: O=C(Cc1ccc(OCC[C@@H]2C[C@@H]2C2CCN(c3ncc(Cl)cn3)CC2)cc1F)NCC1CCCCC1] | 529 | 6.1 |
| 113 | 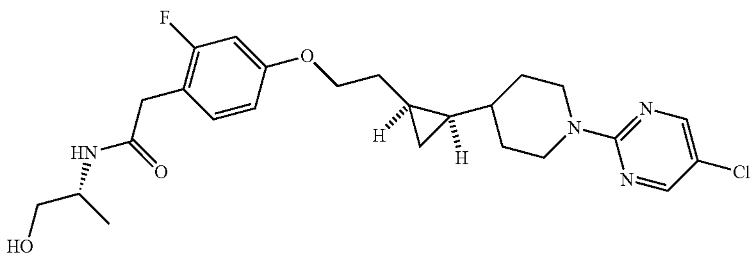 [SMILES: C[C@H](CO)NC(=O)Cc1ccc(OCC[C@@H]2C[C@@H]2C2CCN(c3ncc(Cl)cn3)CC2)cc1F] | 491 | 3.9 |
| 114 | 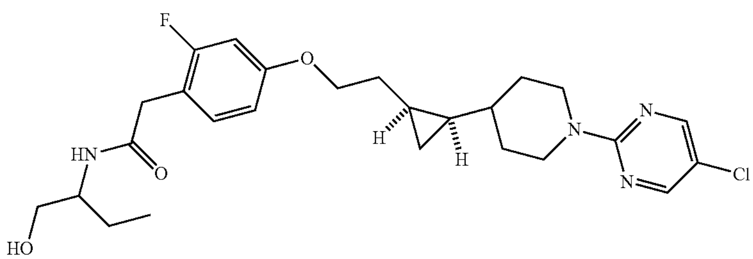 [SMILES: CCC(CO)NC(=O)Cc1ccc(OCC[C@@H]2C[C@@H]2C2CCN(c3ncc(Cl)cn3)CC2)cc1F] | 505 | 3.7 |
| 115 | 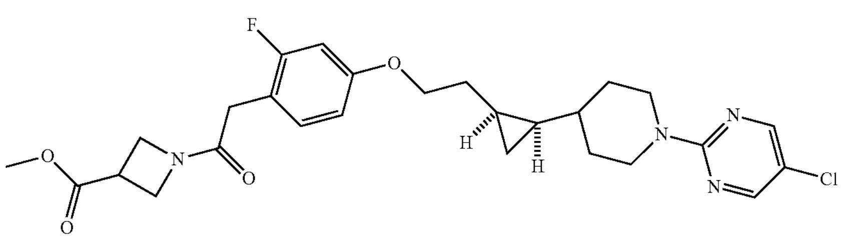 [SMILES: COC(=O)C1CN(C(=O)Cc2ccc(OCC[C@@H]3C[C@@H]3C3CCN(c4ncc(Cl)cn4)CC3)cc2F)C1] | 531 | 2.2 |
| 116 | 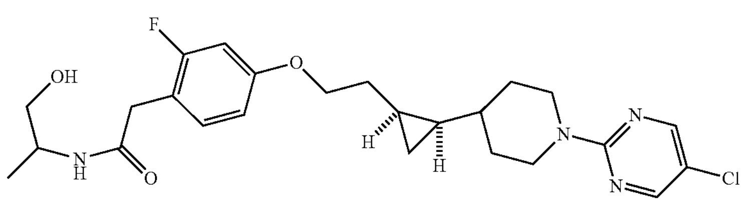 [SMILES: CC(CO)NC(=O)Cc1ccc(OCC[C@@H]2C[C@@H]2C2CCN(c3ncc(Cl)cn3)CC2)cc1F] | 491 | 9.2 |
| 117 | 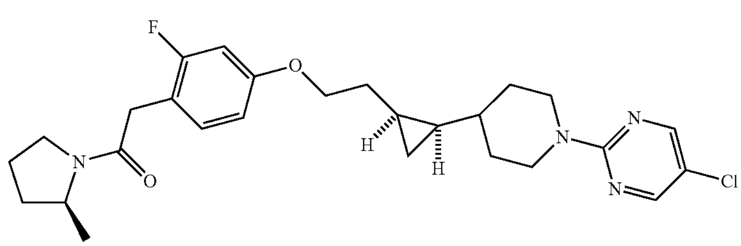 [SMILES: C[C@H]1CCCN1C(=O)Cc1ccc(OCC[C@@H]2C[C@@H]2C2CCN(c3ncc(Cl)cn3)CC2)cc1F] | 501 | 1.7 |

TABLE 12-continued

| Example # | Chemical Structure | Observed Mass [M + H]+ | GPR119 Human EC50 (nM) |
|---|---|---|---|
| 118 | 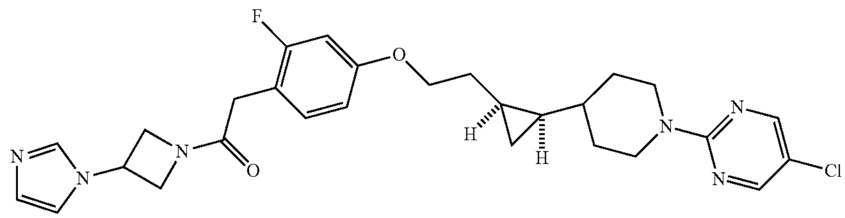 [SMILES: O=C(Cc1ccc(OCC[C@@H]2C[C@@H]2C2CCN(c3ncc(Cl)cn3)CC2)cc1F)N1CC(n2ccnc2)C1] | 539 | 1.1 |
| 119 | 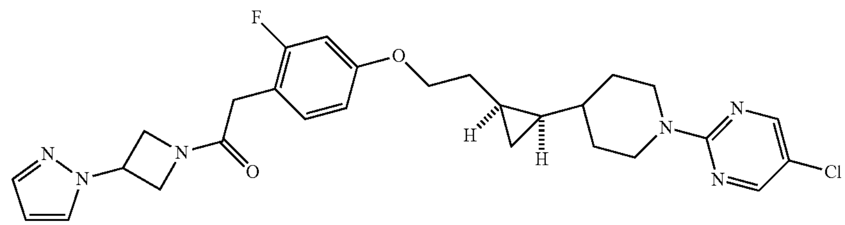 [SMILES: O=C(Cc1ccc(OCC[C@@H]2C[C@@H]2C2CCN(c3ncc(Cl)cn3)CC2)cc1F)N1CC(n2cccn2)C1] | 539 | 0.81 |
| 120 | 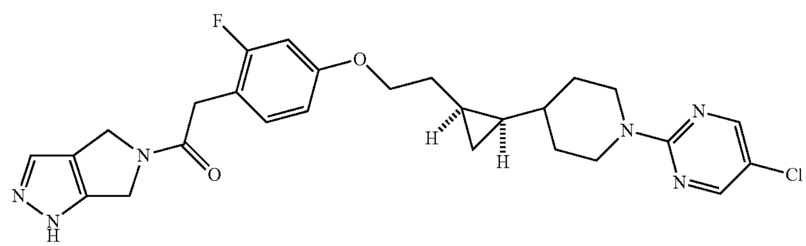 [SMILES: O=C(Cc1ccc(OCC[C@@H]2C[C@@H]2C2CCN(c3ncc(Cl)cn3)CC2)cc1F)N1Cc2cn[nH]c2C1] | 525 | 1.0 |
| 121 | 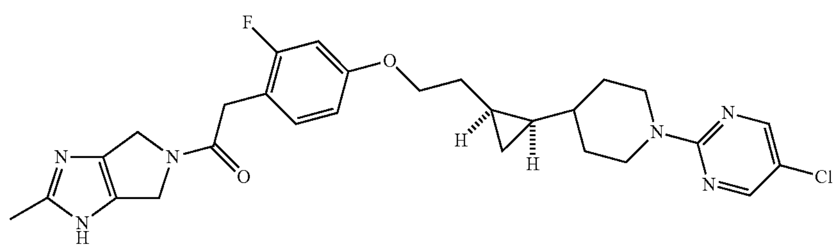 [SMILES: Cc1nc2c([nH]1)CN(C(=O)Cc1ccc(OCC[C@@H]3C[C@@H]3C3CCN(c4ncc(Cl)cn4)CC3)cc1F)C2] | 539 | 2.2 |
| 122 | 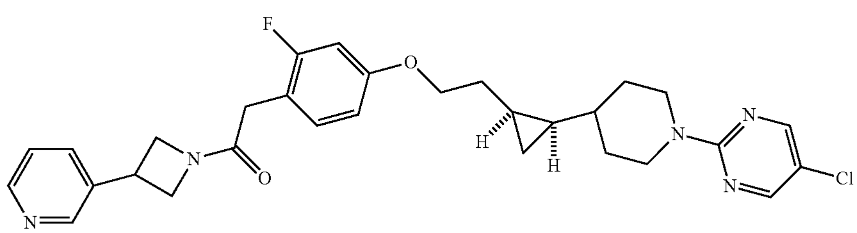 [SMILES: O=C(Cc1ccc(OCC[C@@H]2C[C@@H]2C2CCN(c3ncc(Cl)cn3)CC2)cc1F)N1CC(c2cccnc2)C1] | 550 | 0.66 |
| 123 | 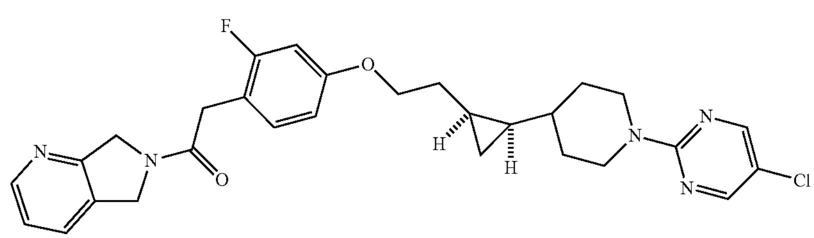 [SMILES: O=C(Cc1ccc(OCC[C@@H]2C[C@@H]2C2CCN(c3ncc(Cl)cn3)CC2)cc1F)N1Cc2cccnc2C1] | 536 | 0.78 |

TABLE 12-continued

| Example # | Chemical Structure | Observed Mass [M + H]+ | GPR119 Human EC50 (nM) |
|---|---|---|---|
| 124 | 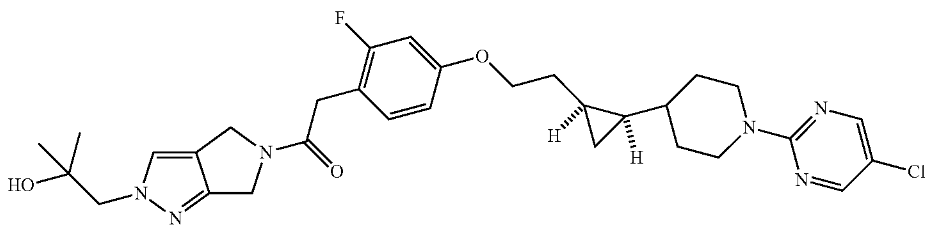 [SMILES: CC(C)(O)Cn1cc2c(n1)CN(C(=O)Cc1ccc(OCC[C@@H]3C[C@@H]3C3CCN(c4ncc(Cl)cn4)CC3)cc1F)C2] | 597 | 3.2 |
| 125 | 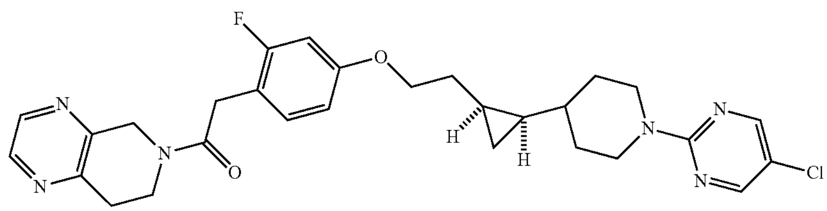 [SMILES: O=C(Cc1ccc(OCC[C@@H]2C[C@@H]2C2CCN(c3ncc(Cl)cn3)CC2)cc1F)N1CCc2nccnc2C1] | 551 | 0.96 |
| 126 | 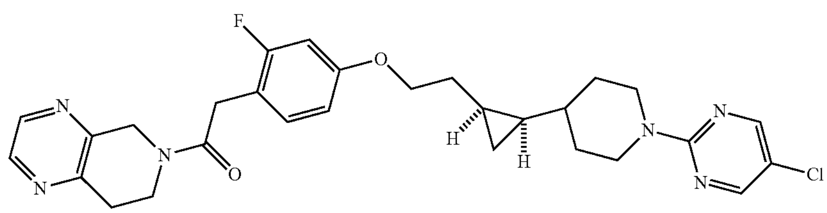 [SMILES: O=C(Cc1ccc(OCC[C@@H]2C[C@@H]2C2CCN(c3ncc(Cl)cn3)CC2)cc1F)N1CCc2nccnc2C1] | 550 | 1.5 |
| 127 | 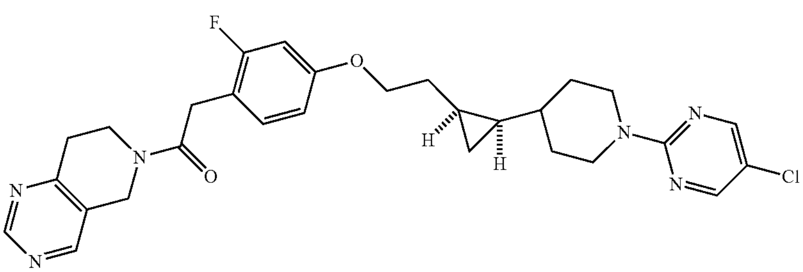 [SMILES: O=C(Cc1ccc(OCC[C@@H]2C[C@@H]2C2CCN(c3ncc(Cl)cn3)CC2)cc1F)N1CCc2ncncc2C1] | 551 | 1.5 |
| 128 | 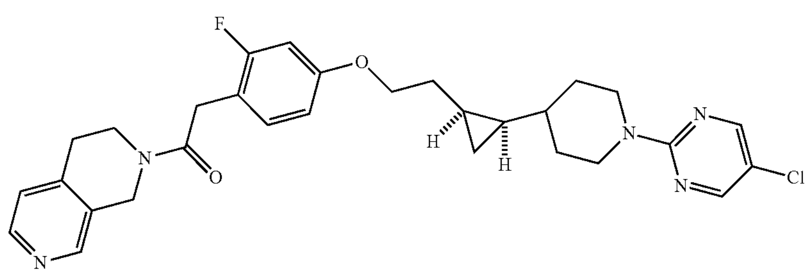 [SMILES: O=C(Cc1ccc(OCC[C@@H]2C[C@@H]2C2CCN(c3ncc(Cl)cn3)CC2)cc1F)N1CCc2ccncc2C1] | 550 | 2.3 |
| 129 | 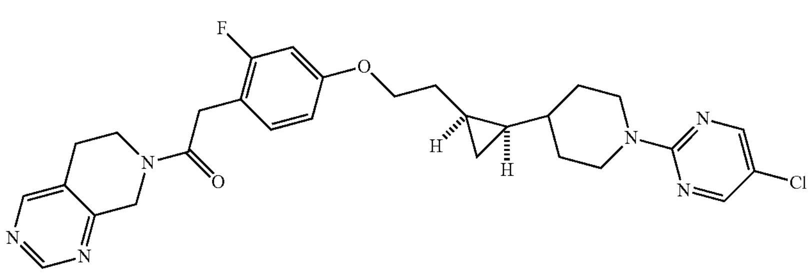 [SMILES: O=C(Cc1ccc(OCC[C@@H]2C[C@@H]2C2CCN(c3ncc(Cl)cn3)CC2)cc1F)N1CCc2cncnc2C1] | 551 | 0.29 |

TABLE 12-continued

| Example # | Chemical Structure | Observed Mass [M + H]+ | GPR119 Human EC$_{50}$ (nM) |
| --- | --- | --- | --- |
| 130 | 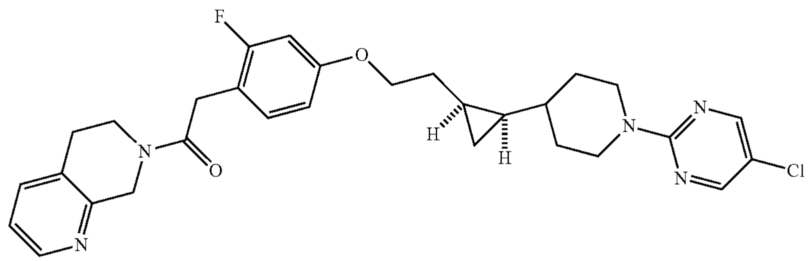 [SMILES: O=C(Cc1ccc(OCC[C@@H]2C[C@@H]2C2CCN(c3ncc(Cl)cn3)CC2)cc1F)N1CCc2cccnc2C1] | 550 | 1.1 |
| 131 | 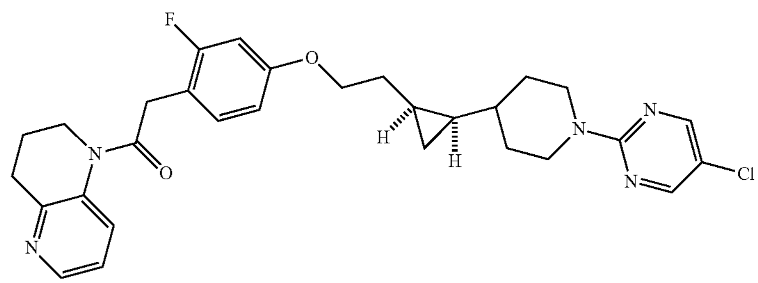 [SMILES: O=C(Cc1ccc(OCC[C@@H]2C[C@@H]2C2CCN(c3ncc(Cl)cn3)CC2)cc1F)N1CCCc2ncccc21] | 550 | 8.0 |
| 132 | 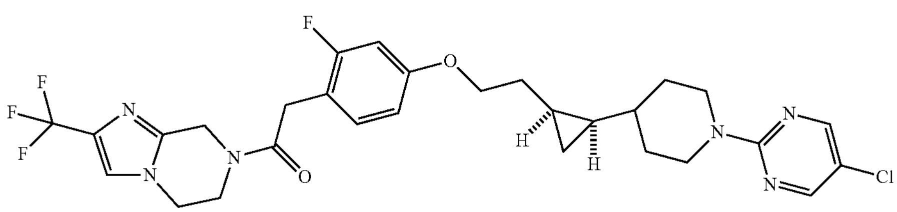 | 607 | 0.55 |
| 133 | 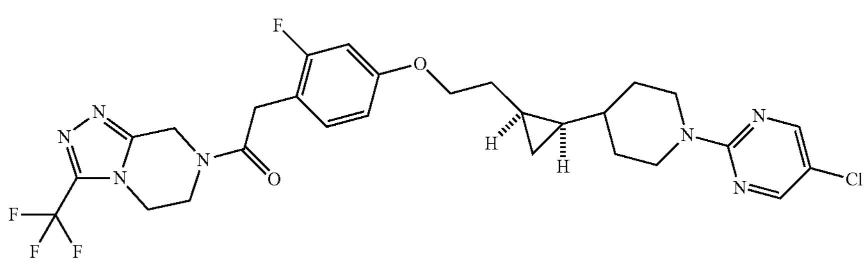 [SMILES: O=C(Cc1ccc(OCC[C@@H]2C[C@@H]2C2CCN(c3ncc(Cl)cn3)CC2)cc1F)N1CCn2c(nnc2C(F)(F)F)C1] | 608 | 0.91 |
| 134 | 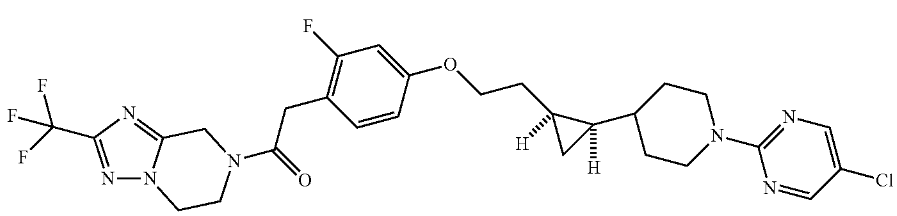 [SMILES: O=C(Cc1ccc(OCC[C@@H]2C[C@@H]2C2CCN(c3ncc(Cl)cn3)CC2)cc1F)N1CCn2nc(C(F)(F)F)nc2C1] | 608 | 1.0 |
| 135 | 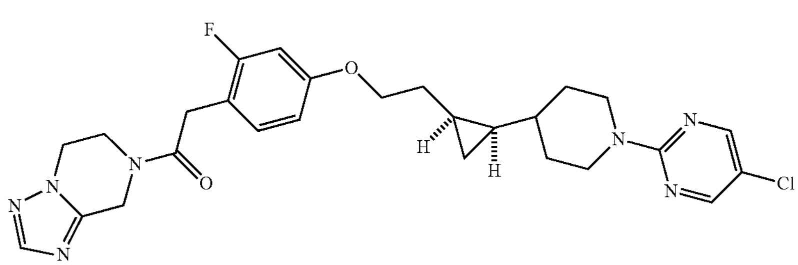 [SMILES: O=C(Cc1ccc(OCC[C@@H]2C[C@@H]2C2CCN(c3ncc(Cl)cn3)CC2)cc1F)N1CCn2ncnc2C1] | 540 | 0.54 |

TABLE 12-continued

| Example # | Chemical Structure | Observed Mass [M + H]+ | GPR119 Human EC50 (nM) |
|---|---|---|---|
| 136 | 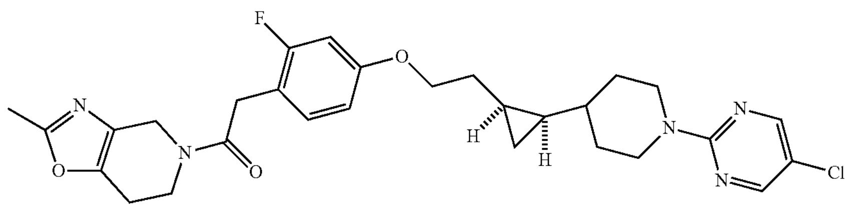 [SMILES: Cc1nc2c(o1)CCN(C(=O)Cc1ccc(OCC[C@@H]3C[C@@H]3C3CCN(c4ncc(Cl)cn4)CC3)cc1F)C2] | 554 | 0.73 |
| 137 | 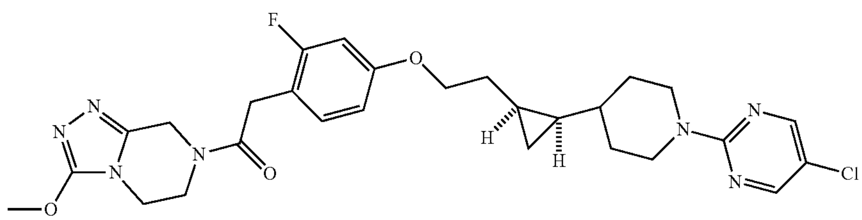 [SMILES: COc1nnc2n1CCN(C(=O)Cc1ccc(OCC[C@@H]3C[C@@H]3C3CCN(c4ncc(Cl)cn4)CC3)cc1F)C2] | 570 | 3.9 |
| 138 | 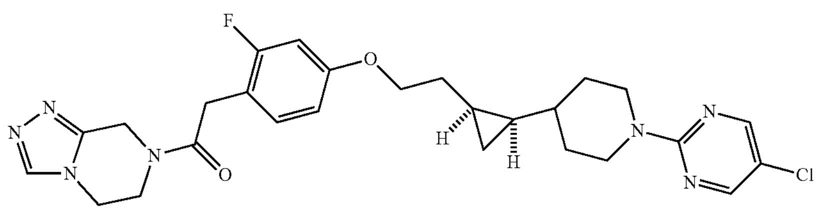 [SMILES: O=C(Cc1ccc(OCC[C@@H]2C[C@@H]2C2CCN(c3ncc(Cl)cn3)CC2)cc1F)N1CCn2cnnc2C1] | 540 | 1.5 |
| 139 | 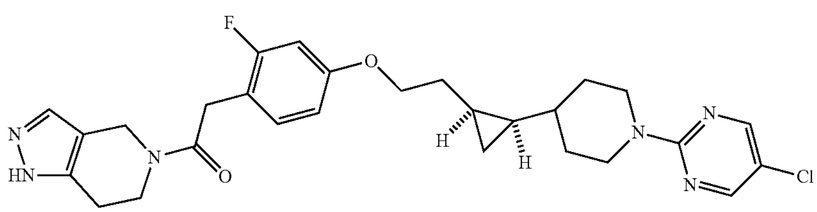 [SMILES: O=C(Cc1ccc(OCC[C@@H]2C[C@@H]2C2CCN(c3ncc(Cl)cn3)CC2)cc1F)N1CCc2[nH]ncc2C1] | 539 | 2.0 |
| 140 | 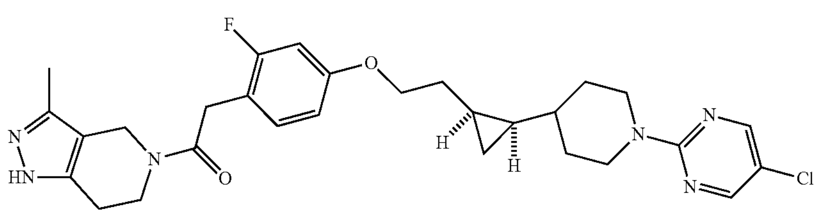 [SMILES: Cc1n[nH]c2c1CN(C(=O)Cc1ccc(OCC[C@@H]3C[C@@H]3C3CCN(c4ncc(Cl)cn4)CC3)cc1F)CC2] | 553 | 3.2 |
| 141 | 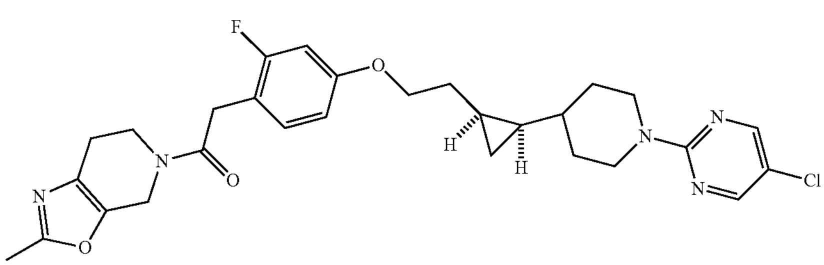 [SMILES: Cc1nc2c(o1)CN(C(=O)Cc1ccc(OCC[C@@H]3C[C@@H]3C3CCN(c4ncc(Cl)cn4)CC3)cc1F)CC2] | 554 | 1.2 |

TABLE 12-continued

| Example # | Chemical Structure | Observed Mass [M + H]+ | GPR119 Human EC$_{50}$ (nM) |
|---|---|---|---|
| 142 | 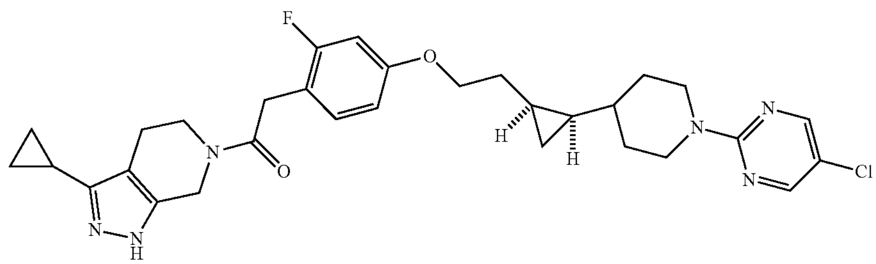 [SMILES: O=C(Cc1ccc(OCC[C@@H]2C[C@@H]2C2CCN(c3ncc(Cl)cn3)CC2)cc1F)N1CCc2c(C3CC3)n[nH]c2C1] | 579 | 3.1 |
| 143 | 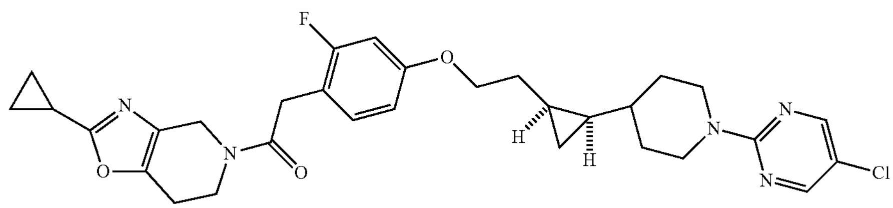 [SMILES: O=C(Cc1ccc(OCC[C@@H]2C[C@@H]2C2CCN(c3ncc(Cl)cn3)CC2)cc1F)N1CCc2oc(C3CC3)nc2C1] | 580 | 4.7 |
| 144 | 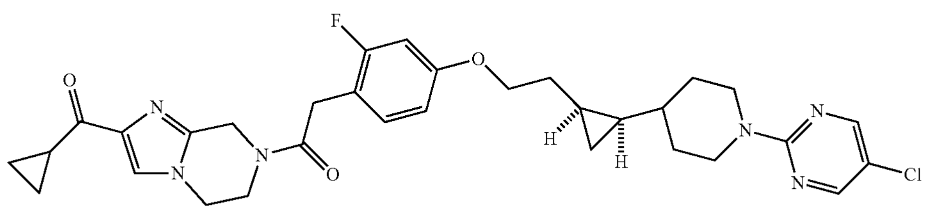 [SMILES: O=C(c1cn2c(n1)CN(C(=O)Cc1ccc(OCC[C@@H]3C[C@@H]3C3CCN(c4ncc(Cl)cn4)CC3)cc1F)CC2)C1CC1] | 607 | 7.2 |
| 145 | 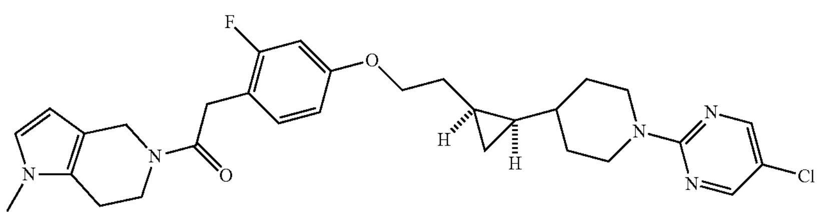 [SMILES: Cn1ccc2c1CCN(C(=O)Cc1ccc(OCC[C@@H]3C[C@@H]3C3CCN(c4ncc(Cl)cn4)CC3)cc1F)C2] | 552 | 6.3 |
| 146 | 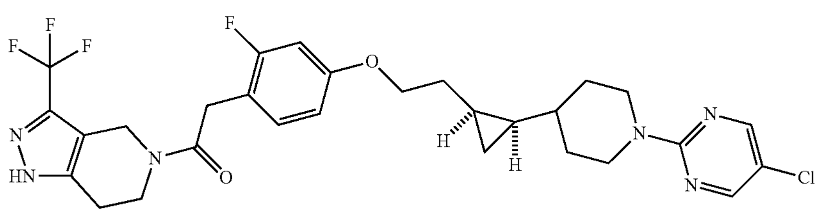 [SMILES: O=C(Cc1ccc(OCC[C@@H]2C[C@@H]2C2CCN(c3ncc(Cl)cn3)CC2)cc1F)N1CCc2[nH]nc(C(F)(F)F)c2C1] | 607 | 3.1 |
| 147 | 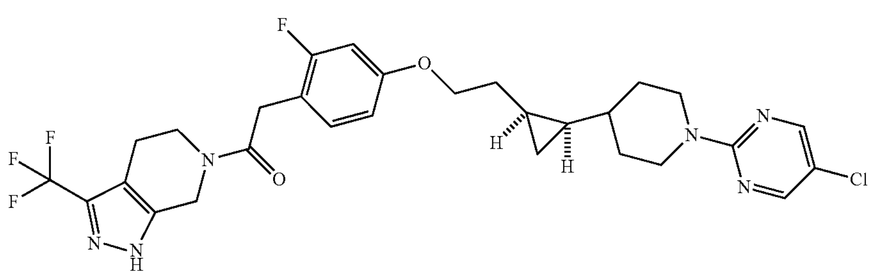 [SMILES: O=C(Cc1ccc(OCC[C@@H]2C[C@@H]2C2CCN(c3ncc(Cl)cn3)CC2)cc1F)N1CCc2c(C(F)(F)F)n[nH]c2C1] | 607 | 2.9 |

TABLE 12-continued

| Example # | Chemical Structure | Observed Mass [M + H]+ | GPR119 Human EC50 (nM) |
|---|---|---|---|
| 148 | 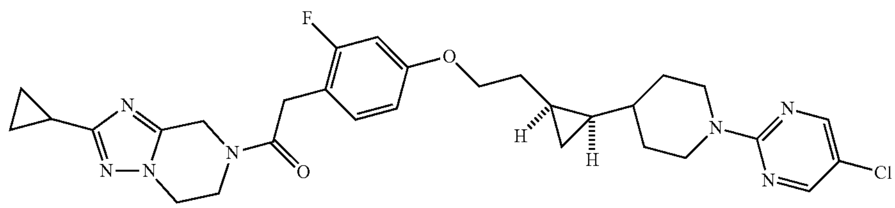 [SMILES: O=C(Cc1ccc(OCC[C@@H]2C[C@@H]2C2CCN(c3ncc(Cl)cn3)CC2)cc1F)N1CCn2nc(C3CC3)nc2C1] | 580 | 1.2 |
| 149 | 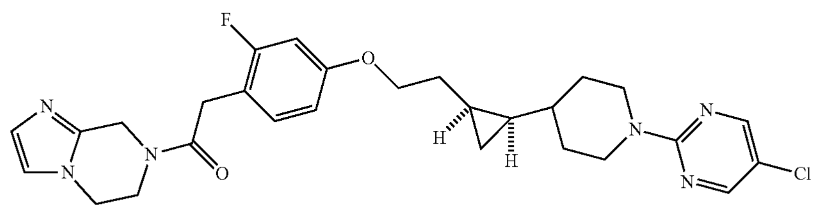 [SMILES: O=C(Cc1ccc(OCC[C@@H]2C[C@@H]2C2CCN(c3ncc(Cl)cn3)CC2)cc1F)N1CCn2ccnc2C1] | 539 | 1.1 |
| 150 | 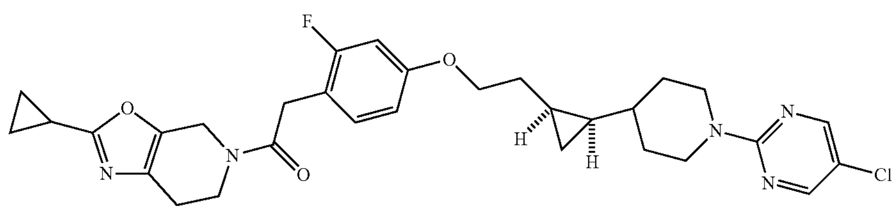 [SMILES: O=C(Cc1ccc(OCC[C@@H]2C[C@@H]2C2CCN(c3ncc(Cl)cn3)CC2)cc1F)N1CCc2nc(C3CC3)oc2C1] | 580 | 3.2 |
| 151 | 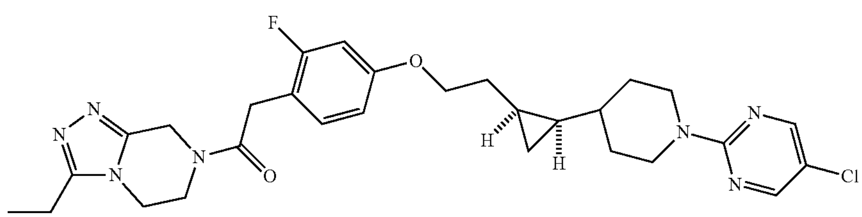 [SMILES: CCc1nnc2n1CCN(C(=O)Cc1ccc(OCC[C@@H]3C[C@@H]3C3CCN(c4ncc(Cl)cn4)CC3)cc1F)C2] | 568 | 4.7 |
| 152 | 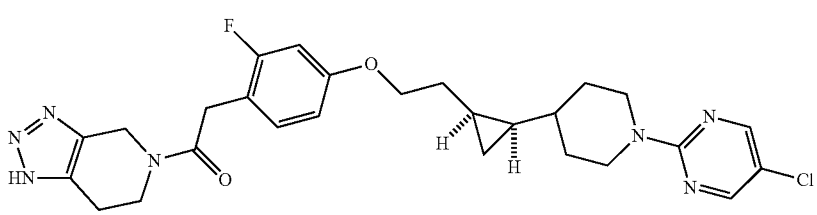 [SMILES: O=C(Cc1ccc(OCC[C@@H]2C[C@@H]2C2CCN(c3ncc(Cl)cn3)CC2)cc1F)N1CCc2[nH]nnc2C1] | 540 | 1.9 |
| 153 | 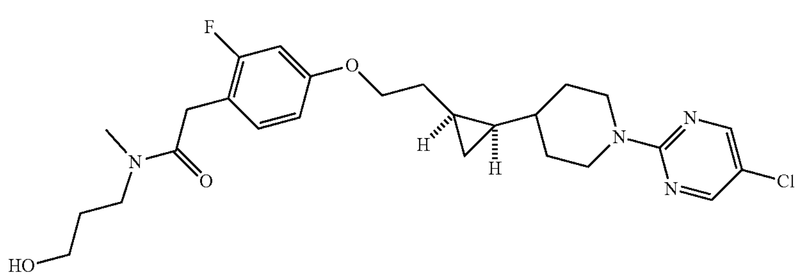 [SMILES: CN(CCCO)C(=O)Cc1ccc(OCC[C@@H]2C[C@@H]2C2CCN(c3ncc(Cl)cn3)CC2)cc1F] | 505 | 1.6 |

TABLE 12-continued

| Example # | Chemical Structure | Observed Mass [M + H]+ | GPR119 Human EC$_{50}$ (nM) |
|---|---|---|---|
| 154 | 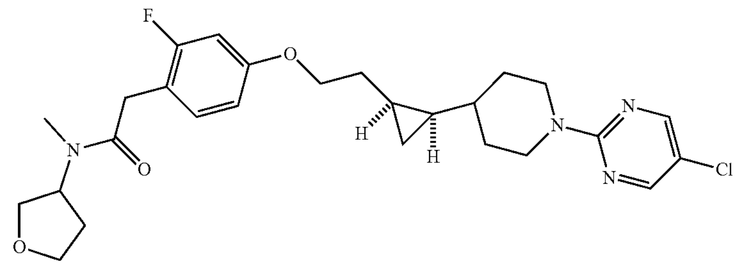 [SMILES: CN(C(=O)Cc1ccc(OCC[C@@H]2C[C@@H]2C2CCN(c3ncc(Cl)cn3)CC2)cc1F)C1CCOC1] | 517 | 0.41 |
| 155 | 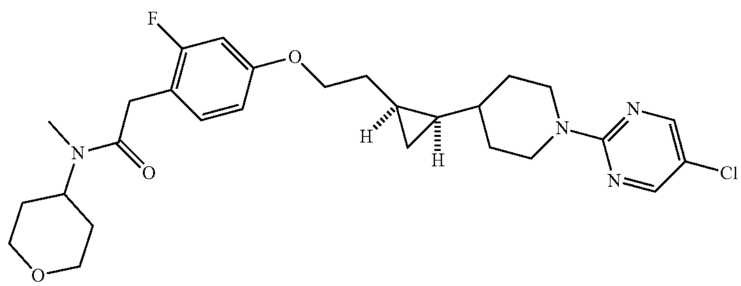 [SMILES: CN(C(=O)Cc1ccc(OCC[C@@H]2C[C@@H]2C2CCN(c3ncc(Cl)cn3)CC2)cc1F)C1CCOCC1] | 531 | 1.3 |
| 156 | 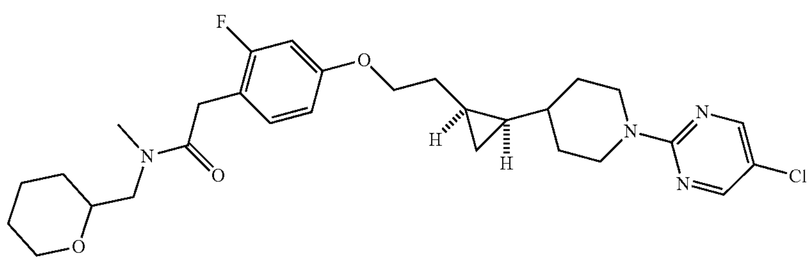 [SMILES: CN(CC1CCCCO1)C(=O)Cc1ccc(OCC[C@@H]2C[C@@H]2C2CCN(c3ncc(Cl)cn3)CC2)cc1F] | 545 | 2.8 |
| 157 | 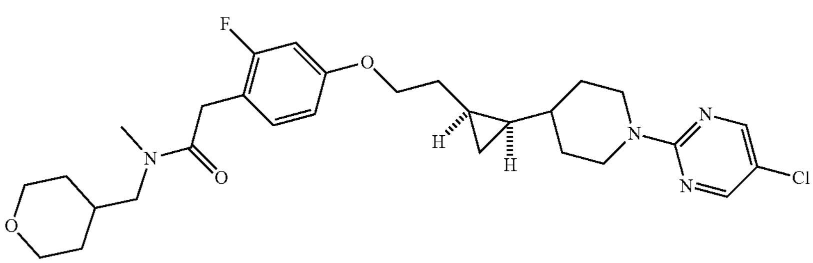 [SMILES: CN(CC1CCOCC1)C(=O)Cc1ccc(OCC[C@@H]2C[C@@H]2C2CCN(c3ncc(Cl)cn3)CC2)cc1F] | 545 | 2.4 |
| 158 | 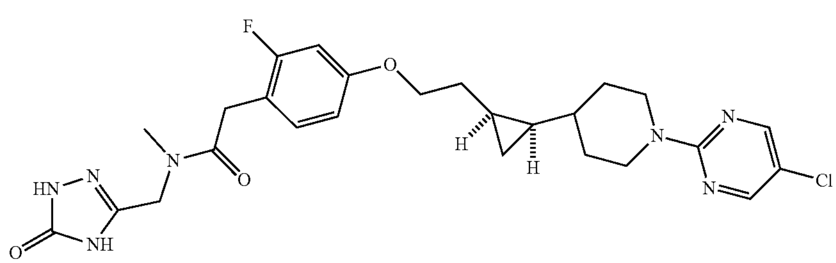 [SMILES: CN(Cc1n[nH]c(=O)[nH]1)C(=O)Cc1ccc(OCC[C@@H]2C[C@@H]2C2CCN(c3ncc(Cl)cn3)CC2)cc1F] | 544 | 6.6 |

TABLE 12-continued

| Example # | Chemical Structure | Observed Mass [M + H]⁺ | GPR119 Human EC$_{50}$ (nM) |
|---|---|---|---|
| 159 | 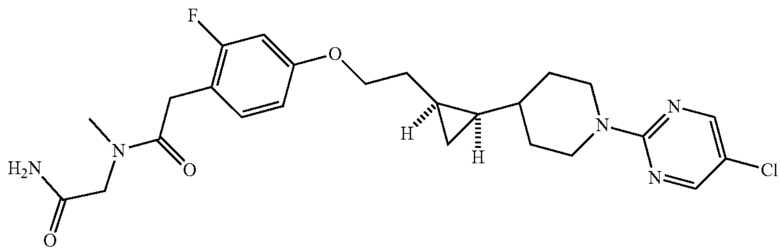 [SMILES: CN(CC(N)=O)C(=O)Cc1ccc(OCC[C@@H]2C[C@@H]2C2CCN(c3ncc(Cl)cn3)CC2)cc1F] | 504 | 3.7 |
| 160 | 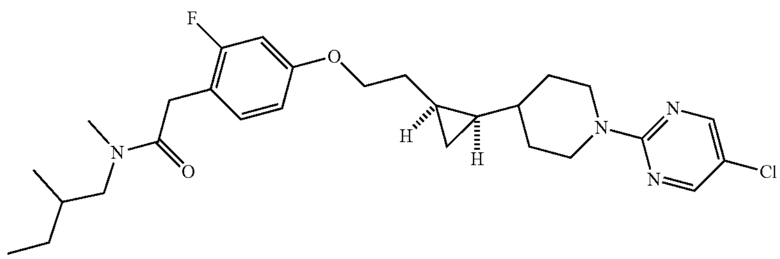 [SMILES: CCC(C)CN(C)C(=O)Cc1ccc(OCC[C@@H]2C[C@@H]2C2CCN(c3ncc(Cl)cn3)CC2)cc1F] | 517 | 3.1 |
| 161 | 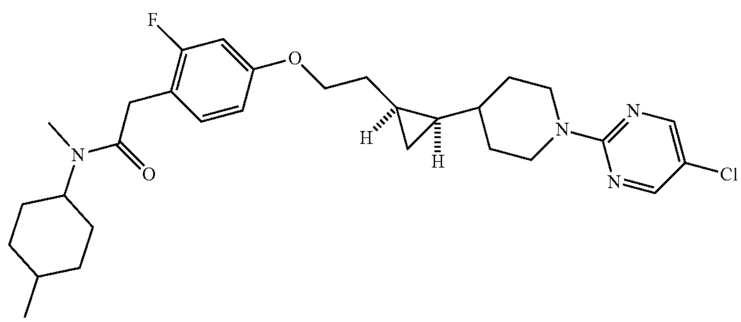 [SMILES: CC1CCC(N(C)C(=O)Cc2ccc(OCC[C@@H]3C[C@@H]3C3CCN(c4ncc(Cl)cn4)CC3)cc2F)CC1] | 543 | 3.7 |
| 162 | 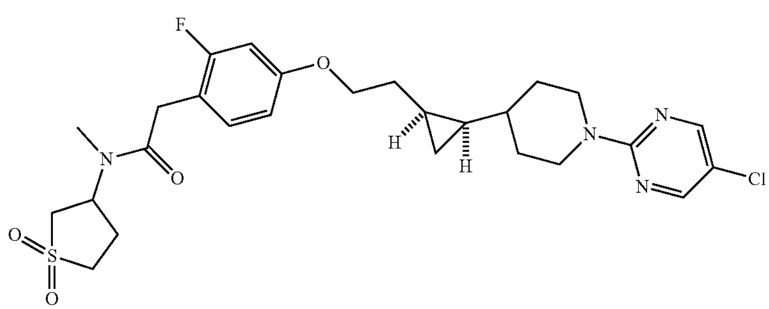 [SMILES: CN(C(=O)Cc1ccc(OCC[C@@H]2C[C@@H]2C2CCN(c3ncc(Cl)cn3)CC2)cc1F)C1CCS(=O)(=O)C1] | 565 | 1.3 |
| 163 | 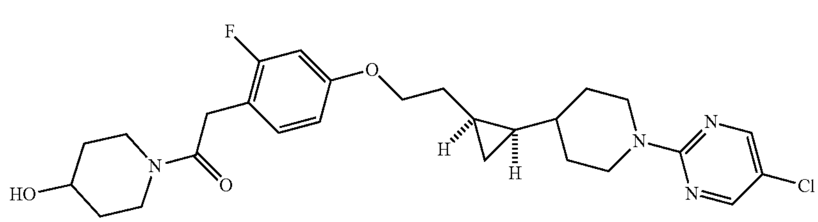 [SMILES: O=C(Cc1ccc(OCC[C@@H]2C[C@@H]2C2CCN(c3ncc(Cl)cn3)CC2)cc1F)N1CCC(O)CC1] | 517 | 1.7 |

TABLE 12-continued

| Example # | Chemical Structure | Observed Mass [M + H]+ | GPR119 Human EC$_{50}$ (nM) |
|---|---|---|---|
| 164 | 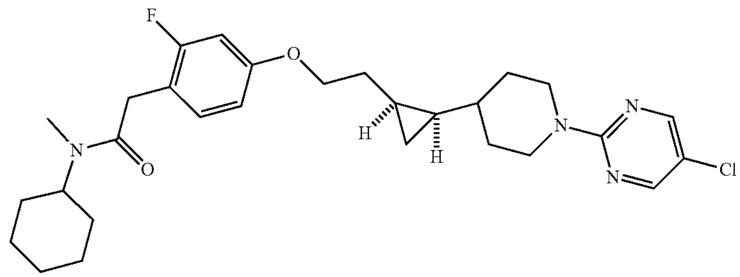 [SMILES: CN(C(=O)Cc1ccc(OCC[C@@H]2C[C@@H]2C2CCN(c3ncc(Cl)cn3)CC2)cc1F)C1CCCCC1] | 529 | 1.6 |
| 165 | 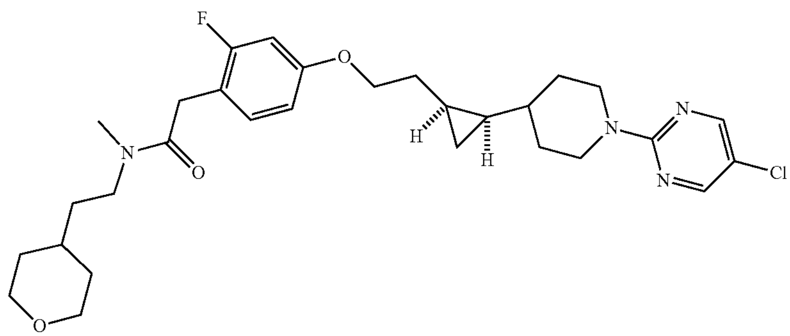 [SMILES: CN(CCC1CCOCC1)C(=O)Cc1ccc(OCC[C@@H]2C[C@@H]2C2CCN(c3ncc(Cl)cn3)CC2)cc1F] | 559 | 2.6 |
| 166 | 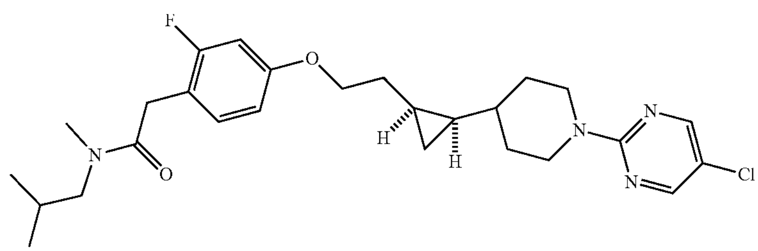 [SMILES: CC(C)CN(C)C(=O)Cc1ccc(OCC[C@@H]2C[C@@H]2C2CCN(c3ncc(Cl)cn3)CC2)cc1F] | 503 | 2.0 |
| 167 | 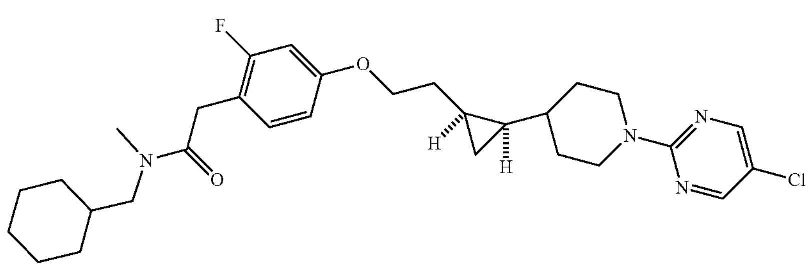 [SMILES: CN(CC1CCCCC1)C(=O)Cc1ccc(OCC[C@@H]2C[C@@H]2C2CCN(c3ncc(Cl)cn3)CC2)cc1F] | 543 | 7.6 |
| 168 | 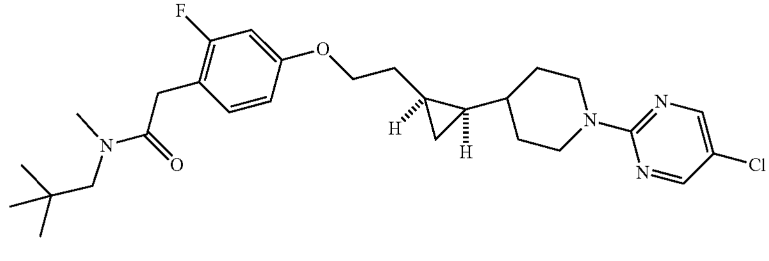 [SMILES: CN(CC(C)(C)C)C(=O)Cc1ccc(OCC[C@@H]2C[C@@H]2C2CCN(c3ncc(Cl)cn3)CC2)cc1F] | 517 | 9.4 |

TABLE 12-continued

| Example # | Chemical Structure | Observed Mass [M + H]+ | GPR119 Human EC$_{50}$ (nM) |
|---|---|---|---|
| 169 | 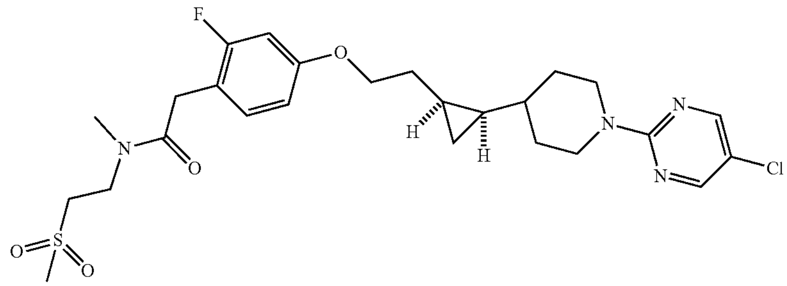 [SMILES: CN(CCS(C)(=O)=O)C(=O)Cc1ccc(OCC[C@@H]2C[C@@H]2C2CCN(c3ncc(Cl)cn3)CC2)cc1F] | 553 | 3.2 |
| 170 | 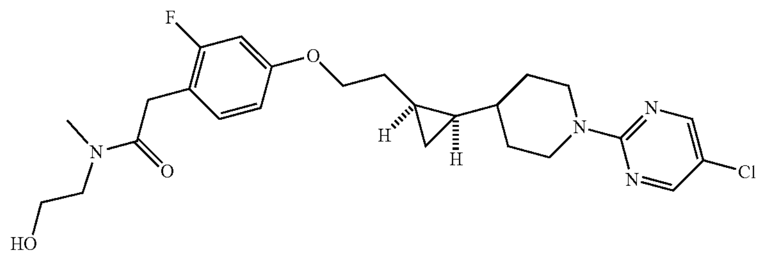 [SMILES: CN(CCO)C(=O)Cc1ccc(OCC[C@@H]2C[C@@H]2C2CCN(c3ncc(Cl)cn3)CC2)cc1F] | 491 | 1.7 |
| 171 | 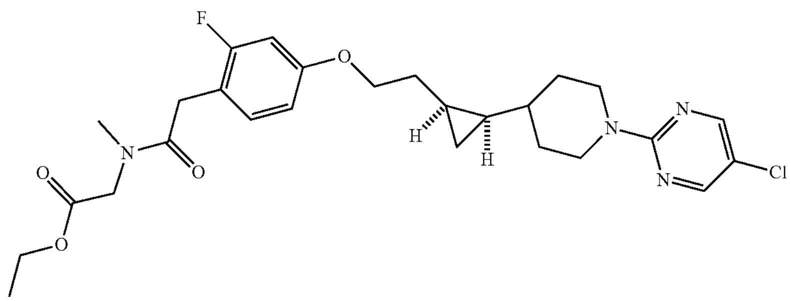 [SMILES: CCOC(=O)CN(C)C(=O)Cc1ccc(OCC[C@@H]2C[C@@H]2C2CCN(c3ncc(Cl)cn3)CC2)cc1F] | 533 | 1.7 |
| 172 | 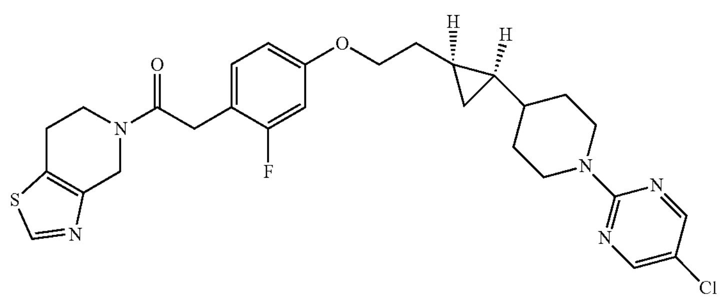 [SMILES: O=C(Cc1ccc(OCC[C@@H]2C[C@@H]2C2CCN(c3ncc(Cl)cn3)CC2)cc1F)N1CCc2scnc2C1] | 556 | 0.60 |
| 173 | 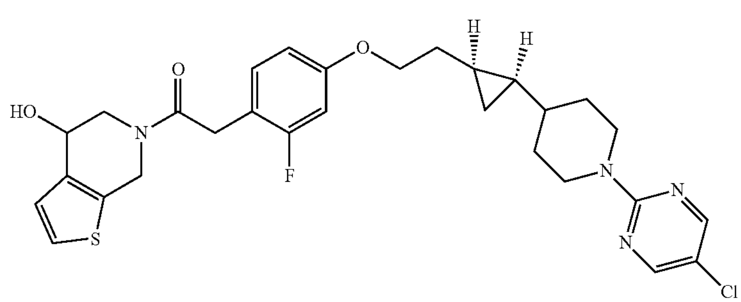 [SMILES: O=C(Cc1ccc(OCC[C@@H]2C[C@@H]2C2CCN(c3ncc(Cl)cn3)CC2)cc1F)N1Cc2sccc2C(O)C1] | 571 | 0.97 |

TABLE 12-continued

| Example # | Chemical Structure | Observed Mass [M + H]+ | GPR119 Human EC$_{50}$ (nM) |
| --- | --- | --- | --- |
| 174 | 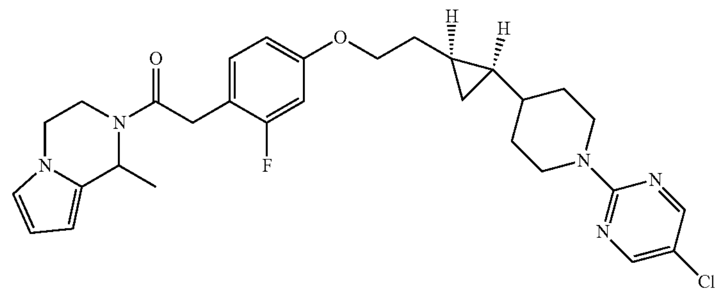 [SMILES: CC1c2cccn2CCN1C(=O)Cc1ccc(OCC[C@@H]2C[C@@H]2C2CCN(c3ncc(Cl)cn3)CC2)cc1F] | 552 | 1.2 |
| 175 | 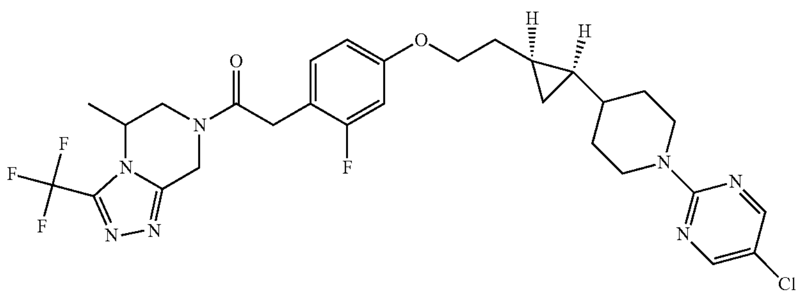 [SMILES: CC1CN(C(=O)Cc2ccc(OCC[C@@H]3C[C@@H]3C3CCN(c4ncc(Cl)cn4)CC3)cc2F)Cc2nnc(C(F)(F)F)n21] | 622 | 1.1 |
| 176 | 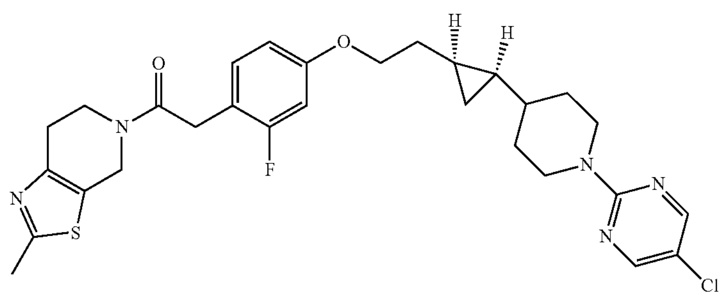 [SMILES: Cc1nc2c(s1)CN(C(=O)Cc1ccc(OCC[C@@H]3C[C@@H]3C3CCN(c4ncc(Cl)cn4)CC3)cc1F)CC2] | 570 | 0.78 |
| 177 | 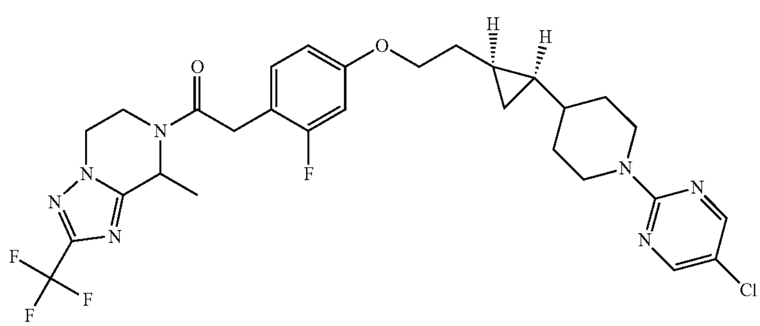 [SMILES: CC1c2nc(C(F)(F)F)nn2CCN1C(=O)Cc1ccc(OCC[C@@H]2C[C@@H]2C2CCN(c3ncc(Cl)cn3)CC2)cc1F] | 622 | 0.60 |
| 178 | 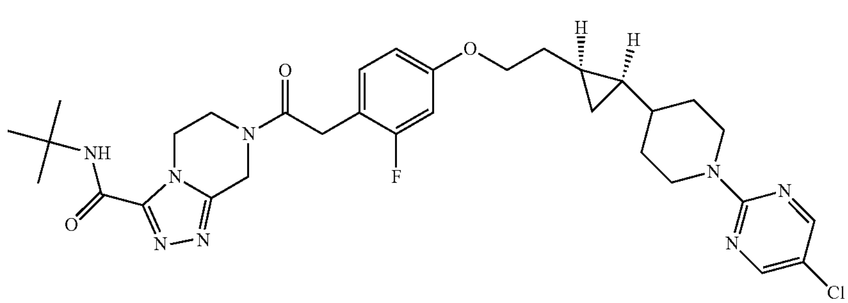 [SMILES: CC(C)(C)NC(=O)c1nnc2n1CCN(C(=O)Cc1ccc(OCC[C@@H]3C[C@@H]3C3CCN(c4ncc(Cl)cn4)CC3)cc1F)C2] | 639 | 2.8 |

TABLE 12-continued

| Example # | Chemical Structure | Observed Mass [M + H]+ | GPR119 Human EC$_{50}$ (nM) |
| --- | --- | --- | --- |
| 179 | 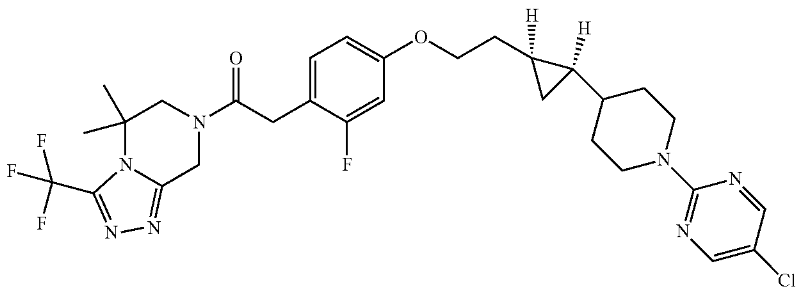 [SMILES: CC1(C)CN(C(=O)Cc2ccc(OCC[C@@H]3C[C@@H]3C3CCN(c4ncc(Cl)cn4)CC3)cc2F)Cc2nnc(C(F)(F)F)n21] | 636 | 1.1 |
| 180 | 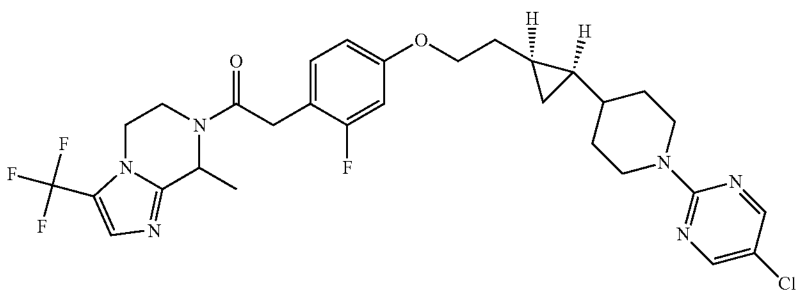 [SMILES: CC1c2ncc(C(F)(F)F)n2CCN1C(=O)Cc1ccc(OCC[C@@H]2C[C@@H]2C2CCN(c3ncc(Cl)cn3)CC2)cc1F] | 621 | 0.82 |
| 181 | 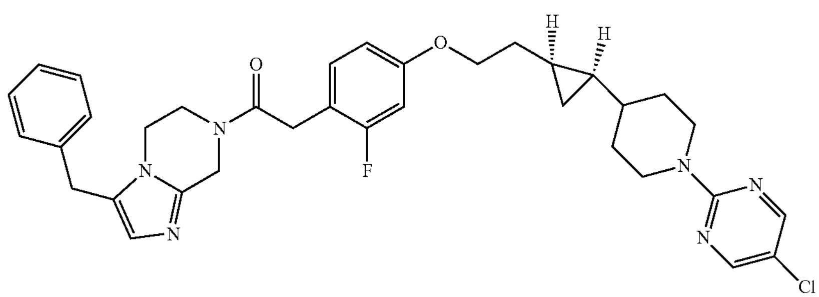 [SMILES: O=C(Cc1ccc(OCC[C@@H]2C[C@@H]2C2CCN(c3ncc(Cl)cn3)CC2)cc1F)N1CCn2c(Cc3ccccc3)cnc2C1] | 629 | 6.1 |
| 182 | 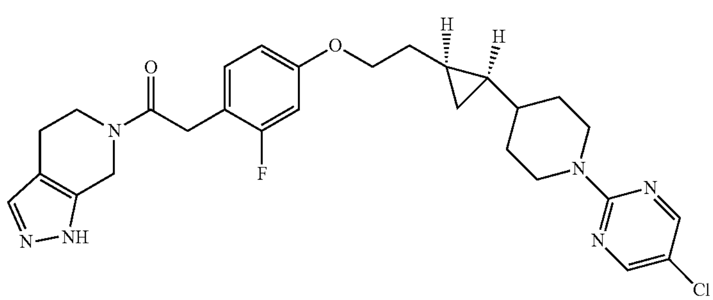 [SMILES: O=C(Cc1ccc(OCC[C@@H]2C[C@@H]2C2CCN(c3ncc(Cl)cn3)CC2)cc1F)N1CCc2cn[nH]c2C1] | 539 | 2.4 |
| 183 | 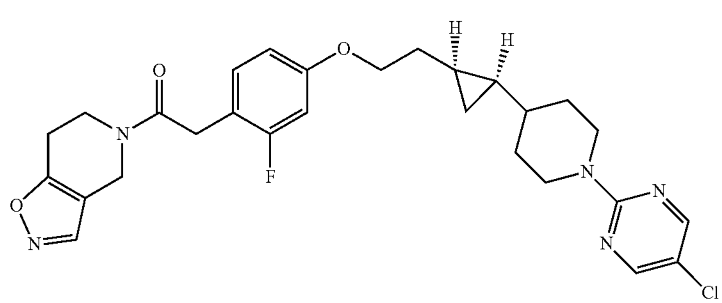 [SMILES: O=C(Cc1ccc(OCC[C@@H]2C[C@@H]2C2CCN(c3ncc(Cl)cn3)CC2)cc1F)N1CCc2oncc2C1] | 540 | 0.93 |

TABLE 12-continued
| Example # | Chemical Structure | Observed Mass [M + H]+ | GPR119 Human EC$_{50}$ (nM) |
|---|---|---|---|
| 184 | 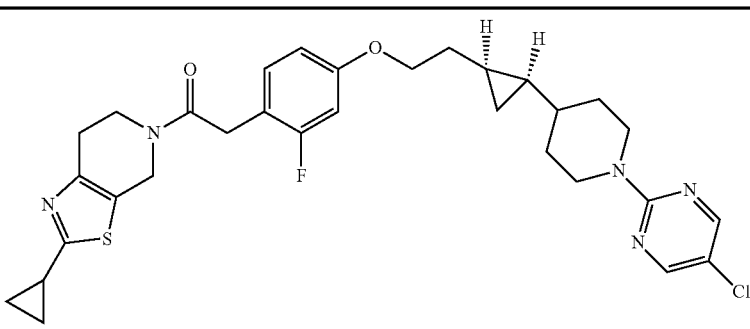 | 596 | 1.7 |
| 185 | 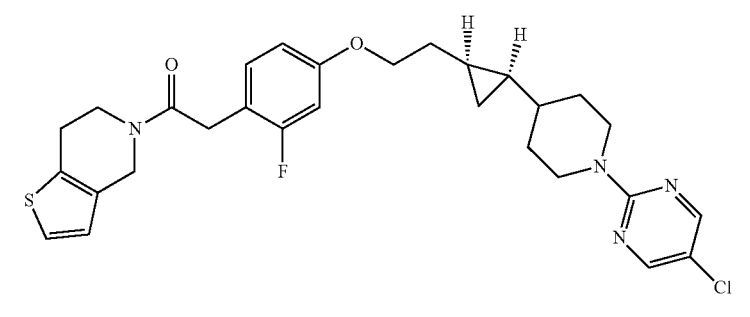 | 555 | 2.2 |
| 186 | 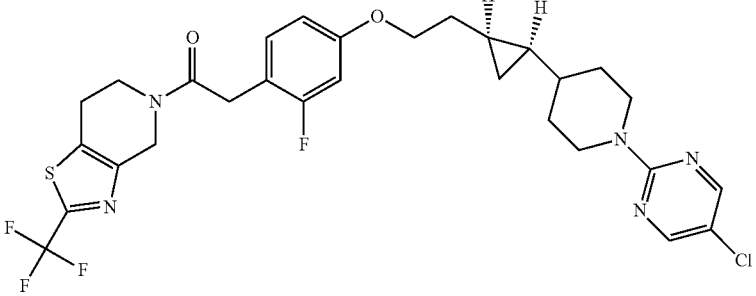 | 624 | 1.7 |
| 187 | 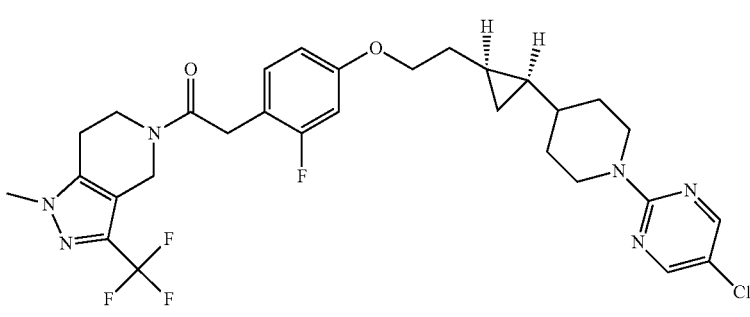 [SMILES: Cn1nc(C(F)(F)F)c2c1CCN(C(=O)Cc1ccc(OCC[C@@H]3C[C@@H]3C3CCN(c4ncc(Cl)cn4)CC3)cc1F)C2] | 621 | 2.0 |
| 188 | 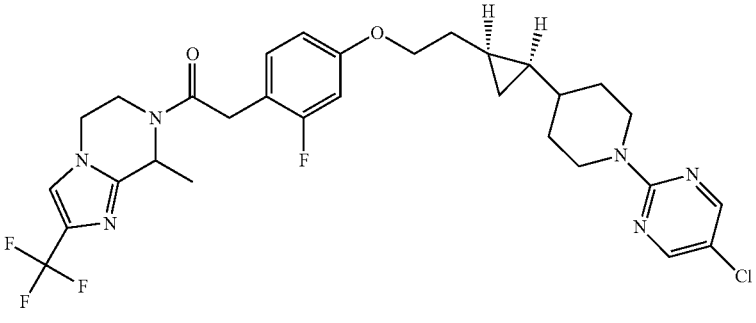 [SMILES: CC1c2nc(C(F)(F)F)cn2CCN1C(=O)Cc1ccc(OCC[C@@H]2C[C@@H]2C2CCN(c3ncc(Cl)cn3)CC2)cc1F] | 621 | 0.55 |

TABLE 12-continued

| Example # | Chemical Structure | Observed Mass [M + H]+ | GPR119 Human EC$_{50}$ (nM) |
|---|---|---|---|
| 189 | 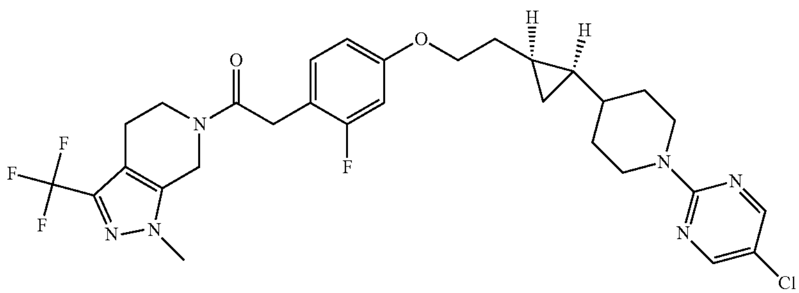 [SMILES: Cn1nc(C(F)(F)F)c2c1CN(C(=O)Cc1ccc(OCC[C@@H]3C[C@@H]3C3CCN(c4ncc(Cl)cn4)CC3)cc1F)CC2] | 621 | 6.0 |
| 190 | 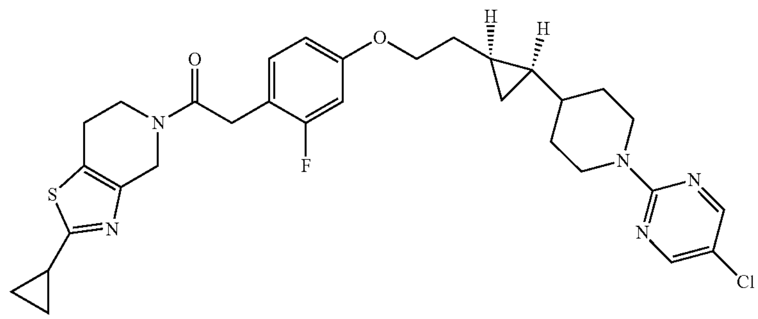 [SMILES: O=C(Cc1ccc(OCC[C@@H]2C[C@@H]2C2CCN(c3ncc(Cl)cn3)CC2)cc1F)N1CCc2sc(C3CC3)nc2C1] | 596 | 6.4 |
| 191 | 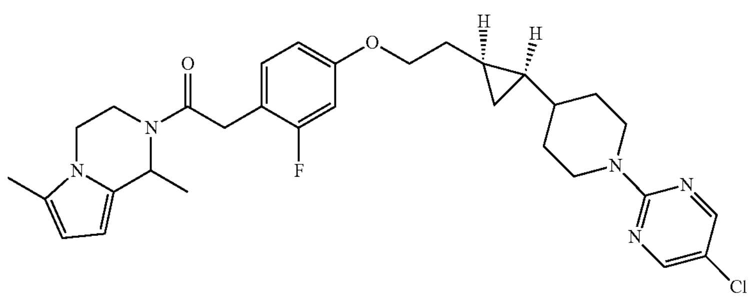 [SMILES: Cc1ccc2n1CCN(C(=O)Cc1ccc(OCC[C@@H]3C[C@@H]3C3CCN(c4ncc(Cl)cn4)CC3)cc1F)C2C] | 566 | 3.4 |
| 192 | 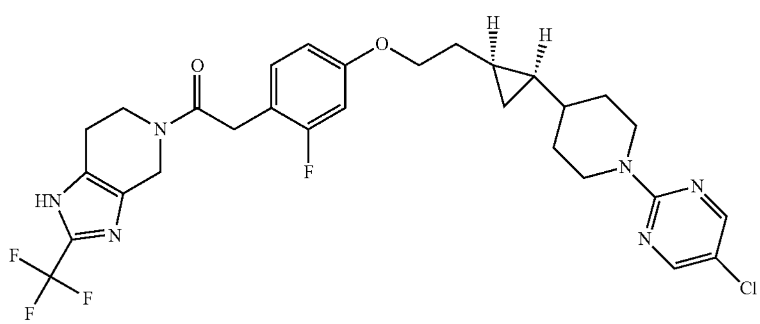 [SMILES: O=C(Cc1ccc(OCC[C@@H]2C[C@@H]2C2CCN(c3ncc(Cl)cn3)CC2)cc1F)N1CCc2[nH]c(C(F)(F)F)nc2C1] | 607 | 2.1 |
| 193 | 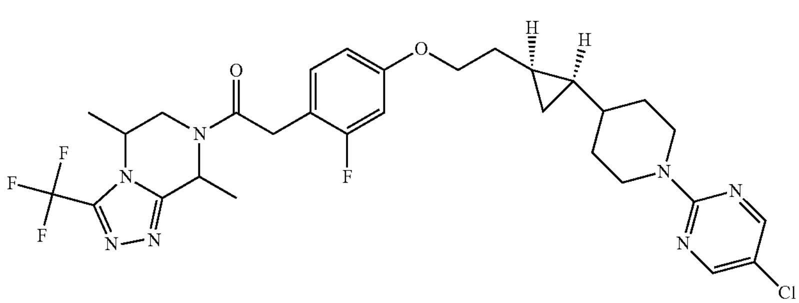 [SMILES: CC1c2nnc(C(F)(F)F)n2C(C)CN1C(=O)Cc1ccc(OCC[C@@H]2C[C@@H]2C2CCN(c3ncc(Cl)cn3)CC2)cc1F] | 636 | 1.1 |

TABLE 12-continued

| Example # | Chemical Structure | Observed Mass [M + H]+ | GPR119 Human EC50 (nM) |
|---|---|---|---|
| 194 | 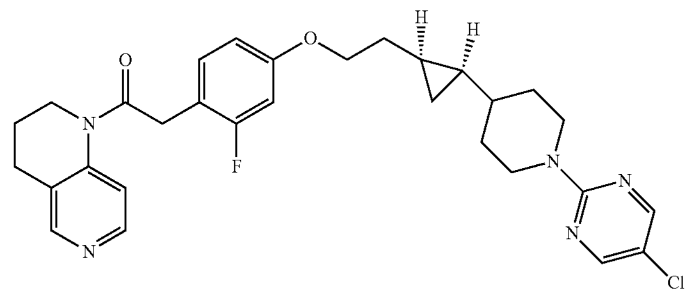 [SMILES: O=C(Cc1ccc(OCC[C@@H]2C[C@@H]2C2CCN(c3ncc(Cl)cn3)CC2)cc1F)N1CCCc2cnccc21] | 550 | 3.6 |
| 195 | 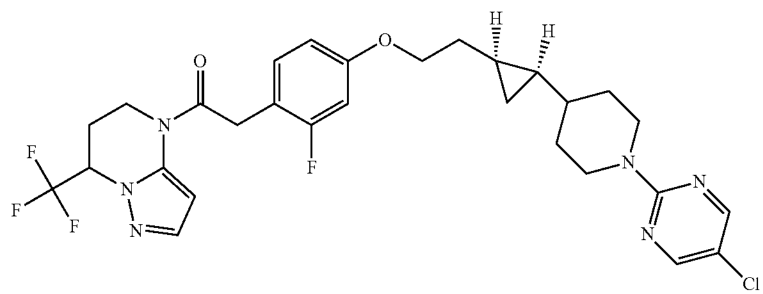 [SMILES: O=C(Cc1ccc(OCC[C@@H]2C[C@@H]2C2CCN(c3ncc(Cl)cn3)CC2)cc1F)N1CCC(C(F)(F)F)n2nccc21] | 607 | 2.9 |
| 196 | 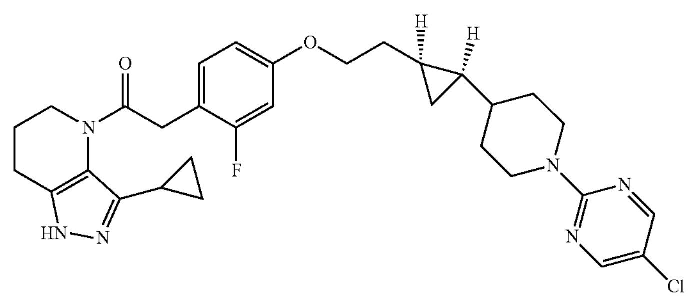 [SMILES: O=C(Cc1ccc(OCC[C@@H]2C[C@@H]2C2CCN(c3ncc(Cl)cn3)CC2)cc1F)N1CCCc2[nH]nc(C3CC3)c21] | 579 | 5.4 |
| 197 | 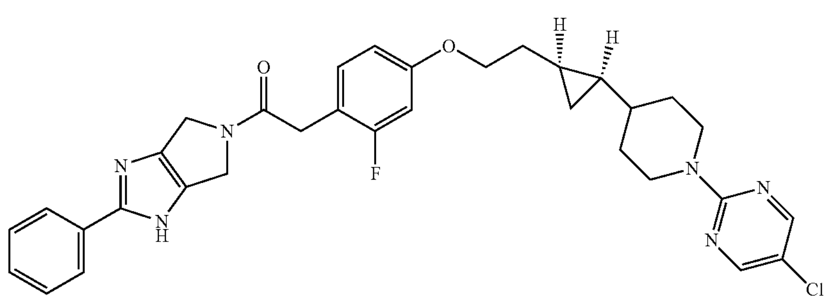 [SMILES: O=C(Cc1ccc(OCC[C@@H]2C[C@@H]2C2CCN(c3ncc(Cl)cn3)CC2)cc1F)N1Cc2nc(-c3ccccc3)[nH]c2C1] | 601 | 6.8 |
| 198 | 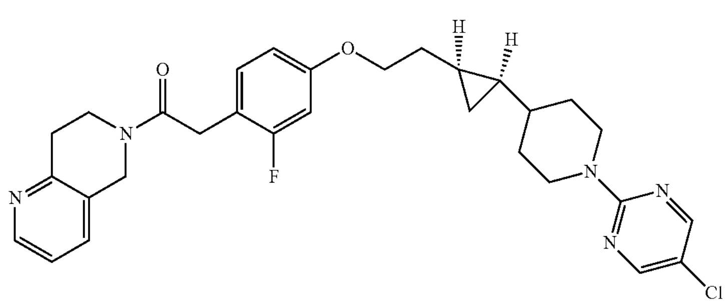 [SMILES: O=C(Cc1ccc(OCC[C@@H]2C[C@@H]2C2CCN(c3ncc(Cl)cn3)CC2)cc1F)N1CCc2ncccc2C1] | 550 | 1.3 |

Example 199

Preparation of 2-(4-{2-[(1S,2R)-2-{1-[5-(ethoxymethyl)pyrimidin-2-yl]piperidin-4-yl}cyclopropyl]ethoxy}-2-fluorophenyl)-1-(3-hydroxyazetidin-1-yl)ethanone

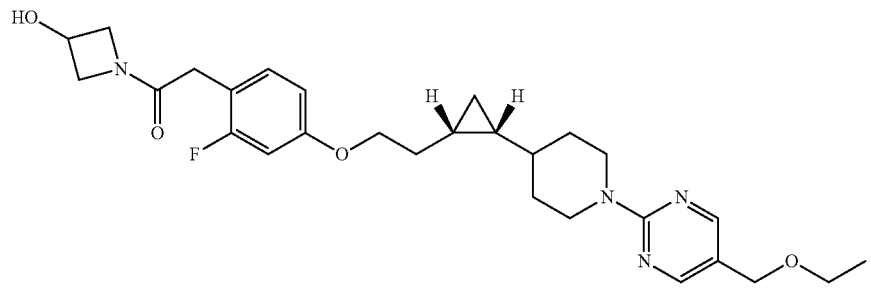 [SMILES: CCOCc1cnc(N2CCC([C@H]3C[C@H]3CCOc3ccc(CC(=O)N4CC(O)C4)c(F)c3)CC2)nc1]

Step A: 2-chloro-5-(ethoxymethyl)pyrimidine

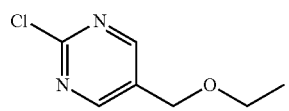

A solution of the (2-chloropyrimidin-5-yl)methanol (1 g, 6.92 mmol) in anhydrous DMF (6.92 ml) was cooled at ice-bath temperature and iodoethane (2.236 ml, 27.7 mmol) added. The solution was stirred for 10 minutes at 0° C. Sodium hydride (0.304 g, 7.61 mmol) was added and the resulting mixture stirred at 0° C. for 0.5 hours and RT for 60 minutes. The mixture was diluted with saturated ammonium chloride (100 mL) and extracted with EtOAc (3×50 mL). The organic fractions were combined, washed with brine (100 mL), dried over Na$_2$SO$_4$, filtered and the volatiles removed in vac. The mixture was purified on a 50 g Biotage KP-SiO$_2$ cartridge using a gradient eluant of 0-100% EtOAc:Hexanes, to afford the title compound. LC/MS (m/z): 173 (M+H)$^+$.

Step B: 2-[(1S,2R)-2-{1-[5-(ethoxymethyl)pyrimidin-2-yl]piperidin-4-yl}cyclopropyl]ethanol

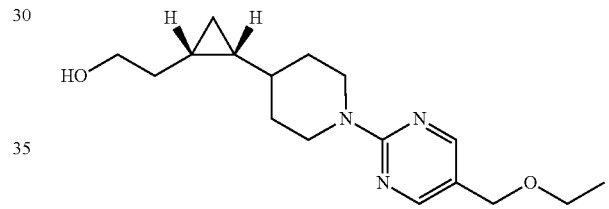

In a 250 ml RBF 2-chloro-5-(ethoxymethyl)pyrimidine (280 mg, 1.622 mmol) and 2-[(1S,2R)-2-(piperidin-4-yl)cyclopropyl]ethanol (334 mg, 1.622 mmol) were dissolved in DMF (1622 µl). Cesium carbonate (1586 mg, 4.87 mmol) was added and the mixture stirred at 70° C. overnight. The mixture was diluted with 4:1 water:brine (200 ml), extracted with EtOAc (3×100 ml), the organic fractions combined, washed with brine, dried over Na$_2$SO$_4$, filtered and the volatiles removed in vacuo. The mixture was purified on a 100 g Biotage HP-SiO$_2$ cartridge using a gradient eluant of 0-100% EtOAc:hexanes to afford the title compound. LC/MS (m/z): 306 (M+H)$^+$.

Step C: Methyl (4-{2-[(1S,2R)-2-{1-[5-(ethoxymethyl)pyrimidin-2-yl]piperidin-4-yl}cyclopropyl]ethoxy}-2-fluorophenyl)acetate

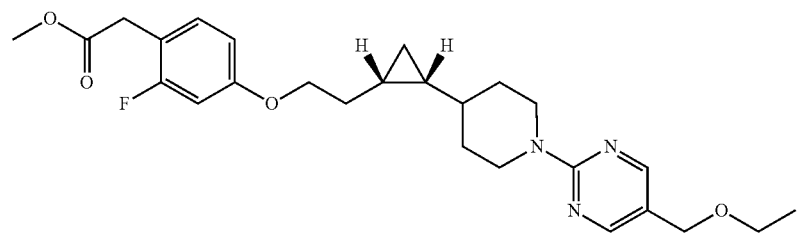 [SMILES: CCOCc1cnc(N2CCC([C@H]3C[C@H]3CCOc3ccc(CC(=O)OC)c(F)c3)CC2)nc1]

DIAD (0.955 ml, 4.91 mmol) was added to a stirred mixture of 2-[(1S,2R)-2-{1-[5-(ethoxymethyl)pyrimidin-2-yl]piperidin-4-yl}cyclopropyl]ethanol (1 g, 3.27 mmol), methyl (2-fluoro-4-hydroxyphenyl)acetate (0.724 g, 3.93 mmol) and triphenylphosphine (1.288 g, 4.91 mmol) in toluene (10 ml). The mixture was stirred at RT for 5 hrs. The mixture was diluted with ethyl acetate (20 mL), washed with brine, dried over MgSO$_4$, filtered and the solvent evaporated in vacuo. The residue was purified by column chromatography on silica gel, Biotage 100M, using a gradient eluant of 0-100% EtOAc/hexanes to afford the title compound. LC/MS (m/z): 472 (M+H)$^+$.

Step D: (4-{2-[(1S,2R)-2-{1-[5-(ethoxymethyl)pyrimidin-2-yl]piperidin-4-yl}cyclopropyl]ethoxy}-2-fluorophenyl)acetic acid

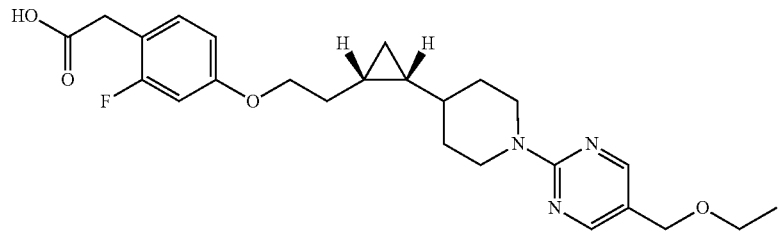 [SMILES: CCOCc1cnc(N2CCC([C@H]3C[C@H]3CCOc3ccc(CC(=O)O)c(F)c3)CC2)nc1]

Methyl (4-{2-[(1S,2R)-2-{1-[5-(ethoxymethyl)pyrimidin-2-yl]piperidin-4-yl}cyclopropyl]ethoxy}-2-fluorophenyl)acetate (1.4 g, 2.97 mmol) was dissolved in THF (3 ml): MeOH (30 ml) and 1M lithium hydroxide (14.84 ml, 14.84 mmol) added. The mixture was stirred at RT overnight. The mixture was concentrated in vacuo and the residue diluted with water (5 mL). The pH of the solution was adjusted to pH~5 by addition of 1N HCl and the aqueous phase was extracted with EtOAc (3×10 mL). The organic fractions were combined, washed with brine, dried over MgSO$_4$ and concentrated under reduced pressure to afford the title compound. LC/MS (m/z): 458 (M+H)$^+$.

Step E: 2-(4-{2-[(1S,2R)-2-{1-[5-(ethoxymethyl)pyrimidin-2-yl]piperidin-4-yl}cyclopropyl]ethoxy}-2-fluorophenyl)-1-(3-hydroxyazetidin-1-yl)ethanone (4-{2-[(1S,2R)-2-{1-[5-(ethoxymethyl)pyrimidin-2-yl]piperidin-4-yl}cyclopropyl]ethoxy}-2-fluorophenyl)acetic acid (50, 0.109 mmol) and 3-hydroxy azetidine hydrochloride (11.97 mg, 0.109 mmol) were dissolved in DMF (1 ml) and HATU (83 mg, 0.219 mmol) and DIEA (0.057 ml, 0.328 mmol) added. The mixture was stirred at RT for 2 hr. The mixture was diluted with ethyl acetate (20 mL), washed with brine, dried over MgSO$_4$, and the solvent was evaporated under reduced pressure. The residue was purified by column chromatography on silica gel, Biotage 25M, using a gradient eluant of MeOH/DCM (0-10%) to to provide the title compound. LC/MS (m/z): 513 (M+H)$^+$. GPR119 Human EC50: 1.9 nM The Examples in Table 13 were synthesized according to the methods described in the prior example (199) employing the appropriate reagents and solvents.

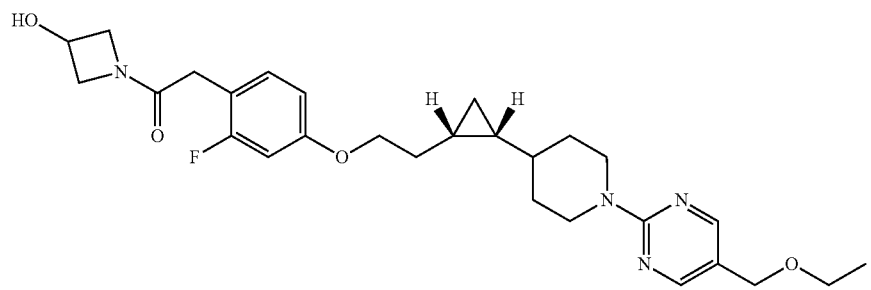 [SMILES: CCOCc1cnc(N2CCC([C@H]3C[C@H]3CCOc3ccc(CC(=O)N4CC(O)C4)c(F)c3)CC2)nc1]

TABLE 13

| Example # | Chemical Structure | Observed Mass [M + H]+ | GPR119 Human EC$_{50}$ (nM) |
|---|---|---|---|
| 200 | 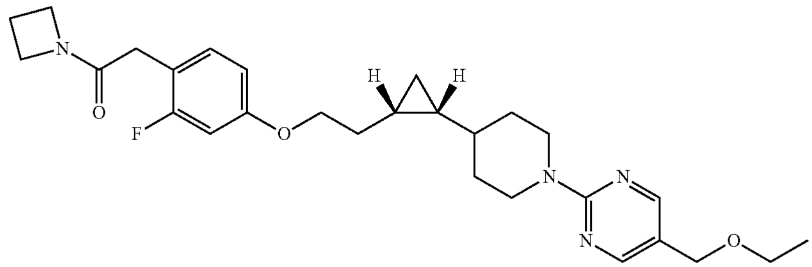 [SMILES: CCOCc1cnc(N2CCC([C@H]3C[C@H]3CCOc3ccc(CC(=O)N4CCC4)c(F)c3)CC2)nc1] | 496 | 0.79 |
| 201 | 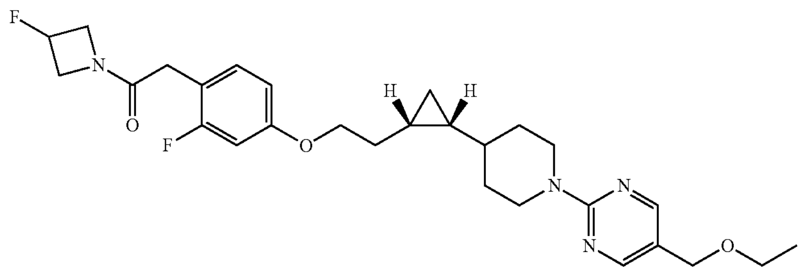 [SMILES: CCOCc1cnc(N2CCC([C@H]3C[C@H]3CCOc3ccc(CC(=O)N4CC(F)C4)c(F)c3)CC2)nc1] | 515 | 0.49 |
| 202 | 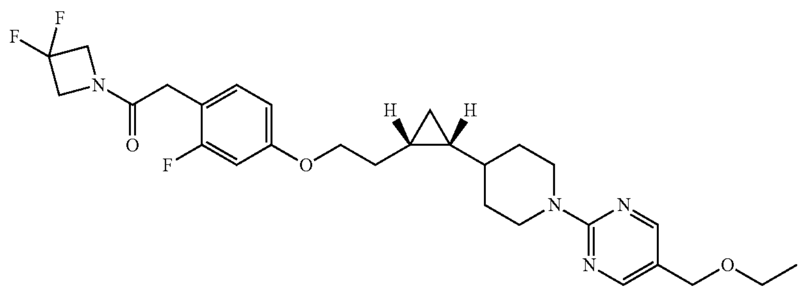 [SMILES: CCOCc1cnc(N2CCC([C@H]3C[C@H]3CCOc3ccc(CC(=O)N4CC(F)(F)C4)c(F)c3)CC2)nc1] | 532 | 0.30 |
| 203 | 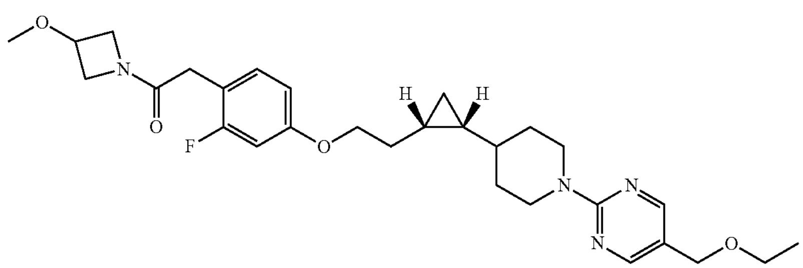 [SMILES: CCOCc1cnc(N2CCC([C@H]3C[C@H]3CCOc3ccc(CC(=O)N4CC(OC)C4)c(F)c3)CC2)nc1] | 526 | 1.2 |
| 204 | 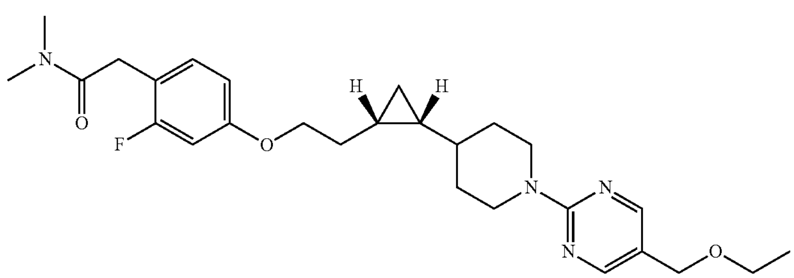 [SMILES: CCOCc1cnc(N2CCC([C@H]3C[C@H]3CCOc3ccc(CC(=O)N(C)C)c(F)c3)CC2)nc1] | 485 | 1.2 |

Example 205

Preparation of 1-(azetidin-1-yl)-2-(2-fluoro-4-{2-[(1S,2R)-2-{1-[5-(2-hydroxypropan-2-yl)pyrimidin-2-yl]piperidin-4-yl}cyclopropyl]ethoxy}phenyl)ethanone

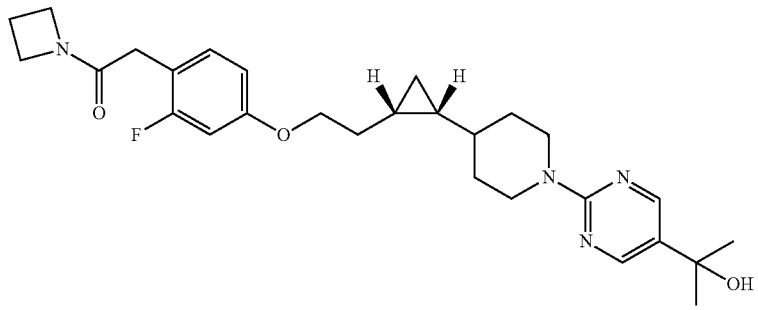 [SMILES: CC(C)(O)c1cnc(N2CCC([C@H]3C[C@H]3CCOc3ccc(CC(=O)N4CCC4)c(F)c3)CC2)nc1]

Step A: 2-(2-{4-[(1R,2S)-2-(2-hydroxyethyl)cyclopropyl]piperidin-1-yl}pyrimidin-5-yl)propan-2-ol

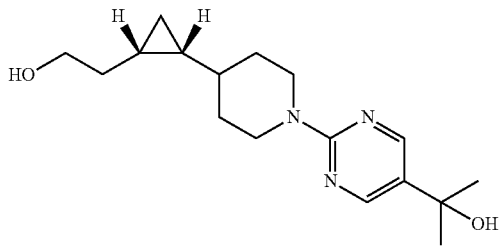 [SMILES: CC(C)(O)c1cnc(N2CCC([C@H]3C[C@H]3CCO)CC2)nc1]

2-((1S,2R)-2-(piperidin-4-yl)cyclopropyl)ethanol (810 mg, 4.79 mmol) and 2-(2-chloropyrimidin-5-yl)propan-2-ol (991 mg, 5.74 mmol) were dissolved in 12 mL of DMF, to which was added cesium carbonate (2.0 g, 6.20 mmol). The mixture was heated at 65° C. overnight. The mixture was cooled to rt, diluted with 20 mL of EtOAc and 20 mL of water. The layers were separated and the aqueous phase extracted with EtOAc (20 mL×2). The combined organic layers were dried over MgSO₄, filtered, and concentrated under reduced pressure. The residue was purified by column chromatography on silica gel (KP-Sil 50 SNAP column, Biotage system) eluting with a range of 40-90% EtOAc/Hex over 12 CV to give the desired compound. LC/MS (m/z): 306 (M+H)$^+$.

Step B: 1-(azetidin-1-yl)-2-(2-fluoro-4-hydroxyphenyl)ethanone

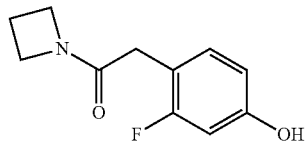 [SMILES: O=C(Cc1ccc(O)cc1F)N1CCC1]

2-(2-fluoro-4-hydroxyphenyl)acetic acid (1 g, 5.88 mmol), HOBT monohydrate (2.7 g, 17.6 mmol), and EDC.HCl (3.38 g, 17.6 mmol) were dissolved in 25 mL of DCM and stirred at rt for 30 min. Azetidine (1 g, 17.6 mmol) was added to this mixture and the reaction aged at rt for 3 hrs. The mixture was concentrated under reduced pressure and the residue purified by column chromatography on silica gel (KP-Sil 50 g SNAP column, Biotage system) eluting with 100% EtOAc over 14 CV to give the desired product. LC/MS (m/z): 210 (M+H)$^+$.

Step C: 1-(azetidin-1-yl)-2-(2-fluoro-4-{2-[(1S,2R)-2-{1-[5-(2-hydroxypropan-2-yl)pyrimidin-2-yl]piperidin-4-yl}cyclopropyl]ethoxy}phenyl)ethanone

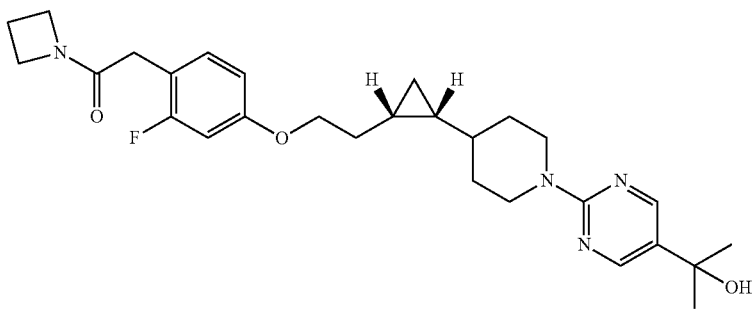 [SMILES: CC(C)(O)c1cnc(N2CCC([C@H]3C[C@H]3CCOc3ccc(CC(=O)N4CCC4)c(F)c3)CC2)nc1]

DIAD (95 μL, 0.491 mmol) was slowly added to a solution of 2-(2-{4-[(1R,2S)-2-(2-hydroxyethyl)cyclopropyl]piperidin-1-yl}pyrimidin-5-yl)propan-2-ol (100 mg, 0.327 mmol), 1-(azetidin-1-yl)-2-(2-fluoro-4-hydroxyphenyl)ethanone (72 mg, 0.344 mmol), and triphenylphosphine (129 mg, 0.491 mmol) in DCM (1.6 mL). The mixture was stirred at rt for 3 hrs. The mixture was diluted with DCM (8 mL) and washed with 2 N NaOH solution (5 mL×1). The organic phase was dried over MgSO$_4$, filtered, and concentrated under reduced pressure. The residue was purified by preparative TLC using 2×2000 micron silica preparative TLC plates (uv 254 active) which were developed using 100% EtOAc. The desired band (Rf=0.5 @ 100% EtOAc) was collected and extracted to give the title compound. $^1$H NMR (500 MHz, CD$_3$CN) δ 8.41 (s, 2H), 7.17 (t, 1H), 6.72 (t, 2H), 4.68 (t, 2H), 4.19 (t, 2H), 4.06 (m, 2H), 3.91 (t, 211), 3.36 (s, 2H), 2.83 (t, 2H), 2.22 (m, 2H), 2.07 (m, 1H), 1.83 (m, 2H), 1.57 (m, 1H), 1.48 (s, 6H), 1.35-1.10 (m, 3H), 0.91 (m, 1H), 0.60 (m, 2H), −0.05 (m, 1H). LC/MS (m/z): 497 (M+H)$^+$, GPR119 Human EC$_{50}$: 7.5 nM.

The example in Table 14 was synthesized according to the methods described in the prior example (205) employing the appropriate reagents and solvents.

Step A: Methyl [4-(2-{(1S,2R)-2-[1-(5-ethylpyrimidin-2-yl)piperidin-4-yl]cyclopropyl}ethoxy)-2-fluorophenyl]acetate

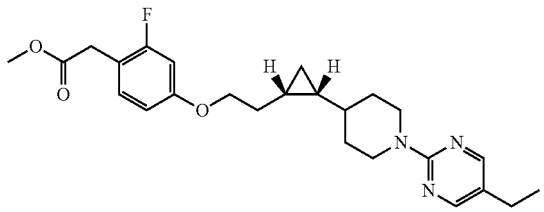 [SMILES: CCc1cnc(N2CCC([C@H]3C[C@H]3CCOc3ccc(CC(=O)OC)c(F)c3)CC2)nc1]

To a solution of 2-[4-(2-{(1S,2R)-2-[1-(5-ethylpyrimidin-2-yl)piperidin-4-yl]cyclopropyl}ethoxy)-2-fluorophenyl]ethanol (0.200 g, 0.726 mmol) in 5 ml anhydrous dichloromethane at RT was added a solution of 1-(azetidin-1-yl)-2-(2,6-difluoro-4-hydroxyphenyl) ethanone (0.160 g, 0.871 mmol) in 5 ml anhydrous dichloromethane. Triphenylphosphine, polymer-bound (0.571 g, 1.90 mmol), and di-tert-butyl azodicarboxylate (0.334 g, 1.45 mmol) was added and the slurry stirred at RT for 3 hours. The mixture was filtered through Celite and the filtrate concentrated in vacuo. The residue was purified by column chromatography on silica gel (Biotage column, 50 g) using a gradient eluent of 0-50% ethyl acetate in hexanes (700 ml) to afford the title compound. LC/MS (m/z) 442.3 (M+H)$^+$.

Step B: [4-(2-{(1S,2R)-2-[1-(5-ethylpyrimidin-2-yl)piperidin-4-yl]cyclopropyl}ethoxy)-2-fluorophenyl]acetic acid

TABLE 14

| Example # | Chemical Structure | Observed Mass [M + H]$^+$ | GPR119 Human EC$_{50}$ (nM) |
|---|---|---|---|
| 206 | 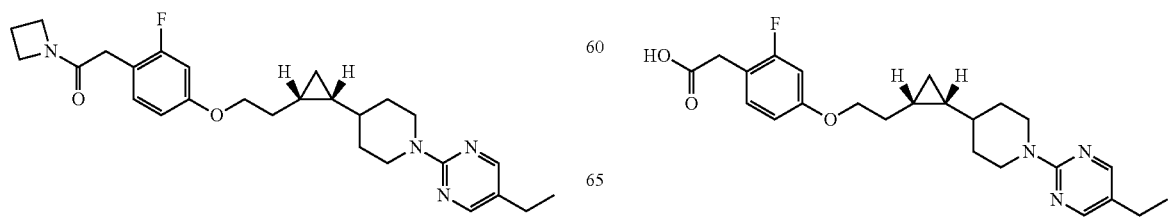 | 515 | 0.71 |

Example 207

Preparation of 1-(azetidin-1-yl)-2-[4-(2-{(1S,2R)-2-[1-(5-ethylpyrimidin-2-yl)piperidin-4-yl]cyclopropyl}ethoxy)-2-fluorophenyl]ethanone To a solution of methyl [4-(2-{(1S,2R)-2-[1-(5-ethylpyrimidin-2-yl)piperidin-4-yl]cyclopropyl}ethoxy)-2-fluorophenyl]acetate (0.300 g, 0,679 mmol) in 6 ml anhydrous tetrahydrofuran was added by 2 ml methanol and 2 ml water. Lithium hydroxide (81.0 mg, 3.40 mmol) was added, and the mixture stirred at RT overnight. 1 M hydrochloric acid was added and the pH adjusted to 4. The volatiles were removed under reduced pressure, and the aqueous phase extracted with dichloromethane (3×20 ml). The organics were combined, dried over magnesium sulphate, filtered, and the filtrate concentrated under reduced pressure. The residue was purified by column chromatography on silica gel (50 g silica gel) using a gradient eluent of 0-70% ethyl acetate in hexanes (700 ml) to afford the title compound. LC/MS (m/z) 428.2 (M+H)+.

Step C: 1-(azetidin-1-yl)-2-[4-(2-{(1S,2R)-2-[1-(5-ethylpyrimidin-2-yl)piperidin-4-yl] cyclopropyl}ethoxy)-2-fluorophenyl]ethanone

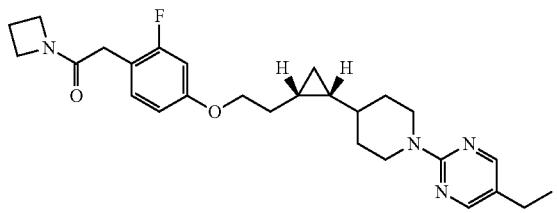 [SMILES: CCc1cnc(N2CCC([C@H]3C[C@H]3CCOc3ccc(CC(=O)N4CCC4)c(F)c3)CC2)nc1]

To a solution of [4-(2-{(1S,2R)-2-[1-(5-ethylpyrimidin-2-yl)piperidin-4-yl]cyclopropyl}ethoxy)-2-fluorophenyl]acetic acid (20.0 mg, 0.047 mmol) in 1 ml anhydrous DMF at RT was added azetidine (4.01 mg, 0.070 mmol) and N,N-diisopropylethylamine (0.201 ml, 1.15 mmol). o-(7-Azabenzotriazol-1-yl)-N,N,N',N'-tetramethyluronium hexafluorophosphate (30.2 mg, 0.234 mmol) was added and the mixture stirred at RT for 4 hrs. The mixture was filtered and purified by reversed-phase HPLC (SunFire Prep C18 OBD 5 um 19×100 mm column; 45-90% acetonitrile in 0.1% formic acid in water gradient) to afford the title compound. LC/MS (m/z): 467.2 (M+H)+. GPR119 Human EC50: 0.40 nM.

The Examples in Table 15 were synthesized according to the methods described in the prior example (207) employing the appropriate reagents and solvents.

Example 209

Preparation of 2-{2,5-difluoro-4-[2-((1S,2R)-2-{1-[5-(methoxymethyl)pyrimidin-2-yl]piperidin-4-yl}cyclopropyl)ethoxy]phenyl}-N, N-dimethylacetamide

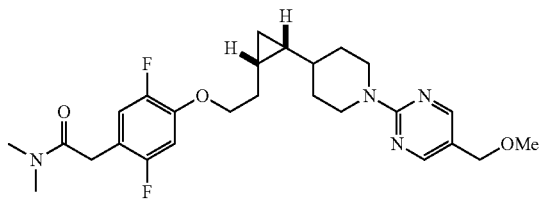 [SMILES: COCc1cnc(N2CCC([C@H]3C[C@H]3CCOc3cc(F)c(CC(=O)N(C)C)cc3F)CC2)nc1]

Step A: Benzyl 4-{(1R,2S)-2-[2-(4-bromo-2,5 difluorophenoxy)ethyl]cyclopropyl}piperidine-1-carboxylate

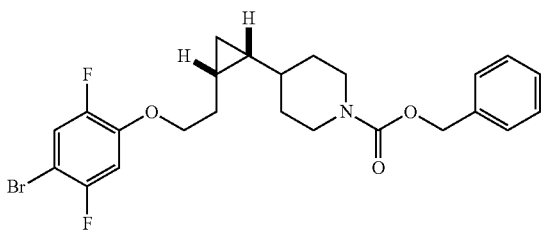 [SMILES: O=C(OCc1ccccc1)N1CCC([C@H]2C[C@H]2CCOc2cc(F)c(Br)cc2F)CC1]

Benzyl 4-[(1R,2S)-2-(2-hydroxyethyl)cyclopropyl]piperidine-1-carboxylate (2.24 g, 7.38 mmol) in DCM (35 ml) was added 4-bromo-2,5-difluorophenol (1.62 g, 7.75 mmol), 3.93 g of triphenylphosphine (polymer-bound, 3.0 mmol/g) and di-tert-butyl diazene-1,2-dicarboxylate (2.21 g, 9.60 mmol). The reaction mixture was stirred at RT for 4 hours. The solid was removed by filtration through celite and the filtrate concentrated. The residue was purified by column chromatography on silica gel (Biotage column, 50 g SNAP) using a gradient 0-20% then 20% EtOAc in hexanes to afford the title compound. LC/MS (m/z): 496.2 (M+H)+.

TABLE 15

| Example # | Chemical Structure | Observed Mass [M + H]+ | GPR119 Human EC50 (nM) |
|---|---|---|---|
| 208 | 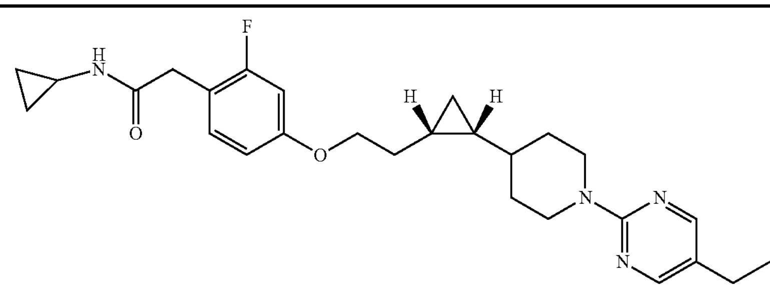 | 467 | 1.9 |

Step B: Benzyl 4-{(1R,2S)-2-[2-(2-tert-butoxy-2-oxoethyl-2,5-difluorophenoxy)ethyl]cyclopropyl}piperidine-1-carboxylate

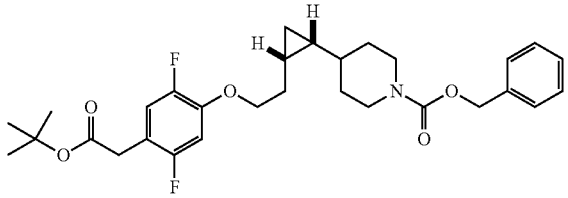 [SMILES: CC(C)(C)OC(=O)Cc1cc(F)c(OCC[C@@H]2C[C@@H]2C2CCN(C(=O)OCc3ccccc3)CC2)cc1F]

Benzyl 4-{(1R,2S)-2-[2-(4-bromo-2,5 difluorophenoxy)ethyl]cyclopropyl}piperidine-1-carboxylate (0.540 g, 1.09 mmol) in THF (5 ml) was added 0.5 M 2-tert-butoxy-2-oxoethylzinc chloride in diethyl ether (5.46 ml, 2.73 mmol), followed by Pd$_2$(dba)$_3$ (50 mg, 0.055 mmol) and 52 mg X-Phos. The vessel was evacuated and back filled with nitrogen (3×) and the mixture was heated at 65° C. overnight. Saturated ammonium chloride (10 ml) was added and the mixture extracted with EtOAc (15 ml). The organic layer was separated, dried over Na$_2$SO$_4$, and concentrated. The residue was purified by column chromatography on silica gel (Biotage SNAP column, 25 g) using a gradient 0-15% then 15% EtOAc in hexanes to afford the title compound. LC/MS (m/z): 552.4 (M+Na)$^+$.

Step C: (4-{2-[(1S,2R)-2-{1-[(benzyloxy)carbonyl]piperidin-4-yl}cyclopropyl]ethoxy}-2,5-difluorophenyl)acetic acid

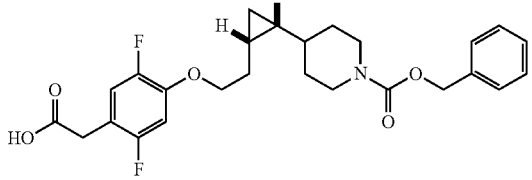

Benzyl 4-{(1R,2S)-2-[2-(2-tert-butoxy-2-oxoethyl-2,5-difluorophenoxy)ethyl]cyclopropyl}piperidine-1-carboxylate (0.350 g, 0.661 ml) was dissolved in dichloromethane (1.5 ml) and TFA (1.5 ml) added. The mixture was stirred at RT for 3.5 h and the volatiles removed under vacuum to afford the title compound. LC/MS (m/z): 474.3 (M+H)$^+$.

Step D: Benzyl 4-[(1R,2S)-2-(2-{4-[2-(dimethylamino)-2-oxoethyl]-2,5-difluorophenoxy}ethyl)cyclopropyl]piperidine-1-carboxylate

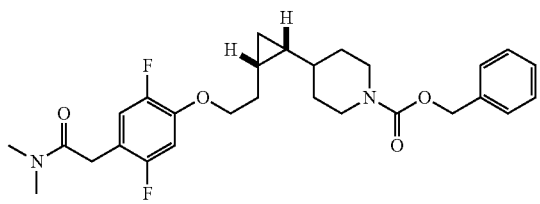 [SMILES: CN(C)C(=O)Cc1cc(F)c(OCC[C@@H]2C[C@@H]2C2CCN(C(=O)OCc3ccccc3)CC2)cc1F]

To a solution of {4-[2-((1S,2R)-2-{1-[(benzyloxy)carbonyl]piperidin-4-yl}cyclopropyl)ethoxy]-2,5-difluorophenyl}acetic acid (313 mg, 0.661 mmol) in 2.5 ml anhydrous DMF at RT was added dimethylamine (2.0 M solution in THF, 0.661 ml, 1.32 mmol) and N,N-diisopropylethylamine (0.562 ml, 3.31 mmol). 0-(7-Azabenzotriazol-1-yl)-N,N,N',N'-tetramethyluronium hexafluorophosphate (503 mg, 1.32 mmol) was then added to the solution and the mixture stirred at RT overnight. The reaction was quenched by addition of water (12 ml) and the mixture extracted with ethyl acetate (12 ml). The layers were separated and the organic layer was dried over sodium sulfate, filtered, and the filtrate was concentrated under reduced pressure. The residue was purified by column chromatography on silica gel (Biotage column, 25 g) using a gradient eluent of 0-50% ethyl acetate in hexanes (800 ml) to afford the title compound. LC/MS (m/z): 501.4 (M+H)$^+$.

Step E: 2-(2,5-Difluoro-4-{2-[(1S,2R)-2-piperidin-4-ylcyclopropyl]ethoxy}phenyl-)-N,N-dimethylacetamide

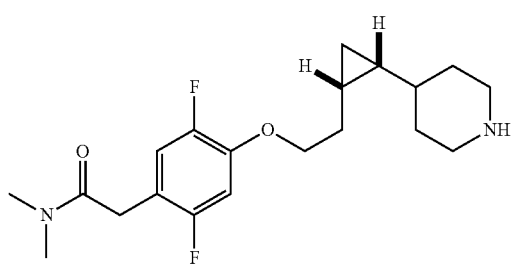 [SMILES: CN(C)C(=O)Cc1cc(F)c(OCC[C@@H]2C[C@@H]2C2CCNCC2)cc1F]

To a solution of benzyl 4-[(1R,2S)-2-(2-{4-[2-(dimethylamino)-2-oxoethyl]-2,5-difluorophenoxy}ethyl)cyclopropyl]piperidine-1-carboxylate (226 mg, 0.451 mmol) in 2 ml anhydrous methanol at RT was added 10% palladium on carbon (25.0 mg). The reaction mixture was stirred under a hydrogen atmosphere for 2 hours. The slurry was filtered through celite, and the filtrate concentrated to afford the title compound. LC/MS (m/z): 368.4 (M+H)$^+$.

Step F: 2-{2,5-Difluoro-4-[2-((1S,2R)-2-{1-[5-(methoxymethyl)pyrimidin-2-yl]piperidin-4-yl}cyclopropyl)ethoxy]phenyl}-N,N-dimethylacetamide

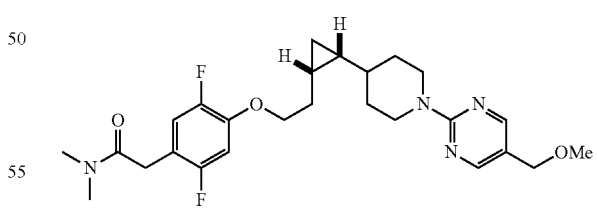

To a solution of 2-(2,5-difluoro-4-{2-[(1S,2R)-2-piperidin-4-ylcyclopropyl]ethoxy}phenyl-)-N,N-dimethylacetamide (40.0 mg, 0.109 mmol) in 1 ml anhydrous DMF at RT was added triethylamine (0.046 ml, 0.33 mmol) and 2-chloro-5-(methoxymethyl)pyrimidine (20.8 mg, 0.131 mmol). The mixture was stirred at RT for 2 hours. The mixture was filtered and purified by reverse-phase HPLC (SunFire Prep C18 OBD Sum 19×100 mm column; 35-65% acetonitrile in 0.1% formic acid in water gradient) to afford the title compound. LC/MS (m/z): 489.5 (M+H)$^+$. Human EC50: 1.6 nM

Example 210

Preparation of 2-[2,6-difluoro-4-(2-{(1S,2R)-2-[1-(5-methoxypyrimidin-2-yl)piperidin-4-yl]cyclopropyl}ethoxy)phenyl]-1-(3-hydroxyazetidin-1-yl)ethanone

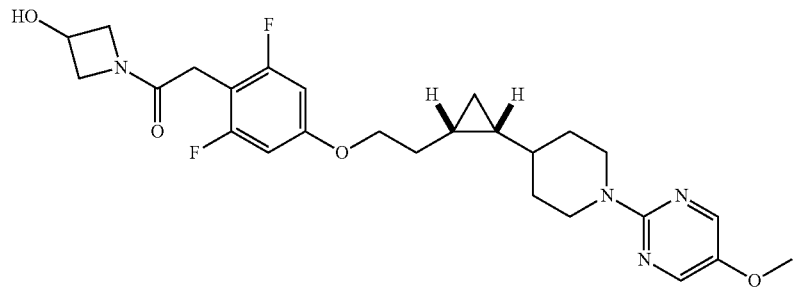 [SMILES: COc1cnc(N2CCC([C@H]3C[C@H]3CCOc3cc(F)c(CC(=O)N4CC(O)C4)c(F)c3)CC2)nc1]

Step A: 2-{(1S,2R)-2-[1-(5-methoxypyrimidin-2-yl)piperidin-4-yl]cyclopropyl}ethanol

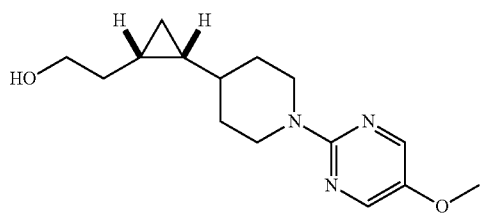

2-((1S,2R)-2-(piperidin-4-yl)cyclopropyl)ethanol (2.5 g, 14.77 mmol) was dissolved in DMF (30 ml) at RT under $N_2$ and cesium carbonate (7.22 g, 22.15 mmol) was added. The mixture was stirred at RT for 5 min and 2-chloro-5-methoxypyrimidine (2.56 g, 17.72 mmol) was added. The mixture was stirred at 100° C. overnight. The mixture was diluted with EtOAc (100 ml), washed with sat. NH$_4$Cl (100 ml), dried over MgSO$_4$, and the volatiles evaporated under reduced pressure. The crude material was purified by silica gel column chromatography (100 g SNAP, 20~60% EtOAc in hexane) to afford the titled compound. LC/MS (m/z): 278 (M+H)$^+$. Rf was 0.4 @ 50% EtOAc in hexanes (blue spot on CAM stain).

Step B: 2-(4-{(1R,2S)-2-[2-(4-bromo-3,5-difluorophenoxy)ethyl]cyclopropyl}piperidin-1-yl)-5-methoxypyrimidine

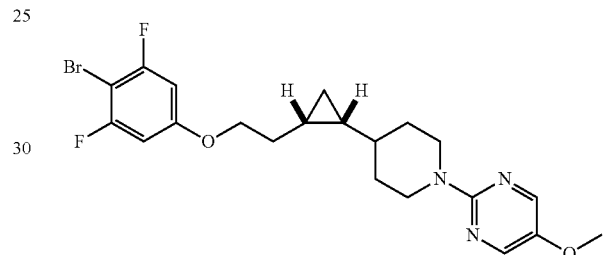

2-((1S,2R)-2-(1-(5-methoxypyrimidin-2-yl)piperidin-4-yl)cyclopropyl)ethanol (1.4 g, 5.05 mmol), 4-bromo-3,5-difluorophenol (1.26 g, 6.06 mmol) and triphenylphosphine (1.98 g, 7.57 mmol) were dissolved in dichloromethane (25 ml). The mixture was stirred at RT under $N_2$ for 5 min and diisopropyl azodicarboxylate (1.53 g, 7.57 mmol) added. The mixture was stirred at RT overnight. The mixture was diluted with DCM (50 ml), washed with 0.5 N NaOH (50 ml), brine, dried over sodium sulfate and the volatiles removed in vacuo. The residue was purified by silica gel column chromatography (50 g SNAP, 10~40% EtOAc in hexane) to afford 1.86 g (79%) of the titled compound. LC/MS (m/z): 469 (M+H)$^+$. Rf was 0.3 @ 30% EtOAc in hexanes (blue spot on CAM stain)

Step C: tert-butyl 2-[2,6-difluoro-4-(2-{(1S,2R)-2-(1-(5-methoxypyrimidin-2-yl)piperidin-4-yl]cyclopropyl}ethoxy)phenyl)acetate

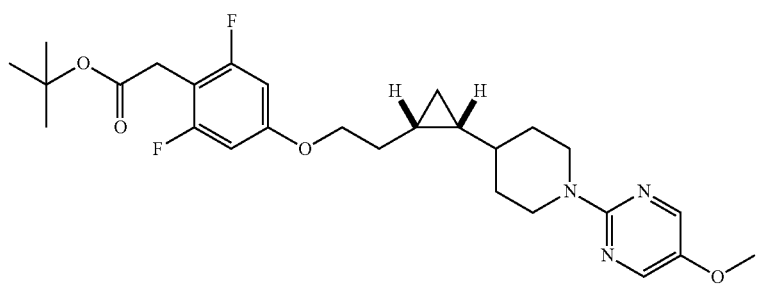 [SMILES: COc1cnc(N2CCC([C@H]3C[C@H]3CCOc3cc(F)c(CC(=O)OC(C)(C)C)c(F)c3)CC2)nc1]

To 2-(4-((1R,2S)-2-(2-(4-bromo-3,5-difluorophenoxy)ethyl)cyclopropyl)piperidin-1-yl)-5-methoxypyrimidine (1.86 g, 3.97 mmol) in THF (5 ml) was added tris(dibenzylideneacetone)dipalladium(0) (0.364 g, 0.397 mmol) and X-PHOS (0.379 g, 0.794 mmol), followed by (2-tert-butoxy-2-oxoethyl)zinc(II) bromide (0.5 M in ethyl ether, 23.83 ml, 11.91 mmol). The mixture was degassed under $N_2$ for 10 min then heated at 60° C. overnight. The mixture was diluted with sat. $NH_4Cl$ (50 ml), and the aqueous phase extracted with EtOAc (50 ml×2). The organic fractions were combined, washed with brine, dried over sodium sulfate, and concentrated under reduced pressure. The residue was purified by silica gel column chromatography (50 g SNAP, 5~30% EtOAc in hexane) to afford the titled compound. LC/MS (m/z): 504 (M+H)$^+$. Rf was 0.28 @ 25% EtOAc in hexanes (blue spot on CAM stain)

Step D: [2,6-difluoro-4-(2-{(1S,2R)-2-[1-(5-methoxypyrimidin-2-yl]piperidin-4-yl)cyclopropyl}ethoxy)phenyl]acetic acid

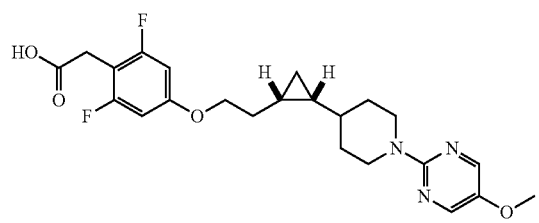 [SMILES: COc1cnc(N2CCC([C@H]3C[C@H]3CCOc3cc(F)c(CC(=O)O)c(F)c3)CC2)nc1]

Tert-butyl 2-(2,6-difluoro-4-(2-((1S,2R)-2-(1-(5-methoxypyrimidin-2-yl)piperidin-4-yl)cyclopropyl)ethoxy)phenyl)acetate (1.87 g, 3.71 mmol) was dissolved in DCM (10 ml) and hydrochloric acid (9.28 ml, 4 M solution in dioxane, 37.1 mmol) was added. The mixture was stirred at 35° C. for 5 h. The volatiles were removed under reduced pressure to afford the titled compound. LC/MS (m/z): 448 (M+H)$^+$.

Step E: 2-[2,6-difluoro-4-(2-{(1S,2R)-2-[1-(5-methoxypyrimidin-2-yl)piperidin-4-yl]cyclopropyl}ethoxy)phenyl]-1-(3-hydroxyazetidin-1-yl)ethanone

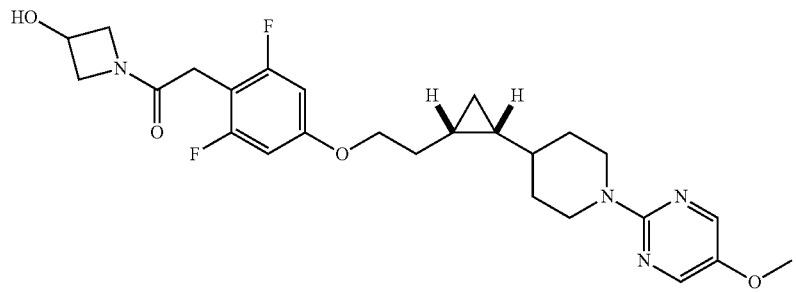 [SMILES: COc1cnc(N2CCC([C@H]3C[C@H]3CCOc3cc(F)c(CC(=O)N4CC(O)C4)c(F)c3)CC2)nc1]

2-(2,6-difluoro-4-(2-((1S,2R)-2-(1-(5-methoxypyrimidin-2-yl)piperidin-4-yl)cyclopropyl)ethoxy)phenyl)acetic acid (80 mg, 0.179 mmol), 1-hydroxybenzotriazole hydrate (41.1 mg, 0.268 mmol), 3-hydroxyazetidine hydrochloride (29.4 mg, 0.268 mmol) and (E)-3-(ethyldiazenyl)-N,N-dimethylpropan-1-amine hydrochloride (48.2 mg, 0.268 mmol) were dissolved in $CH_2Cl_2$ (4 ml). The mixture was stirred at RT for 5 min and triethylamine (0.075 ml, 0.536 mmol) was added. The mixture was stirred at RT overnight and purified by loading directly onto a Preparative TLC plate that was developed with pure EtOAc. The desired product (Rf=0.40 @ pure EtOAc) was collected to give the title compound. $^1$H NMR (500 MHz, CDCl$_3$) δ 8.15 (s, 2H), 6.50 (d, 2H), 4.60 (m, 3H), 4.40 (m, 1H), 4.30 (m, 1H), 4.05 (m, 2H), 3.90 (m, 11-1), 3.80 (s, 3H), 3.41 (s, 2H), 3.05 (broad, s, 1H), 2.85 (m, 2H), 2.15 (m, 1H), 1.92 (m, 2H), 1.55 (m, 1H), 1.40 (m, 2H), 0.95 (m, 2H), 0.68 (m, 2H), −0.40 (m, 1H). LC/MS (m/z): 503 (M+H)$^+$, GPR119 Human EC$_{50}$: 0.59 nM.

The Examples in Table 16 were synthesized according to the methods described in the prior example (210) employing the appropriate reagents and solvents.

TABLE 16

| Example # | Chemical Structure | Observed Mass [M + H]+ | GPR119 Human EC$_{50}$ (nM) |
|---|---|---|---|
| 211 | 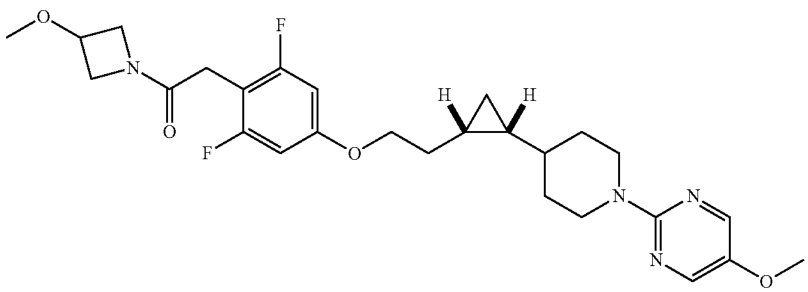 | 517 | 0.11 |
| 212 | 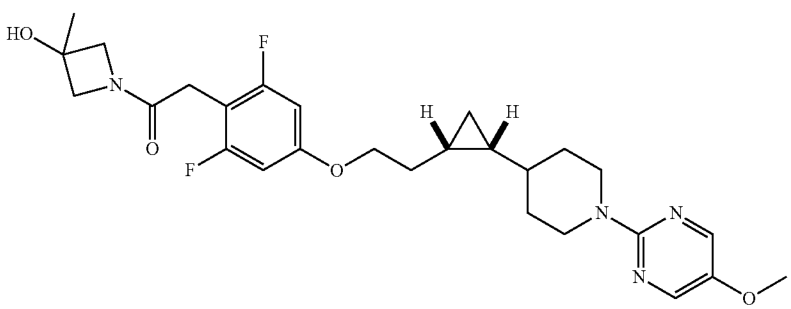 [SMILES: COc1cnc(N2CCC([C@H]3C[C@H]3CCOc3cc(F)c(CC(=O)N4CC(C)(O)C4)c(F)c3)CC2)nc1] | 517 | 0.88 |
| 213 | 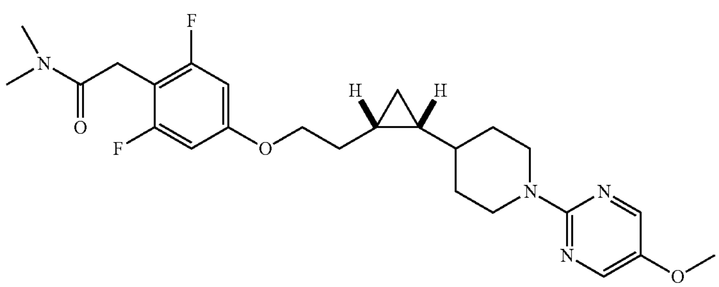 | 475 | 0.23 |
| 214 | 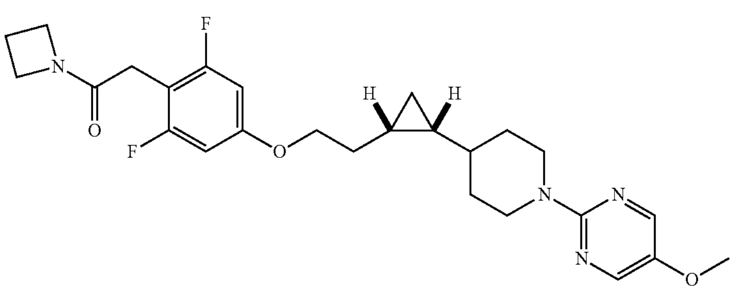 [SMILES: COc1cnc(N2CCC([C@H]3C[C@H]3CCOc3cc(F)c(CC(=O)N4CCC4)c(F)c3)CC2)nc1] | 487 | 0.20 |
| 215 | 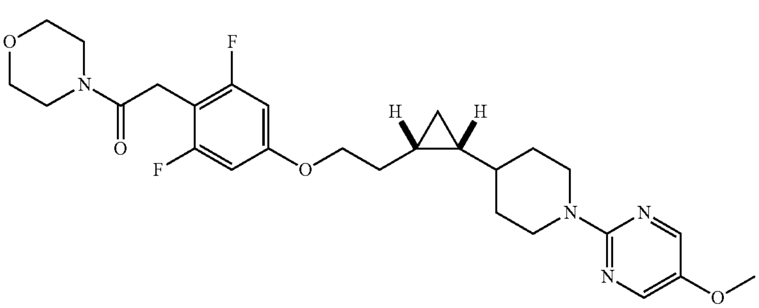 [SMILES: COc1cnc(N2CCC([C@H]3C[C@H]3CCOc3cc(F)c(CC(=O)N4CCOCC4)c(F)c3)CC2)nc1] | 517 | 0.29 |

TABLE 16-continued

| Example # | Chemical Structure | Observed Mass [M + H]⁺ | GPR119 Human EC$_{50}$ (nM) |
|---|---|---|---|
| 216 | 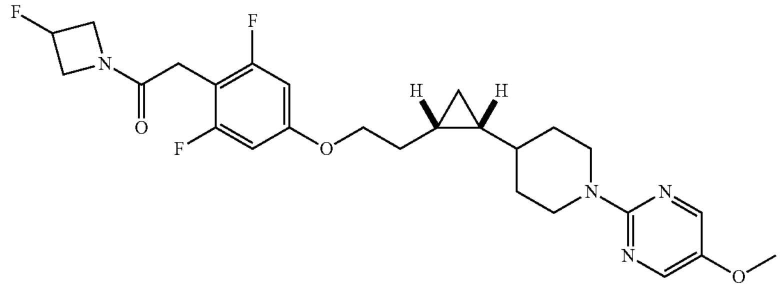 [SMILES: COc1cnc(N2CCC([C@H]3C[C@H]3CCOc3cc(F)c(CC(=O)N4CC(F)C4)c(F)c3)CC2)nc1] | 505 | 0.09 |
| 217 | 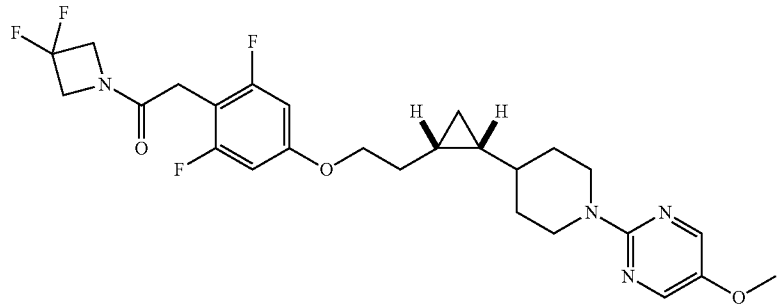 [SMILES: COc1cnc(N2CCC([C@H]3C[C@H]3CCOc3cc(F)c(CC(=O)N4CC(F)(F)C4)c(F)c3)CC2)nc1] | 523 | 0.07 |

Example 218

Preparation of 1-({2,6-difluoro-4-[2-((1S,2R)-2-{1-[5-(methoxymethyl)pyrimidin-2-yl]piperidin-4-yl}cyclopropyl)ethoxy]phenyl}acetyl)azetidin-3-ol

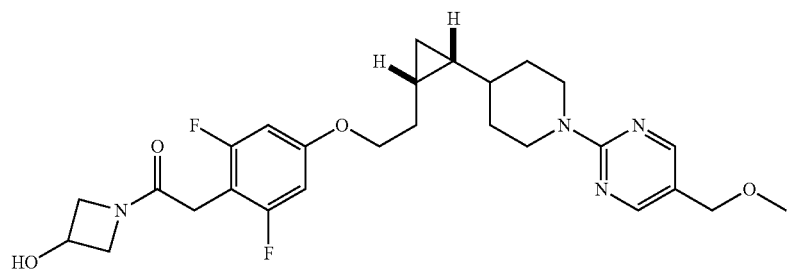 [SMILES: COCc1cnc(N2CCC([C@H]3C[C@H]3CCOc3cc(F)c(CC(=O)N4CC(O)C4)c(F)c3)CC2)nc1]

Step A: methyl (2,6-difluoro-4-hydroxyphenyl)acetate

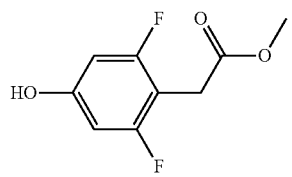

To a stirred solution of (2,6-difluoro-4-methoxyphenyl) acetic acid (1.50 g, 7.42 mmol) in 20 ml anhydrous dichloromethane at 0° C. was added a solution of boron tribromide (4.29 ml, 44.5 mmol) in 10 ml anhydrous dichloromethane. The cooling bath was removed and the mixture allowed to warm to RT for 2 hours. The reaction was diluted with 20 ml anhydrous methanol, and stirred for 30 minutes. The mixture was concentrated under reduced pressure, and the residue purified by column chromatography on silica gel, (Biotage column, 50 g) using a gradient eluent of 0-30% ethyl acetate in hexanes (700 ml) to afford the title compound. $^1$H NMR (CDCl$_3$): δ 6.30 (d, J=8.3 Hz, 2H), 6.12 (br, 1H), 3.76 (s, 3H), 3.63 (s, 2H).

Step B: Methyl{2,6-difluoro-4-[2-((1S,2R)-2-{1-[5-(methoxymethyl)pyrimidin-2-yl]piperidin-4-yl}cyclopropyl)ethoxy]phenyl}acetate

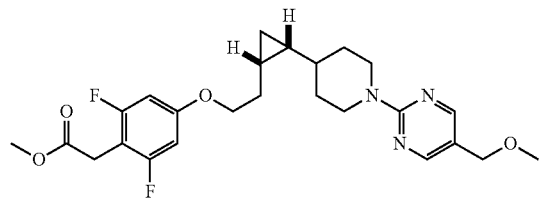

To a stirred solution of methyl (2,6-difluoro-4-hydroxyphenyl)acetate (1.46 g, 7.22 mmol) in 10 ml anhydrous dichloromethane at RT was added a solution of 2-((1S,2R)-2-{1-[5-(methoxymethyl)pyrimidin-2-yl]piperidin-4-yl}cyclopropyl)ethanol (2.10 g, 7.22 mmol) in 20 ml anhydrous dichloromethane, followed by triphenylphosphine (polymer-bound, 3.79 g, 11.4 mmol), and di-tert-butyl azodicarboxylate (1.83 g, 7.94 mmol). The reaction mixture was stirred at RT for 3 hours. The mixture was filtered through Celite and concentrated under reduced pressure. The residue was purified by column chromatography on silica gel (Biotage column, 50 g) using a gradient eluent of 0-40% ethyl acetate in hexanes (900 ml) to afford the title compound. LC/MS (m/z) 476.4 (M+H)⁺.

Step C: {2,6-difluoro-4-[2-((1S,2R)-2-{1-[5-(methoxymethyl)pyrimidin-2-yl]piperidin-4-yl}cyclopropyl)ethoxy]phenyl}acetic acid

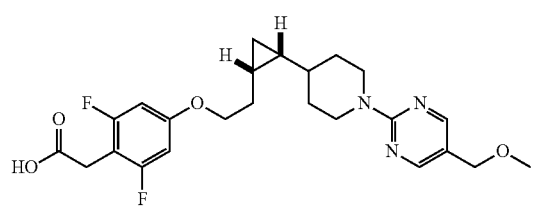

To a solution of methyl {2,6-difluoro-4-[2-((1S,2R)-2-{1-[5-(methoxymethyl)pyrimidin-2-yl]piperidin-4-yl}cyclopropyl)ethoxy]phenyl}acetate (3.15 g, 6.62 mmol) in 21 ml of tetrahydrofuran was added 14 ml of methanol and 14 ml of water. 5 M sodium hydroxide (4.50 ml, 22.5 mmol) was added and the mixture stirred at RT overnight. 2 M hydrochloric acid (11.3 ml, 22.5 mmol) was added to adjust the pH of the solution to 4. The volatiles were removed under vacuum, and the aqueous phase extracted with dichloromethane (3×30 ml). The organic layers were combined, dried over magnesium sulphate, filtered, and the filtrate was concentrated under reduced pressure. The residue was purified by column chromatography on silica gel (Biotage column, 50 g) using a gradient eluent of 0-60% EtOAc:hexanes (700 ml) to afford the title compound. $^1$H NMR (CDCl$_3$): δ 8.29 (s, 2H), 6.48 (d, J=9.1 Hz, 2H), 4.67-4.74 (m, 2H), 4.26 (s, 2H), 4.00-4.04 (m, 2H), 3.67 (s, 2H), 3.34 (s, 3H), 2.84-2.91 (m, 2H), 2.12-2.18 (m, 1H), 1.83 (d, J=12.4 Hz, 2H), 1.48-1.55 (m, 1H), 1.33-1.41 (m, 2H), 1.05-1.12 (m, 1H), 0.87-0.94 (m, 1H), 0.64-0.71 (m, 1H), 0.58-0.64 (m, 1H), −0.10 (m, 1H). LC/MS (m/z) 463.4 (M+H)⁺.

Step D: 1-({2,6-difluoro-4-[2-((1S,2R)-2-{1-[5-(methoxymethyl)pyrimidin-2-yl]piperidin-4-yl}cyclopropyl)ethoxy]phenyl}acetyl)azetidin-3-ol

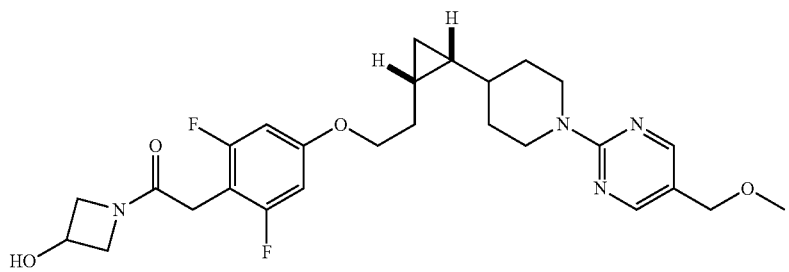 [SMILES: COCc1cnc(N2CCC([C@H]3C[C@H]3CCOc3cc(F)c(CC(=O)N4CC(O)C4)c(F)c3)CC2)nc1]

To a solution of {2,6-difluoro-4-[2-((1S,2R)-2-{1-[5-(methoxymethyl)pyrimidin-2-yl]piperidin-4-yl}cyclopropyl)ethoxy]phenyl}acetic acid (1.00 g, 2.17 mmol) in 8 ml anhydrous DMF at RT was added azetidin-3-ol hydrochloride (0.475 g, 4.33 mmol) and N,N-diisopropylethylamine (1.84 ml, 10.8 mmol). O-(7-Azabenzotriazol-1-yl)-N,N,N',N'-tetramethyluronium hexafluorophosphate (1.65 g, 4.33 mmol) was added and the mixture stirred at RT overnight. The mixture was filtered and purified by reverse-phase HPLC column chromatography (SunFire Prep C18 OBD Sum 19×100 mm column; 35-75% acetonitrile in 0.1% formic acid in water gradient) to afford the title compound. $^1$H NMR (CD$_3$OD): δ 8.26 (s, 2H), 6.57 (d, J=9.4 Hz, 2H), 4.69 (t, J=12.5 Hz, 2H), 4.57-4.59 (m, 1H), 4.45-4.49 (m, 1H), 4.27 (s, 2H), 4.18-4.22 (m, 1H), 4.01-4.09 (m, 3H), 3.75-3.78 (m, 1H), 3.47 (s, 2H), 3.34 (s, 3H), 2.86-2.93 (m, 2H), 2.09-2.12 (m, 1H), 1.82-1.88 (m, 2H), 1.56-1.58 (m, 1H), 1.31-1.35 (m, 2H), 1.16-1.18 (m, 1H), 0.95-0.97 (m, 1H), 0.59-0.68 (m, 2H), −0.04 (m, 1H). LC/MS (m/z): 517.5 (M+H)⁺. Human EC50: 1.6 nM

Example 219

Preparation of 1-(azetidin-1yl)-2-(2,6-difluoro-4-{2 [(1S,2R)-2-{1-[5-(methoxylmethyl)pyrimidin-2yl] piperidin-4-yl}cyclopropyl]ethoxyl}phenyl)ethanone

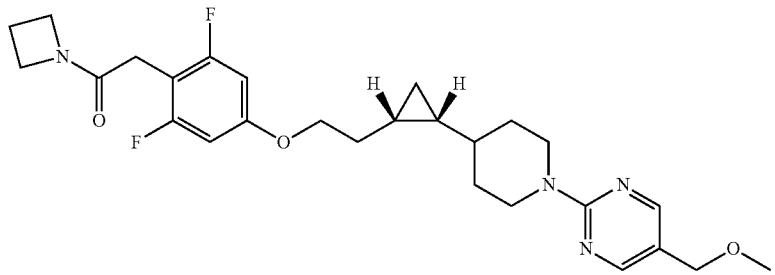 [SMILES: COCc1cnc(N2CCC([C@H]3C[C@H]3CCOc3cc(F)c(CC(=O)N4CCC4)c(F)c3)CC2)nc1]

To a solution of {2,6-difluoro-4-[2-((1S,2R)-2-{1-[5-(methoxymethyl)pyrimidin-2-yl]piperidin-4-yl}cyclopropyl)ethoxy}phenyl]acetic acid (5.00 g, 10.8 mmol) in 8 ml anhydrous DMF at RT was added azetidine (0.928 g, 16.3 mmol) and N,N-diisopropylethylamine (3.78 ml, 21.7 mmol). o-(7-Azabenzotriazol-1-yl)-N,N,N',N'-tetramethyluronium hexafluorophosphate (6.18 g, 16.3 mmol) was added to the solution and the mixture stirred at RT for 4 hrs. The residue was purified by preparative biotage reverse phase (C-18) (100 g column), eluting with Acetonitrile/Water+0.1% formic acid (35% to 90%). The solid was purified by column chromatography on silica gel (Biotage 40M), eluting with EtOAc/hexanes (30% to 90%). The product was further purified by preparative biotage Reverse phase (C-18) (100 g), eluting with Acetonitrile/Water+0.1% formic acid (35% to 90%) to give the title compound. $^1$H NMR (500 MHz, DMSO-d$_6$) δ 8.28 (s, 2H), 6.67 (d, J=9.4 Hz, 2H), 4.67 (t, J=13.9 Hz, 2H), 4.18 (m, 4H), 4.06 (m, 211), 3.85 (t, J=7.8 Hz, 2H), 3.38 (s, 2H), 3.23 (s, 3H), 2.85 (m, 2H), 2.20 (m, 211), 2.03 (m, 1H), 1.75 (t, J=14.2 Hz, 2H), 1.51 (m, 114), 1.21-1.25 (m, 3H), 0.87 (m, 1H), 0.57 (m, 2H), −0.08 (m, 1H). LC/MS (m/z): 501.4 (M+H)$^+$. GPR119 Human EC50: 0.18 nM The Examples in Table 17 were synthesized according to the methods described in the prior examples (218 and 219) employing the appropriate reagents and solvents.

TABLE 17

| Example # | Chemical Structure | Observed Mass [M + H]$^+$ | GPR119 Human EC$_{50}$ (nM) |
|---|---|---|---|
| 220 | 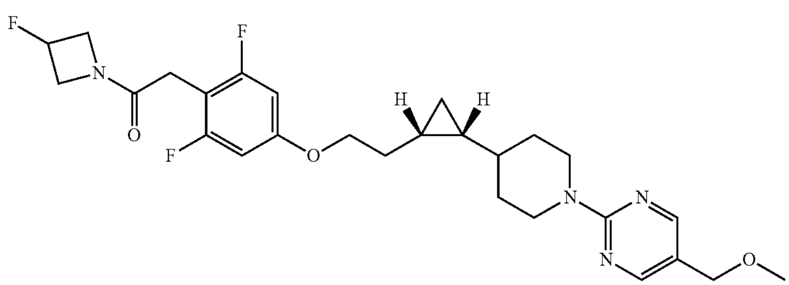 [SMILES: COCc1cnc(N2CCC([C@H]3C[C@H]3CCOc3cc(F)c(CC(=O)N4CC(F)C4)c(F)c3)CC2)nc1] | 519 | 0.14 |
| 221 | 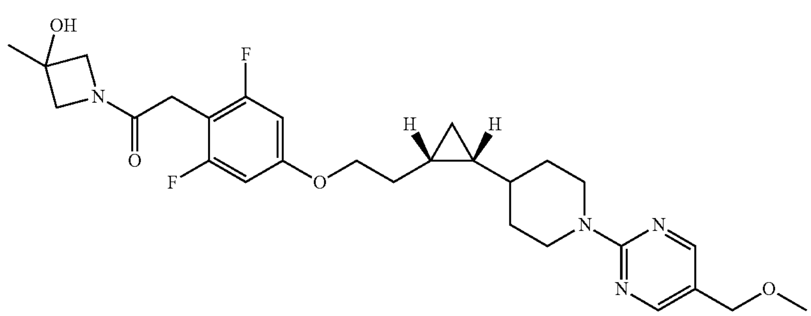 | 531 | 2.1 |

TABLE 17-continued
| Example # | Chemical Structure | Observed Mass [M + H]+ | GPR119 Human EC50 (nM) |
|---|---|---|---|
| 222 | 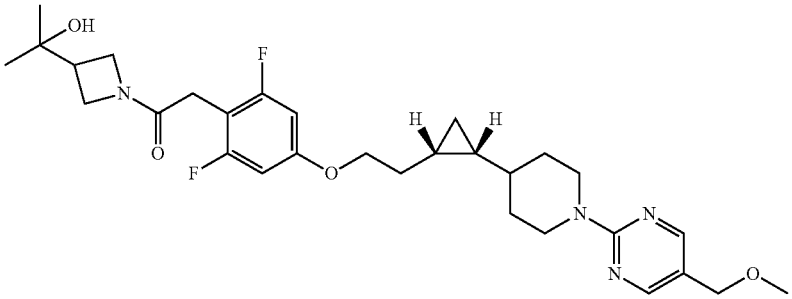 [SMILES: COCc1cnc(N2CCC([C@H]3C[C@H]3CCOc3cc(F)c(CC(=O)N4CC(C(C)(C)O)C4)c(F)c3)CC2)nc1] | 559 | 2.0 |
| 223 | 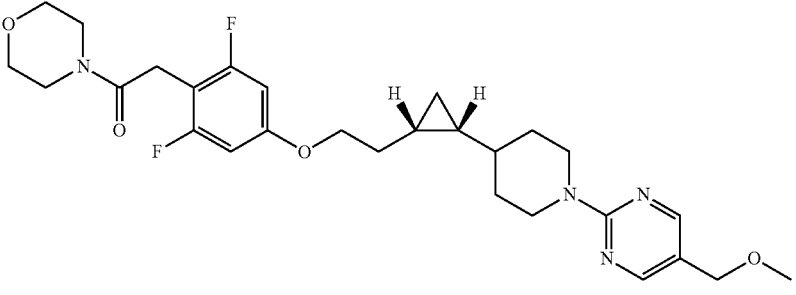 [SMILES: COCc1cnc(N2CCC([C@H]3C[C@H]3CCOc3cc(F)c(CC(=O)N4CCOCC4)c(F)c3)CC2)nc1] | 531 | 0.38 |
| 224 | 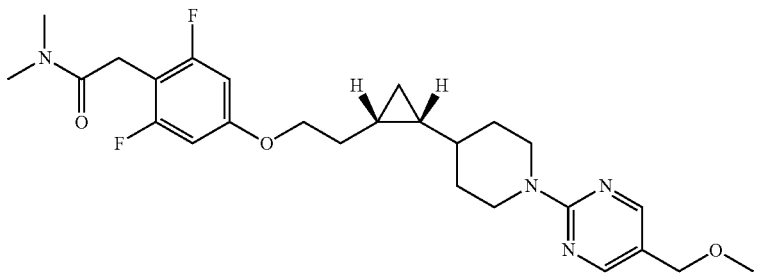 | 489 | 0.40 |
| 225 | 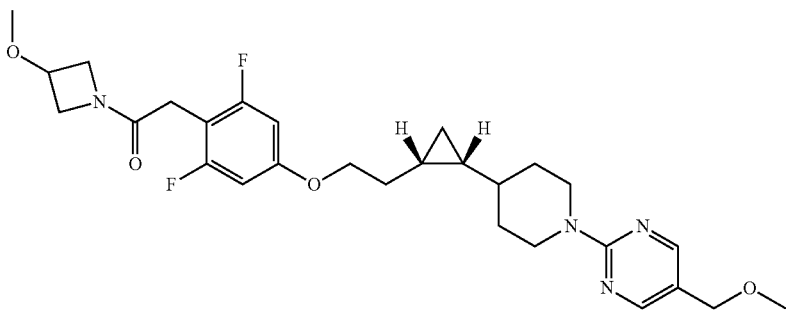 [SMILES: COCc1cnc(N2CCC([C@H]3C[C@H]3CCOc3cc(F)c(CC(=O)N4CC(OC)C4)c(F)c3)CC2)nc1] | 531 | 0.35 |
| 226 | 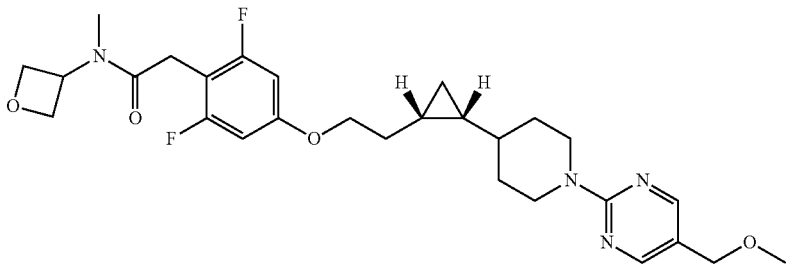 [SMILES: COCc1cnc(N2CCC([C@H]3C[C@H]3CCOc3cc(F)c(CC(=O)N(C)C4COC4)c(F)c3)CC2)nc1] | 531 | 0.41 |

TABLE 17-continued

| Example # | Chemical Structure | Observed Mass [M + H]+ | GPR119 Human EC50 (nM) |
|---|---|---|---|
| 227 | 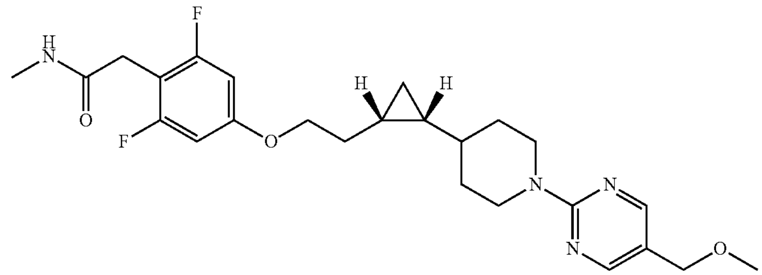 | 475 | 2.5 |
| 228 | 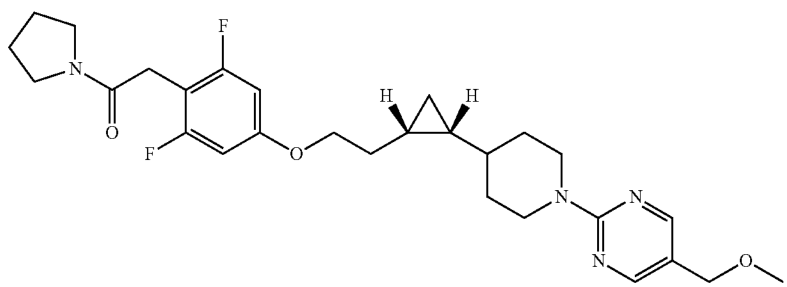 [SMILES: COCc1cnc(N2CCC([C@H]3C[C@H]3CCOc3cc(F)c(CC(=O)N4CCCC4)c(F)c3)CC2)nc1] | 515 | 0.20 |

Example 229

Preparation of 1-(azetidin-1-yl)-2-[4-(2-{(1S,2R)-2-[1-(5-ethoxypyrimidin-2-yl)piperidin-4-yl]cyclopropyl}ethoxy)-2,6-difluorophenyl]ethanone Step A: 2-{(1S,2R)-2-[1-(5-ethoxypyrimidin-2-yl)piperidin-4-yl]cyclopropyl}ethanol

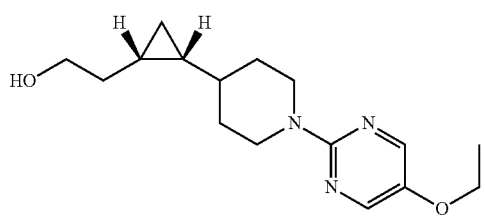 [SMILES: CCOc1cnc(N2CCC([C@H]3C[C@H]3CCO)CC2)nc1]

2-((1S,2R)-2-(piperidin-4-yl)cyclopropyl)ethanol (4.0 g, 23.6 mmol) and 2-chloro-5-ethoxypyrimidine (4.12 g, 26.0 mmol) were dissolved in 40 mL of DMA, to which was added cesium carbonate (10.0 g, 30.7 mmol). The reaction was heated at 105° C. overnight. The reaction mixture was cooled to rt and diluted with 40 mL of EtOAc and 40 mL of water. The layers were separated and the aqueous phase extracted with EtOAc (30 mL×2). The combined organic layers were dried over MgSO4, filtered, and concentrated under reduced pressure. The residue was purified by column chromatography on silica gel (KP-Sil 340 g SNAP column, Biotage system) eluting with 15-80% EtOAc:hexanes over 11 CV to afford the title compound. LC/MS (m/z): 292 (M+H)+.

Step B: 2-(4-{(1R,2S)-2-[2-(4-bromo-3,5-difluorophenoxy)ethyl]cyclopropyl}piperidin-1-yl)-5-ethoxypyrimidine

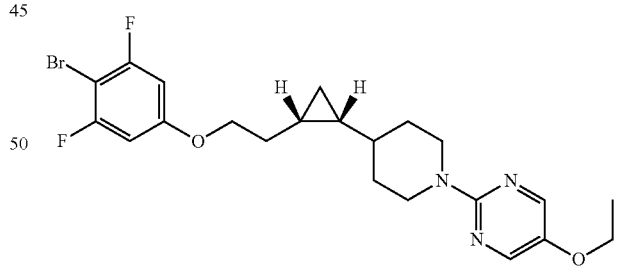

DIAD (2.45 mL, 12.6 mmol) was slowly added to a solution of 2-((1S,2R)-2-(1-(5-ethoxypyrimidin-2-yl)piperidin-4-yl)cyclopropyl)ethanol (2.45 g, 8.41 mmol), 4-bromo-3,5-difluorophenol (1.93 g, 9.25 mmol), and triphenylphosphine (3.31 g, 12.6 mmol) in DCM (30 mL) that had been cooled to 0° C. The ice bath was removed and the resulting mixture was stirred at rt for 3 hrs. The reaction mixture was diluted with DCM (20 mL) and washed with a 2 N NaOH solution (30 mL×1). The organic phase was dried over MgSO4, filtered, and concentrated under reduced pressure. The residue was purified by column chromatography on silica gel (KP-Sil 100 g SNAP column, Biotage system) eluting with 5-40% EtOAc:hexanes over 12 CV to afford the title compound. LC/MS (m/z): 482 (M+H)+.

Step C: tert-butyl [4-(2-{(1S,2R)-2-[1-(5-ethoxypyrimidin-2-yl)piperidin-4-yl]cyclopropyl}ethoxy)-2,6-difluorophenyl]acetate

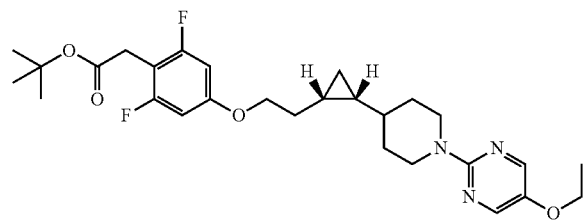 [SMILES: CCOc1cnc(N2CCC([C@H]3C[C@H]3CCOc3cc(F)c(CC(=O)OC(C)(C)C)c(F)c3)CC2)nc1]

A 0.5 M solution of 2-(tert-butyloxy)-2-oxoethylzinc chloride in Et₂O (43 mL, 21.2 mmol) was added to a mixture of 2-(4-((1R,2S)-2-(2-(4-bromo-3,5-difluorophenoxy)ethyl)cyclopropyl)piperidin-1-yl)-5-ethoxypyrimidine (3.4 g, 7.05 mmol), Pd₂(dba)₃ (0.484 g, 0.529 mmol), and X-PHOS (504 mg, 1.06 mmol) in anhydrous THF (10 mL). The mixture was stirred and heated at 65° C. overnight. The mixture was cooled to rt and filtered through celite, washing the filtercake with excess EtOAc. The volatiles were removed and the residue was purified by column chromatography on silica gel (KP-Sil 100 g SNAP column, Biotage system) eluting with 5-40% EtOAc:hexanes over 12 CV to afford the title compound. LC/MS (m/z): 518 (M+H)+.

Step D: [4-(2-{(1S,2R)-2-[1-(5-ethoxypyrimidin-2-yl)piperidin-4-yl]cyclopropyl}ethoxy)-2,6-difluorophenyl]acetic acid

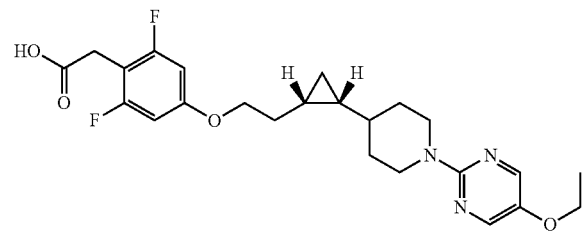 [SMILES: CCOc1cnc(N2CCC([C@H]3C[C@H]3CCOc3cc(F)c(CC(=O)O)c(F)c3)CC2)nc1]

A solution of 4 M HCl in dioxane (16.2 mL, 64.7 mmol) was added to a solution of tert-butyl 2-(4-(2-((1S,2R)-2-(1-(5-ethoxypyrimidin-2-yl)piperidin-4-yl)cyclopropyl)ethoxy)-2,6-difluorophenyl)acetate (3.35 g, 6.47 mmol) in DCM (16 mL). This mixture was stirred at 35° C. for 4 hrs. The mixture was concentrated under reduced pressure to afford the title compound. LC/MS (m/z): 462 (M+H)+.

Step E: 1-(azetidin-1-yl)-2-[4-(2-{(1S,2R)-2-[1-(5-ethoxypyrimidin-2-yl)piperidin-4-yl]cyclopropyl}ethoxy)-2,6-difluorophenyl]ethanone

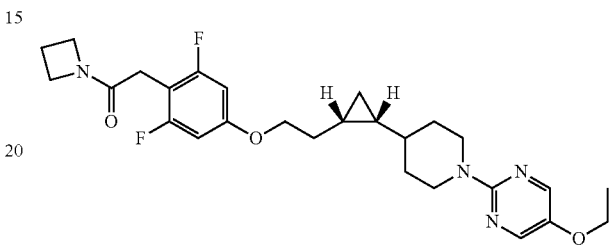

A solution of 2-(4-(2-((1S,2R)-2-(1-(5-ethoxypyrimidin-2-yl)piperidin-4-yl)cyclopropyl)ethoxy)-2,6-difluorophenyl)acetic acid (80 mg, 0.17 mmol), HOBT.H₂O (77 mg, 0.51 mmol), and EDC.HCl (97 mg, 0.51 mmol) dissolved in DCM (1 mL) was stirred for 30 min a rt. Azetidine (45.4 µL, 0.673 mmol) was added to this solution and the reaction aged at rt for 3 hrs. The mixture was diluted with DCM (1 mL) and the solution loaded directly onto 2×2000 micron silica preparative TLC plates (visualized using a UV lamp @ 254 nm) which were developed using 100% EtOAc as the solvent system. The band corresponding to the product (Rf=0.4 @ 100% EtOAc) was collected, washed with EtOAc, the filtrate collected and the volatiles removed in vacuo to afford the title compound. $^1$H NMR (500 MHz, CD₃CN) δ 8.07 (s, 2H), 6.59 (d, 2H), 4.58 (t, 2H), 4.22 (t, 2H), 4.08 (m, 2H), 4.01 (q, 2H), 3.92 (t, 2H), 3.37 (s, 2H), 2.80 (t, 2H), 2.26 (m, 2H), 2.08 (m, 1H), 1.80 (m, 2H), 1.55 (m, 1H), 1.35-1.26 (m, 5H), 1.11 (m, 1H), 0.90 (m, 1H), 0.61 (m, 2H), −0.07 (m, 1H). LC/MS (m/z): 501 (M+H)+, GPR119 Human EC₅₀: 0.14 nM.

The examples in Table 18 were synthesized according to the methods described in the prior example (229) employing the appropriate reagents and solvents.

TABLE 18

| Example # | Chemical Structure | Observed Mass [M + H]+ | GPR119 Human EC$_{50}$ (nM) |
|---|---|---|---|
| 230 | 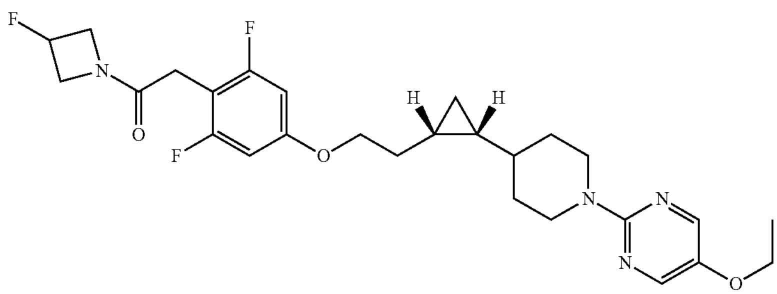 [SMILES: CCOc1cnc(N2CCC([C@H]3C[C@H]3CCOc3cc(F)c(CC(=O)N4CC(F)C4)c(F)c3)CC2)nc1] | 519 | 0.11 |

TABLE 18-continued

| Example # | Chemical Structure | Observed Mass [M + H]+ | GPR119 Human EC$_{50}$ (nM) |
|---|---|---|---|
| 231 | 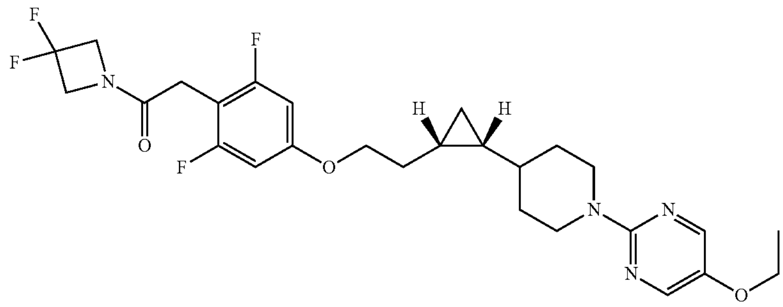 [SMILES: CCOc1cnc(N2CCC([C@H]3C[C@H]3CCOc3cc(F)c(CC(=O)N4CC(F)(F)C4)c(F)c3)CC2)nc1] | 537 | 0.13 |
| 232 | 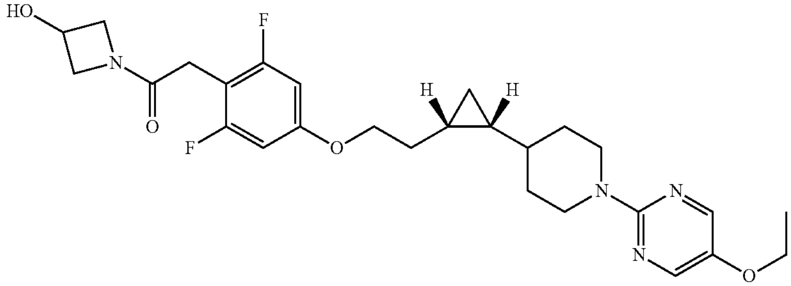 [SMILES: CCOc1cnc(N2CCC([C@H]3C[C@H]3CCOc3cc(F)c(CC(=O)N4CC(O)C4)c(F)c3)CC2)nc1] | 517 | 0.55 |
| 233 | 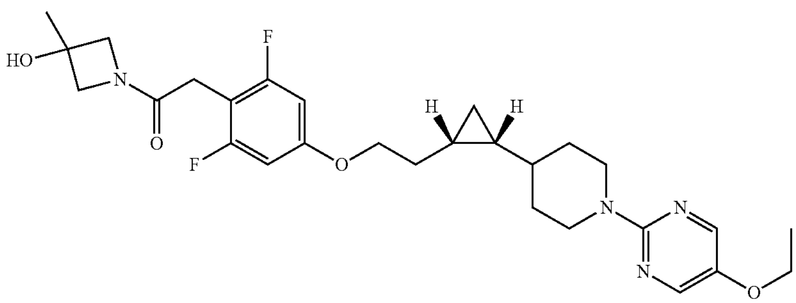 [SMILES: CCOc1cnc(N2CCC([C@H]3C[C@H]3CCOc3cc(F)c(CC(=O)N4CC(C)(O)C4)c(F)c3)CC2)nc1] | 531 | 0.66 |
| 234 | 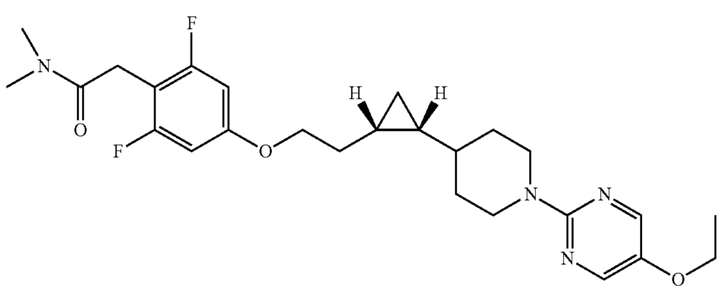 [SMILES: CCOc1cnc(N2CCC([C@H]3C[C@H]3CCOc3cc(F)c(CC(=O)N(C)C)c(F)c3)CC2)nc1] | 489 | 0.26 |
| 235 | 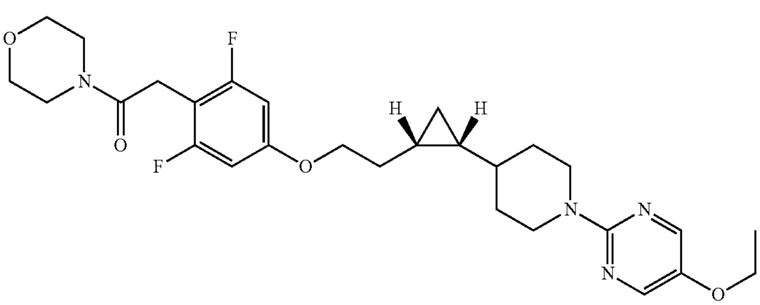 [SMILES: CCOc1cnc(N2CCC([C@H]3C[C@H]3CCOc3cc(F)c(CC(=O)N4CCOCC4)c(F)c3)CC2)nc1] | 531 | 0.26 |

TABLE 18-continued

| Example # | Chemical Structure | Observed Mass [M + H]+ | GPR119 Human EC50 (nM) |
|---|---|---|---|
| 236 | 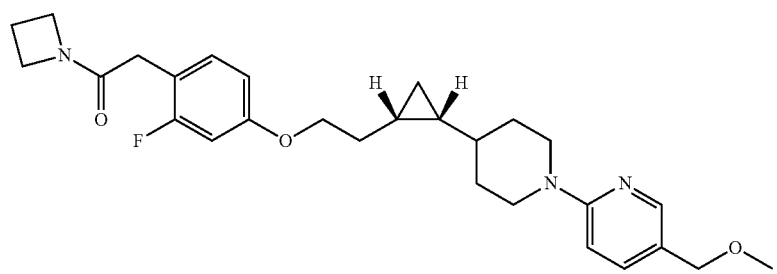 [SMILES: COCc1ccc(N2CCC([C@H]3C[C@H]3CCOc3ccc(CC(=O)N4CCC4)c(F)c3)CC2)nc1] | 531 | 0.12 |

Example 237

Preparation of 1-(azetidin-1-yl)-2-(2-fluoro-4-{2-[(1S,2R)-2-{1-[5-(methoxymethyl)pyridin-2-yl]piperidin-4-yl}cyclopropyl]ethoxy}phenyl)ethanone Step A: 6-{4-[(1R,2S)-2-(2-hydroxyethyl)cyclopropyl]piperidin-1-yl}pyridine-3-carbaldehyde

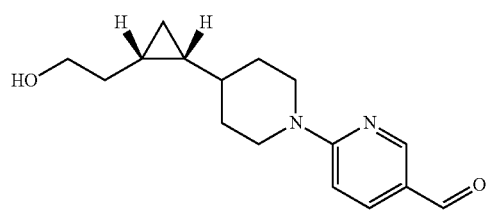 [SMILES: O=Cc1ccc(N2CCC([C@H]3C[C@H]3CCO)CC2)nc1]

In a 250 ml RBF the 6-chloropyridine-3-carbaldehyde (1.907 g, 13.47 mmol) and 2-[(1S,2R)-2-(piperidin-4-yl)cyclopropyl]ethanol (2.28 g, 13.47 mmol) were dissolved in DMF (13.47 ml). Cesium carbonate (13.17 g, 40.4 mmol) was added and the mixture stirred at RT overnight. The mixture was poured into 4:1 water:brine (200 ml), extracted with EtOAc (3×100 ml), the organic fractions combined, washed with brine, dried over $Na_2SO_4$, filtered and the volatiles removed in vacuo. The residue was purified by column chromatography on silica gel, Biotage 100M, using a gradient eluant of 0-100% EtOAc/hexanes to afford the title compound. LC/MS (m/z): 275 (M+H)+.

Step B: 6-{4-[(1R,2S)-2-(2-{[tert-butyl(dimethyl)silyl]oxy}ethyl)cyclopropyl]piperidin-1-yl}pyridine-3-carbaldehyde

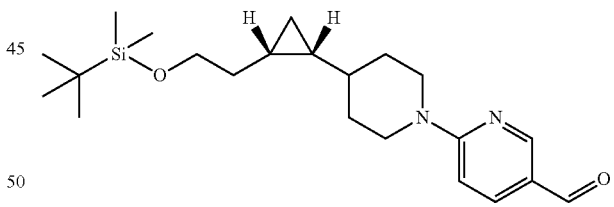

6-{4-[(1R,2S)-2-(2-hydroxyethyl)cyclopropyl]piperidin-1-yl}pyridine-3-carbaldehyde (1.5 g, 5.47 mmol) was dissolved in DMF (5.47 ml), and imidazole (0.558 g, 8.20 mmol) was added. The mixture was cooled to 0° C., TBDMS-Cl (0.989 g, 6.56 mmol) added and the mixture was allowed to warm to RT and stirred overnight. The mixture was diluted with 4:1 water:saturated sodium bicarbonate (100 ml), extracted with EtOAc (3×75 ml), the organic fractions combined, washed with brine, dried over $Na_2SO_4$, filtered and the volatiles removed in vac. The residue was purified by column chromatography on silica gel, Biotage 50 g, using a gradient eluant of 0-100% EtOAc/hexanes to afford the title compound. LC/MS (m/z): 389 (M+H)+.

Step C: (6-{4-[(1R,2S)-2-(2-{[tert-butyl(dimethyl)silyl]oxy}ethyl)cyclopropyl]piperidin-1-yl}pyridin-3-yl)methanol

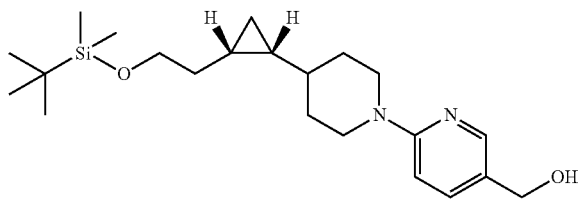 [SMILES: CC(C)(C)[Si](C)(C)OCC[C@@H]1C[C@@H]1C1CCN(c2ccc(CO)cn2)CC1]

6-{4-[(1R,2S)-2-(2-{[tert-butyl(dimethyl)silyl]oxy}ethyl)cyclopropyl]piperidin-1-yl}pyridine-3-carbaldehyde (1.75 g, 4.50 mmol) was placed in a 250 ml flask and dissolved in MeOH (11.26 ml). Sodium borohydride (0.170 g, 4.50 mmol) was added and the mixture stirred at RT for 1 hour. The mixture was concentrated, dissolved in EtOAc (200 ml) and washed with 1:1 brine:saturated sodium bicarbonate (200 ml). The layers were separated, the aqueous phase extracted with EtOAc (2×70 ml), the organic fractions combined, washed with brine, dried over sodium sulfate filtered, and concentrated under reduced pressure to afford the title compound. LC/MS (m/z): 391 (M+H)$^+$.

Step D: 2-{4-[(1R,2S)-2-(2-{[tert-butyl(dimethyl)silyl]oxy}ethyl)cyclopropyl]piperidin-1-yl}-5-(methoxymethyl)pyridine

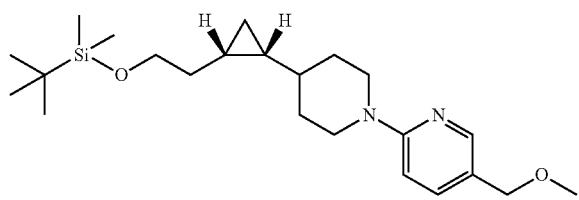 [SMILES: COCc1ccc(N2CCC([C@H]3C[C@H]3CCO[Si](C)(C)C(C)(C)C)CC2)nc1]

A solution of the (6-{4-[(1R,2S)-2-(2-{[tert-butyl(dimethyl)silyl]oxy}ethyl)cyclopropyl]piperidin-1-yl}pyridin-3-yl)methanol (0.3 g, 0.768 mmol) in THF (1.920 ml) was cooled at ice-bath temperature. A solution of NaHMDS (0.922 ml, 0.922 mmol) was added followed by addition of methyl iodide (0.067 ml, 1.075 mmol). The bath was removed and the resulting mixture stirred at room temperature for 2 hours. The mixture was diluted with 1N NaOH (50 ml), extracted with EtOAc (3×30 ml), the organic fractions combined, washed with brine, dried over sodium sulfate, filtered and the volatiles removed in vacuo. The residue was purified by column chromatography on silica gel, Biotage 25 g, using a gradient eluant of 0-30% EtOAc/hexanes to afford the title compound. LC/MS (m/z): 405 (M+H)$^+$.

Step E: 2-[(1S,2R)-2-{1-[5-(methoxymethyl)pyridin-2-yl]piperidin-4-yl}cyclopropyl]ethanol

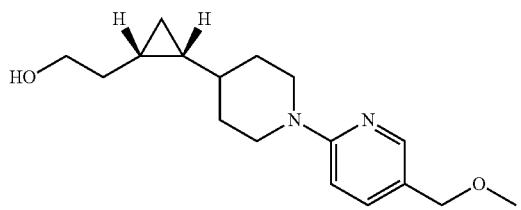 [SMILES: COCc1ccc(N2CCC([C@H]3C[C@H]3CCO)CC2)nc1]

The (6-{4-[(1R,2S)-2-(2-{[tert-butyl(dimethyl)silyl]oxy}ethyl)cyclopropyl]piperidin-1-yl}pyridin-3-yl)methanol (2.471 ml, 0.494 mmol) was dissolved in THF (1.236 ml) and TBAF (0.741 ml, 0.741 mmol) added. The mixture was stirred at room temperature for 1 hour. The mixture was diluted with 1N NaOH (50 ml), extracted with EtOAc (3×30 ml), the organic fractions combined, washed with brine, dried over sodium sulfate, filtered and the volatiles removed in vacuo. The residue was purified by column chromatography on silica gel, Biotage 25 g, using a gradient eluant of 0-100% EtOAc/hexanes to afford the title compound. LC/MS (m/z): 291 (M+H)$^+$.

Step F: 1-(azetidin-1-yl)-2-(2-fluoro-4-{2-[(1S,2R)-2-{1-[5-(methoxymethyl)pyridin-2-yl]piperidin-4-yl}cyclopropyl]ethoxy}phenyl)ethanone

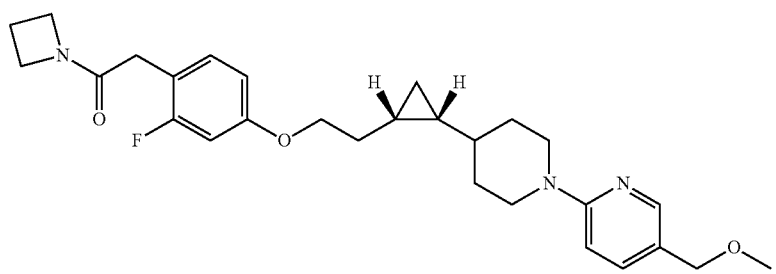 [SMILES: COCc1ccc(N2CCC([C@H]3C[C@H]3CCOc3ccc(CC(=O)N4CCC4)c(F)c3)CC2)nc1]

DIAD (38.2 μl, 0.196 mmol) was added to a stirred mixture of 1-(azetidin-1-yl)-2-(2-fluoro-4-hydroxyphenyl)ethanone (41.1 mg, 0.196 mmol), 2-[(1S,2R)-2-{1-[5-(methoxymethyl)pyridin-2-yl]piperidin-4-yl}cyclopropyl]ethanol (57 mg, 0.196 mmol), and triphenyl phosphine (51.5 mg, 0.196 mmol) in toluene (327 μl). The mixture was degassed (3×) and stirred at RT for 2 hours. The mixture was diluted with ethyl acetate (20 mL), washed with water (20 ml), the layers separated, the aqueous phase extracted with EtOAc (20 ml), the organic fractions combined, washed with brine (35 ml), dried over sodium sulfate, filtered and the volatiles removed in vac. The residue was purified by column chromatography on silica gel, Biotage 25 g, using a gradient eluant of 0-100% EtOAc/hexanes to afford the title compound. LC/MS (m/z): 482 (M+H)$^+$. GPR119 Human EC50: 0.94 nM Example 238

Preparation of 1-(azetidin-1-yl)-2-[4-(2-{(1S,2R)-2-[1-(5-ethylpyrimidin-2-yl)piperidin-4-yl]cyclopropyl}ethoxy)-2,6-difluorophenyl]ethanone

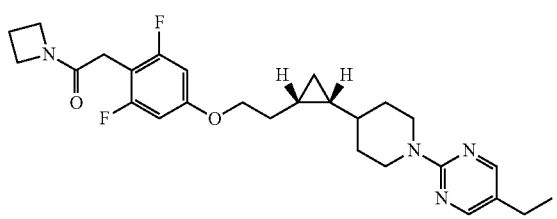 [SMILES: CCc1cnc(N2CCC([C@H]3C[C@H]3CCOc3cc(F)c(CC(=O)N4CCC4)c(F)c3)CC2)nc1]

Step A: 1-(azetidin-1-yl)-2-(2,6-difluoro-4-hydroxyphenyl)ethanone

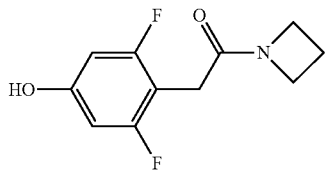 [SMILES: O=C(Cc1c(F)cc(O)cc1F)N1CCC1]

To a solution of (2,6-difluoro-4-hydroxyphenyl)acetic acid (0.98 g, 4.95 mmol) in 8 ml anhydrous DMF at RT was added azetidine (0.565 g, 9.89 mmol) and N,N-diisopropylethylamine (2.15 ml, 12.3 mmol). o-(7-Azabenzotriazol-1-yl)-N,N,N',N'-tetramethyluronium hexafluorophosphate (3.76 g, 9.89 mmol) was added to the solution and the reaction mixture was stirred at RT for 4 hrs. The solution was purified by preparative biotage Reverse phase (C-18) (50 g column), eluting with Acetonitrile/Water+0.1% formic acid (35% to 100%), to afford the title compound. LC/MS (m/z) 242.3 (M+15)$^+$.

Step B: 1-(azetidin-1-yl)-2-[4-(2-{(1S,2R)-2-[1-(5-ethylpyrimidin-2-yl)piperidin-4-yl]cyclopropyl}ethoxy)-2,6-difluorophenyl]ethanone

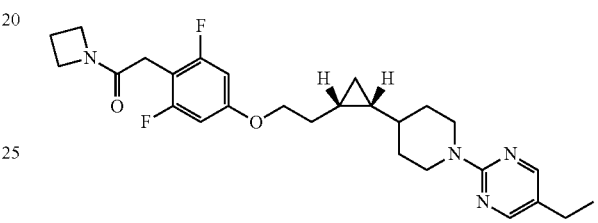

To a solution of 1-(azetidin-1-yl)-2-(2,6-difluoro-4-hydroxyphenyl)ethanone (50.0 mg, 0.128 mmol) in 5 ml anhydrous dichloromethane at RT was added a solution of 2-{(1S,2R)-2-[1-(5-ethylpyrimidin-2-yl)piperidin-4-yl]cyclopropyl}ethanol (38.0 mg, 0.182 mmol), triphenylphosphine (polymer-bound, 143 mg, 0.412 mmol), and di-tert-butyl azodicarboxylate (84.0 mg, 0.363 mmol). The reaction mixture was stirred at RT for 3 hours. The mixture was filtered through Celite and concentrated under reduced pressure. The residue was filtered and purified by reverse-phase HPLC (SunFire Prep C18 OBD 5 um 19×100 mm column; 35-100% acetonitrile in 0.1% formic acid in water gradient), to give the title compound. LC/MS (m/z) 485.3 (M+H)$^+$.

The Example in Table 19 was synthesized according to the methods described in the prior example (238) employing the appropriate reagents and solvents.

TABLE 19

| Example # | Chemical Structure | Observed Mass [M + H]$^+$ | GPR119 Human EC$_{50}$ (nM) |
|---|---|---|---|
| 239 | 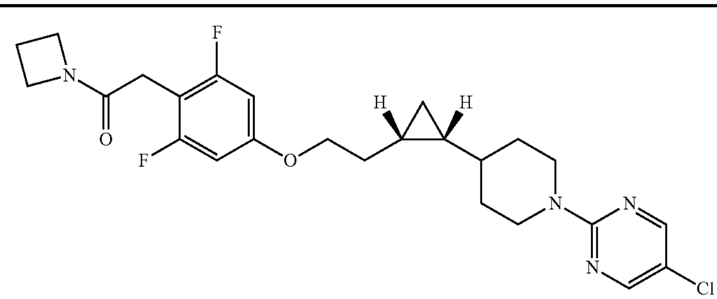 | 485 | 0.090 |

Example 240

2-{2,6-Difluoro-4-[2-((1R,2R)-2-{1-[5-(methoxymethyl) pyrimidin-2-yl]piperidin-4-yl}cyclopropyl)ethoxy] phenyl}ethanol

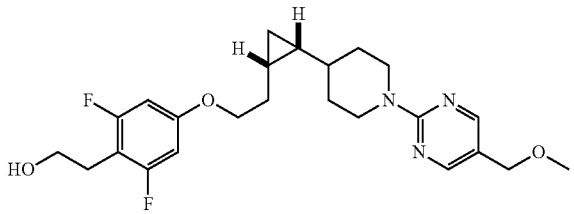 [SMILES: COCc1cnc(N2CCC([C@H]3C[C@H]3CCOc3cc(F)c(CCO)c(F)c3)CC2)nc1]

To a solution of {2,6-difluoro-4-[2-((1R,2R)-2-{1-[5-(methoxymethyl)pyrimidin-2-yl]piperidin-4-yl}cyclopropyl)ethoxy]phenyl}acetic acid (72.0 mg, 0.125 mmol) in 1 ml anhydrous tetrahydrofuran at 0° C. was added 1 M borane-tetrahydrofuran complex (0.375 ml, 0.375 mmol) dropwise. The reaction mixture was stirred at 50° C. for an hour. The mixture was diluted by addition of 1 ml of methanol, concentrated under reduced pressure, and the residue purified by reverse-phase HPLC (SunFire Prep C18 OBD 5 um 19×100 mm column; 25-95% acetonitrile in 0.1% formic acid in water gradient) to afford the title compound. LC/MS (m/z): 448.4 (M+H)$^+$. Human EC50: 7.2 nM

Example 241

Preparation of 1-(azetidin-1-yl)-2-[6-(2-{(1S,2R)-2-[1-(5-ethylpyrimidin-2-yl)piperidin-4-yl] cyclopropyl}ethoxy)pyridin-3-yl)ethanone

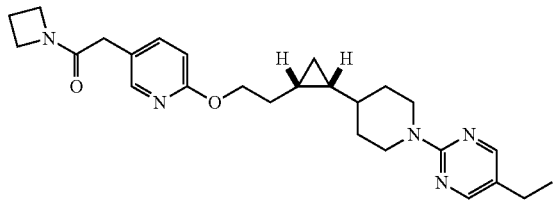 [SMILES: CCc1cnc(N2CCC([C@H]3C[C@H]3CCOc3ccc(CC(=O)N4CCC4)cn3)CC2)nc1]

2-((1S,2R)-2-(1-(5-Ethylpyrimidin-2-yl)piperidin-4-yl) cyclopropyl)ethanol (40 mg, 0.145 mmol) was dissolved in DMF (2 ml) at RT under N$_2$ and potassium tert-butoxide (0.218 ml, 0.218 mmol) was added. The mixture was stirred at RT for 5 min and 1-(azetidin-1-yl)-2-(6-chloropyridin-3-yl) ethanone (36.7 mg, 0.174 mmol) was added. The mixture was microwaved at 100° C. for 30 min. and 150° C. for 30 min. The mixture was diluted with CH$_3$CN, filtered and purified by reverse-phase HPLC (SunFire Prep C18 OBD Sum 19×100 mm column; 25-95% acetonitrile in 0.1% formic acid in water gradient) to afford the title compound. $^1$H NMR (500 MHz, CDCl$_3$) δ 8.10 (s, 2H), 8.01 (s, 1H), 7.61 (d, 1H), 6.75 (d, 1H), 4.70 (m, 2H), 4.39 (t, 2H), 4.21 (t, 2H), 4.03 (t, 2H), 3.38 (s, 2H), 2.85 (m, 2H), 2.45 (m, 2H), 2.31 (m, 2H), 2.18 (m, 1H), 1.84 (m, 2H), 1.58 (m, 1H), 1.40 (m, 2H), 1.10-1.20 (m, 5H), 0.95 (m, 2H), 0.68 (m, 2H), −0.40 (m, 1H). LC/MS (m/z): 450 (M+H)$^+$, GPR119 Human EC$_{50}$: 7.4 nM.

The Example in Table 20 was synthesized according to the methods described in the prior example (241) employing the appropriate reagents and solvents.

TABLE 20

| Example # | Chemical Structure | Observed Mass [M + H]$^+$ | GPR119 Human EC$_{50}$ (nM) |
|---|---|---|---|
| 242 | 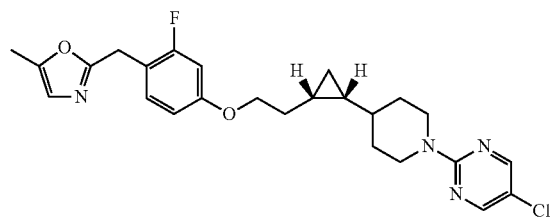 [SMILES: Cc1cnc(Cc2ccc(OCC[C@@H]3C[C@@H]3C3CCN(c4ncc(Cl)cn4)CC3)cc2F)o1] | 456 | 9.4 |

Example 243

Preparation of 5-chloro-2-{4-[(1R,2S)-2-(2-{3-fluoro-4-[(5-methyl-1,3-oxazol-2-yl)methyl] phenoxy}ethyl)cyclopropyl]piperidin-1-yl}pyrimidine

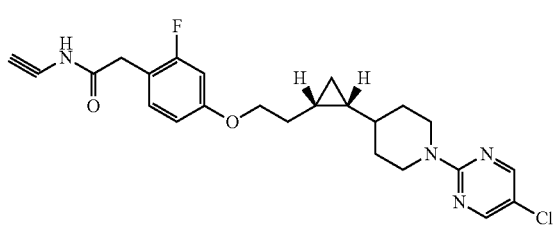 [SMILES: C#CNC(=O)Cc1ccc(OCC[C@@H]2C[C@@H]2C2CCN(c3ncc(Cl)cn3)CC2)cc1F]

Step A: 2-[4-(2-{(1S,2R)-2-[1-(5-chloropyrimidin-2-yl)piperidin-4-yl]cyclopropyl}ethoxy)-2-fluorophenyl]-N-ethynylacetamide To a solution of [4-(2-{(1S,2R)-2-[1-(5-chloropyrimidin-2-yl)piperidin-4-yl]cyclopropyl}ethoxy)-2-fluorophenyl]

acetic acid (80.0 mg, 0.184 mmol) and acetylenamine (11.68 mg, 0.190) in anhydrous DMF (1 mL) was added HOBt (28.2 mg, 0.184 mmol) followed by EDC (70.7 mg, 0.368 mmol) and the mixture was stirred at room temperature under nitrogen atmosphere for 16 hours. The mixture was diluted with water and ethyl acetate (5 mL). The layers were separated, the aqueous phase extracted with EtOAc (5 ml), the organic fractions combined, dried over sodium sulfate, filtered and concentrated in vacuo. The residue was purified via preparative TLC plate (1000 μM) using 40% ethyl acetate in hexane. The band containing product was removed from the plate and the silica washed with EtOAc. The filtrate was collected and the volatiles removed in vacuo to afford the title compound. HPLC/MS; 1.49 min (2 minute run), 471 (M+H)$^+$.

Step B: 5-chloro-2-{4-[(1R,2S)-2-(2-{3-fluoro-4-[(5-methyl-1,3-oxazol-2-yl)methyl]phenoxy}ethyl)cyclopropyl]piperidin-1-yl}pyrimidine

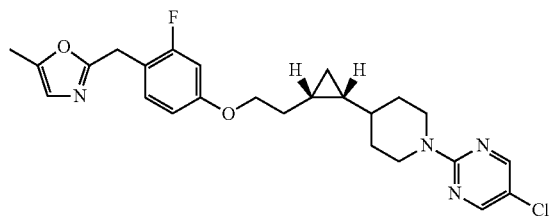 [SMILES: Cc1cnc(Cc2ccc(OCC[C@@H]3C[C@@H]3C3CCN(c4ncc(Cl)cn4)CC3)cc2F)o1]

To a solution of 2-[4-(2-{(1S,2R)-2-[1-(5-chloropyrimidin-2-yl)piperidin-4-yl]cyclopropyl}ethoxy)-2-fluorophenyl]-N-ethynylacetamide (20 mg, 0.042 mmol) in a 10:1 solution of DCM:acetonitrile (0.55 mL) was added gold chloride (~1.3 mg, 0.004 mmol) and the resulting mixture stirred at room temperature for 2 days. The mixture was concentrated under reduced pressure. The material was purified using preparative RP-HPLC eluting with a gradient of 10-90% acetonitrile in water with 0.05% TFA buffer to afford the title compound. HPLC/MS; 1.52 min (2 minute run), 471 (M+H)$^+$. GPR119 Human EC50: 2.5 nM Example 244

Preparation of 5-chloro-2-{4-[(1R,2S)-2-(2-{3-fluoro-4-[(5-methyl-1,3,4-oxadizol-2-yl)methyl]phenoxy}ethyl)cyclopropyl]piperidin-1-yl}pyrimidine

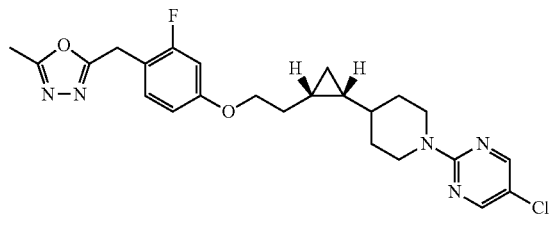 [SMILES: Cc1nnc(Cc2ccc(OCC[C@@H]3C[C@@H]3C3CCN(c4ncc(Cl)cn4)CC3)cc2F)o1]

Step A: 2-[4-(2-{(1S,2R)-2-[1-(5-chloropyrimidin-2-yl)piperidin-4-yl]cyclopropyl}ethoxy)-2-fluorophenyl]-acetohydrazide

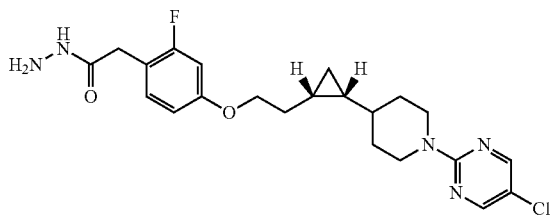 [SMILES: NNC(=O)Cc1ccc(OCC[C@@H]2C[C@@H]2C2CCN(c3ncc(Cl)cn3)CC2)cc1F]

A solution of [4-(2-{(1S,2R)-2-[1-(5-chloropyrimidin-2-yl)piperidin-4-yl]cyclopropyl}ethoxy)-2-fluorophenyl]acetic acid (500 mg, 1.152 mmol) in 5 mL of THF cooled to −10° C. and TEA (0.177 mL, 1.268 mmol) was added. Methyl chloroformate (0.098 mL, 1.268 mmol) was added and the mixture stirred for 30 minutes at −10° C. The mixture was filtered and the filtercake washed with 10 mL THF. The filtrate was collected and concentrated under reduced pressure. The residue (265 mg, 0.539 mmol) was dissolved in 1 mL of DMF and hydrazine monohydrate (0.052 mL, 1.077 mmol) added. The mixture was stirred overnight at room temperature. The mixture was diluted with ethyl acetate (3 mL) and washed with water (2 mL) and brine (2 mL). The organics fractions were combined, dried over sodium sulfate, filtered, and concentrated under reduced pressure. The residue was purified using preparative TLC (1000 μM, silica gel) developing with 5% methanol in DCM. The band containing the product was collected and the silica washed with 10% methanol in DCM to elute the product. The solution was concentrated under reduced pressure to afford the title compound. HPLC/MS; 1.22 min(2 minute run), 448 (M+H)$^+$.

Step B: 5-chloro-2-{4-[(1R,2S)-2-(2-{3-fluoro-4-[(5-methyl-1,3,4-oxadizol-2-yl)methyl]phenoxy}ethyl)cyclopropyl]piperidin-1-yl}pyrimidine

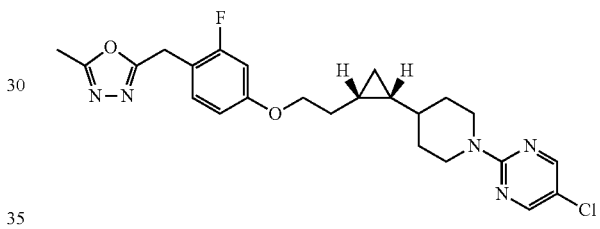

2-[4-(2-{(1S,2R)-2-[1-(5-chloropyrimidin-2-yl)piperidin-4-yl]cyclopropyl}ethoxy)-2-fluorophenyl]acetohydrazide (25 mg, 0.056 mmol) was taken up in 1 mL of trimethyl orthoacetate. The solution was placed under a nitrogen atmosphere and heated to reflux for overnight. The mixture was cooled to room temperature and concentrated under reduced pressure. The residue was purified by Mass directed RP-HPLC eluting with a gradient of 10-90% acetonitrile in water with 0.05% TFA buffer to afford the title compound. HPLC/MS; 1.39 min (2 minute run), 472 (M+H)$^+$. GPR119 Human EC50: 5.1 nM Example 245

Preparation of 5-chloro-2-{4-[(1R,2S)-2-(2-{3-fluoro-4-[(1,3,4-oxadizol-2-yl)methyl]phenoxy}ethyl)cyclopropyl]piperidin-1-yl}pyrimidine

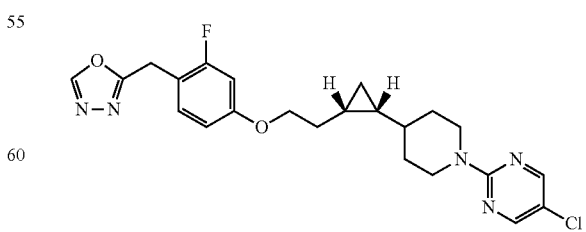

2-[4-(2-{(1S,2R)-2-[1(5-chloropyrimidin-2-yl)piperidin-4-yl]cyclopropyl}ethoxy)-2-fluorophenyl]-acetohydrazide (25 mg, 0.056 mmol) was dissolved in 1 mL of trimethyl orthoacetate. The solution placed under a nitrogen atmo sphere and heated to reflux overnight. The mixture was cooled to room temperature and concentrated under reduced pressure. The residue was purified by Mass directed RP-HPLC eluting with a gradient of 10-90% acetonitrile in water with 0.05% TFA buffer to afford the title compound. HPLC/MS; 2.58 min (4 minute run), 458 (M+H)+. GPR119 Human EC50: 4.1 nM The Examples in Table 22 were synthesized according to the methods described in the prior examples employing the appropriate reagents and solvents.

TABLE 22

| Example # | Chemical Structure | Observed Mass [M + H]+ | GPR119 Human EC$_{50}$ (nM) |
|---|---|---|---|
| 246 | 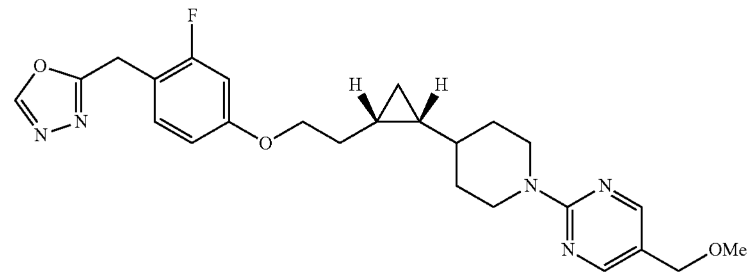 [SMILES: COCc1cnc(N2CCC([C@H]3C[C@H]3CCOc3ccc(Cc4nnco4)c(F)c3)CC2)nc1] | 468 | 7.7 |
| 247 | 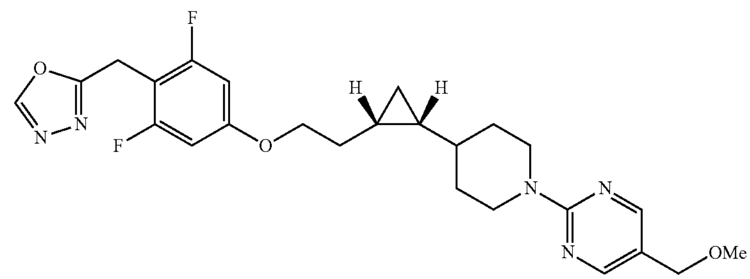 [SMILES: COCc1cnc(N2CCC([C@H]3C[C@H]3CCOc3cc(F)c(Cc4nnco4)c(F)c3)CC2)nc1] | 486 | 6.7 |

Example 248

Preparation of 2-[4-((1R,2S)-2-{2-[3-fluoro-4-(1,3,4-thiadiazol-2-ylmethyl)phenoxy]ethyl}cyclopropyl)piperidin-1-yl]-5-(methoxymethyl)pyrimidine

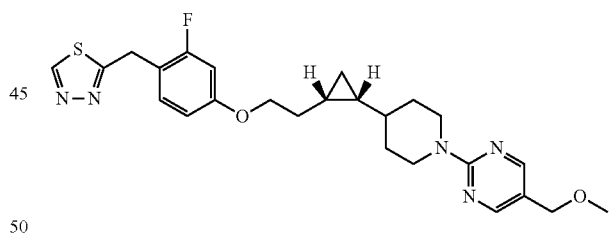

Step A: 2-[2-fluoro-4-(2-[(1S,2R)-2-{1-[5-(methoxymethyl)pyrimidine-2-yl]piperidin-4-yl]cyclopropyl}ethoxy)phenyl]acetohydrazide

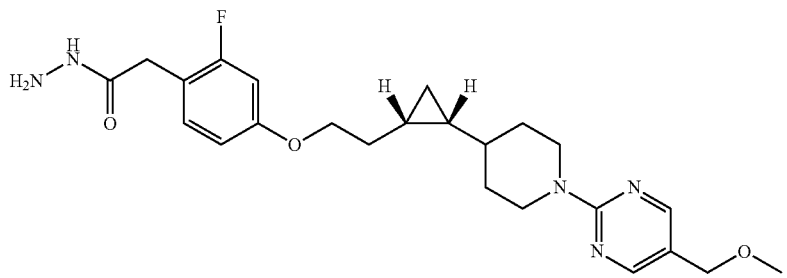 [SMILES: COCc1cnc(N2CCC([C@H]3C[C@H]3CCOc3ccc(CC(=O)NN)c(F)c3)CC2)nc1]

A solution [2-fluoro-4-(2-{(1S,2R)-2-{1-[5-(methoxymethyl)pyrimidin-2-yl]piperidin-4-yl}cyclopropyl}ethoxy)phenyl]acetic acid (500 mg, 1.152 mmol) in 5 mL of THF was cooled to −10° C. TEA (0.177 mL, 1.268 mmol) and methyl chloroformate (0.098 mL, 1.268 mmol) were added and the mixture stirred for 30 minutes at −10° C. The precipitate was filtered and the filtercake washed with 10 mL of THF. The filtrate was collected, concentrated under reduced pressure. The residue (265 mg, 0.539 mmol) was dissolved in 1 mL of DMF and hydrazine monohydrate (0.052 mL, 1.077 mmol) added. The resulting mixture was stirred overnight at room temperature, diluted with ethyl acetate (3 mL), washed with water (2 mL), and brine (2 mL). The organic fractions were dried over sodium sulfate, filtered, and concentrated under reduced pressure. The residue was purified via preparative TLC (1000 μM, silica gel) developing with 5% methanol in DCM. The band containing the product was collected and the silica washed with 10% methanol in DCM. The filtrate was collected and concentrated under reduced pressure to afford the title compound. HPLC/MS; 1.31 min(2 minute run), 458 (M+H)+.

Step B: 2-[4-((1R,2S)-2-{2-[3-fluoro-4-(1,3,4-thiadiazol-2-ylmethyl)phenoxy]ethyl}cyclopropyl)piperidin-1-yl]-5-(methoxymethyl)pyrimidine

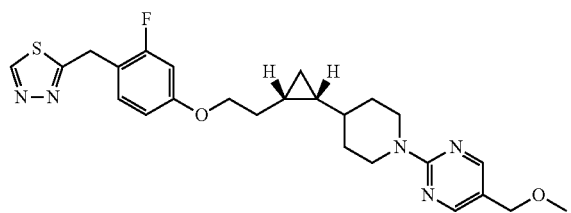 [SMILES: COCc1cnc(N2CCC([C@H]3C[C@H]3CCOc3ccc(Cc4nncs4)c(F)c3)CC2)nc1]

2-[2-fluoro-4-(2-{(1S,2R)-2-{1-[5-(methoxymethyl)pyrimidine-2-yl]piperidin-4-yl]cyclopropyl}ethoxy)phenyl]acetohydrazide (46 mg, 0.10 mmol) was dissolved in formic acid (1 mL) and the solution stirred at room temperature overnight. The mixture was concentrated under reduced pressure. The residue was dissolved in anhydrous dioxane (1 mL) and Lawesson's Reagent (50 mg, 0.13 mmol) added and the mixture stirred at 100° C. for 3 hours. The mixture was diluted with ethyl acetate (10 mL) and washed with water (5 mL). The aqueous fraction was extracted with ethyl acetate (2×5 mL). The organic fractions were combined, washed with brine, dried over sodium sulfate and filtered. The filtrate was concentrated under reduced pressure. The residue was purified using preparative TLC (2 plates, 1000 μM) developing with 50% ethyl acetate in hexane. The bands containing the product were removed, the silica gel washed with 100% ethyl acetate. The filtrate was collected and concentrated under reduced pressure. The sample was purified using an HP mass-directed RP-HPLC using a gradient eluant of 10-90% acetonitrile in water with 0.05% TFA as buffer to afford the title compound. HPLC/MS; 1.67 min (2 minute run), 484 (M+H)+. GPR119 Human EC$_{50}$: 4.2 nM Example 249

Preparation of 1-(azetidin-1-yl)-2-[4-(2-{(1S,2R)-2-[1-(5-ethylpyrimidin-2-yl)piperidin-4-yl]cyclopropyl}ethoxy)-3-fluorophenyl]ethanone

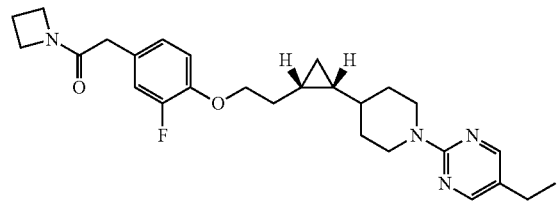 [SMILES: CCc1cnc(N2CCC([C@H]3C[C@H]3CCOc3ccc(CC(=O)N4CCC4)cc3F)CC2)nc1]

Step A: 1-(azetidin-1-yl)-2-(3-fluoro-4-hydroxyphenyl)ethanone

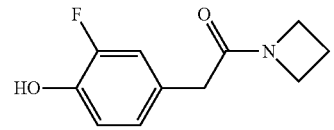 [SMILES: O=C(Cc1ccc(O)c(F)c1)N1CCC1]

To a solution of (3-fluoro-4-methoxyphenyl)acetic acid (0.94 g, 5.52 mmol) in 8 ml anhydrous DMF at RT was added azetidine (0.379 g, 6.63 mmol) and N,N-diisopropylethylamine (2.89 ml, 16.6 mmol). EDC (1.59 g, 8.29 mmol) was and the mixture stirred at RT for 4 hrs. The residue was purified by reverse-phase HPLC (SunFire Prep C18 OBD 5 um 19×100 mm column; 10-100% acetonitrile in 0.1% formic acid in water gradient), to give the title compound. LC/MS (m/z) 210.2 (M+15)+.

Step B: 1-(azetidin-1-yl)-2-[4-(2-{(1S,2R)-2-[1-(5-ethylpyrimidin-2-yl)piperidin-4-yl]cyclopropyl}ethoxy)-3-fluorophenyl]ethanone

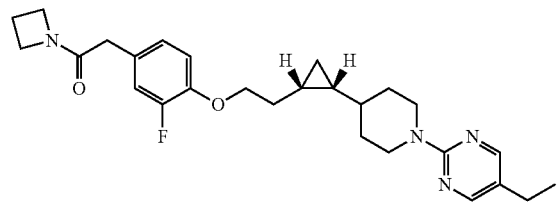 [SMILES: CCc1cnc(N2CCC([C@H]3C[C@H]3CCOc3ccc(CC(=O)N4CCC4)cc3F)CC2)nc1]

To a solution of 1-(azetidin-1-yl)-2-(3-fluoro-4-hydroxyphenyl)ethanone (65.0 mg, 0.236 mmol) in 5 ml anhydrous dichloromethane at RT was added a solution of 2-{(1S,2R)-2-[1-(5-ethylpyrimidin-2-yl)piperidin-4-yl]cyclopropyl}ethanol (59.0 mg, 0.283 mmol), triphenylphosphine (polymer-bound, 186 mg, 0.534 mmol), and di-tert-butyl azodicarboxylate (109 mg, 0.472 mmol). The reaction mixture as stirred at RT for 3 hours. The mixture was filtered by Celite and concentrated. The residue was filtered and purified by reverse-phase HPLC (SunFire Prep C18 OBD 5 um 19×100 mm column; 35-100% acetonitrile in 0.1% formic acid in water gradient), to give the title compound. LC/MS (m/z) 467.3 (M+H)+.

The Example in Table 15 was synthesized according to the methods described in the prior examples employing the appropriate reagents and solvents.

TABLE 15

| Example # | Chemical Structure | Observed Mass [M + H]$^+$ | GPR119 Human EC$_{50}$ (nM) |
|---|---|---|---|
| 250 | 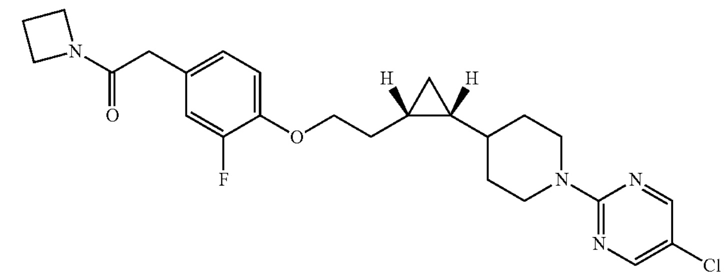 [SMILES: O=C(Cc1ccc(OCC[C@@H]2C[C@@H]2C2CCN(c3ncc(Cl)cn3)CC2)c(F)c1)N1CCC1] | 473 | 2.2 |
| 251 | 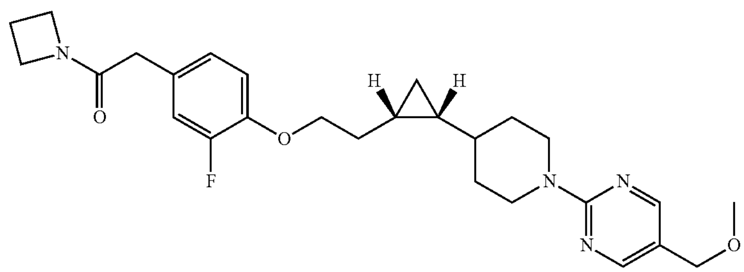 [SMILES: COCc1cnc(N2CCC([C@H]3C[C@H]3CCOc3ccc(CC(=O)N4CCC4)cc3F)CC2)nc1] | 483 | 5.5 |

Example of a Pharmaceutical Formulation

As a specific embodiment of an oral composition of a compound of the present invention, 50 mg of any of the examples is formulated with sufficient finely divided lactose to provide a total amount of 580 to 590 mg to fill a size 0 hard gelatin capsule.

While the invention has been described and illustrated in reference to specific embodiments thereof, various changes, modifications, and substitutions can be made therein without departing from the invention. For example, alternative effective dosages may be applicable, based upon the responsiveness of the patient being treated. Likewise, the pharmacologic response may vary depending upon the particular active compound selected, formulation and mode of administration. All such variations are included within the present invention.

What is claimed is:
1. A compound represented by the formula:

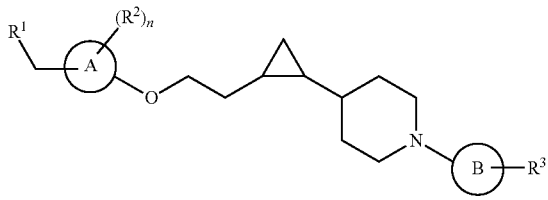

I or a pharmaceutically acceptable salt thereof, wherein:
Ring A is a 6-membered heteroaryl containing 1-3 N, or phenyl;
ring B is a 6-membered heteroaryl containing 1-3 N;
$R^1$ is selected from the group consisting of
(1) 5- or 6-membered heteroaryl containing 1-4 O, S, or N, optionally substituted by $C_{1-3}$alkyl,
(2) 3-8 membered heterocyclyl containing 1-3 O, S, or N,
(3) $C_{1-3}$alkyl-OH,
(4) $C(O)_2C_{1-3}$alkyl, and
(5) $C(O)NR^4R^5$;
each $R^2$ is selected from the group consisting of
(1) $C_{1-3}$alkyl,
(2) $C_{1-3}$alkoxy,
(3) halo$C_{1-3}$alkyl,
(4) halo$C_{1-3}$alkoxy,
(5) halo, and
(6) cyano;
$R^3$ is selected from the group consisting of
(1) CN,
(2) halo,
(3) —$C_{1-6}$alkyl,
(4) -halo$C_{1-6}$alkyl,
(5) —$C_{1-6}$alkoxy,
(6) -halo$C_{1-6}$alkoxy,
(7) —$C_{1-6}$alkyl-OH,
(8) —$C_{1-3}$alkyl-O—$C_{1-3}$alkyl, and
(9) —$C_{1-3}$alkyl-S—$C_{1-3}$alkyl;
$R^4$ and $R^5$ are independently selected from the group consisting of
(1) hydrogen,
(2) hydroxy,
(3) $C_{1-6}$alkyl,
(4) $C_{1-6}$alkyl-OH,
(5) $C_{1-6}$alkyl-O—$C_{1-3}$alkyl,
(6) halo$C_{1-6}$alkyl,
(7) $C_{1-6}$alkoxy,
(8) $C_{3-6}$cycloalkyl,
(9) $C_{1-3}$alkyl-$C_{3-6}$cycloalkyl, wherein the alkyl group is optionally substituted by hydroxy, or 1-3 fluoro,
(10) $C_{1-3}$alkyl($C_{3-6}$cycloalkyl)$_2$,

(11) $C_{1-3}$alkyl-$C_{3-5}$heterocyclyl containing 1-3 N, O, or S, wherein the heterocyclyl is optionally substituted by 1-2 oxo,
(12) $C_{3-5}$heterocyclyl containing 1-3 N, O or S, wherein the heterocyclyl is optionally substituted by 1-2 oxo,
(13) $C_{1-3}$alkyl-C(O)NH$_2$,
(14) $C_{1-3}$alkyl-S(O)$_2$C$_{1-3}$alkyl,
(15) $C_{1-3}$alkyl-C(O)$_2$C$_{1-3}$alkyl,
(16) C(O)C$_{1-6}$alkyl,
(17) C(O)C$_{3-6}$cycloalkyl,
(18) S(O)$_2$C$_{1-6}$alkyl, and
(19) S(O)$_2$C$_{3-6}$cycloalkyl,
or $R^4$ and $R^5$ are linked together with the nitrogen to which they are both attached to form a 3-9 membered monocyclic or bicyclic heterocyclic ring, comprising C, O, N, or S ring atoms, wherein the heterocyclic ring is optionally substituted with 1-3 $R^6$;
each $R^6$ is selected from the group consisting of:
(1) $C_{1-3}$alkyl,
(2) halo$C_{1-3}$alkyl,
(3) $C_{1-3}$alkoxy,
(4) $C_{1-3}$alkyl-OH,
(5) $C_{1-3}$alkyl-O—$C_{1-3}$alkyl,
(6) halo,
(7) hydroxy,
(8) oxo,
(9) C(O)$_2$C$_{1-3}$alkyl,
(10) C(O)NH$_2$,
(11) C(O)N(H)C$_{1-6}$alkyl,
(12) C(O)C$_{3-6}$cycloalkyl,
(13) $C_{3-6}$cycloalkyl,
(14) $C_{1-3}$alkyl-phenyl,
(15) phenyl, and
(16) 5- or 6-membered heteroaryl, containing 1-3 N, O, or S; and
n is 0, 1, 2 or 3.

2. The compound of claim 1, wherein ring A is pyridinyl, pyrimidinyl, pyridazinyl, pyrazinyl, triazinyl, or phenyl, or a pharmaceutically acceptable salt thereof.

3. The compound of claim 2, wherein ring A is pyridinyl, pyrimidinyl, or phenyl, or a pharmaceutically acceptable salt thereof.

4. The compound of claim 3, wherein ring A is phenyl, or a pharmaceutically acceptable salt thereof.

5. The compound of claim 1, wherein ring B is pyridinyl, pyrimidinyl, pyridazinyl, pyrazinyl, or triazinyl, or a pharmaceutically acceptable salt thereof.

6. The compound of claim 5, wherein ring B is pyridinyl or pyrimidinyl, or a pharmaceutically acceptable salt thereof.

7. The compound of claim 6, wherein ring B is pyrimidinyl, or a pharmaceutically acceptable salt thereof.

8. The compound of claim 7, wherein ring B is

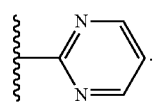

or a pharmaceutically acceptable salt thereof.

9. The compound of claim 1, wherein $R^3$ is selected from the group consisting of:

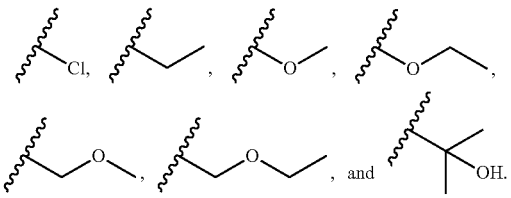

or a pharmaceutically acceptable salt thereof.

10. The compound of claim 9, wherein $R^3$ is selected from the group consisting of:

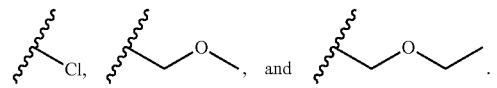

or a pharmaceutically acceptable salt thereof.

11. The compound of claim 10, wherein $R^3$ is

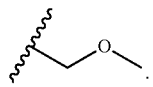 [SMILES: *COC]

or a pharmaceutically acceptable salt thereof.

12. The compound of claim 1, wherein the cyclopropyl ring of formula I is the cis cyclopropyl isomer, or a pharmaceutically acceptable salt thereof.

13. The compound of claim 12, wherein the cyclopropyl ring of formula I has the 1S and 2R stereocenters, or a pharmaceutically acceptable salt thereof.

14. The compound of claim 13, or a pharmaceutically acceptable salt thereof, wherein the compound is present in at least 90% diastereomeric excess, or a pharmaceutically acceptable salt thereof.

15. The compound of claim 1, wherein ring A is phenyl; and ring B is pyrimidinyl, or a pharmaceutically acceptable salt thereof.

16. The compound of claim 15, wherein $R^3$ is

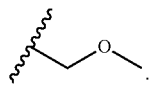 [SMILES: *COC]

or a pharmaceutically acceptable salt thereof.

17. A compound represented by the formula Ic:

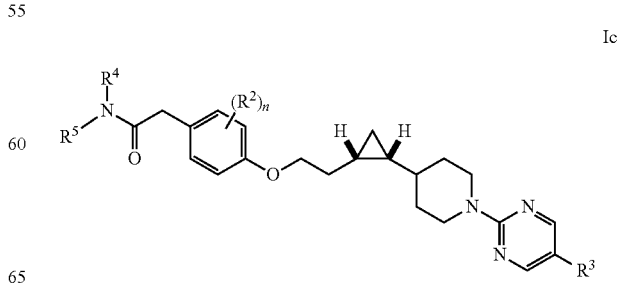

or a pharmaceutically acceptable salt thereof, wherein:
  each $R^2$ is selected from the group consisting of
    (1) $C_{1-3}$alkyl,
    (2) $C_{1-3}$alkoxy,
    (3) halo$C_{1-3}$alkyl,
    (4) halo$C_{1-3}$alkoxy,
    (5) halo, and
    (6) cyano;
  $R^3$ is selected from the group consisting of
    (1) CN,
    (2) halo,
    (3) —$C_{1-6}$alkyl,
    (4) -halo$C_{1-6}$alkyl,
    (5) —$C_{1-6}$alkoxy,
    (6) -halo$C_{1-6}$alkoxy,
    (7) —$C_{1-6}$alkyl-OH,
    (8) —$C_{1-3}$alkyl-O—$C_{1-3}$alkyl, and
    (9) —$C_{1-3}$alkyl-S—$C_{1-3}$alkyl;
  $R^4$ and $R^5$ are independently selected from the group consisting of
    (1) hydrogen,
    (2) hydroxy,
    (3) $C_{1-6}$alkyl,
    (4) $C_{1-6}$alkyl-OH,
    (5) $C_{1-6}$alkyl-O—$C_{1-3}$alkyl,
    (6) halo$C_{1-6}$alkyl,
    (7) $C_{1-6}$alkoxy,
    (8) $C_{3-6}$cycloalkyl,
    (9) $C_{1-3}$alkyl-$C_{3-6}$cycloalkyl, wherein the alkyl group is optionally substituted by hydroxy, or 1-3 fluoro,
    (10) $C_{1-3}$alkyl($C_{3-6}$cycloalkyl)$_2$,
    (11) $C_{1-3}$alkyl-$C_{3-5}$heterocyclyl containing 1-3 N, O, or S, wherein the heterocyclyl is optionally substituted by 1-2 oxo,
    (12) $C_{3-5}$heterocyclyl containing 1-3 N, O or S, wherein the heterocyclyl is optionally substituted by 1-2 oxo,
    (13) $C_{1-3}$alkyl-C(O)NH$_2$,
    (14) $C_{1-3}$alkyl-S(O)$_2$C$_{1-3}$alkyl,
    (15) $C_{1-3}$alkyl-C(O)$_2$C$_{1-3}$alkyl,
    (16) C(O)C$_{1-6}$alkyl,
    (17) C(O)C$_{3-6}$cycloalkyl,
    (18) S(O)$_2$C$_{1-6}$alkyl, and
    (19) S(O)$_2$C$_{3-6}$cycloalkyl,
  or $R^4$ and $R^5$ are linked together with the nitrogen to which they are both attached to form a 3-9 membered monocyclic or bicyclic heterocyclic ring, comprising C, O, N, or S ring atoms, wherein the heterocyclic ring is optionally substituted with 1-3 $R^6$;
  each $R^6$ is selected from the group consisting of:
    (1) $C_{1-3}$alkyl,
    (2) halo$C_{1-3}$alkyl,
    (3) $C_{1-3}$alkoxy,
    (4) $C_{1-3}$alkyl-OH,
    (5) $C_{1-3}$alkyl-O—$C_{1-3}$alkyl,
    (6) halo,
    (7) hydroxy,
    (8) oxo,
    (9) C(O)$_2$C$_{1-3}$alkyl,
    (10) C(O)NH$_2$,
    (11) C(O)N(H)C$_{1-6}$alkyl,
    (12) C(O)C$_{3-6}$cycloalkyl,
    (13) $C_{3-6}$cycloalkyl,
    (14) $C_{1-3}$alkyl-phenyl,
    (15) phenyl,
    (16) 5- or 6-membered heteroaryl, containing 1-3 N, O, or S; and
  n is 0, 1, 2, or 3.

18. A compound represented by the formula Id:

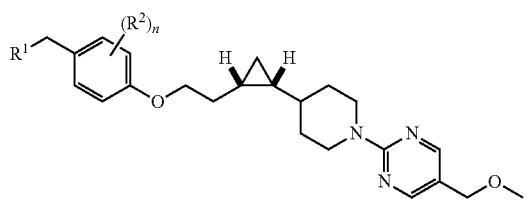

or a pharmaceutically acceptable salt thereof, wherein:
  $R^1$ is selected from the group consisting of
    (1) 5-membered heteroaryl containing 1-4 O, S, or N, optionally substituted by $C_{1-3}$alkyl,
    (2) 3-8 membered heterocyclyl containing 1-3 O, S, or N,
    (3) $C_{1-3}$alkyl-OH,
    (4) C(O)$_2$C$_{1-3}$alkyl, and
    (5) C(O)NR$^4$R$^5$;
  each $R^2$ is selected from the group consisting of
    (1) $C_{1-3}$alkyl,
    (2) $C_{1-3}$alkoxy,
    (3) halo$C_{1-3}$alkyl,
    (4) halo$C_{1-3}$alkoxy,
    (5) halo, and
    (6) cyano;
  $R^4$ and $R^5$ are independently selected from the group consisting of
    (1) hydrogen,
    (2) hydroxy,
    (3) $C_{1-6}$alkyl,
    (4) $C_{1-6}$alkyl-OH,
    (5) $C_{1-6}$alkyl-O—$C_{1-3}$alkyl,
    (6) halo$C_{1-6}$alkyl,
    (7) $C_{1-6}$alkoxy,
    (8) $C_{3-6}$cycloalkyl,
    (9) $C_{1-3}$alkyl-$C_{3-6}$cycloalkyl, wherein the alkyl group is optionally substituted by hydroxy, or 1-3 fluoro,
    (10) $C_{1-3}$alkyl($C_{3-6}$cycloalkyl)$_2$,
    (11) $C_{1-3}$alkyl-$C_{3-5}$heterocyclyl containing 1-3 N, O, or S, wherein the heterocyclyl is optionally substituted by 1-2 oxo,
    (12) $C_{3-5}$heterocyclyl containing 1-3 N, O or S, wherein the heterocyclyl is optionally substituted by 1-2 oxo,
    (13) $C_{1-3}$alkyl-C(O)NH$_2$,
    (14) $C_{1-3}$alkyl-S(O)$_2$C$_{1-3}$alkyl,
    (15) $C_{1-3}$alkyl-C(O)$_2$C$_{1-3}$alkyl,
    (16) C(O)C$_{1-6}$alkyl,
    (17) C(O)C$_{3-6}$cycloalkyl,
    (18) S(O)$_2$C$_{1-6}$alkyl, and
    (19) S(O)$_2$C$_{3-6}$cycloalkyl,
  or $R^4$ and $R^5$ are linked together with the nitrogen to which they are both attached to form a 3-9 membered monocyclic or bicyclic heterocyclic ring, comprising C, O, N, or S ring atoms, wherein the heterocyclic ring is optionally substituted with 1-3 $R^6$;
  each $R^6$ is selected from the group consisting of:
    (1) $C_{1-3}$alkyl,
    (2) halo$C_{1-3}$alkyl,
    (3) $C_{1-3}$alkoxy,
    (4) $C_{1-3}$alkyl-OH,
    (5) $C_{1-3}$alkyl-O—$C_{1-3}$alkyl,
    (6) halo, (7) hydroxy,
(8) oxo,
(9) C(O)$_2$C$_{1-3}$alkyl,
(10) C(O)NH$_2$,
(11) C(O)N(H)C$_{1-6}$alkyl,
(12) C(O)C$_{3-6}$cycloalkyl,
(13) C$_{3-6}$cycloalkyl,
(14) C$_{1-3}$alkyl-phenyl,
(15) phenyl,
(16) 5- or 6-membered heteroaryl, containing 1-3 N, O, or S; and
n is 0, 1, 2, or 3.
19. The compound of claim 1, or a pharmaceutically acceptable salt thereof, selected from the group consisting of:
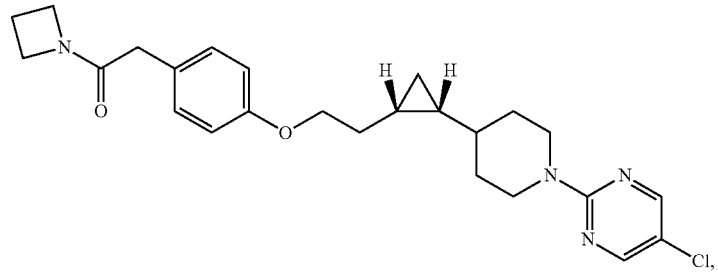
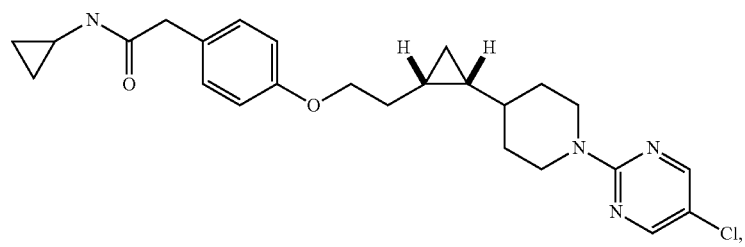
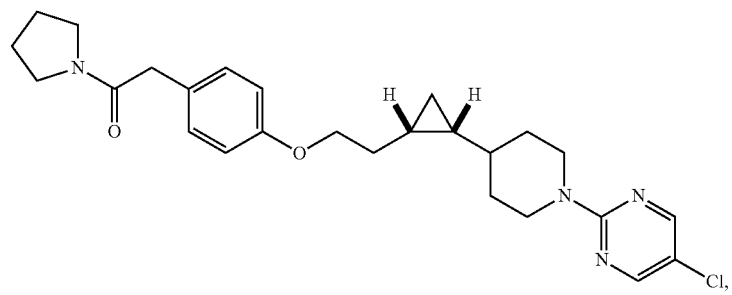
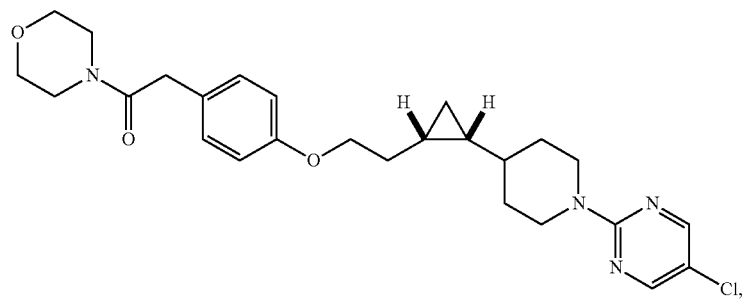
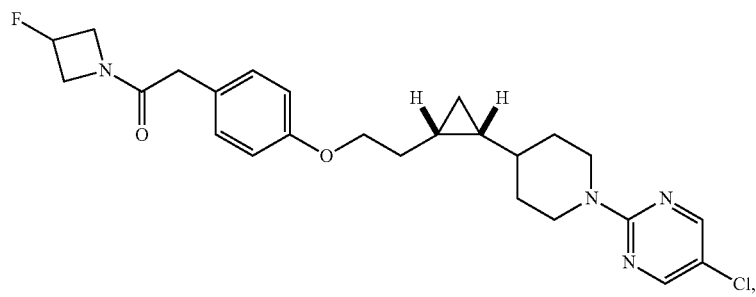

-continued
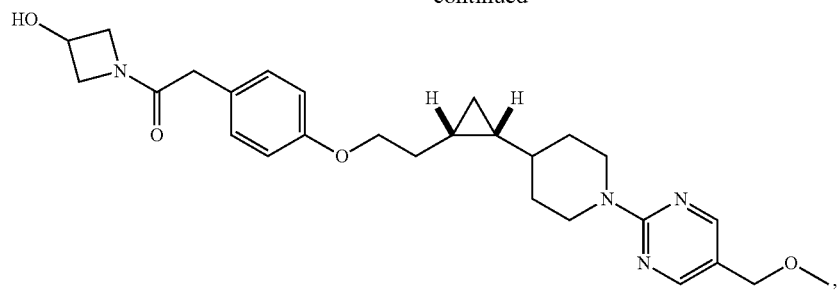
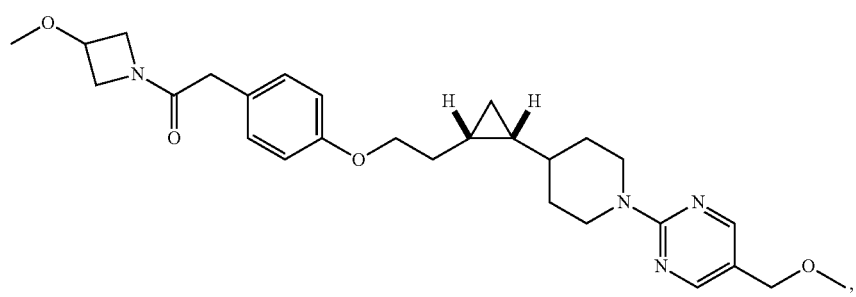
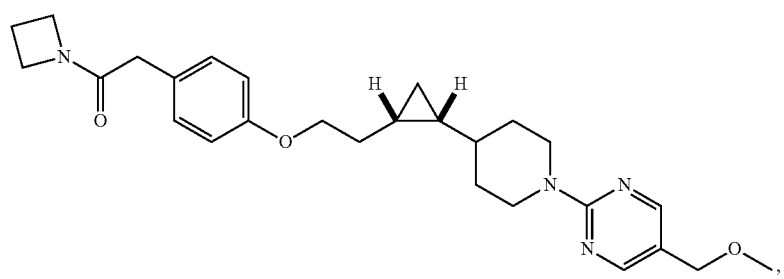
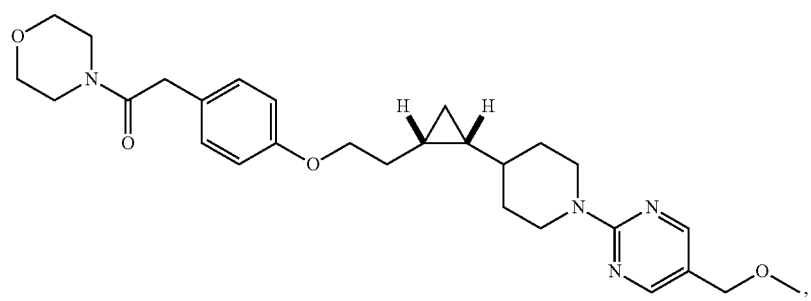
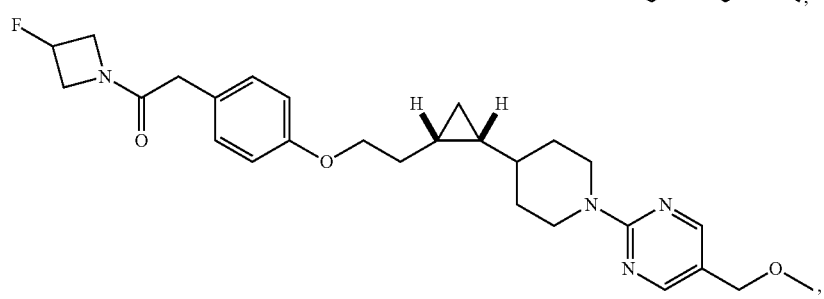

-continued
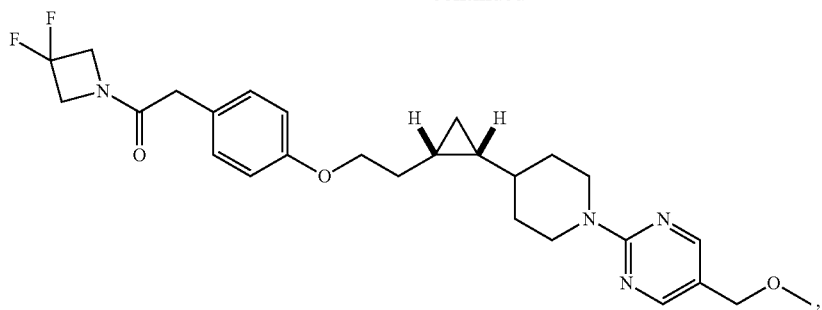
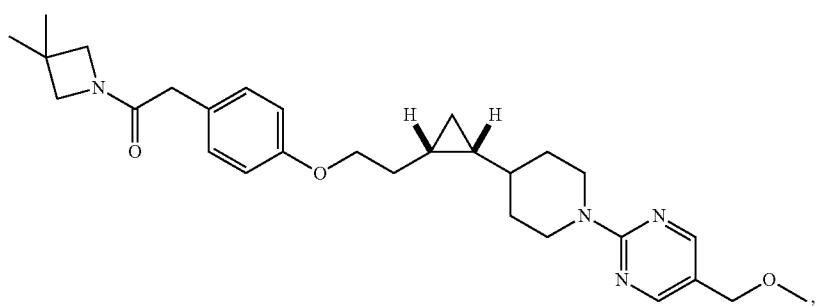
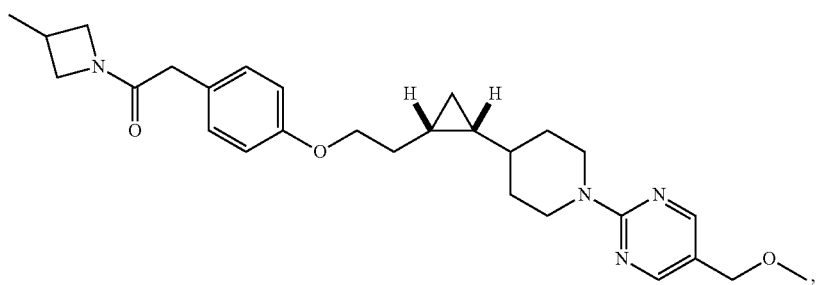
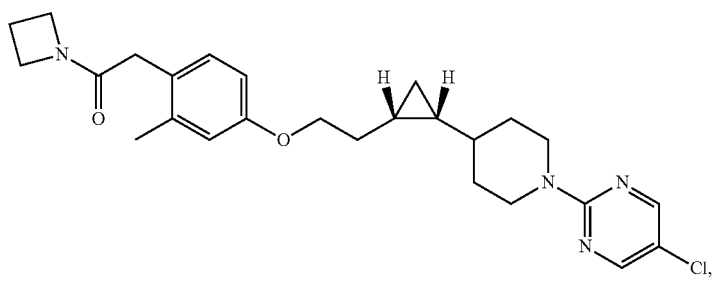
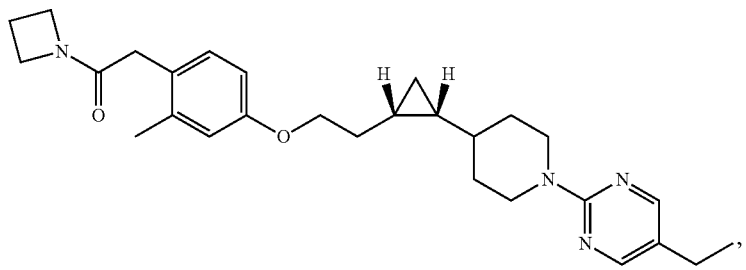
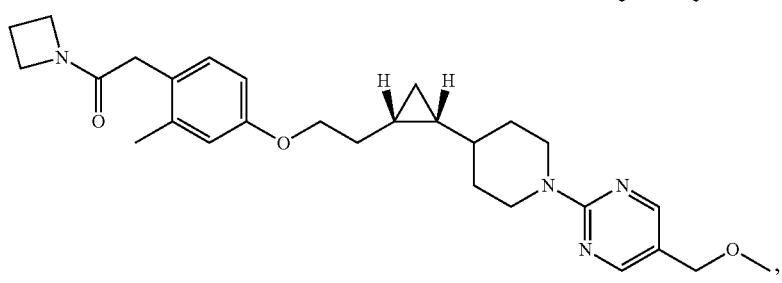

-continued
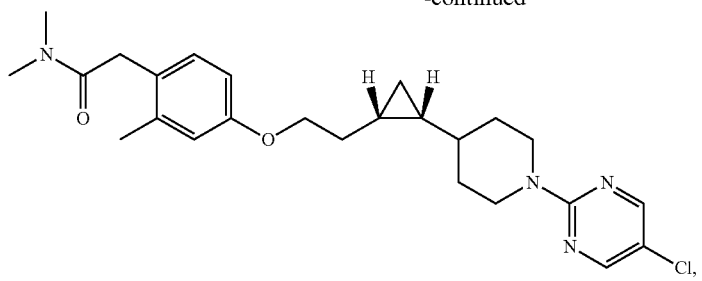
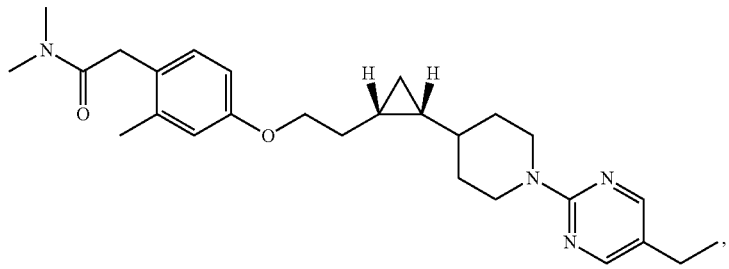
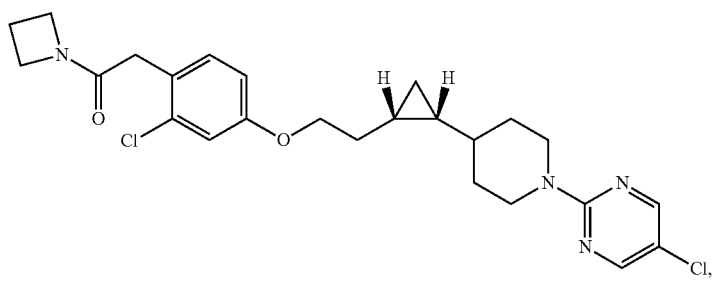
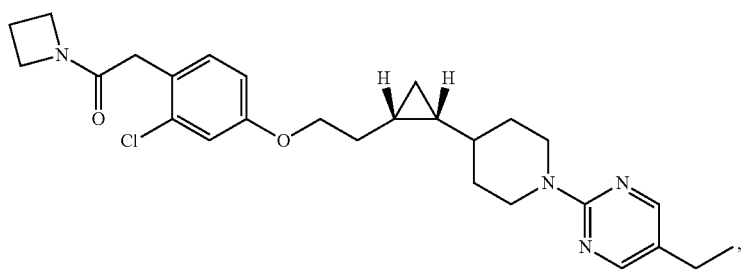
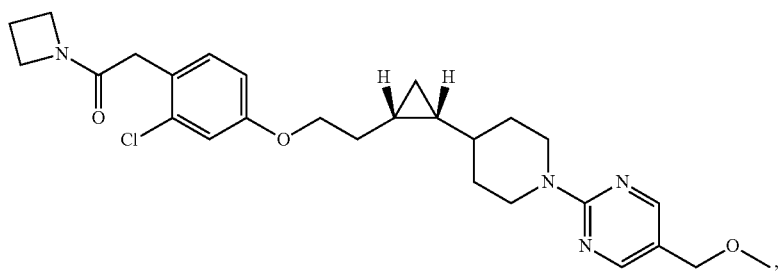
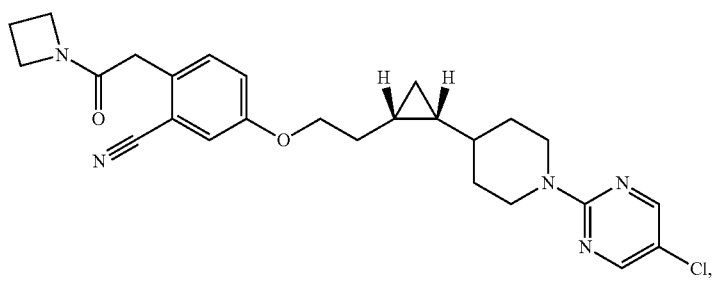

-continued
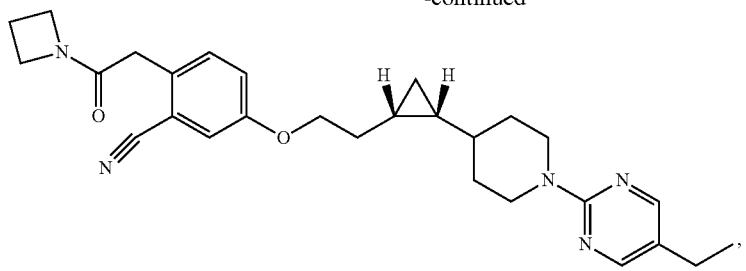
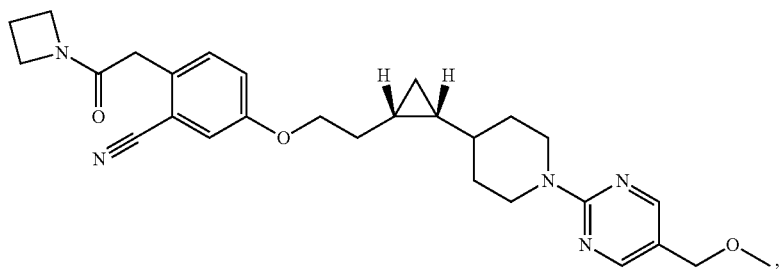
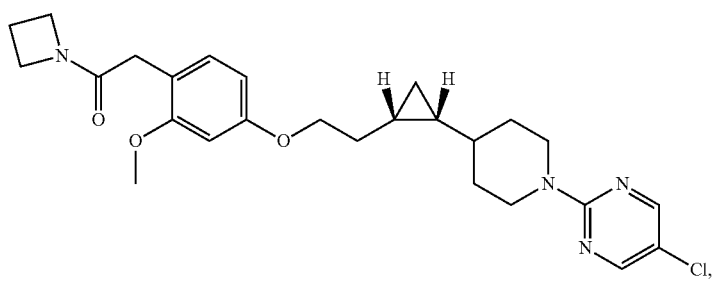
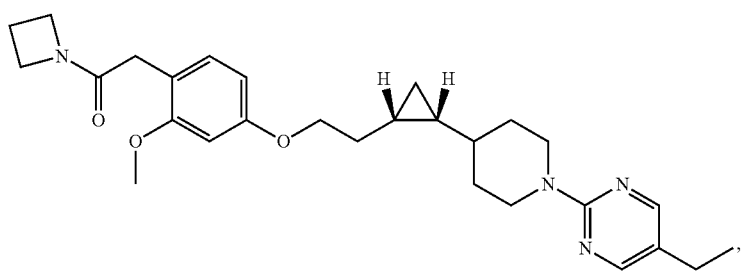
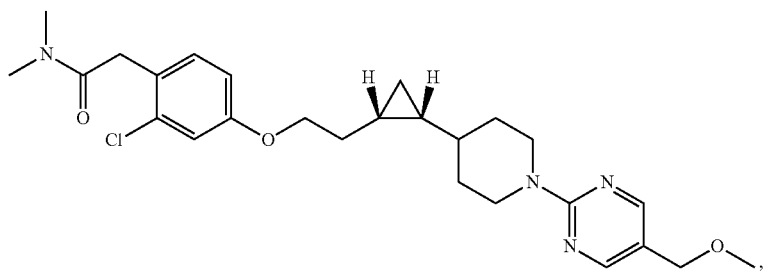
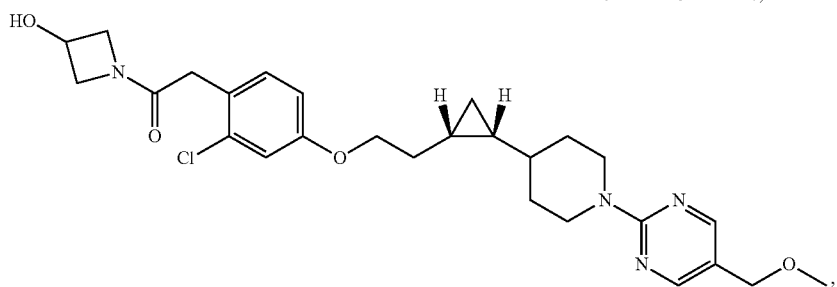

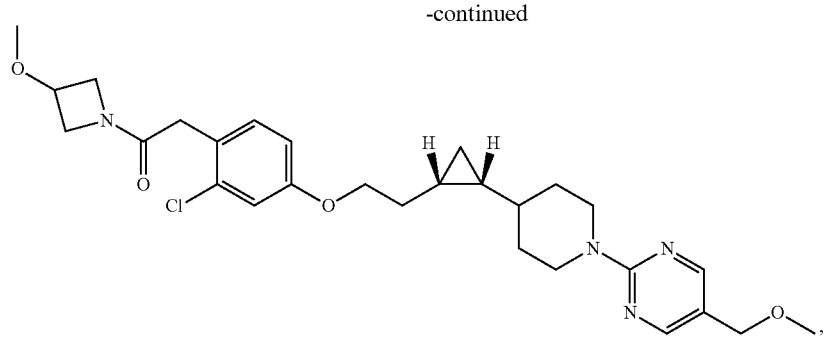
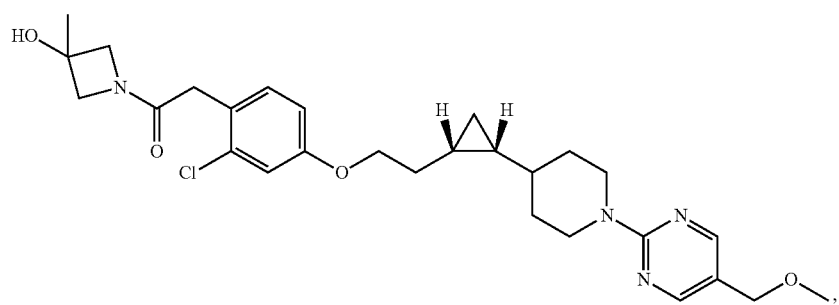
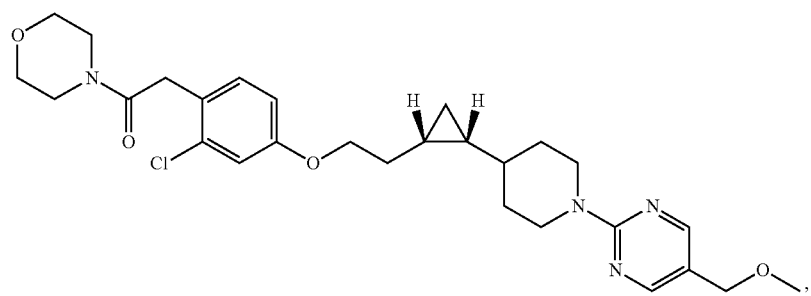
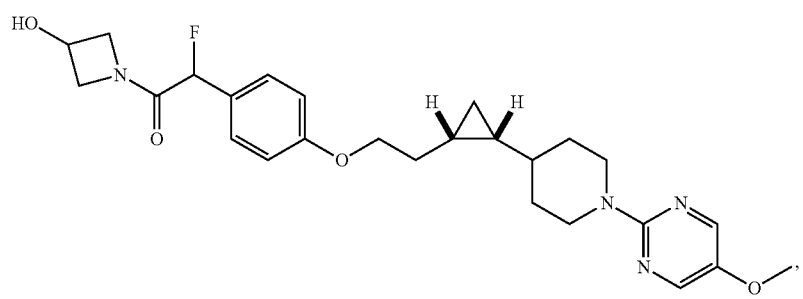
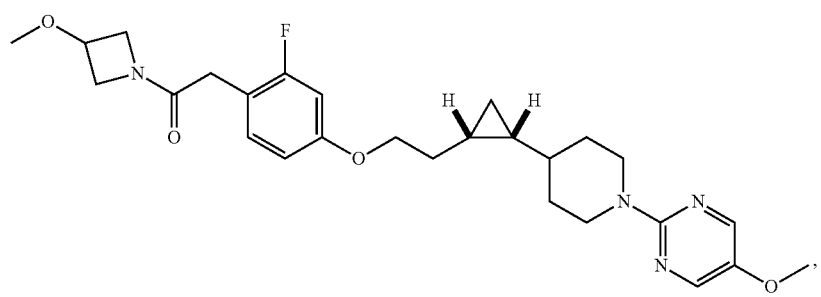

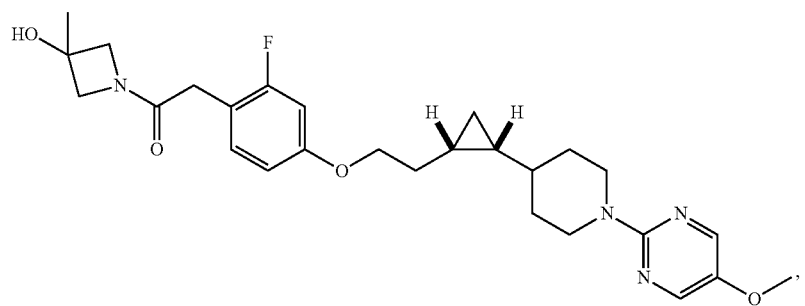
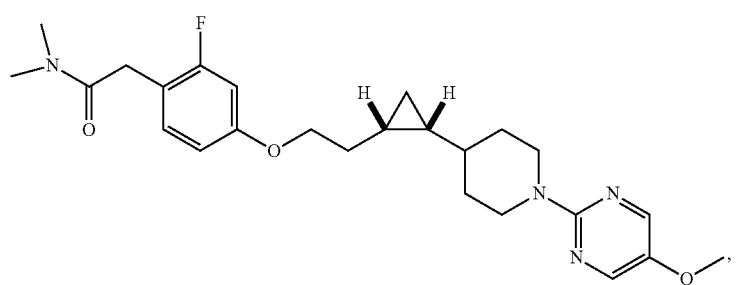
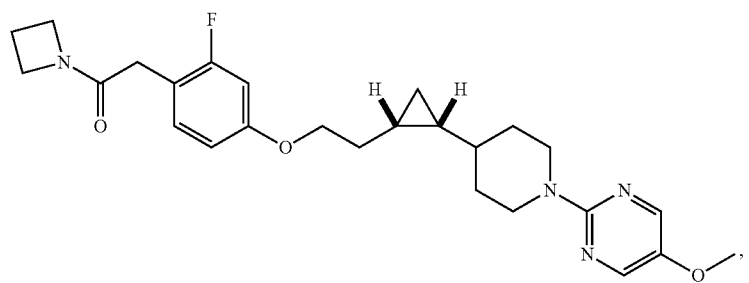
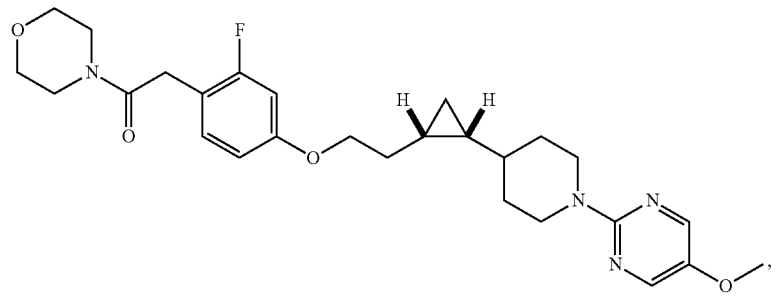
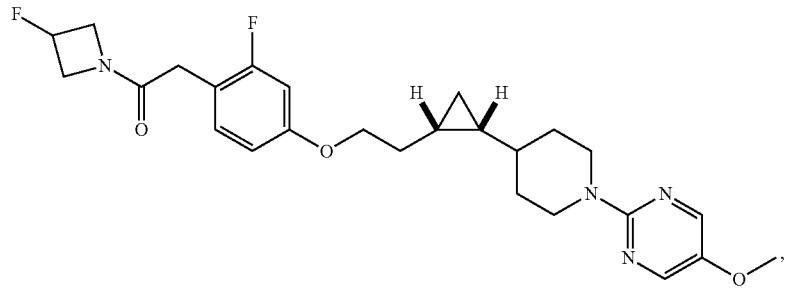

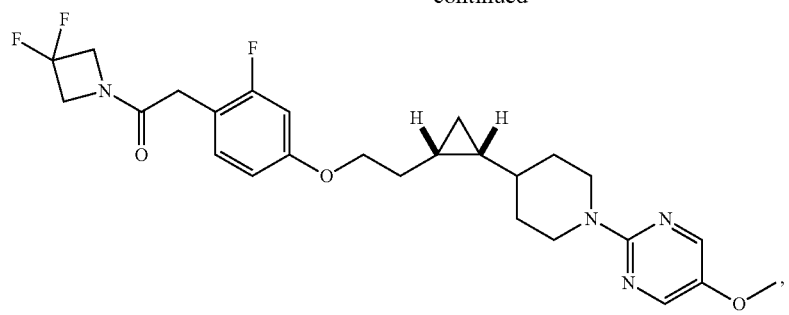
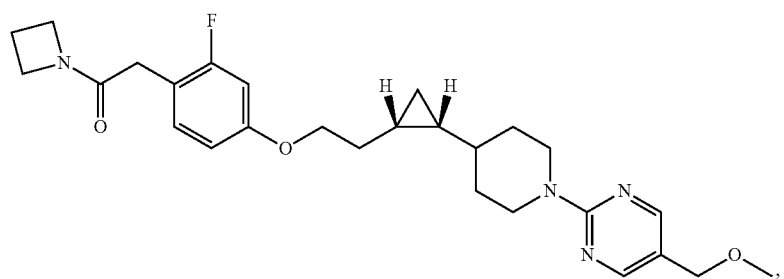
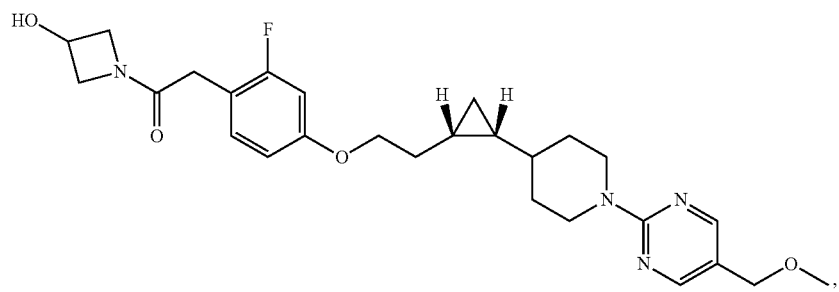
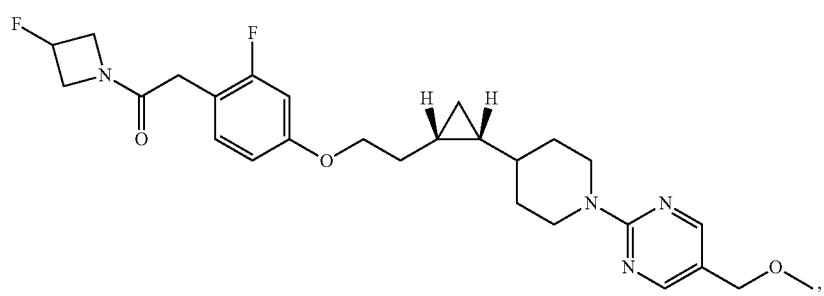
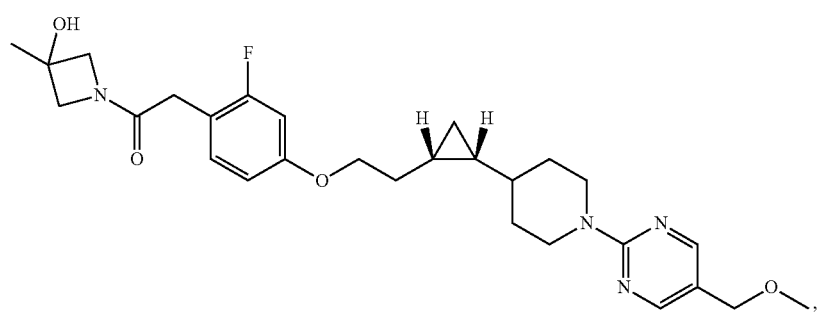

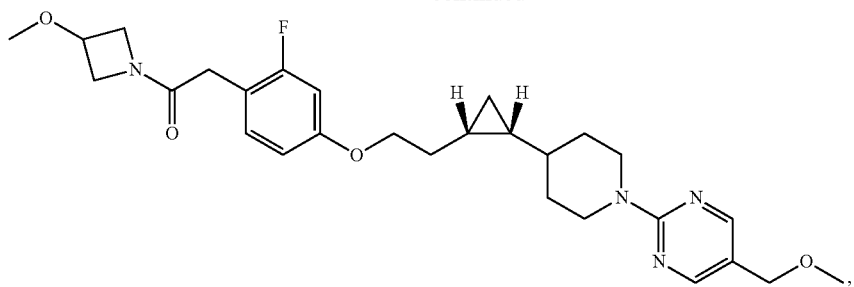
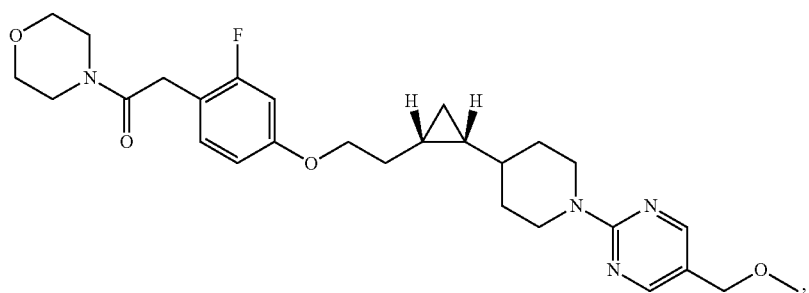
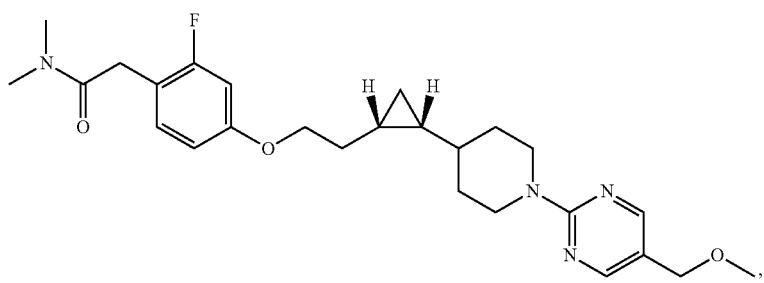
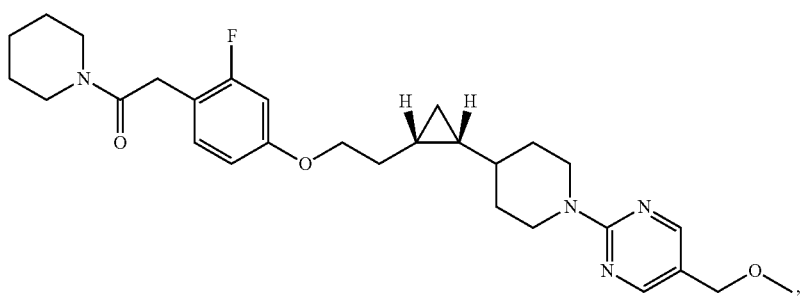
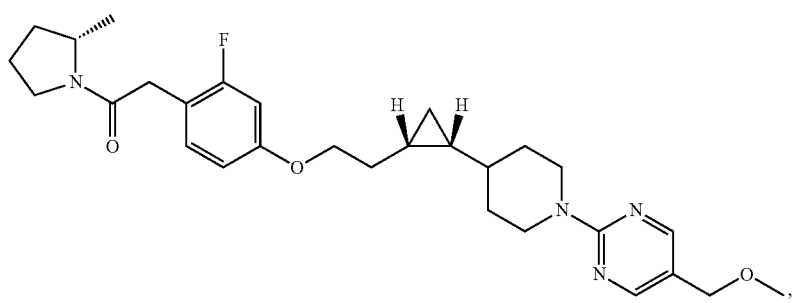

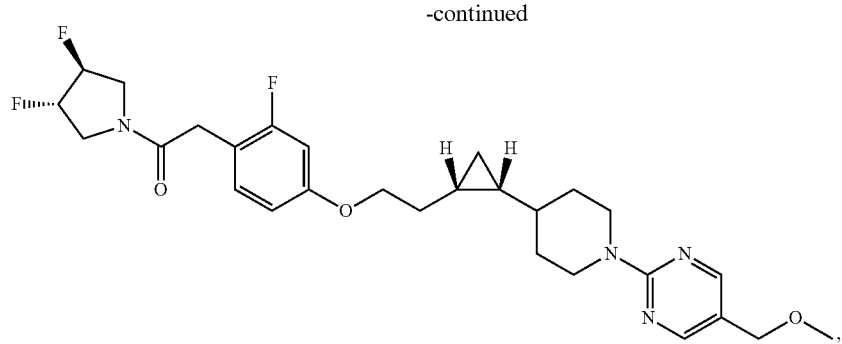
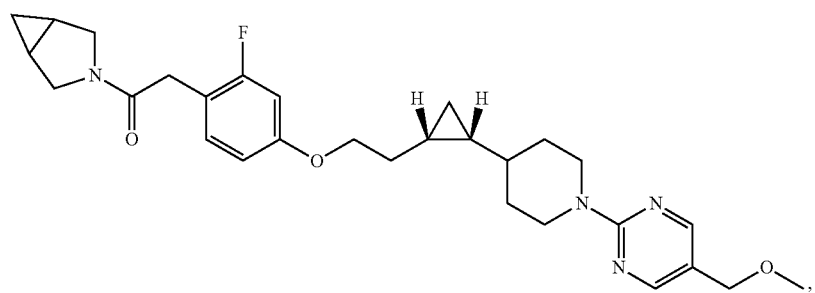
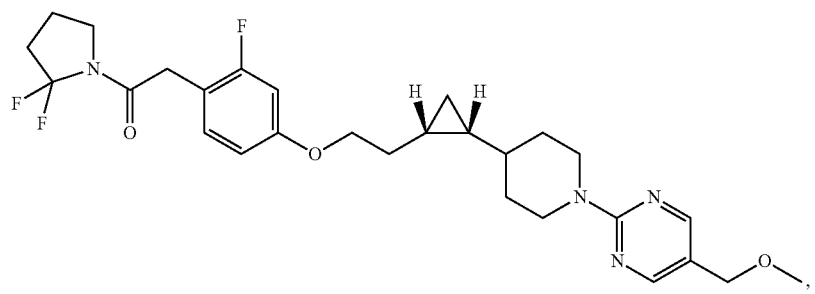
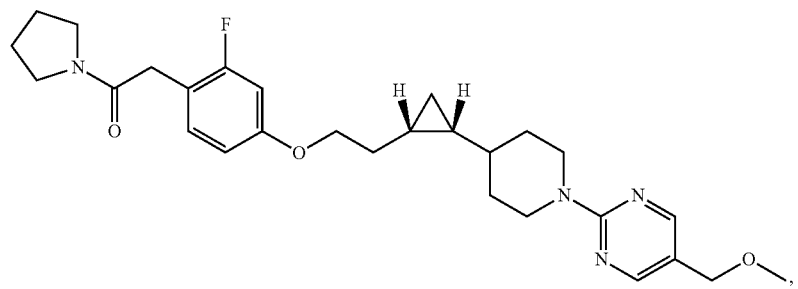
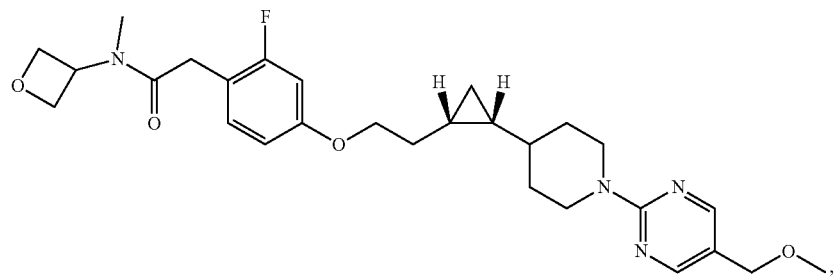

-continued
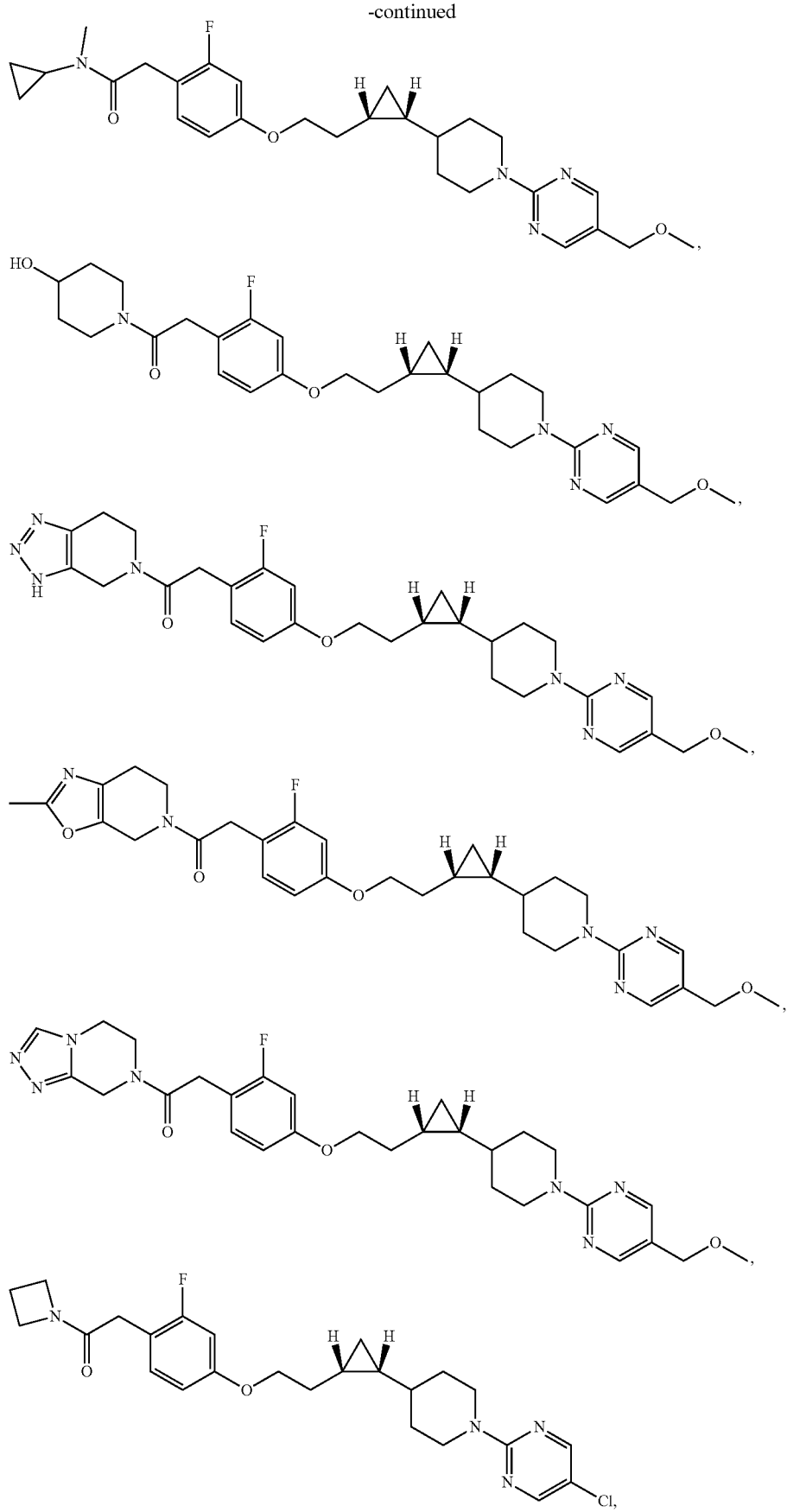

-continued
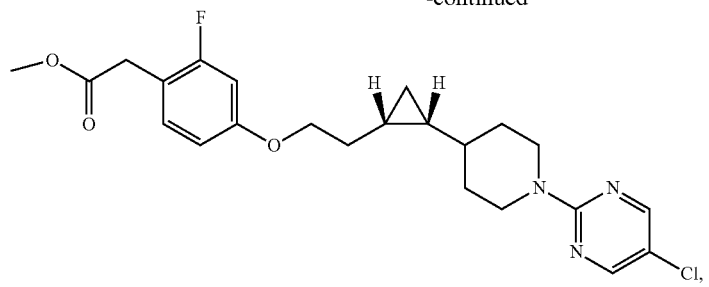
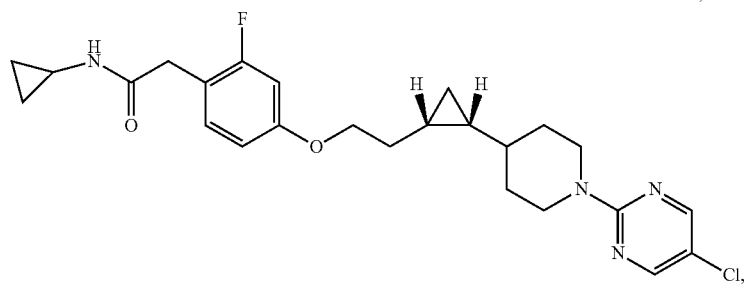
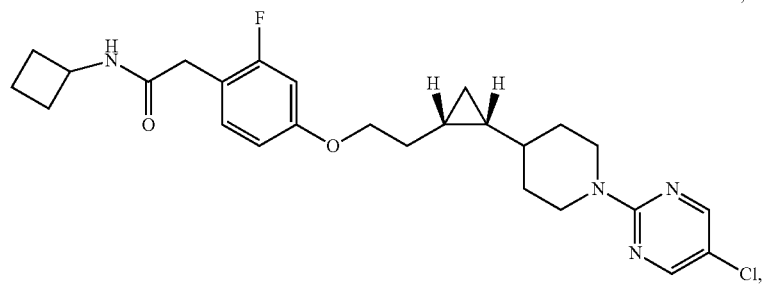
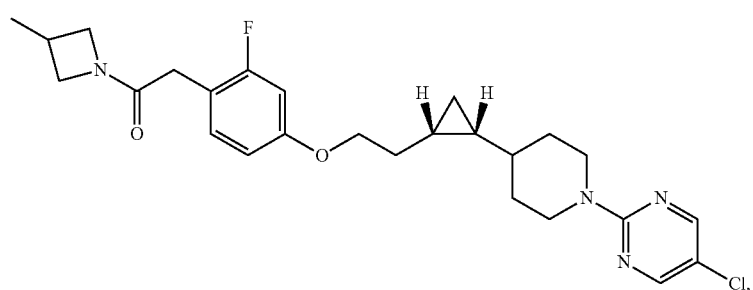
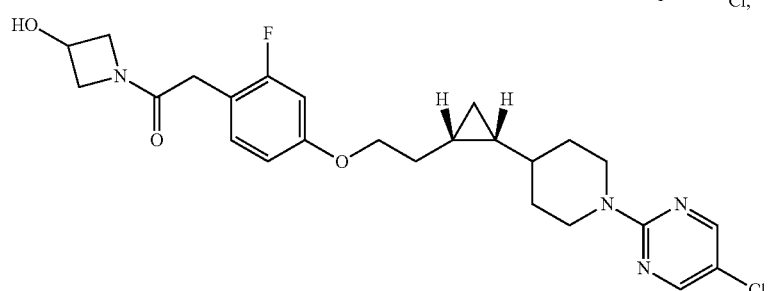
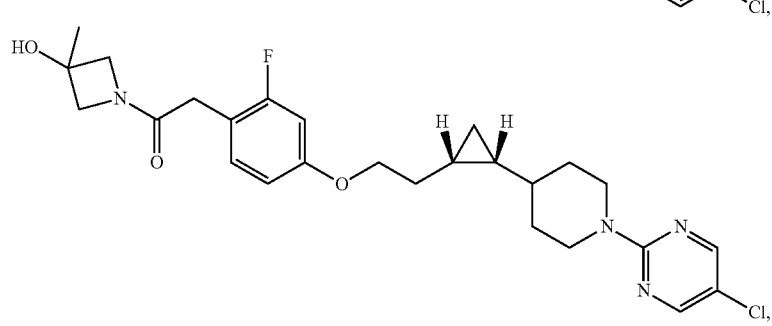

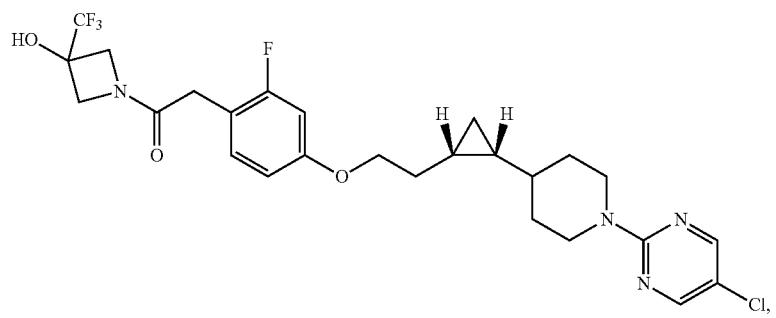
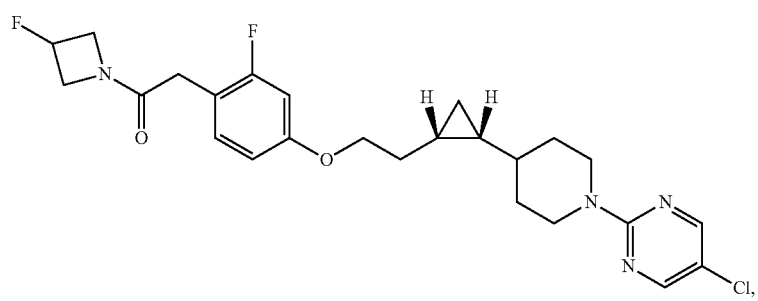
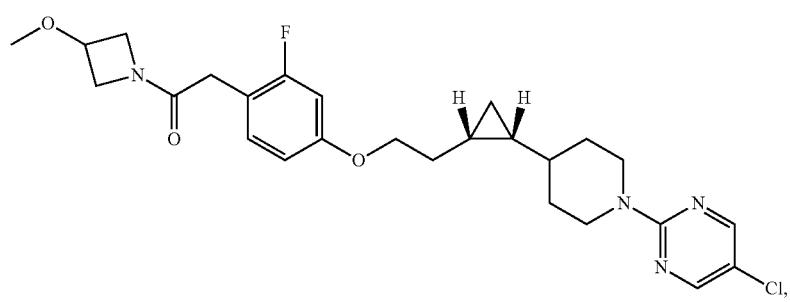
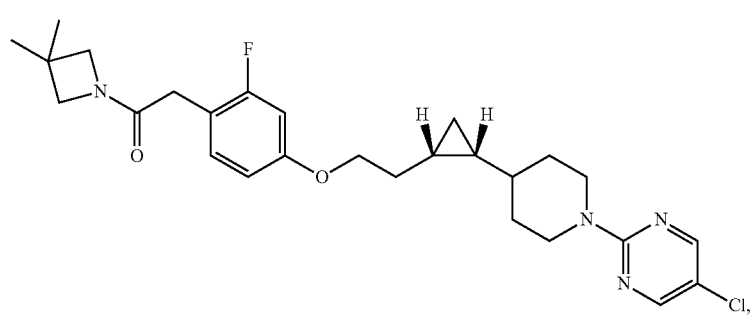
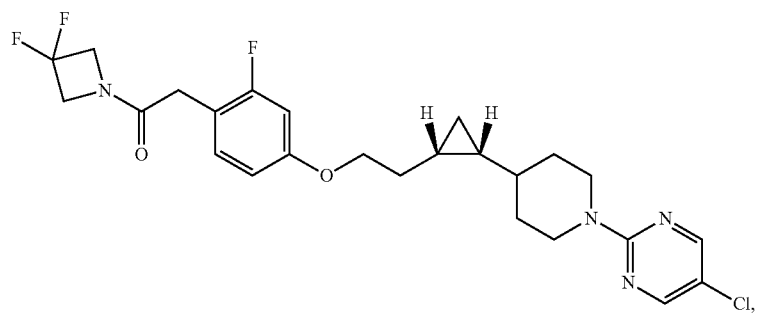

-continued
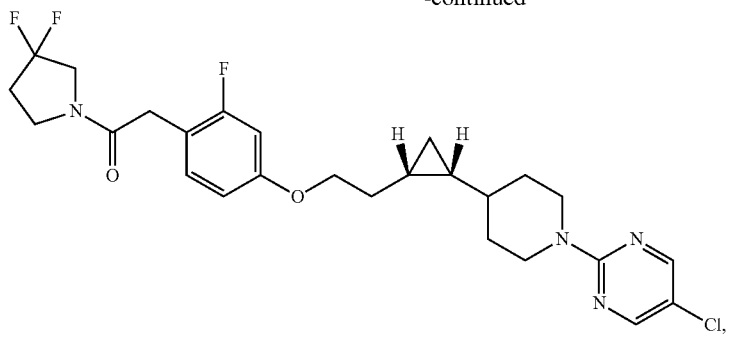
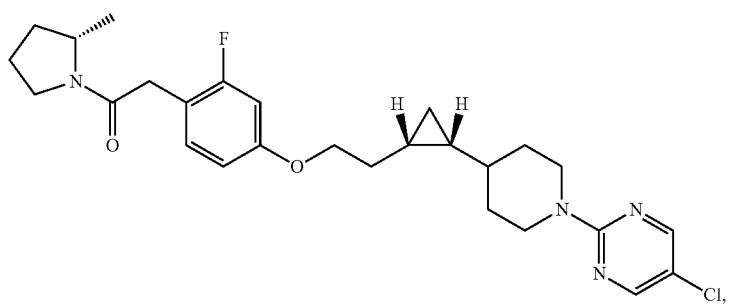
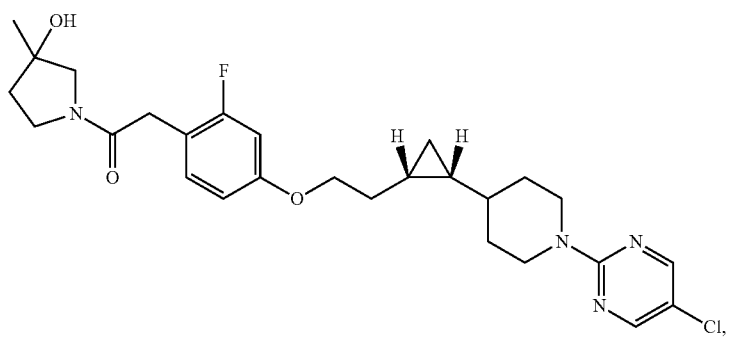
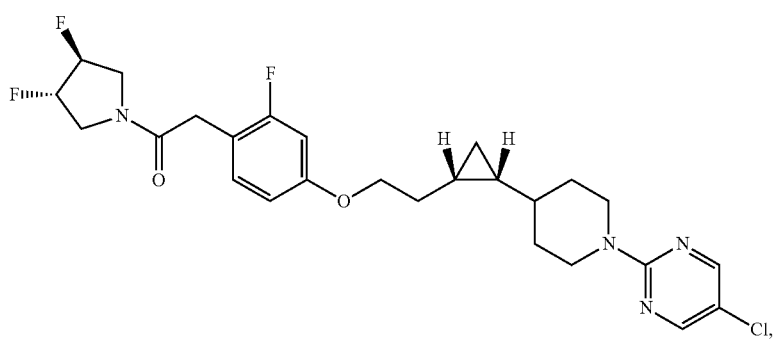
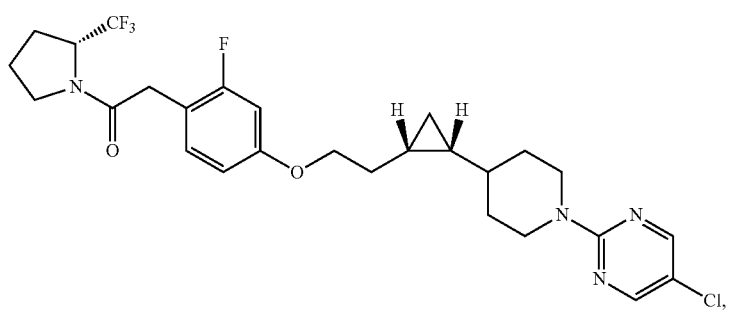

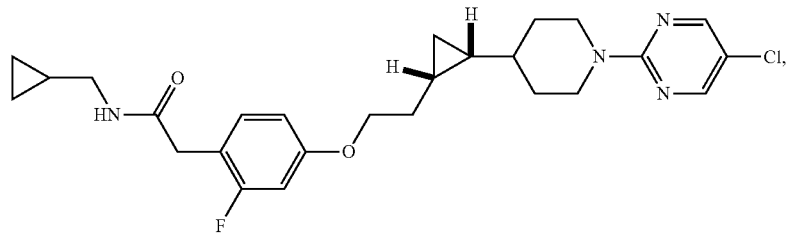
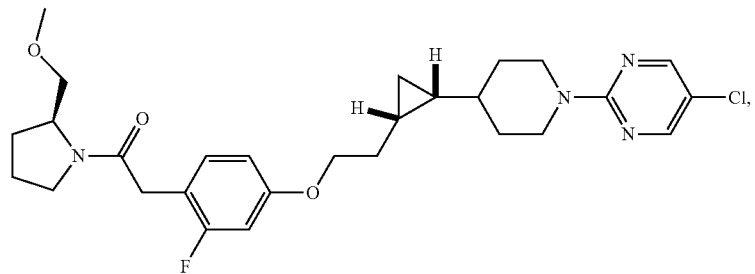
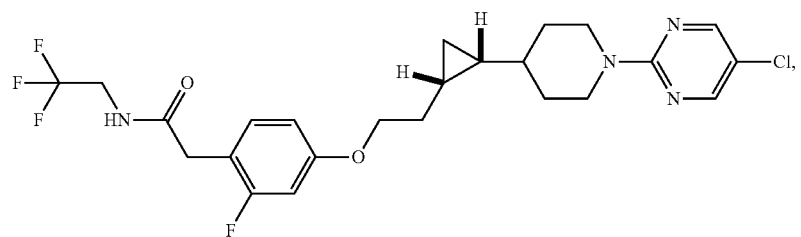
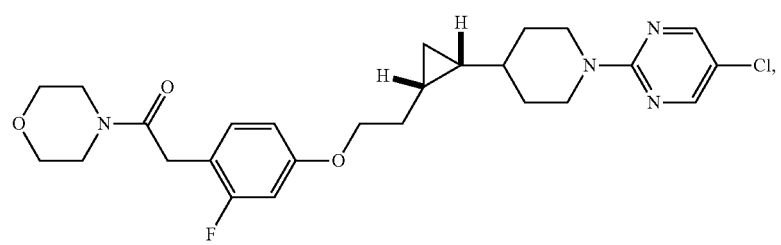
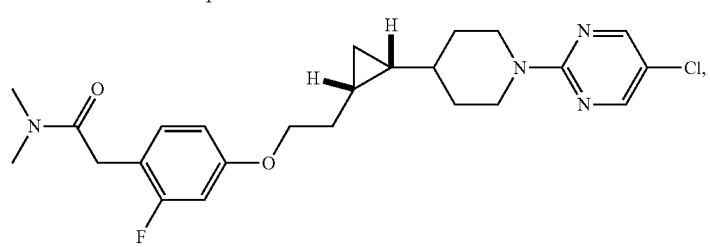
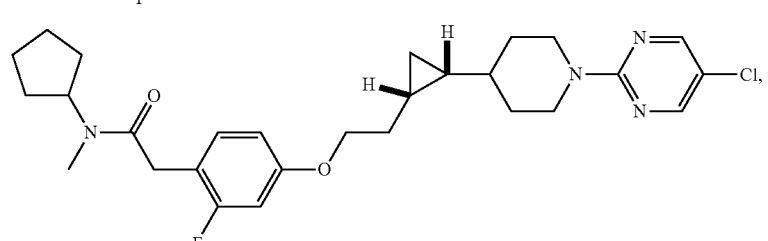
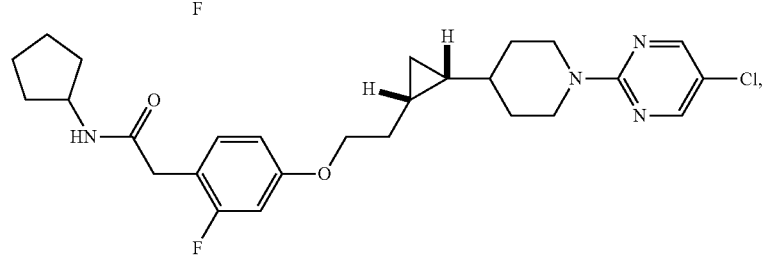

-continued
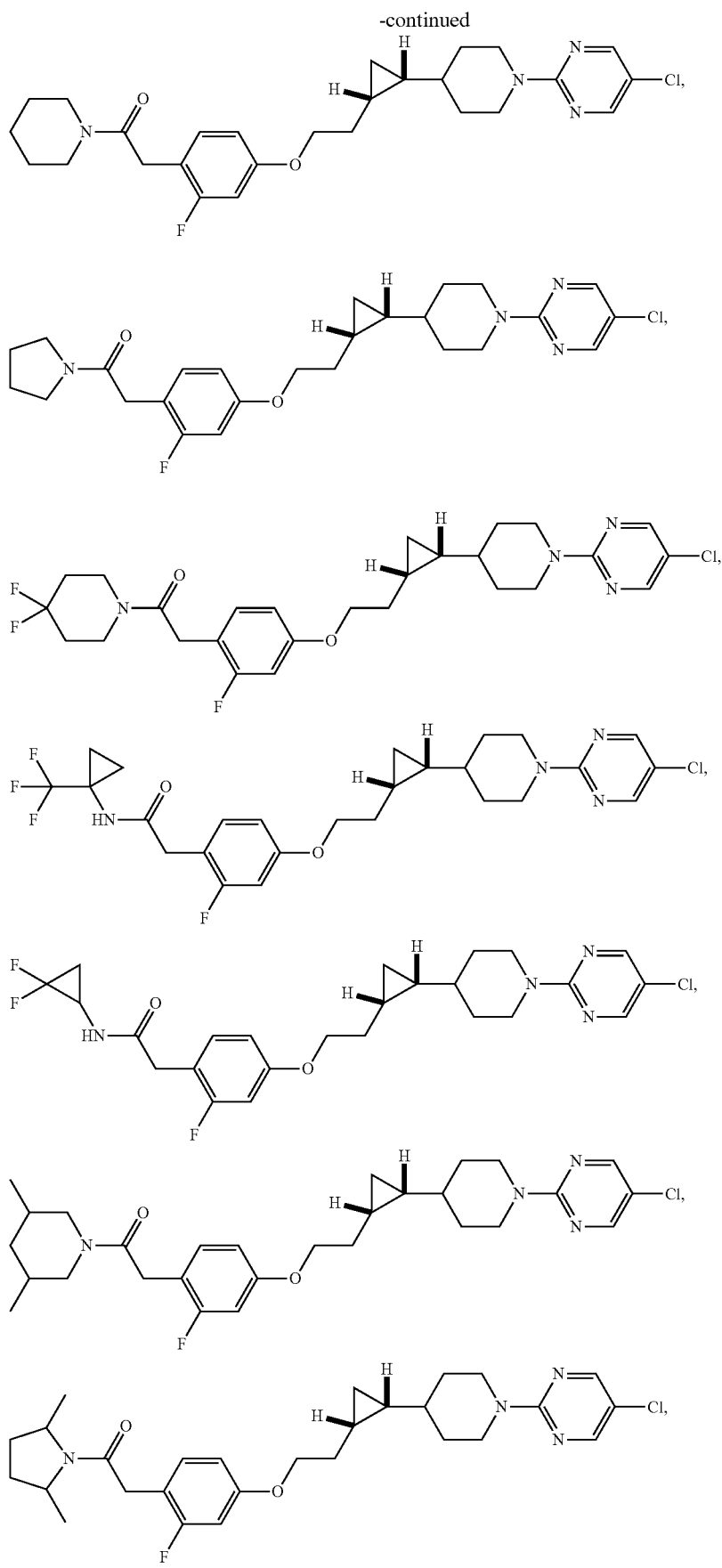

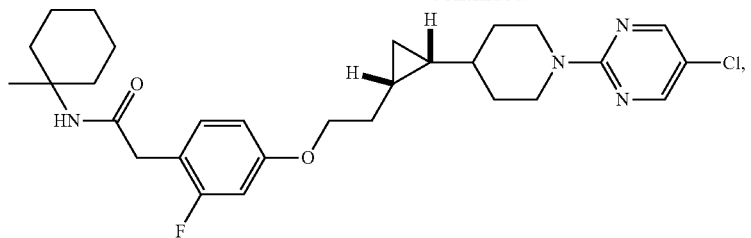
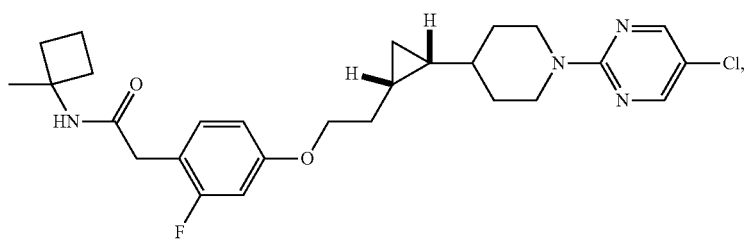
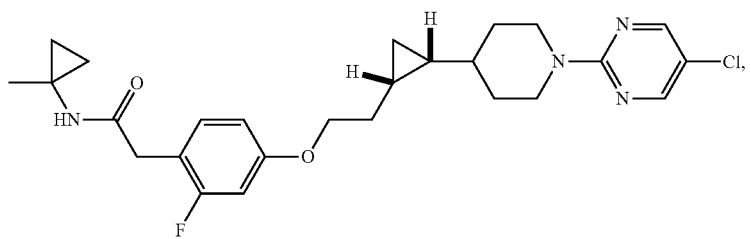
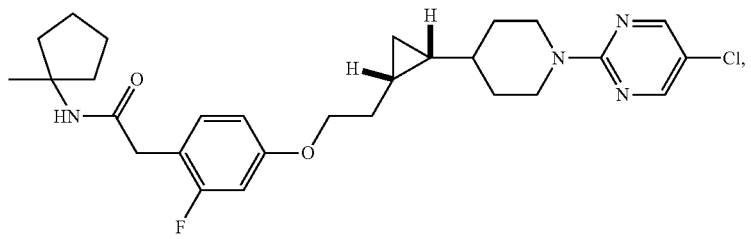
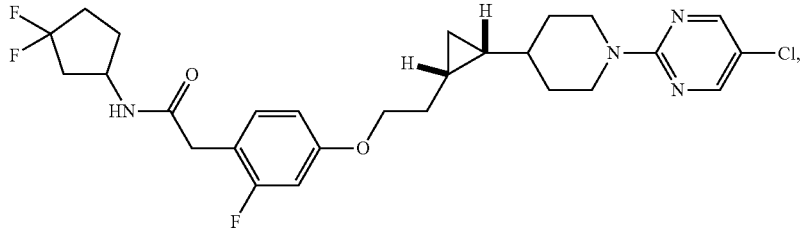
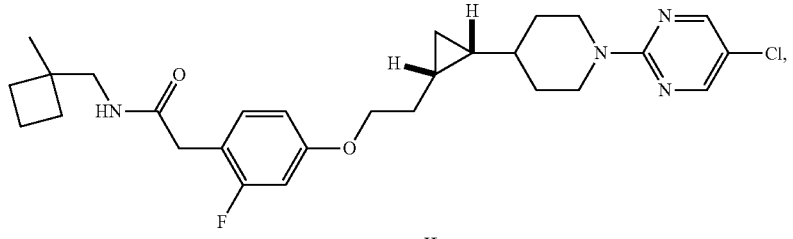
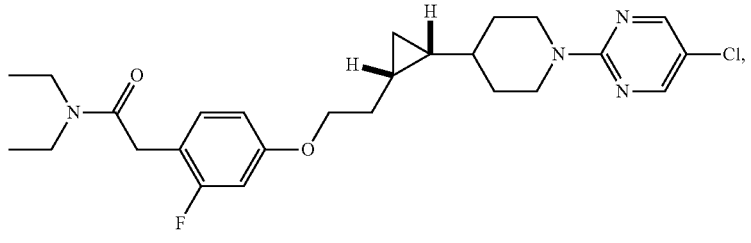

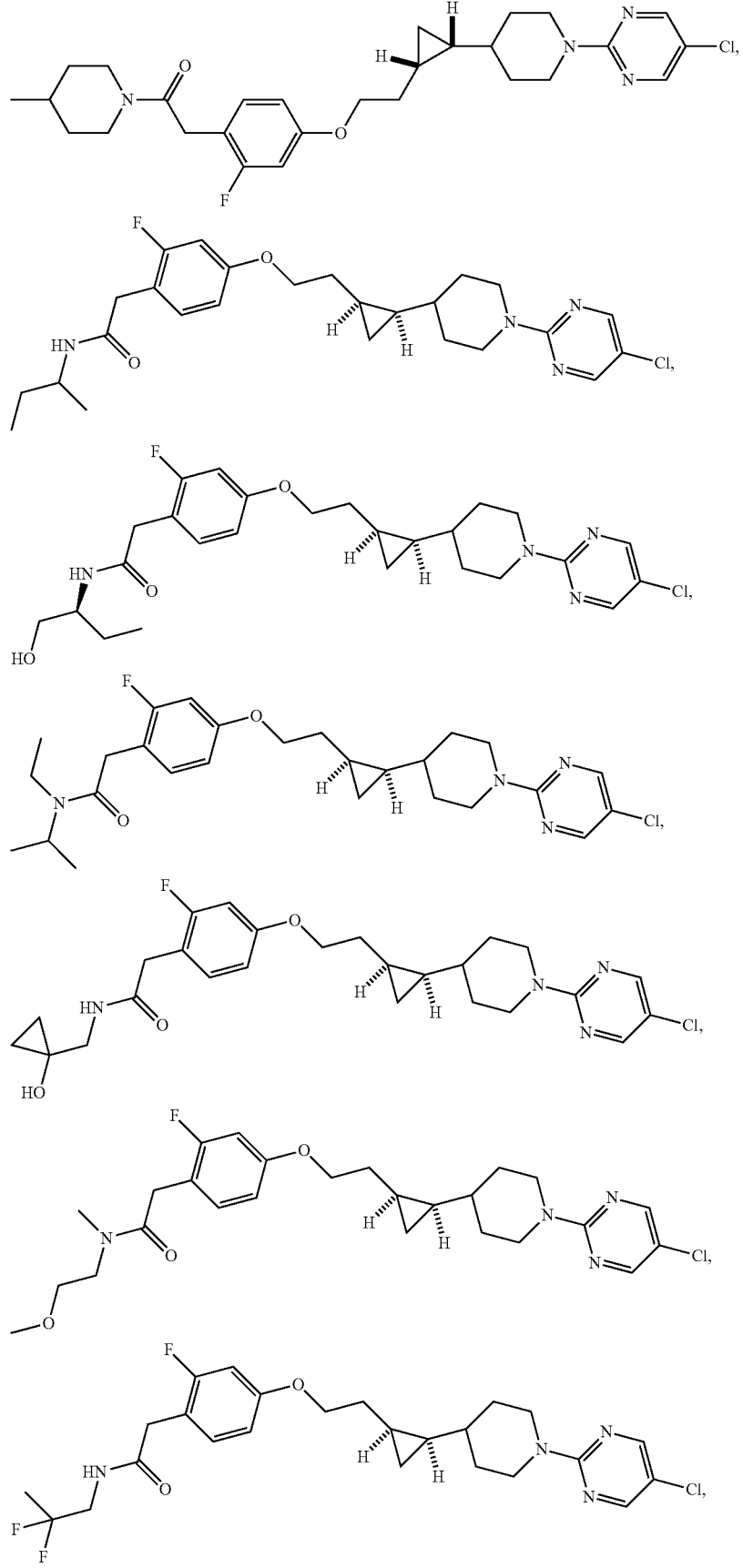

-continued
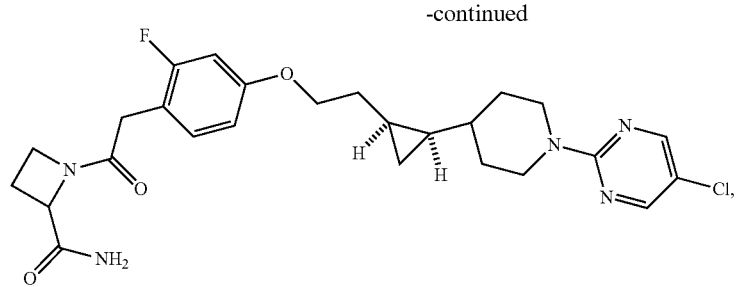
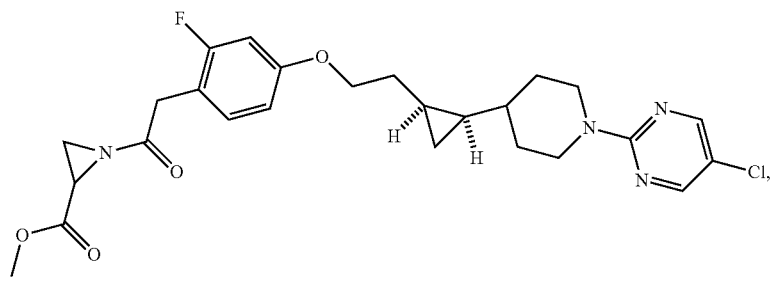
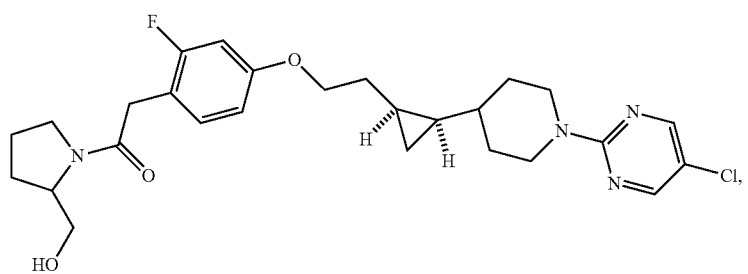
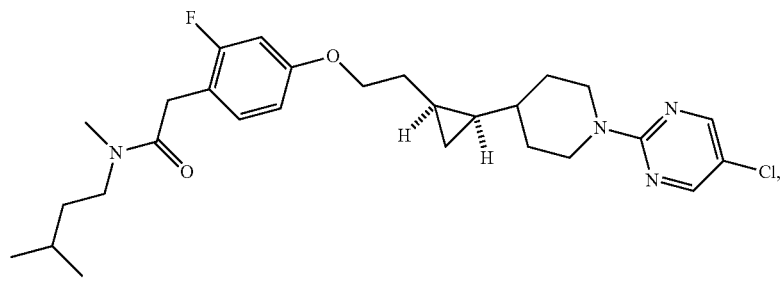
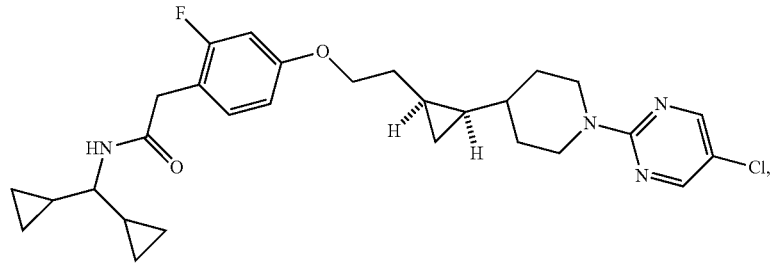
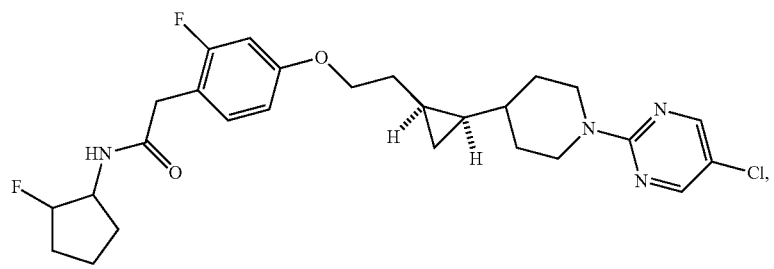

-continued
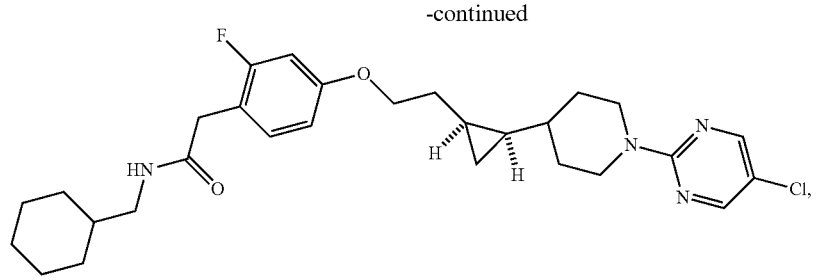
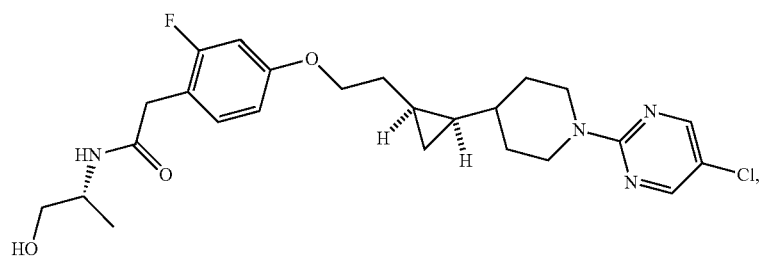
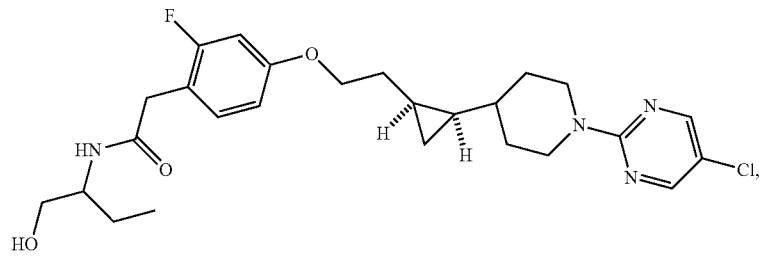
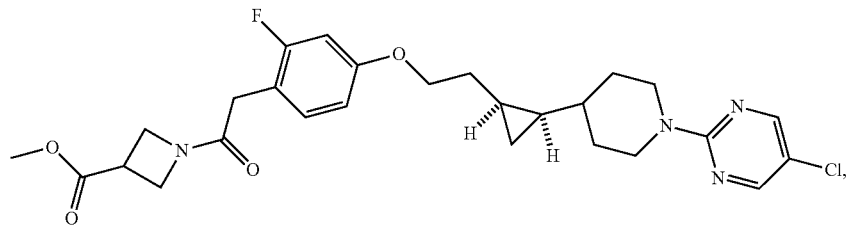
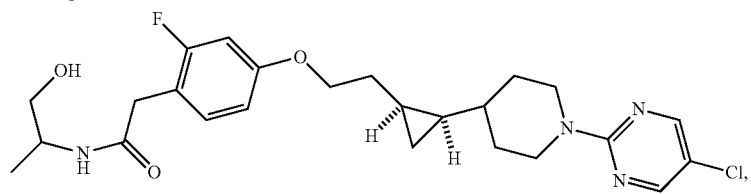
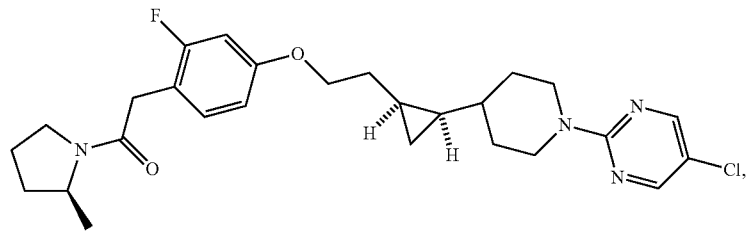
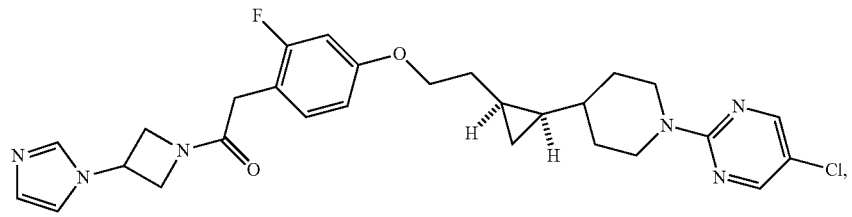

-continued
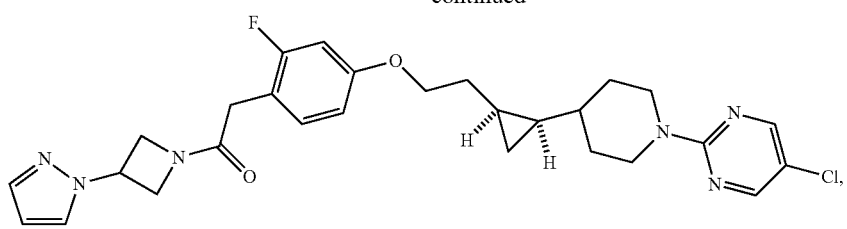
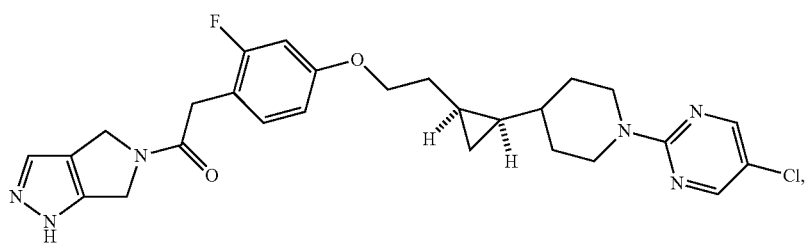
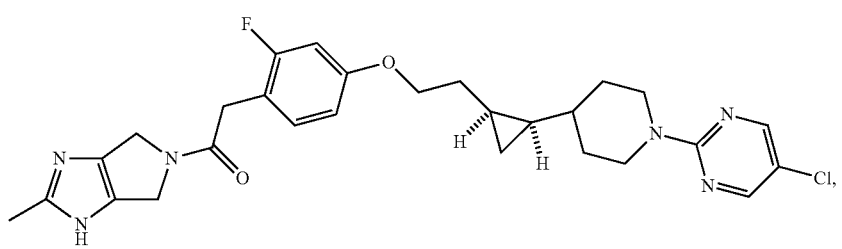
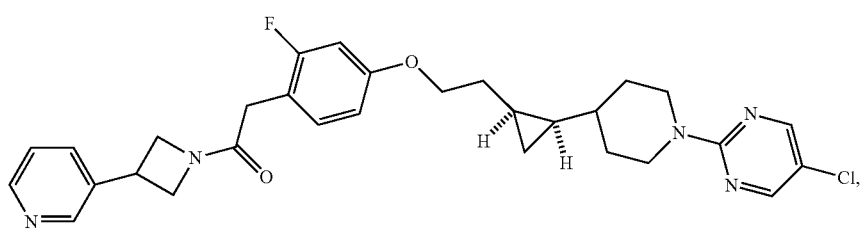
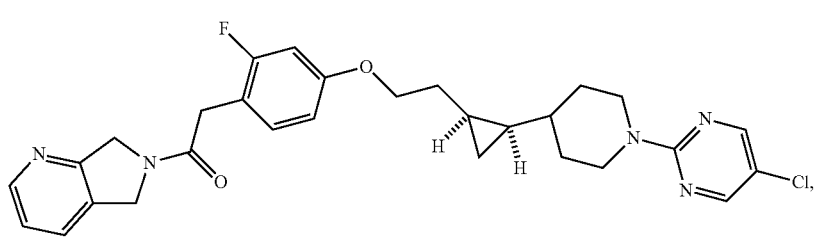
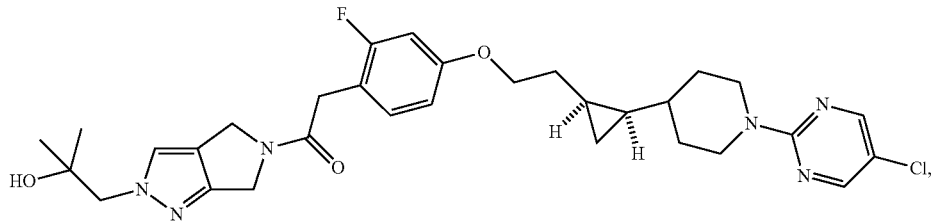
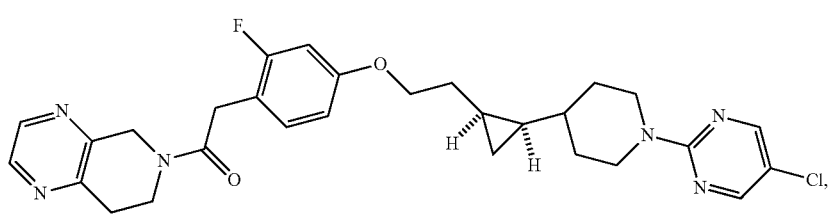

-continued
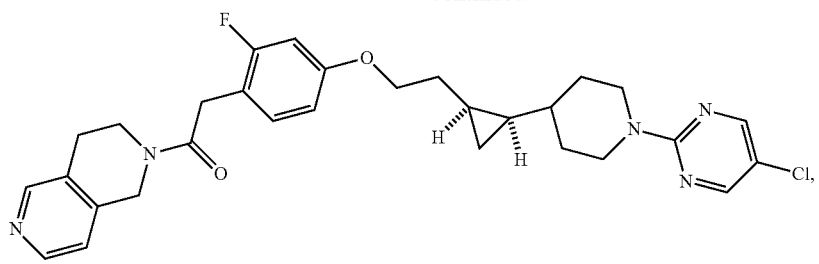
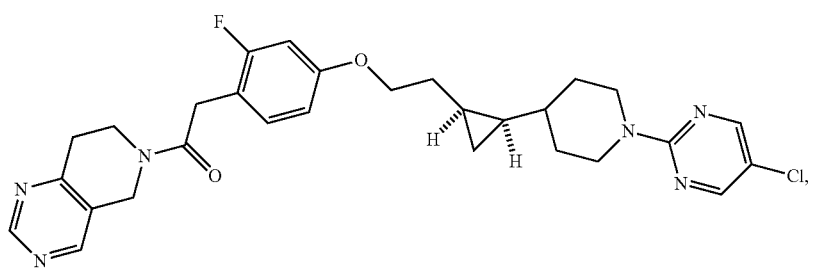
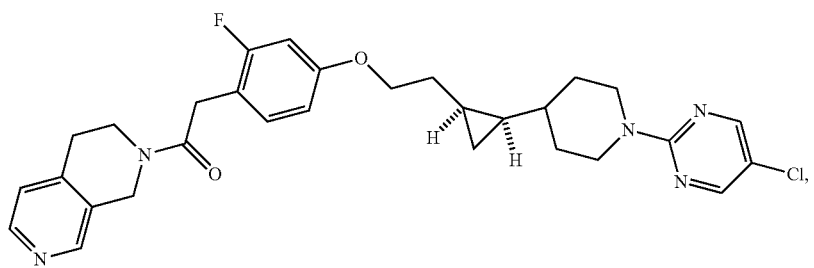
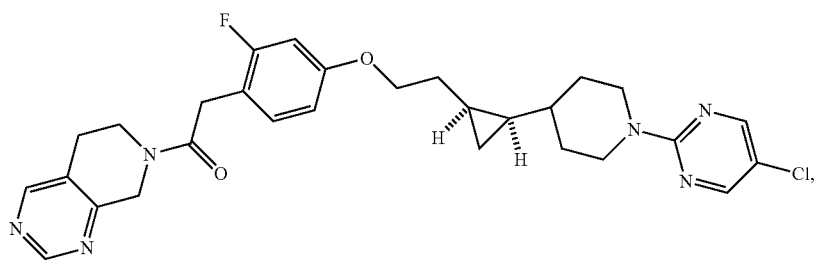
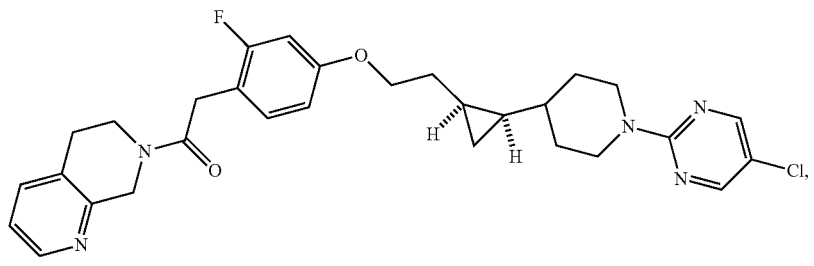
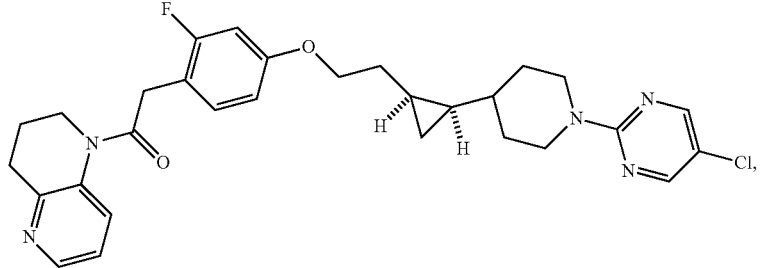

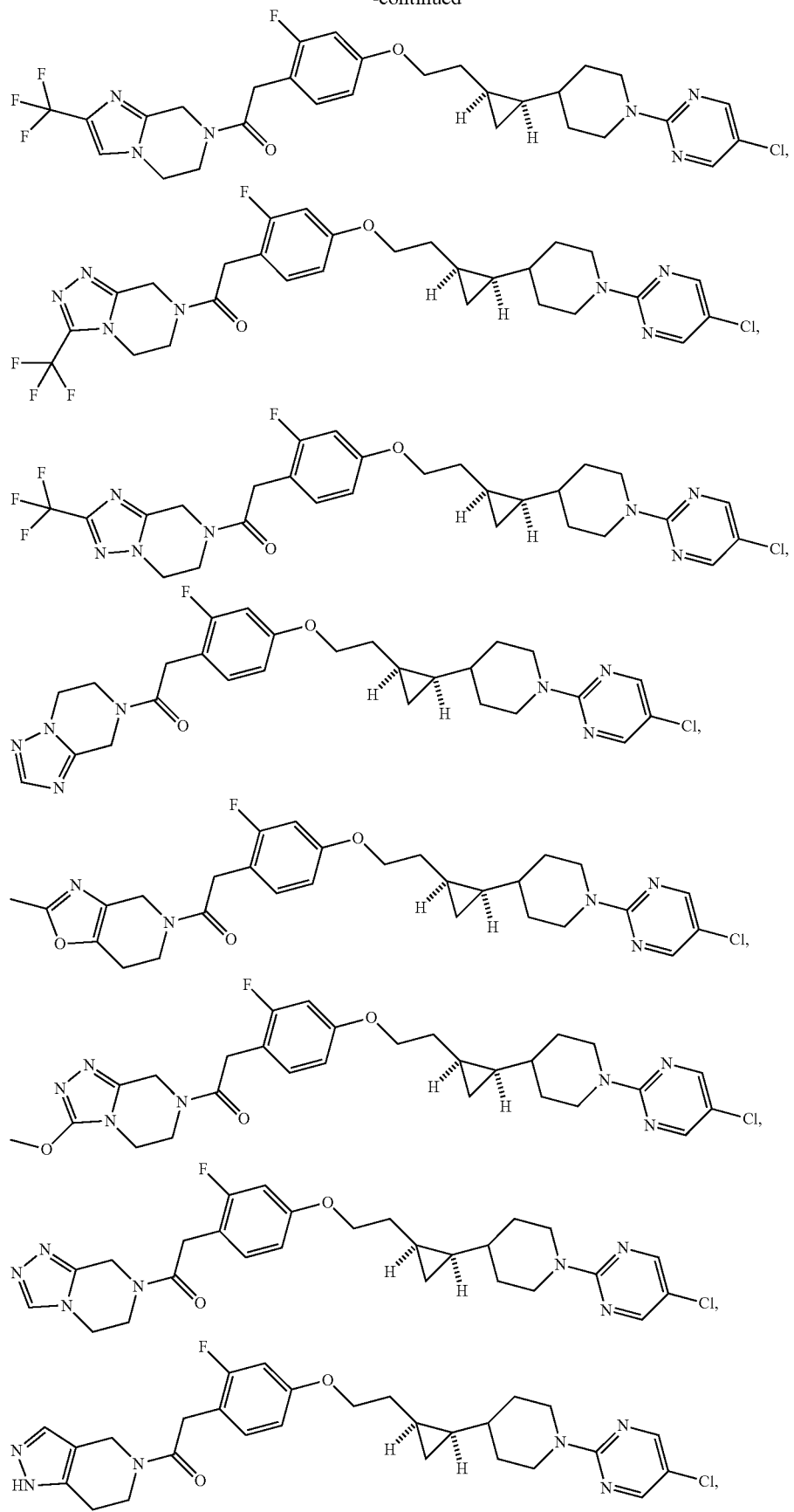

-continued
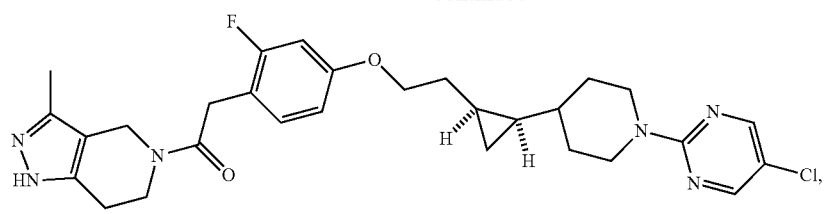
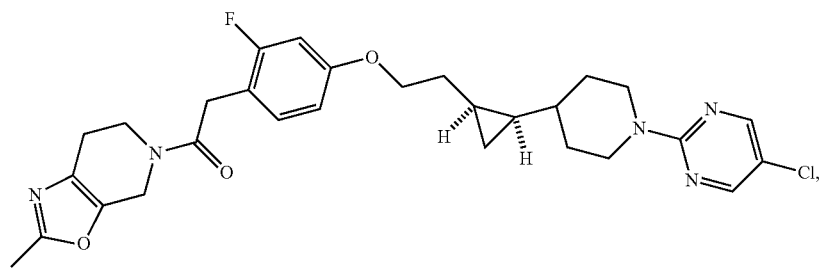
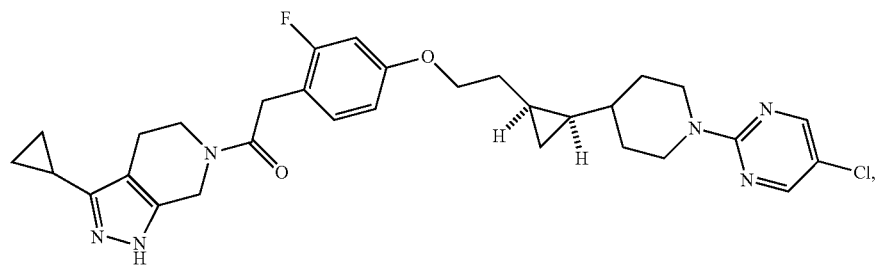
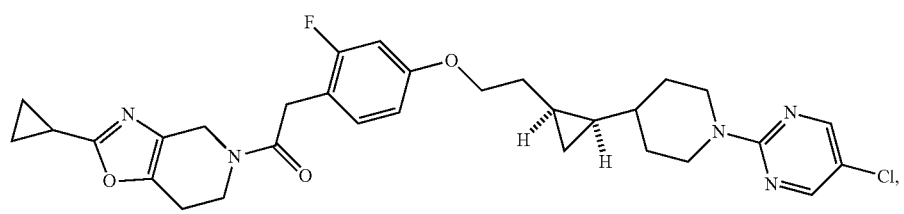
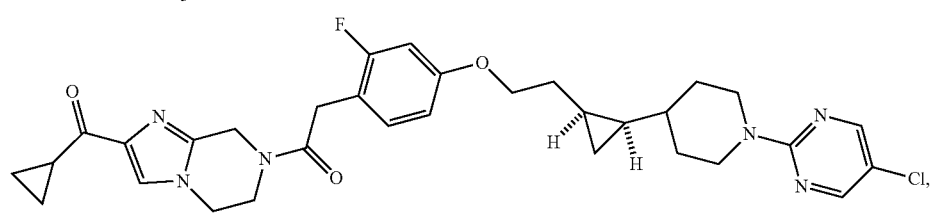
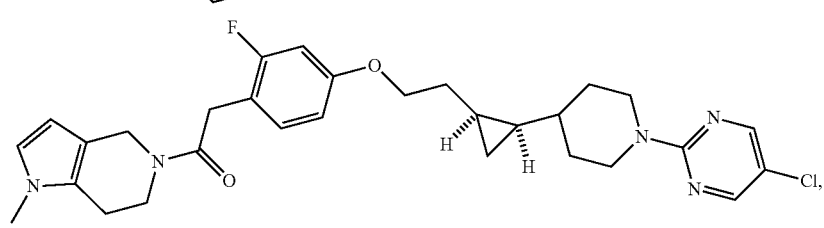
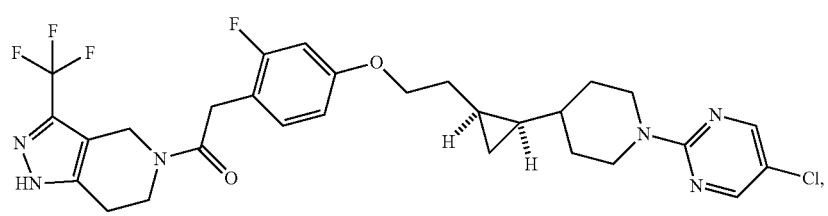

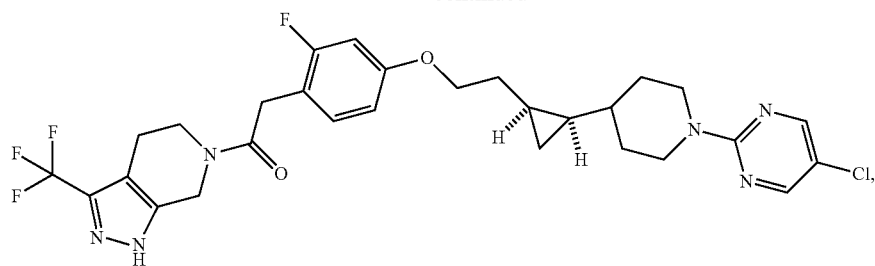
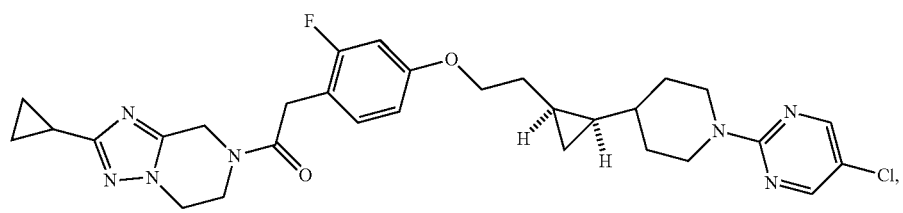
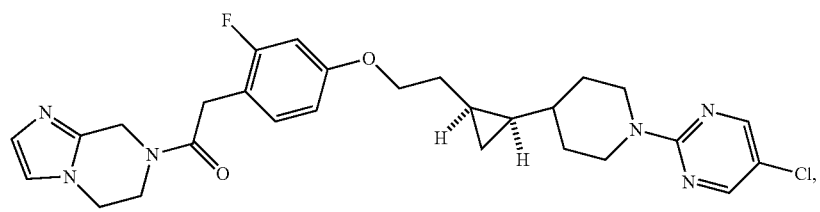
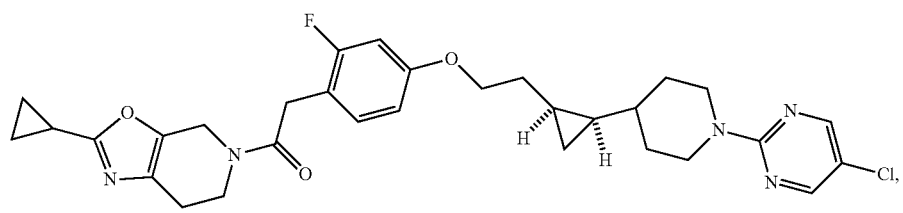
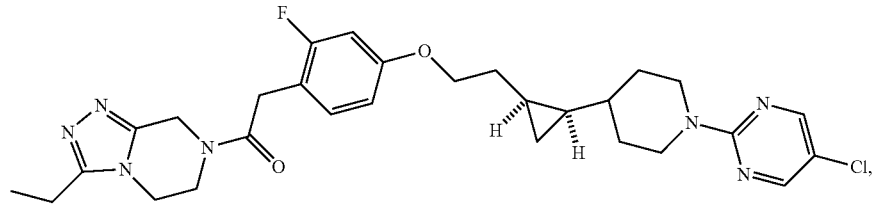
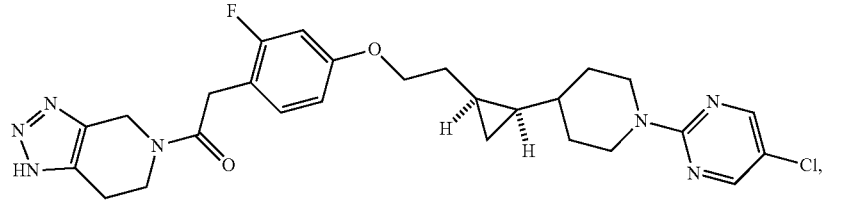
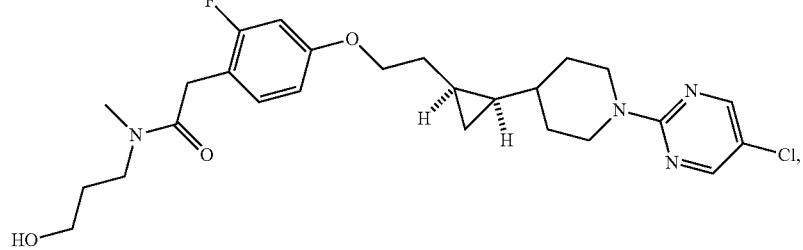

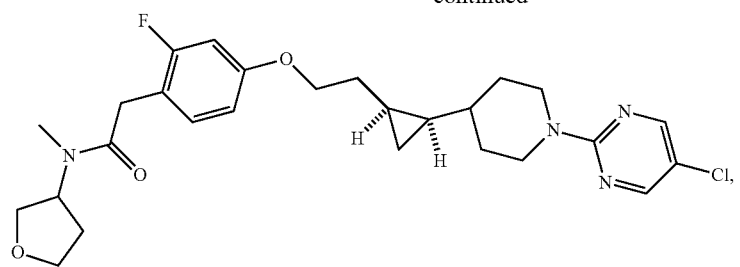
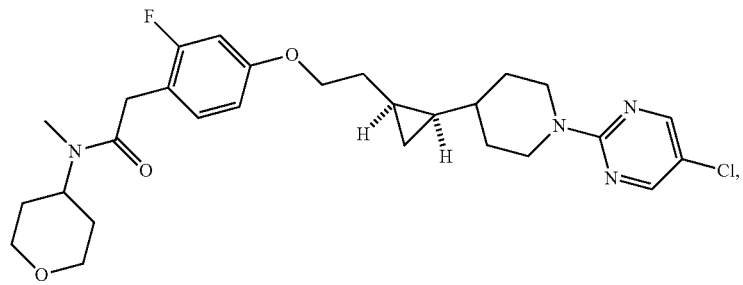
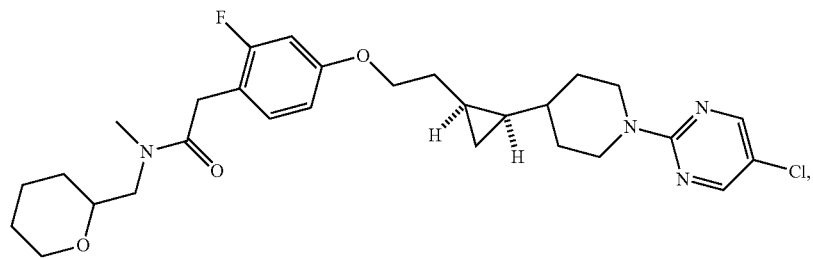
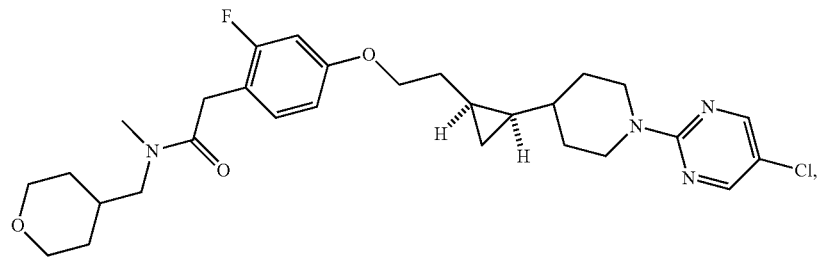
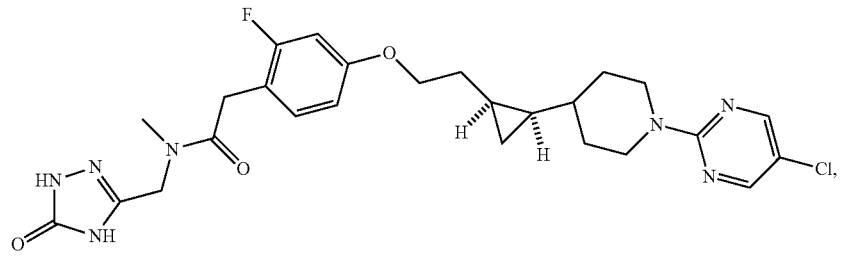
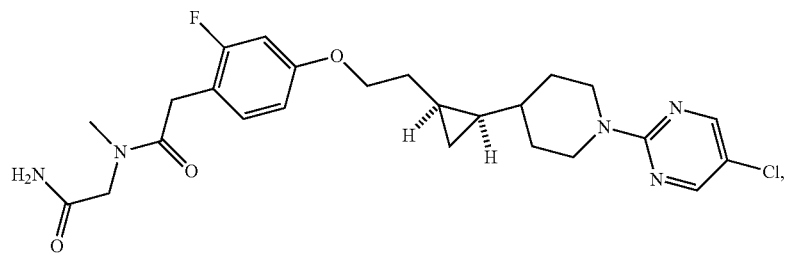

-continued
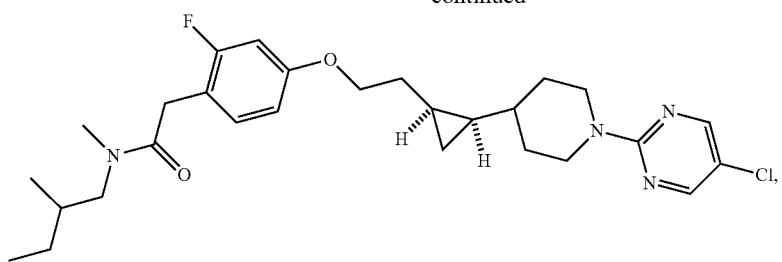
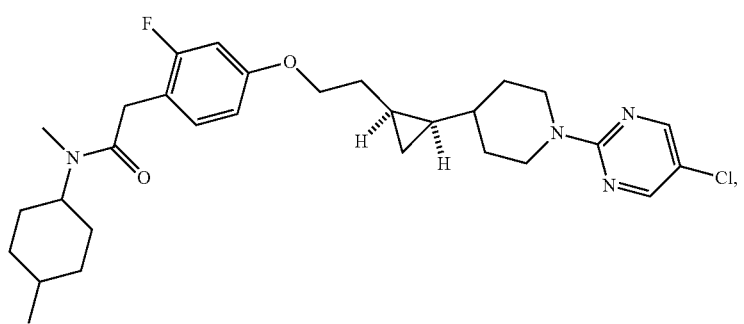
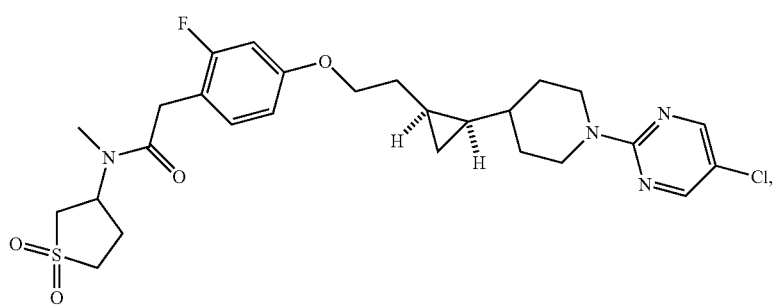
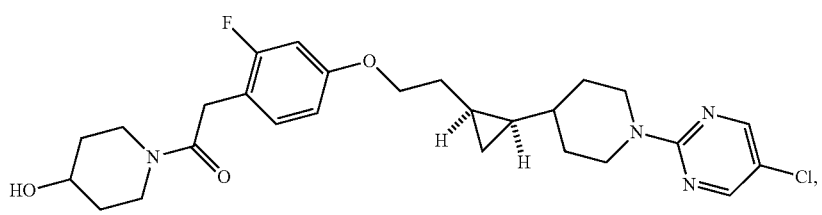
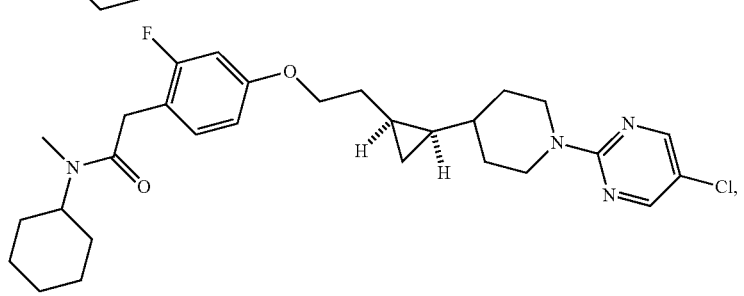
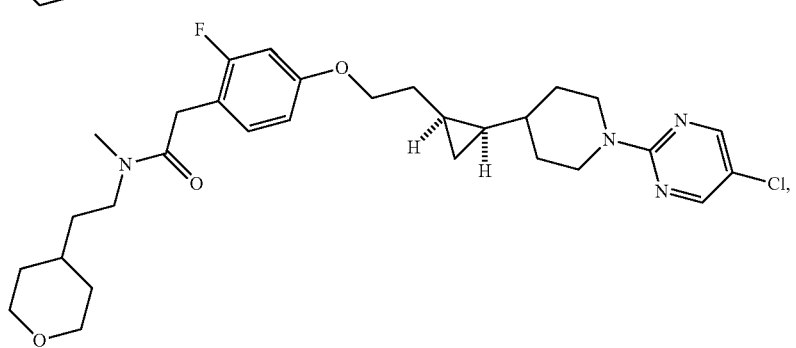

-continued
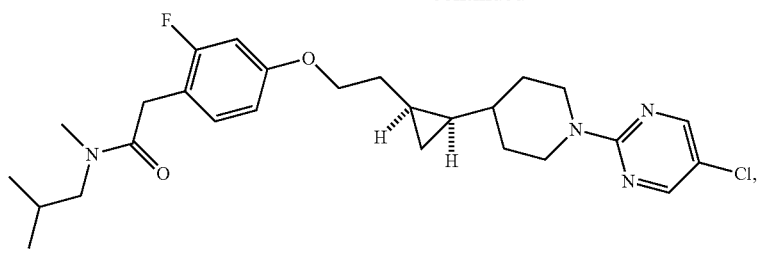
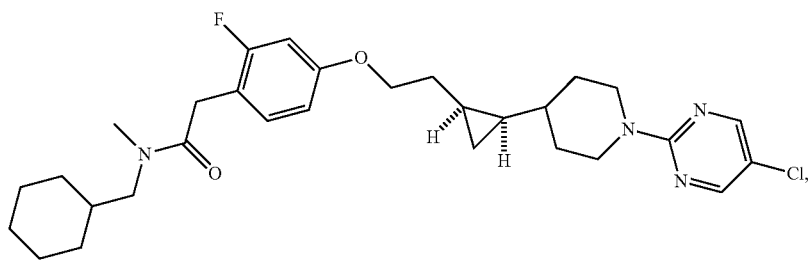
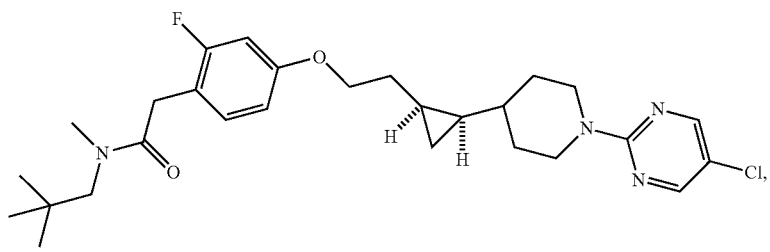
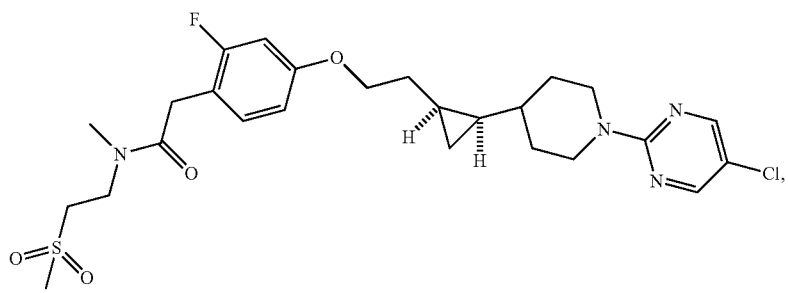
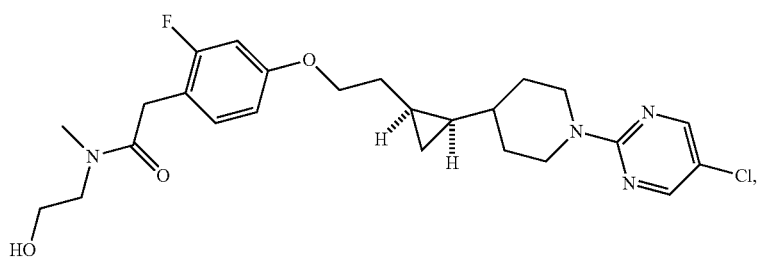
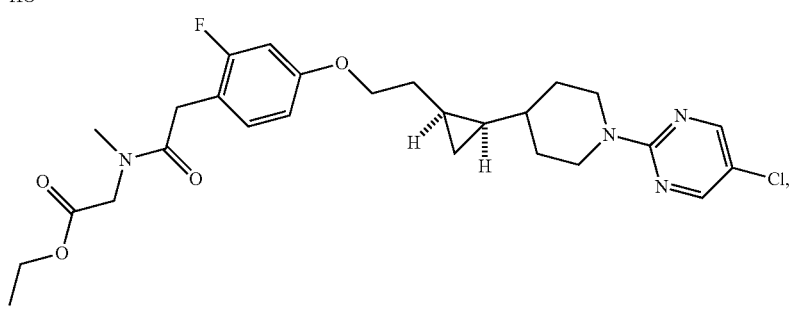

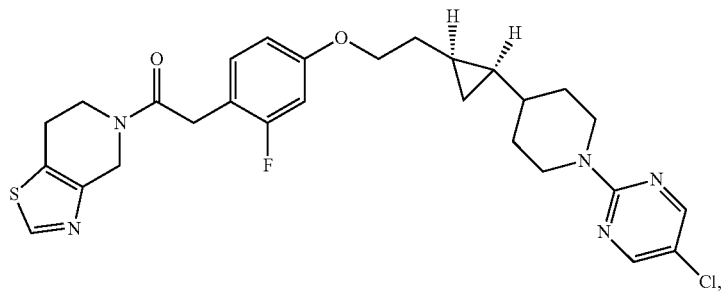
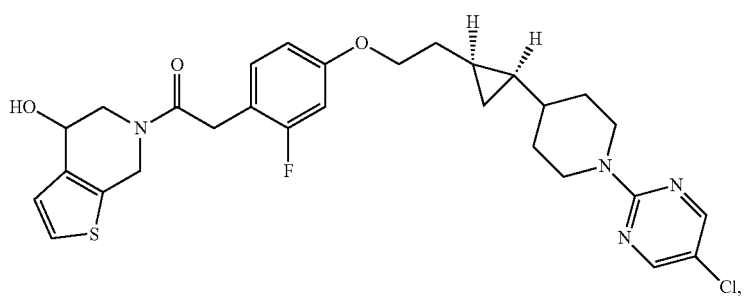
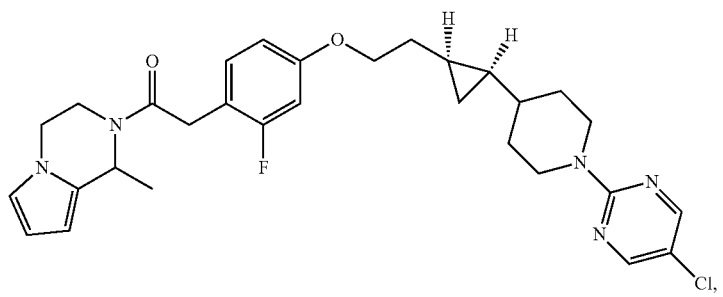
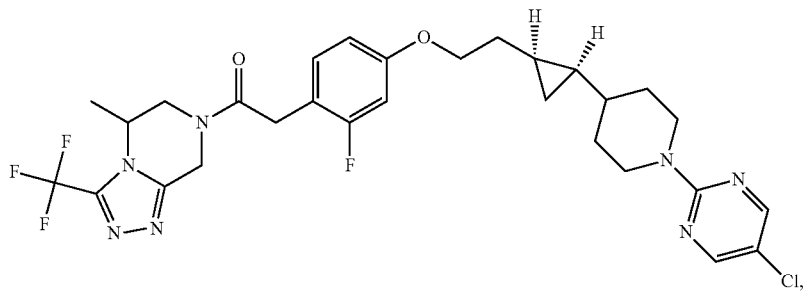
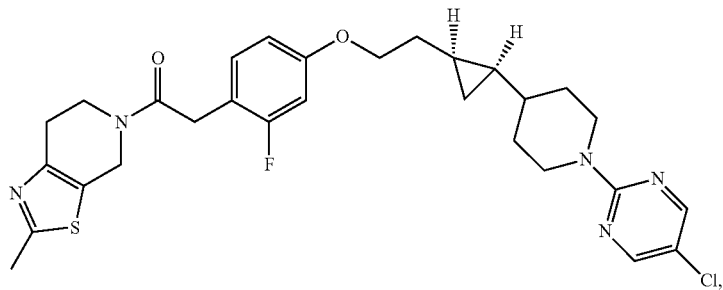

-continued
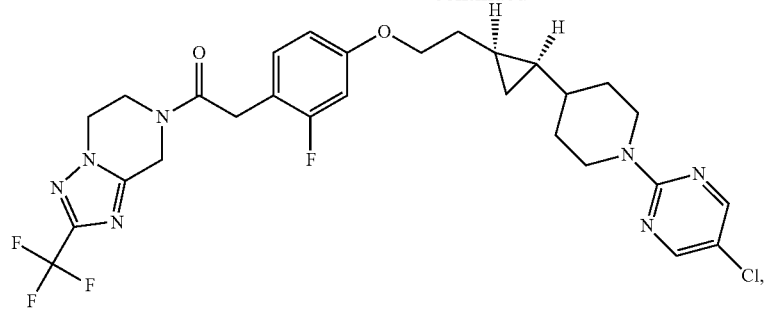
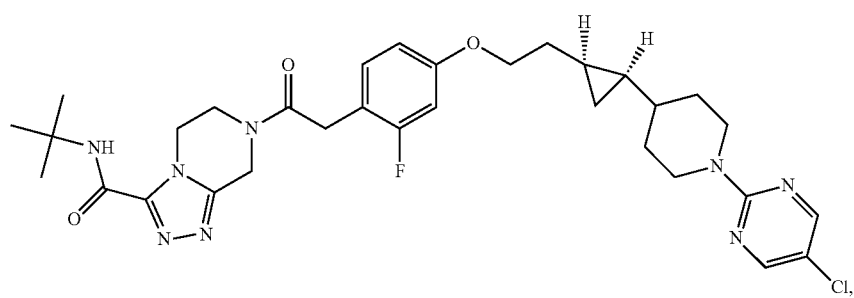
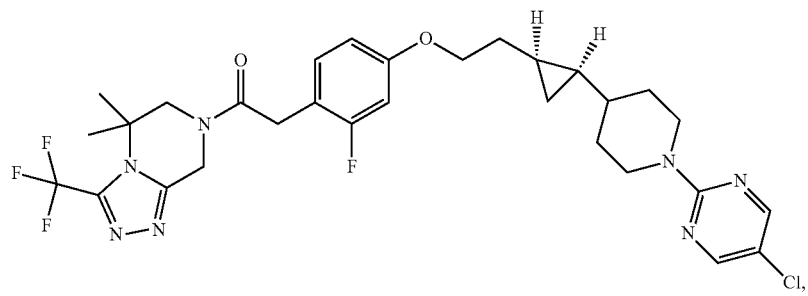
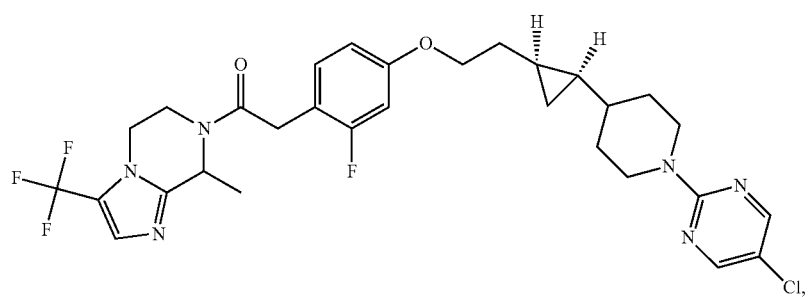
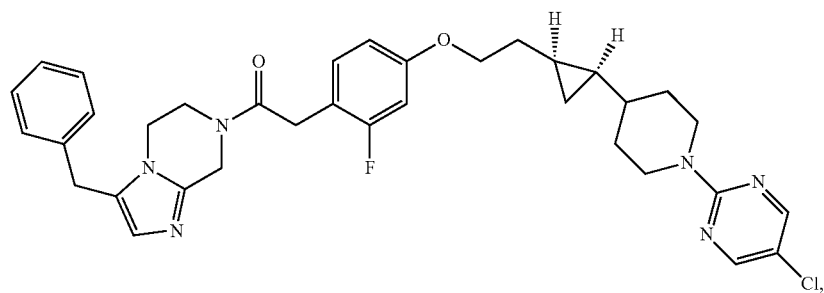

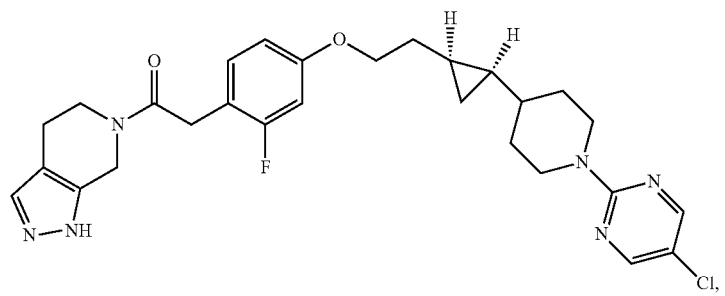
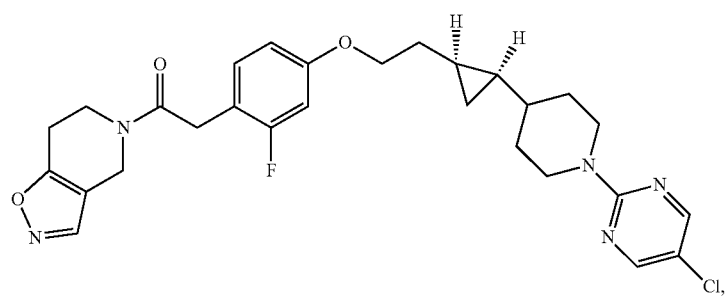
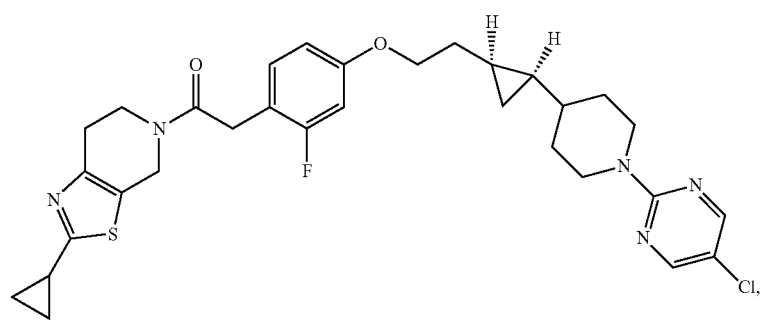
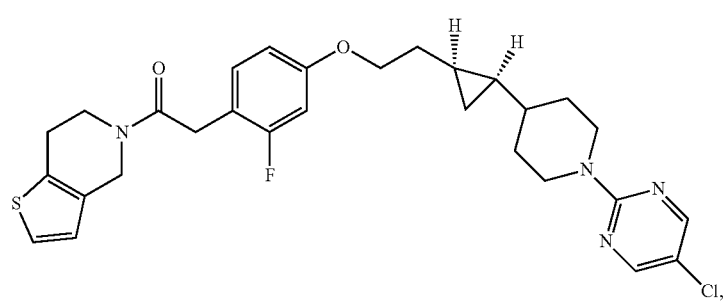
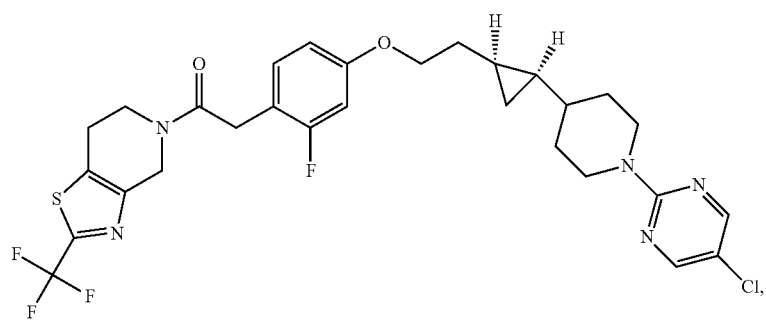

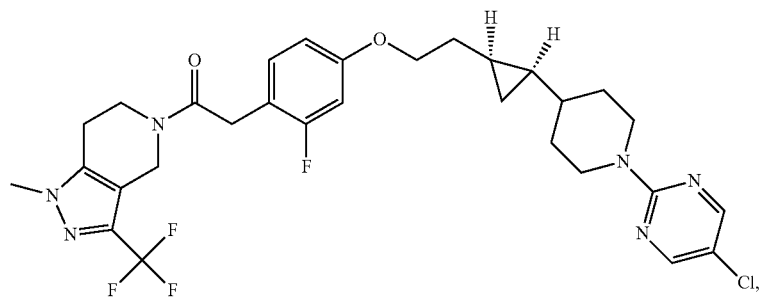
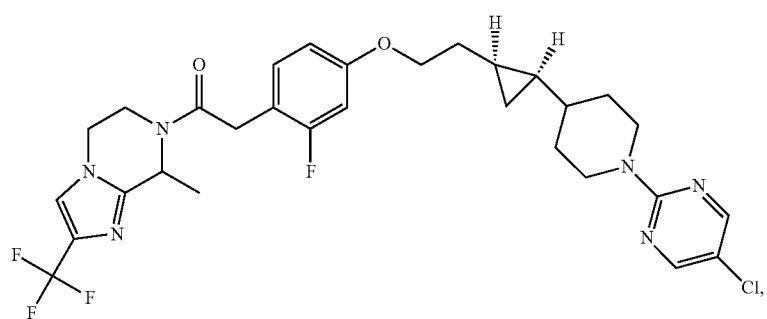
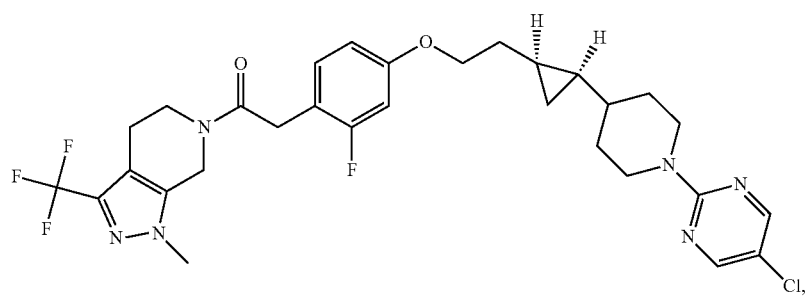
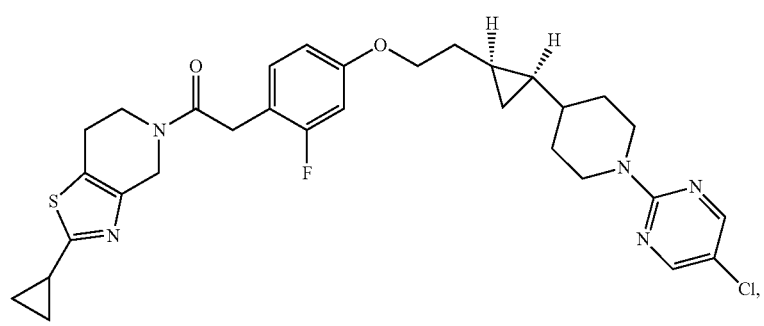
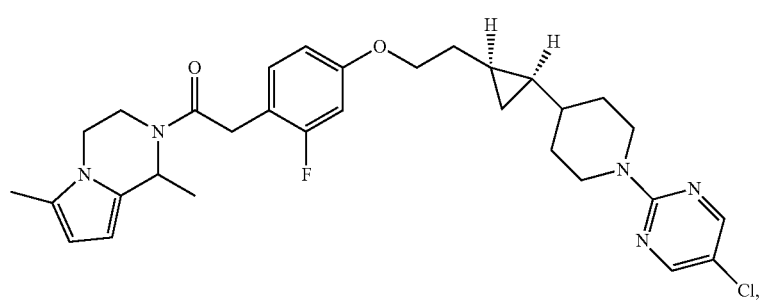

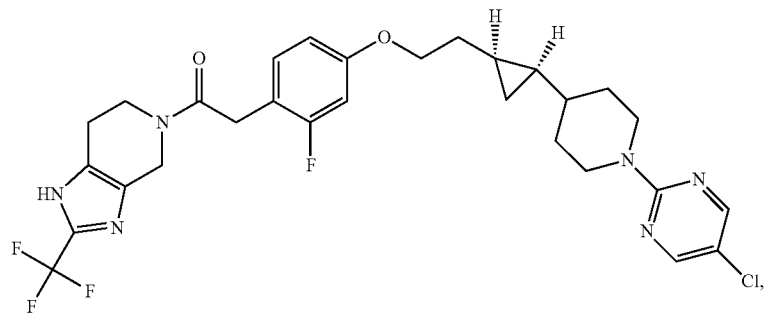
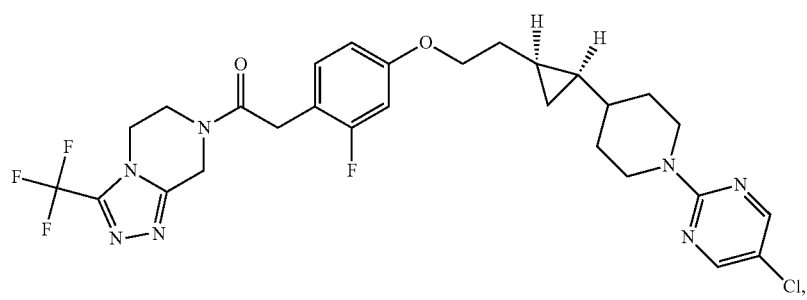
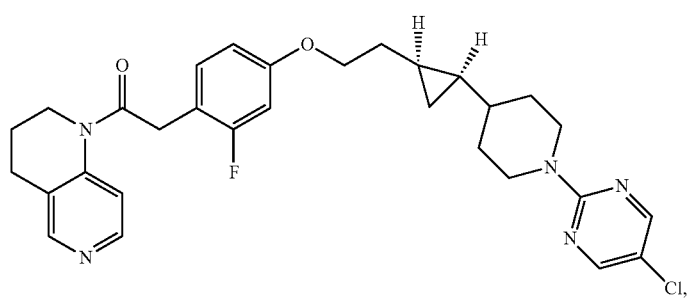
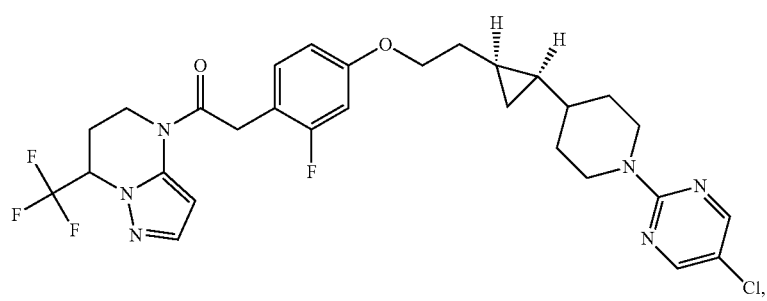
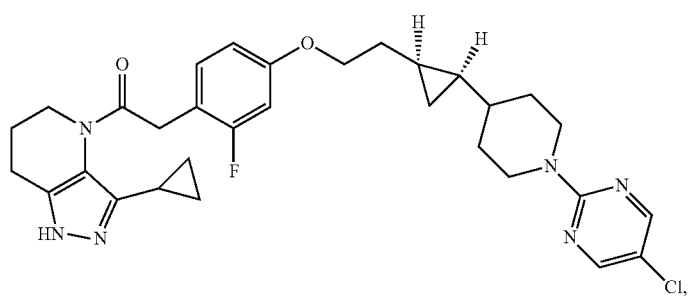

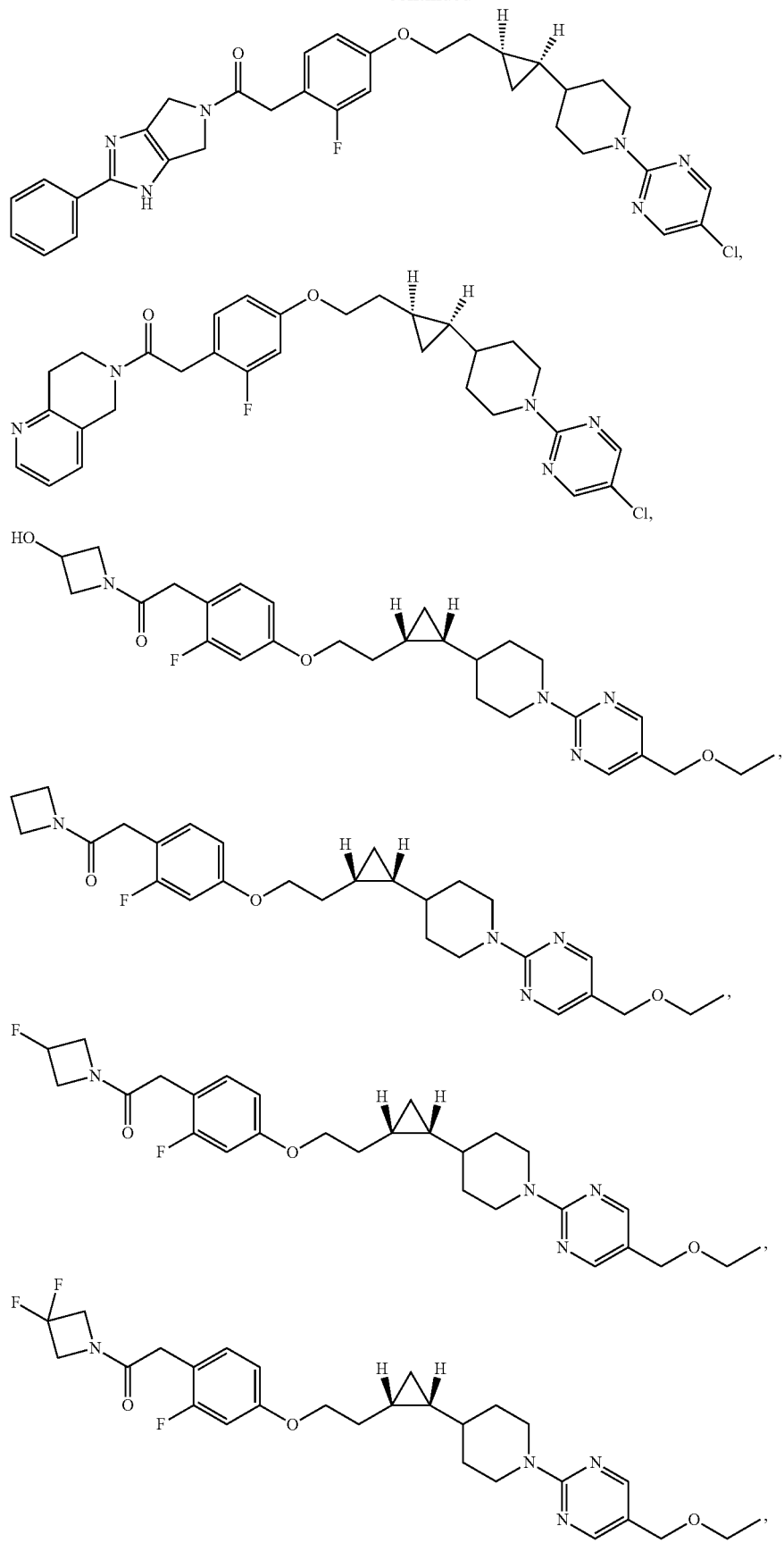

-continued
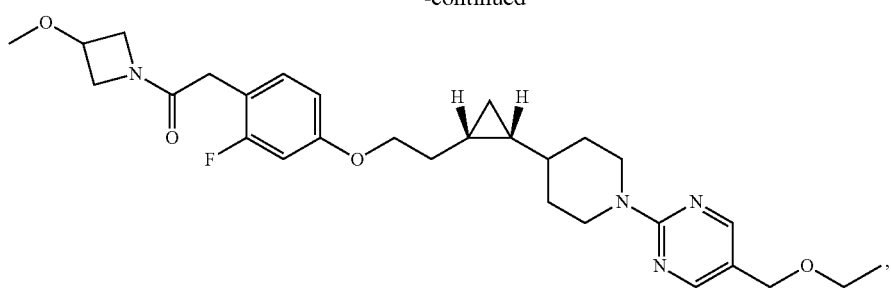
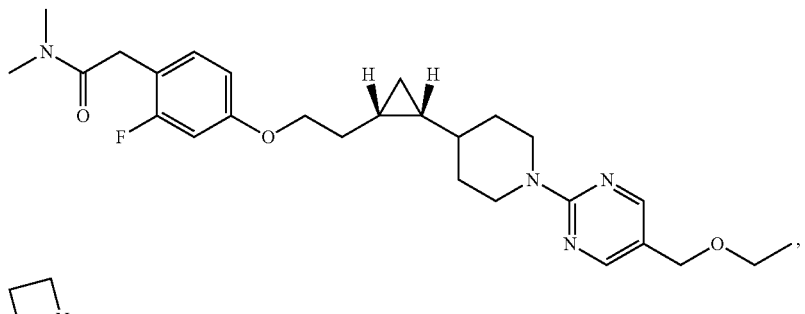
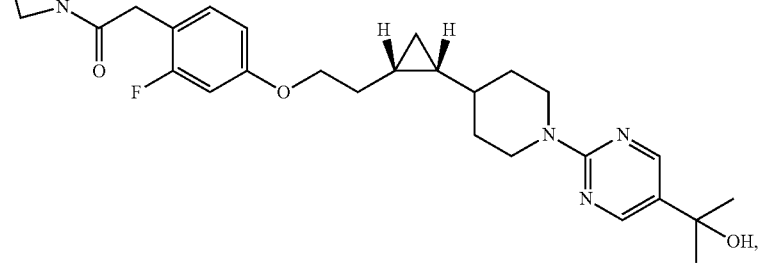
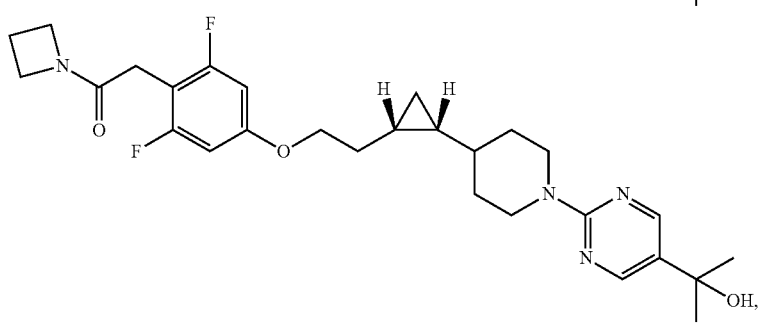
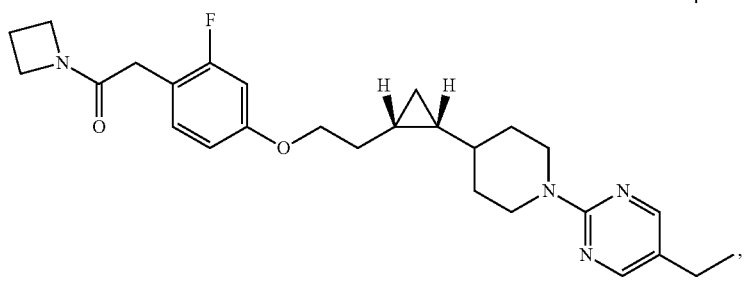
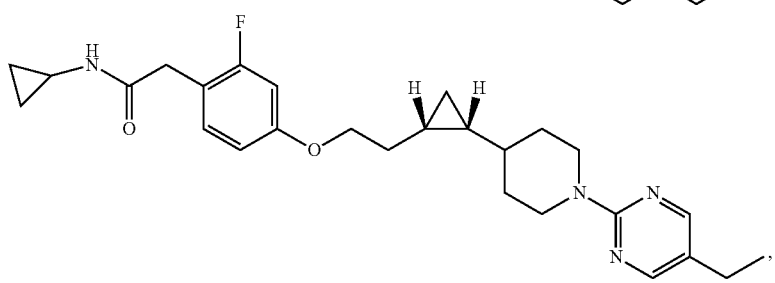

-continued
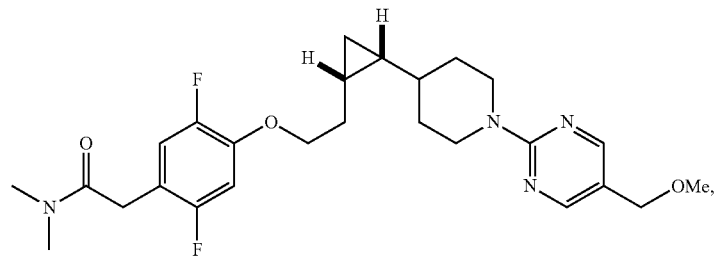
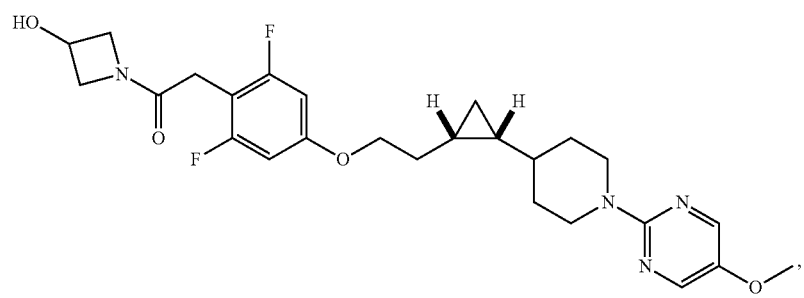
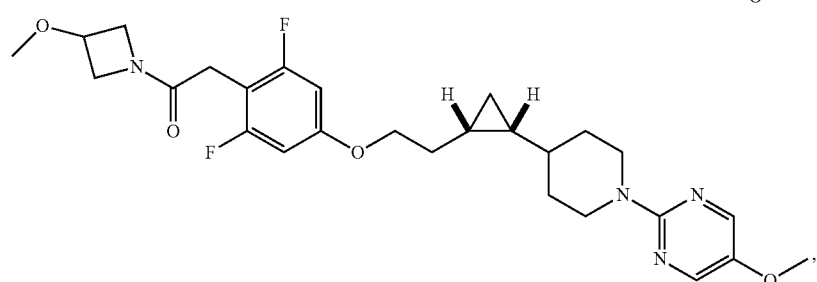
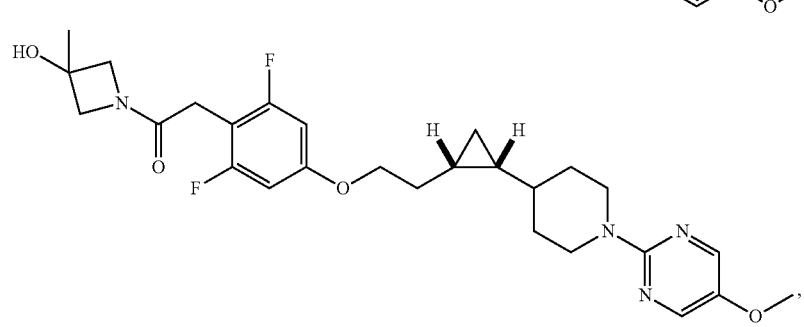
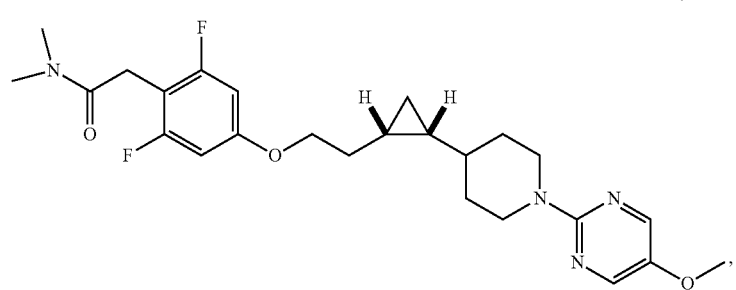
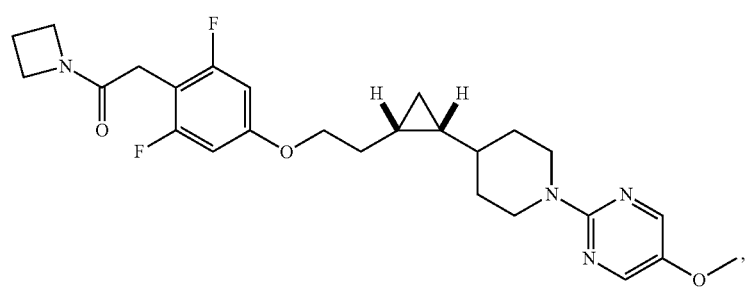

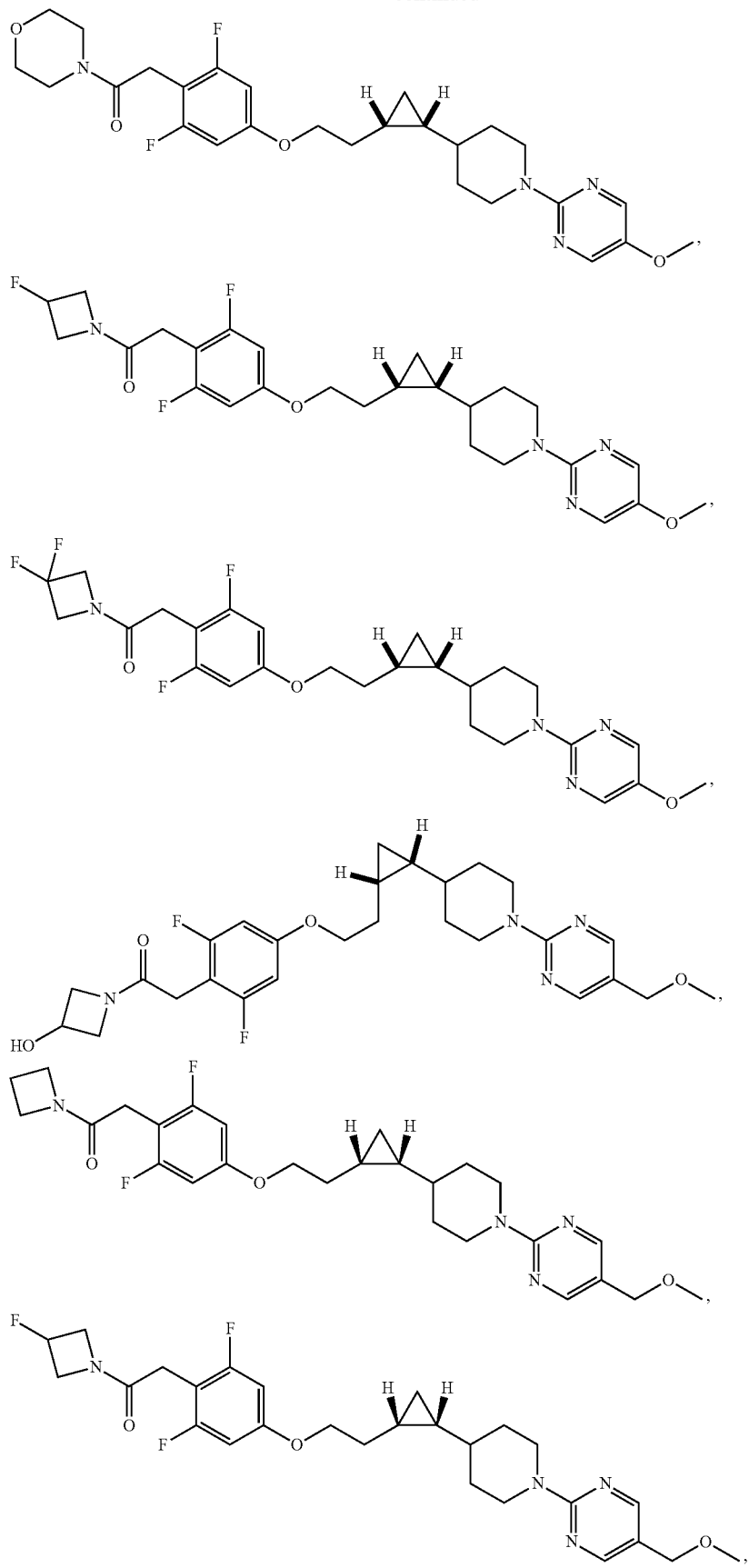

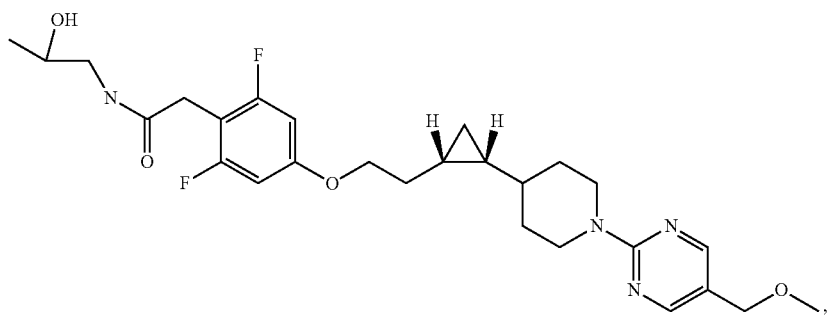
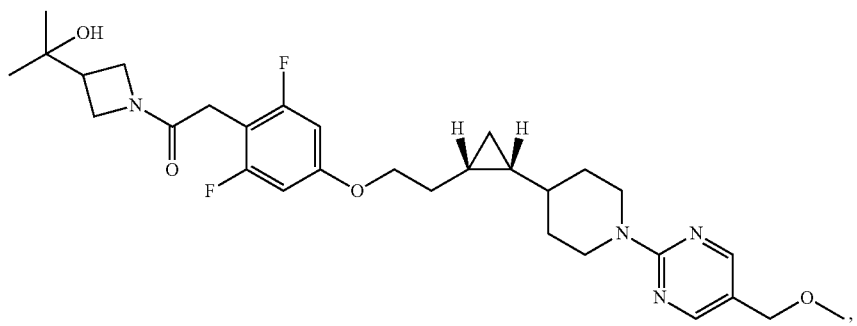
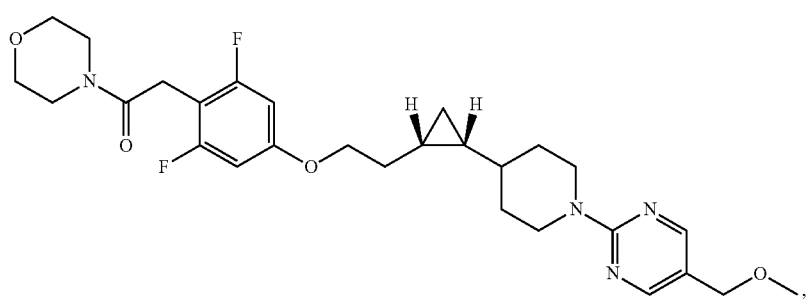
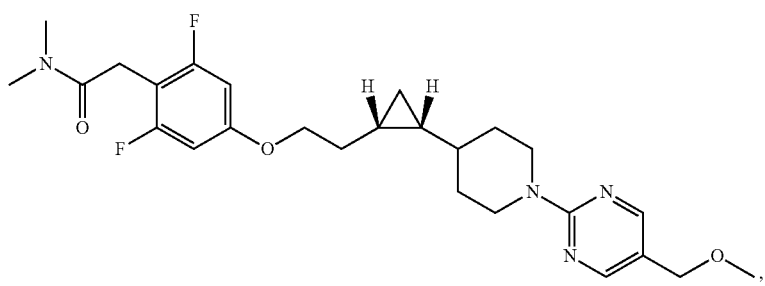
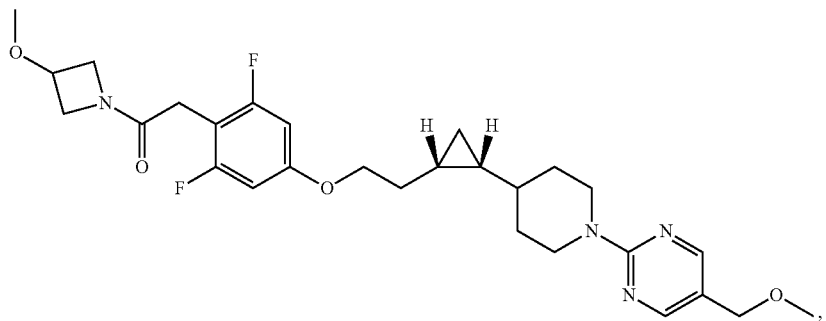

-continued
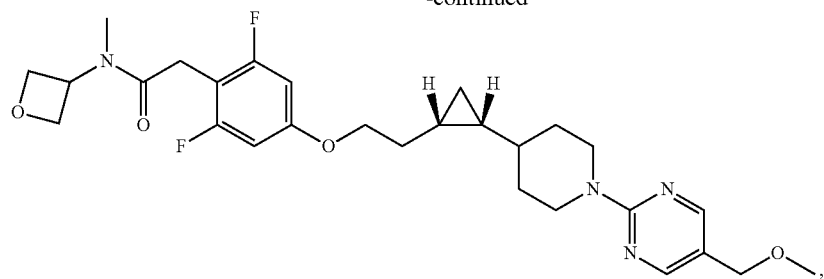
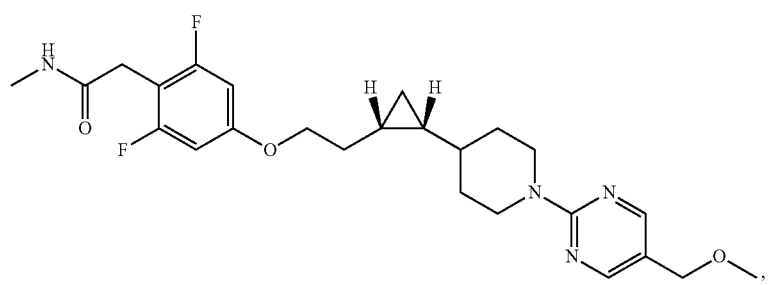
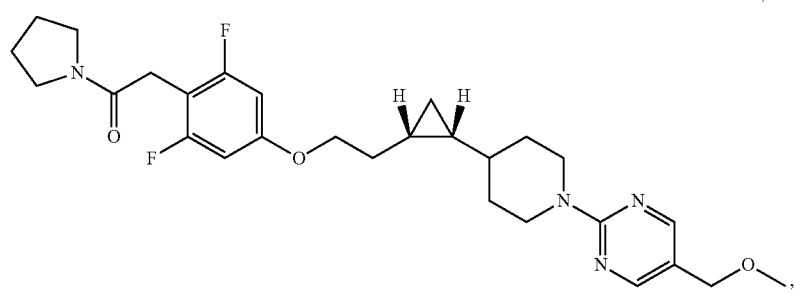
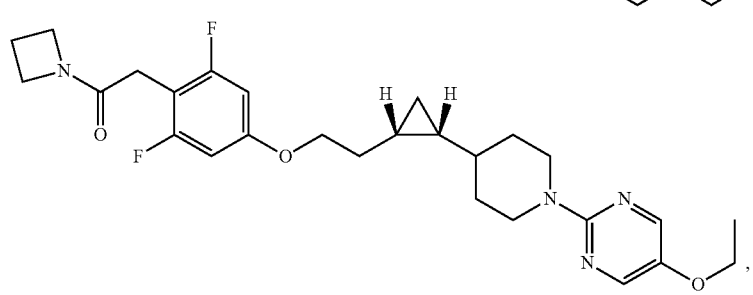
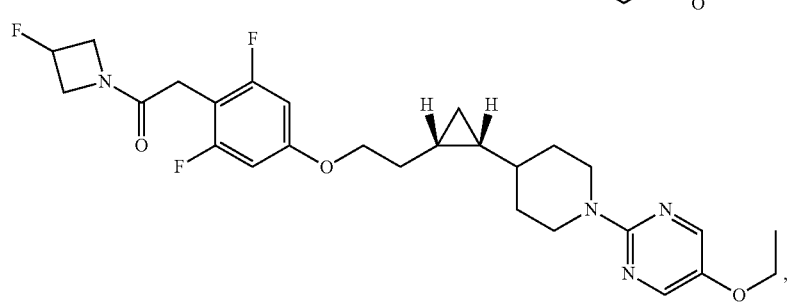
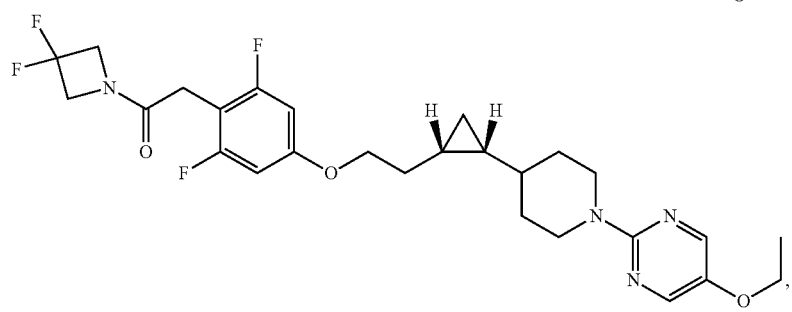

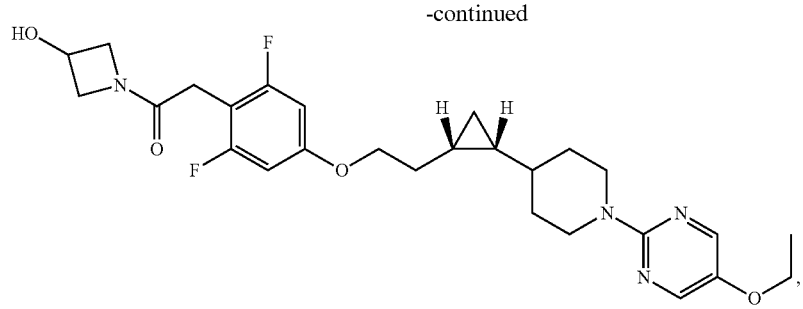
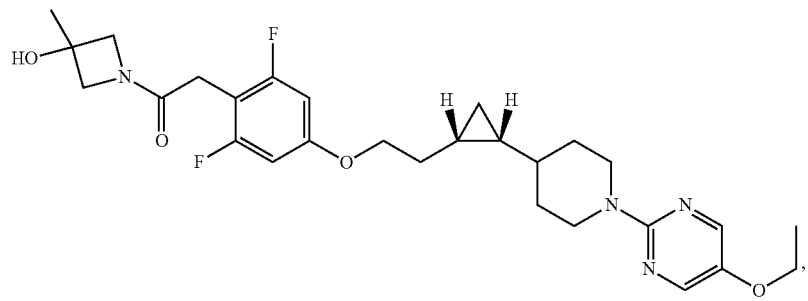
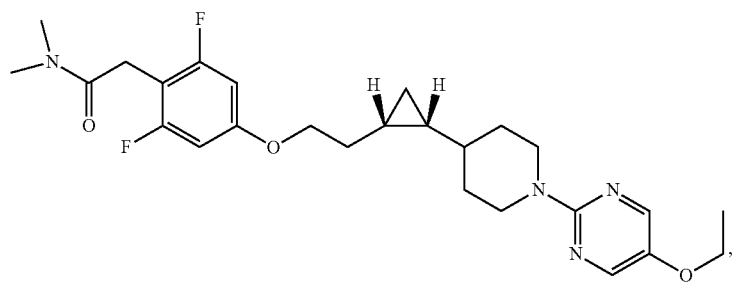
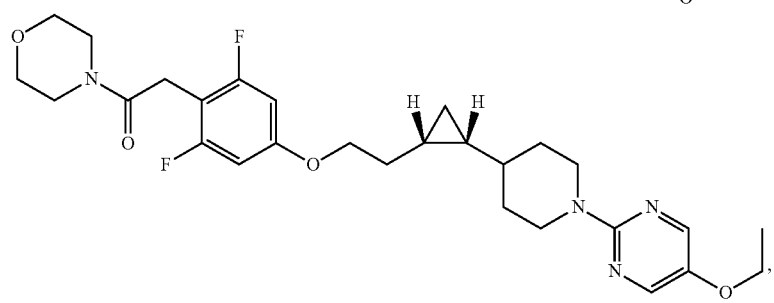
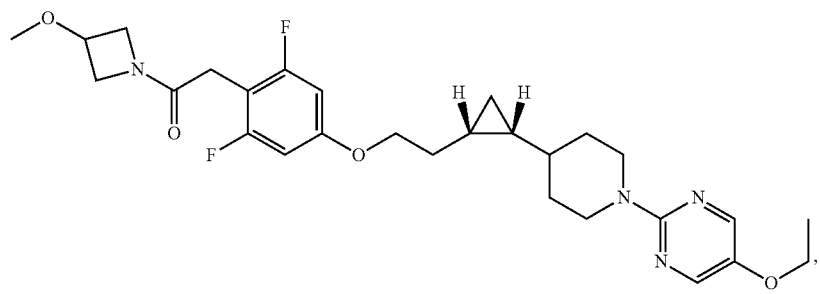
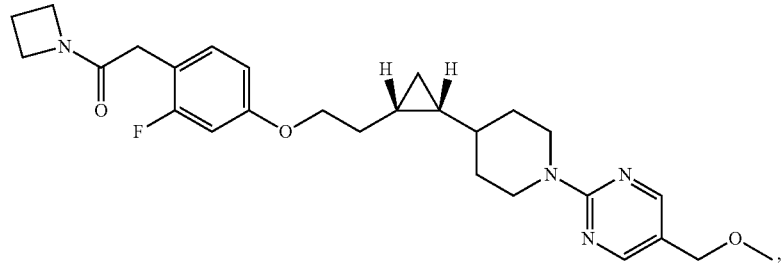

-continued
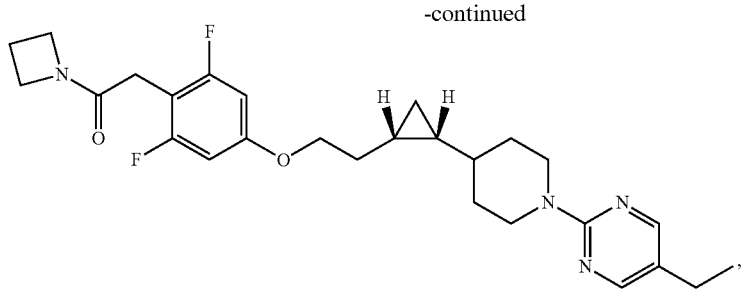
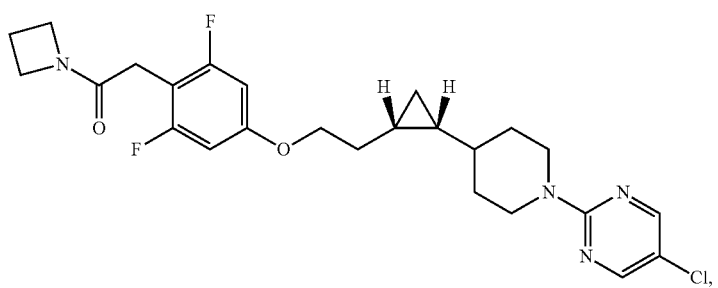
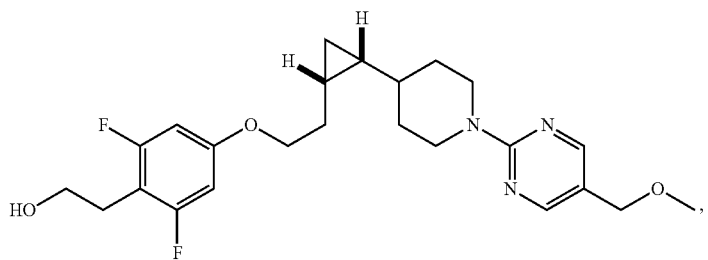
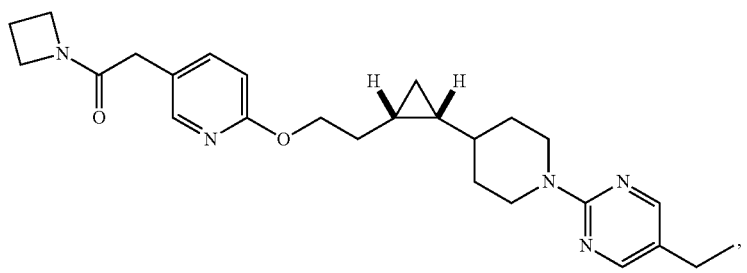
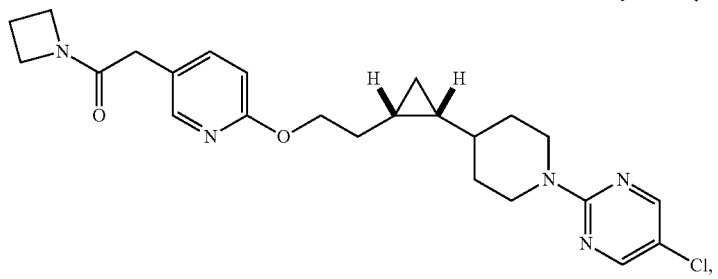
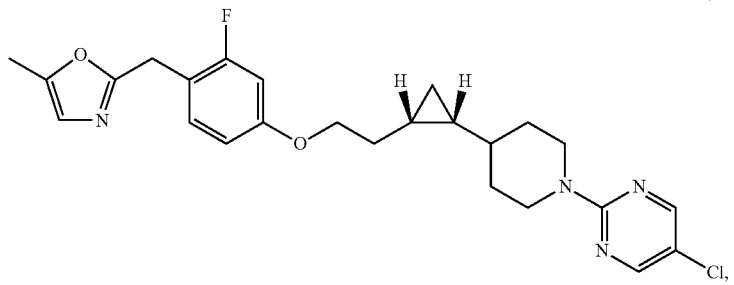

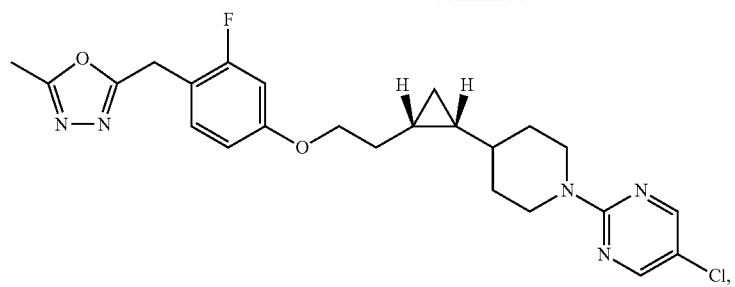
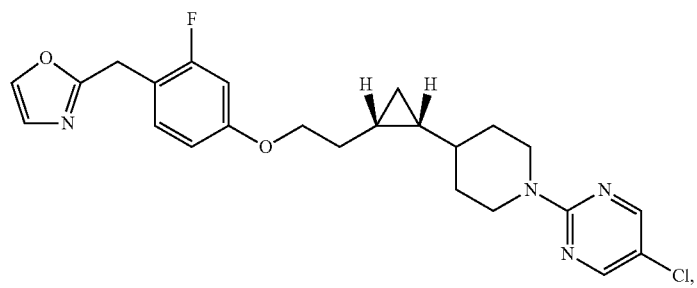
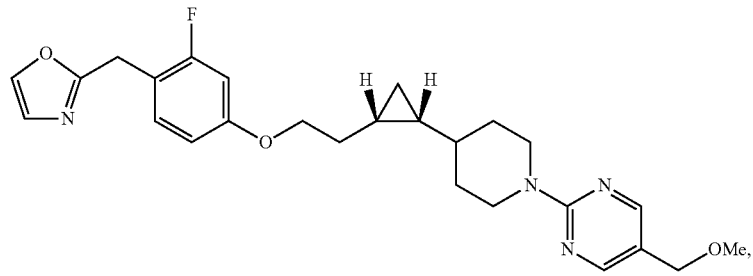
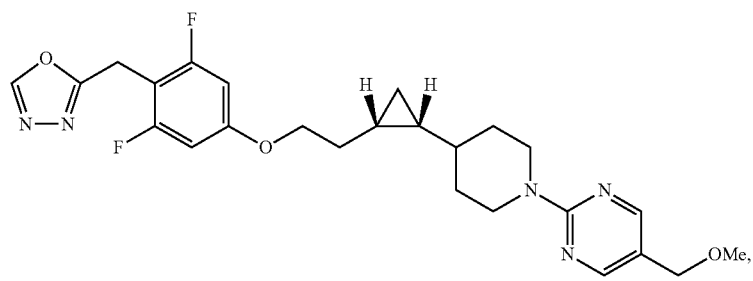
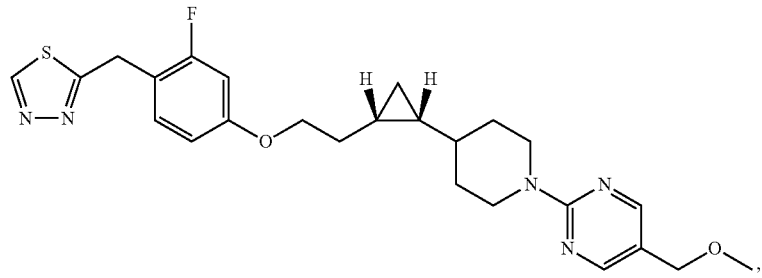
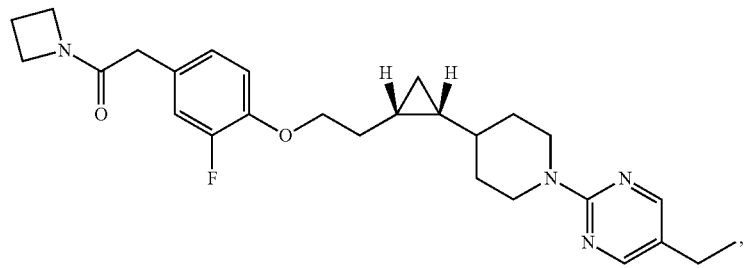

-continued
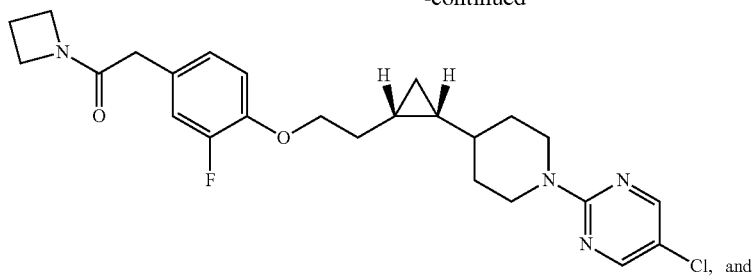
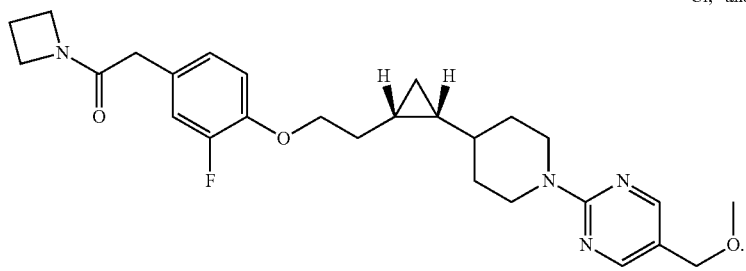
20. The compound of claim 1, or a pharmaceutically acceptable salt thereof, wherein the compound is
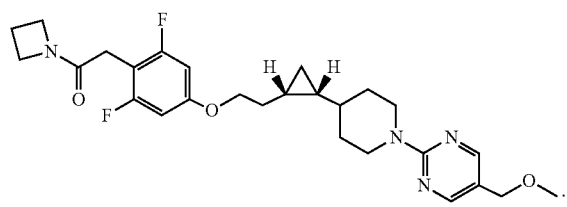 [SMILES: COCc1cnc(N2CCC([C@H]3C[C@H]3CCOc3cc(F)c(CC(=O)N4CCC4)c(F)c3)CC2)nc1]
21. The compound of claim 1, or a pharmaceutically acceptable salt thereof, wherein the compound is
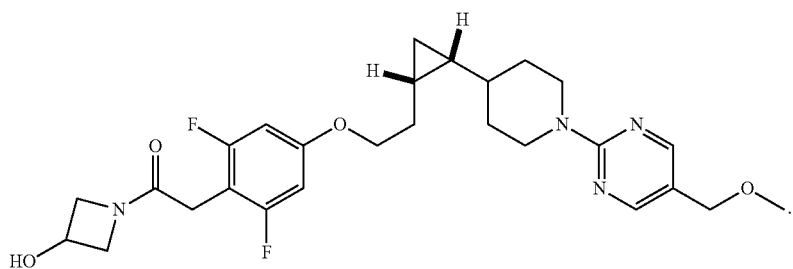 [SMILES: COCc1cnc(N2CCC([C@H]3C[C@H]3CCOc3cc(F)c(CC(=O)N4CC(O)C4)c(F)c3)CC2)nc1]
22. The compound of claim 1, or a pharmaceutically acceptable salt thereof, wherein the compound is
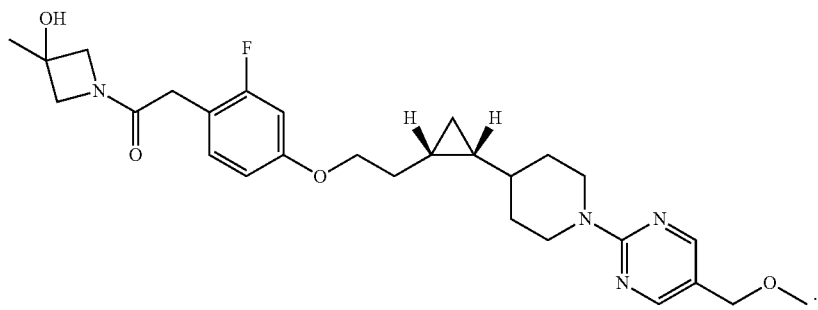

23. The compound of claim 1, or a pharmaceutically acceptable salt thereof, wherein the compound is

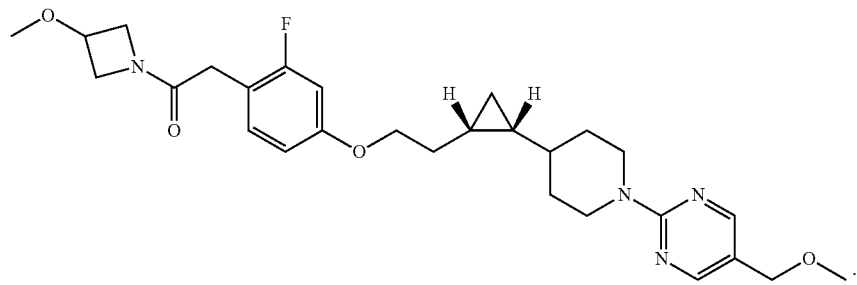

24. A pharmaceutical composition comprising a compound of claim 1, or a pharmaceutically acceptable salt thereof, and a pharmaceutically acceptable carrier.

25. A method for the treatment of a condition selected from the group consisting of obesity and diabetes comprising administering to an individual a pharmaceutical composition comprising the compound of claim 1 or a pharmaceutically acceptable salt thereof.

* * * * *